(12) United States Patent
Groves et al.

(10) Patent No.: US 12,098,191 B2
(45) Date of Patent: *Sep. 24, 2024

(54) ANTIBODIES TO AMYLOID BETA

(71) Applicant: MedImmune Limited, Cambridge (GB)

(72) Inventors: Maria Groves, Cambridge (GB); Suzanne Gustavsson, Huddinge (SE); Kina Höglund, Solna (SE); Chris Lloyd, Cambridge (GB); Adrian Nickson, Cambridge (GB); Camilla Niva, Arsta (SE); Sylvia Simon, Stockholm (SE); David Lowne, Cambridge (GB); Fraser Welsh, Cambridge (GB); Per-Ola Freskgard, Södertälje (SE)

(73) Assignee: MEDIMMUNE LIMITED, Cambridge (GB)

( * ) Notice: Subject to any disclaimer, the term of this patent is extended or adjusted under 35 U.S.C. 154(b) by 185 days.

This patent is subject to a terminal disclaimer.

(21) Appl. No.: 17/673,449

(22) Filed: Feb. 16, 2022

(65) Prior Publication Data

US 2022/0251181 A1    Aug. 11, 2022

Related U.S. Application Data

(63) Continuation of application No. 16/864,439, filed on May 1, 2020, now Pat. No. 11,286,297, which is a continuation of application No. 15/793,510, filed on Oct. 25, 2017, now Pat. No. 10,662,239, which is a continuation of application No. 14/435,520, filed as application No. PCT/EP2013/071567 on Oct. 15, 2013, now Pat. No. 9,834,598.

(60) Provisional application No. 61/713,996, filed on Oct. 15, 2012.

(51) Int. Cl.
| | | |
|---|---|---|
| *C07K 16/18* | (2006.01) | |
| *A61K 38/17* | (2006.01) | |
| *A61K 39/00* | (2006.01) | |
| *A61K 39/395* | (2006.01) | |
| *A61P 25/28* | (2006.01) | |

(52) U.S. Cl.
CPC ............ *C07K 16/18* (2013.01); *A61P 25/28* (2018.01); *A61K 38/1716* (2013.01); *A61K 39/3955* (2013.01); *A61K 2039/505* (2013.01); *C07K 2317/21* (2013.01); *C07K 2317/33* (2013.01); *C07K 2317/51* (2013.01); *C07K 2317/515* (2013.01); *C07K 2317/55* (2013.01); *C07K 2317/565* (2013.01); *C07K 2317/567* (2013.01); *C07K 2317/60* (2013.01); *C07K 2317/622* (2013.01); *C07K 2317/92* (2013.01)

(58) Field of Classification Search
CPC ............ C07K 16/18; C07K 2317/21; C07K 2317/33; C07K 2317/51; C07K 2317/515; C07K 2317/55; C07K 2317/565; C07K 2317/567; C07K 2317/60; C07K 2317/622; C07K 2317/92; A61P 25/28; A61K 38/1716; A61K 39/3955; A61K 2039/505; A61K 39/395; C12N 15/63

See application file for complete search history.

(56) References Cited

U.S. PATENT DOCUMENTS

| | | |
|---|---|---|
| 9,834,598 B2 | 12/2017 | Groves et al. |
| 10,662,239 B2 | 5/2020 | Groves et al. |
| 2018/0105585 A1 | 4/2018 | Groves et al. |

FOREIGN PATENT DOCUMENTS

| | | |
|---|---|---|
| CN | 1646559 A | 7/2005 |
| CN | 101076543 A | 11/2007 |
| CN | 101827862 | 9/2010 |
| CN | 101878301 A | 11/2010 |
| CN | 102076714 A | 5/2011 |
| EP | 1160256 | 12/2001 |
| EP | 1717250 | 11/2006 |
| EP | 2906597 | 8/2015 |
| RU | 2009/104769 | 8/2010 |
| WO | WO2003/015691 | 2/2003 |
| WO | WO2006/072620 | 7/2006 |
| WO | WO2008/011348 | 1/2008 |
| WO | WO 2014/060444 | 4/2014 |
| WO | WO2017/158064 | 9/2017 |
| WO | WO2017/160622 | 9/2017 |

OTHER PUBLICATIONS

Bannister et al., "Parallel, high-throughput purification of recombinant antibodies for in vivo cell assays," Biotechnol Bioeng., 94(5): 931-937 (2006).
Bard et al., "Peripherally administered antibodies against amyloid beta-peptide enter the central nervous system and reduce pathology in a mouse model of Alzheimer disease," Nat. Med. 6(8): 916-919 (2000).
Borchelt et al., "Familial Alzheimer's disease-linked presenilin 1 variants elevate Abeta1-42/1-40 ratio in vitro and in vivo," Neuron., 17(5):1005-1013 (1996).

(Continued)

*Primary Examiner* — Kimberly Ballard
*Assistant Examiner* — Stacey N MacFarlane
(74) *Attorney, Agent, or Firm* — Morgan, Lewis & Bockius LLP

(57) ABSTRACT

Antibody for human amyloid beta. Antibody selectively binds human amyloid beta 42 peptide over human amyloid beta 40 peptide. Antibodies specific for amyloid beta 42 as therapeutic agents for binding amyloid beta 42 peptide and treating conditions associated with amyloidosis, such as Alzheimer's disease.

12 Claims, 19 Drawing Sheets

Specification includes a Sequence Listing.

(56) References Cited

OTHER PUBLICATIONS

Calingasan et al., "β-amyloid 42 accumulation in the lumbar spinal cord motor neurons of amyotrophic lateral sclerosis patients," Neurobiology Disease, vol. 19(1): 340-347 (2005).
Citron et al., "Additive effects of PS1 and APP mutations on secretion of the 42-residue amyloid beta-protein," Neurobiol Dis., 5(2):107-116 (1998).
De Strooper, "Loss-of-function presenilin mutations in Alzheimer disease. Talking Point on the role of presenilin mutations in Alzheimer disease," EMBO Rep., 8(2):141-146 (2007).
DeMattos et al., "Peripheral anti-A beta antibody alters CNS and plasma A beta clearance and decreases brain A beta burden in a mouse model of Alzheimer's disease," PNAC USA, 98(15):8850-8855 (2001).
Duff et al., "Increased amyloid-beta42(43) in brains of mice expressing mutant presenilin 1," Nature, 383(6602):710-713 (1996).
EMD Millipore Corp. "Anti-Amyloid Beta (ABeta) x-42, clone 12F4", certificate of analysis, copyright 2008.
Gilman et al., "Clinical effects of Abeta immunization (AN1792) in patients with AD in an interrupted trial," Neurology, 64(9):1553-1562 (2005).
Glabe, "Does Alzheimer disease tilt the scales of amyloid degradation versus accumulation?" Nat Med., 6(2):133-134 (2000).
Golde et al., "Quantitative and mechanistic studies of Abeta immunotherapy," CNS & Neuro. Dis. Drug Targets, 8(1):31-49 (2009).
Greeve et al., "Age-dependent neurodegeneration and Alzheimer-amyloid plaque formation in transgenic *Drosophila*," J. Neurosci., 24(16):3899-3906 (2004).
Groves et al., "Applications of ribosome display to antibody drug discovery," Expert Opin Biol Ther., 5(1):125-135 (2005).
Hanes et al., "In vitro selection and evolution of functional proteins by using ribosome display," PNAS USA, 94(10):4937-4942 (1997).
Hanes et al., "Selecting and evolving functional proteins in vitro by ribosome display," Methods Enzymol., 328:404-430 (2000).
Hartman T., et al., "Distinct sites of intracellular production for Alzheimer's disease A beta40/42 amyloid peptides," Nature Medicine 3(9) pp. 1016-1020 (1997).
Hoet et al., "Generation of high-affinity human antibodies by combining donor-derived and synthetic complementarity-determining-region diversity," Nat Biotechnol., 23(3):344-348 (2005).
Human Amyloid β 1-42 (Aβ 1-42) Kit, Technical Data Sheeet, Copyright 2009, PerkinElmer, Inc. [Online] Retrieved from internet Feb. 23, 2016.
Lijima et al., "Dissecting the pathological effects of human Abeta40 and Abeta42 in *Drosophila*: a potential model for Alzheimer's disease," PNAS USA, 101(7):6623-6628 (2004).
Kim et al., "A β40 Inhibits Amyloid Deposition In Vivo," The Journal of Neuroscience, 27(3): 627-633 (2007).
Kuperstein et al., "Neurotoxicity of Alzheimer's disease Aβ peptides is induced by small changes in the Aβ42 to Aβ40 ratio," EMBO J., 29(19):3408-3420 (2010).
Lambert et al., "Diffusible, nonfibrillar ligands derived from Abeta1-42 are potent central nervous system neurotoxins," PNAS USA 95(11):6448-6453 (1998).
Levites et al., "Anti-Abeta42- and anti-Abeta40-specific mAbs attenuate amyloid deposition in an Alzheimer disease mouse model," J Clin Invest., 116(1):193-201 (2005).
Matsuoka et al., "Novel therapeutic approach for the treatment of Alzheimer's disease by peripheral administration of agents with an affinity to beta-amyloid,"J.Neurosci., 23(1):29-33 (2003).
McGowan et al., "Abeta42 is essential for parenchymal and vascular amyloid deposition in mice," Neuron., 47(2):191-199 (2005).
Mucke et al., "High-level neuronal expression of abeta 1-42 in wild-type human amyloid protein precursor transgenic mice: synaptotoxicity without plaque formation," J. Neurosci., 20(11):4050-4058 (2000).
Oganesyan et al., Structural characterization of a human Fc fragment engineered for lack of effector functions, Acta Crystallogr. D Bioi. Crystallogr., 64(Pt 6):700-704 (2008).
Orgogozo et al., "Subacute meningoencephalitis in a subset of patients with AD after Abeta42 immunization," neurology, 61(1):46-54 (2003).
Osbourn et al., "Generation of a panel of related human scFv antibodies with high affinities for human CEA," Immunotechnology, 2(3):181-196 (1996).
Persic et al., "An integrated vector system for the eukaryotic expression of antibodies or their fragments after selection from phage display libraries," Gene, 187(1):9-18 (1997).
Portelius et al., "Mass spectrometric characterization of brain amyloid beta isoform signatures in familial and sporadic Alzheimer's disease," Acta Neurppathol., 120(2):185-193 (2010).
Pride et al., "Progress in the active immunotherapeutic approach to Alzheimer's disease: clinical investigations into AN1792-associated meningoencephalitis," Neurodegener Dis., 5(3-4):194-196 (2008).
Schenk et al., "beta-peptide immunization: a possible new treatment for Alzheimer disease," Arch Neurol., 57(7):934-936 (2000).
Schenk et al., "Immunization with amyloid-beta attenuates Alzheimer-disease-like pathology in the PDAPP mouse," Nature, 400(6740): 173-177 (1999).
Scheuner et al., "Secreted amyloid beta-protein similar to that in the senile plaques of Alzheimer's disease is increased in vivo by the presenilin 1 and 2 and APP mutations linked to familial Alzheimer's disease," Nat Med., 2(8):864-870 (1996).
Selkoe, "Translating cell biology into therapeutic advances in Alzheimer's disease," Nature, 399:A23-31 (1999).
Tomlinson et al., "The repertoire of human germline VH sequences reveals about fifty groups of VH segments with different hypervariable loops," J Mol Biol., 227(3):776-798 (1992).
Vassar et al., "Beta-secretase cleavage of Alzheimer's amyloid precursor protein by the transmembrane aspartic protease BACE," Science, 286:735-741 (1999).
Vaughan et al., "Human antibodies with sub-nanomolar affinities isolated from a large non-immunized phage display library," Nat Biotechnol., 14(3):309-314 (1996).
Walsh et al., "Certain inhibitors of synthetic amyloid beta-peptide (Abeta) fibrillogenesis block oligomerization of natural Abeta and thereby rescue long-term potentiation," J Neurosci., 25:2455-2462 (2005).
Walsh et al., "Naturally secreted oligomers of amyloid beta protein potently inhibit hippocampal long-term potentiation in vivo," Nature, 416:535-539 (2002).
Walsh et al., "The role of cell-derived oligomers of Abeta in Alzheimer's disease and avenues for therapeutic intervention," Biochem Soc Trans., 33:1087-1090 (2005).
Wang et al., "Soluble oligomers of beta amyloid (1-42) inhibit long-term potentiation but not long-term depression in rat dentate gyrus," Brain Res., 924:133-140 (2002).
Weller et al., "Cerebral amyloid angiopathy: pathogenesis and effects on the ageing and Alzheimer brain," Neurol Res., 25:611-616 (2003).
Wilcock et al., "Deglycosylated anti-amyloid-beta antibodies eliminate cognitive deficits and reduce parenchymal amyloid with minimal vascular consequences in aged amyloid precursor protein transgenic mice," J Neurosci., 26:5340-5346 (2006).
Wilcock et al., "Immunotherapy, vascular pathology, and microhemorrhages in transgenic mice," CNS Neurol Disord Drug Targets, 8:50-64 (2009).
Younkin, "Evidence that A beta 42 is the real culprit in Alzheimer's disease," Ann Neurol., 37:287-288 (1995).
Younkin, "The role of A beta 42 in Alzheimer's disease," J Physiol, 92:289-292 (1998).

C

D

A

B

C

D

A

B

C

D

A

B

C

D

SEQUENCE LISTING

```
<160> NUMBER OF SEQ ID NOS: 578

<210> SEQ ID NO 1
<211> LENGTH: 375
<212> TYPE: DNA
<213> ORGANISM: Homo sapiens
<220> FEATURE:
<223> OTHER INFORMATION: Abet0007

<400> SEQUENCE: 1
gaggtgcagc tgttggagtc tgggggaggc ttggtacagc ctgggggtc cctgagactc      60 tcctgtgcag cctctggatt caccttagc gtttatacta tgtggtgggt ccgccaggct     120
ccagggaagg ggctggagtg ggtctcagtt attggttcta gtggtggtac gacagtttac     180
gcagactccg tgaagggccg gttcaccatc tccagagaca attccaagaa cacgctgtat     240
```

```
ctgcaaatga acagcctgag agccgaggac acggccgtgt attactgtgc gagagaaggg    300
cagcagctgg tacgcccta ctactactac ggtatggacg tctggggca ggggaccctg     360 gtcaccgtct cctca                                                    375
```

```
<210> SEQ ID NO 2
<211> LENGTH: 125
<212> TYPE: PRT
<213> ORGANISM: Homo sapiens
<220> FEATURE:
<223> OTHER INFORMATION: Abet0007

<400> SEQUENCE: 2
```

Glu Val Gln Leu Leu Glu Ser Gly Gly Gly Leu Val Gln Pro Gly Gly
                5                   10                  15

Ser Leu Arg Leu Ser Cys Ala Ala Ser Gly Phe Thr Phe Ser Val Tyr
            20                  25                  30

Thr Met Trp Trp Val Arg Gln Ala Pro Gly Lys Gly Leu Glu Trp Val
        35                  40                  45

Ser Val Ile Gly Ser Ser Gly Gly Thr Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gln Gln Leu Val Arg Pro Tyr Tyr Tyr Tyr Gly Met
            100                 105                 110

Asp Val Trp Gly Gln Gly Thr Leu Val Thr Val Ser Ser
        115                 120                 125

```
<210> SEQ ID NO 3
<211> LENGTH: 5
<212> TYPE: PRT
<213> ORGANISM: Homo sapiens
<220> FEATURE:
<223> OTHER INFORMATION: Abet0007

<400> SEQUENCE: 3
```

Val Tyr Thr Met Trp
                5

```
<210> SEQ ID NO 4
<211> LENGTH: 17
<212> TYPE: PRT
<213> ORGANISM: Homo sapiens
<220> FEATURE:
<223> OTHER INFORMATION: Abet0007

<400> SEQUENCE: 4
```

Val Ile Gly Ser Ser Gly Gly Thr Thr Val Tyr Ala Asp Ser Val Lys
                5                   10                  15

Gly

```
<210> SEQ ID NO 5
<211> LENGTH: 16
<212> TYPE: PRT
<213> ORGANISM: Homo sapiens
<220> FEATURE:
<223> OTHER INFORMATION: Abet0007

<400> SEQUENCE: 5
```

Glu Gly Gln Gln Leu Val Arg Pro Tyr Tyr Tyr Tyr Gly Met Asp Val 5                  10                  15

<210> SEQ ID NO 6
<211> LENGTH: 30
<212> TYPE: PRT
<213> ORGANISM: Homo sapiens
<220> FEATURE:
<223> OTHER INFORMATION: Abet0007

<400> SEQUENCE: 6

Glu Val Gln Leu Leu Glu Ser Gly Gly Gly Leu Val Gln Pro Gly Gly
                  5                  10                  15

Ser Leu Arg Leu Ser Cys Ala Ala Ser Gly Phe Thr Phe Ser
         20                  25                  30

<210> SEQ ID NO 7
<211> LENGTH: 14
<212> TYPE: PRT
<213> ORGANISM: Homo sapiens
<220> FEATURE:
<223> OTHER INFORMATION: Abet0007

<400> SEQUENCE: 7

Trp Val Arg Gln Ala Pro Gly Lys Gly Leu Glu Trp Val Ser
                  5                  10

<210> SEQ ID NO 8
<211> LENGTH: 32
<212> TYPE: PRT
<213> ORGANISM: Homo sapiens
<220> FEATURE:
<223> OTHER INFORMATION: Abet0007

<400> SEQUENCE: 8

Arg Phe Thr Ile Ser Arg Asp Asn Ser Lys Asn Thr Leu Tyr Leu Gln
                  5                  10                  15

Met Asn Ser Leu Arg Ala Glu Asp Thr Ala Val Tyr Tyr Cys Ala Arg
         20                  25                  30

<210> SEQ ID NO 9
<211> LENGTH: 11
<212> TYPE: PRT
<213> ORGANISM: Homo sapiens
<220> FEATURE:
<223> OTHER INFORMATION: Abet0007

<400> SEQUENCE: 9

Trp Gly Gln Gly Thr Leu Val Thr Val Ser Ser
                  5                  10

<210> SEQ ID NO 10
<211> LENGTH: 318
<212> TYPE: DNA
<213> ORGANISM: Homo sapiens
<220> FEATURE:
<223> OTHER INFORMATION: Abet0007

<400> SEQUENCE: 10
cagagcgtct tgactcagcc accctcagtg tccgtgtccc caggacagac ggccagcatc      60
acctgctctg gacataactt ggaagataaa tttgcttcct ggtatcaaca gaagtcaggc     120
cagtcccctg tcctggtcat ctatcgagat gacaagcggc cctcagggat ccctgagcga     180
ttctctgcct ccaactctgg gcacactgcc actctgacca tcagcgggac ccaggctacg     240
gatgaggctg actattactg tcaggcgcag gacagtacca ctcgagtgtt cggcggaggg     300
accaagctga ccgtccta                                                 318

<210> SEQ ID NO 11
<211> LENGTH: 106
<212> TYPE: PRT
<213> ORGANISM: Homo sapiens
<220> FEATURE:
<223> OTHER INFORMATION: Abet0007

<400> SEQUENCE: 11

Gln Ser Val Leu Thr Gln Pro Pro Ser Val Ser Val Ser Pro Gly Gln
                5                  10                  15

Thr Ala Ser Ile Thr Cys Ser Gly His Asn Leu Glu Asp Lys Phe Ala
             20                  25                  30

Ser Trp Tyr Gln Gln Lys Ser Gly Gln Ser Pro Val Leu Val Ile Tyr
         35                  40                  45

Arg Asp Asp Lys Arg Pro Ser Gly Ile Pro Glu Arg Phe Ser Ala Ser
     50                  55                  60

Asn Ser Gly His Thr Ala Thr Leu Thr Ile Ser Gly Thr Gln Ala Thr
 65                  70                  75                  80

Asp Glu Ala Asp Tyr Tyr Cys Gln Ala Gln Asp Ser Thr Thr Arg Val
                 85                  90                  95

Phe Gly Gly Gly Thr Lys Leu Thr Val Leu
            100                 105

<210> SEQ ID NO 12
<211> LENGTH: 11
<212> TYPE: PRT
<213> ORGANISM: Homo sapiens
<220> FEATURE:
<223> OTHER INFORMATION: Abet0007

<400> SEQUENCE: 12

Ser Gly His Asn Leu Glu Asp Lys Phe Ala Ser
                5                  10

<210> SEQ ID NO 13
<211> LENGTH: 7
<212> TYPE: PRT
<213> ORGANISM: Homo sapiens
<220> FEATURE:
<223> OTHER INFORMATION: Abet0007

<400> SEQUENCE: 13

Arg Asp Asp Lys Arg Pro Ser
                5

<210> SEQ ID NO 14
<211> LENGTH: 9
<212> TYPE: PRT
<213> ORGANISM: Homo sapiens
<220> FEATURE:
<223> OTHER INFORMATION: Abet0007

<400> SEQUENCE: 14

Gln Ala Gln Asp Ser Thr Thr Arg Val
                5

<210> SEQ ID NO 15
<211> LENGTH: 22
<212> TYPE: PRT
<213> ORGANISM: Homo sapiens
<220> FEATURE:

<223> OTHER INFORMATION: Abet0007

<400> SEQUENCE: 15

Gln Ser Val Leu Thr Gln Pro Pro Ser Val Ser Val Ser Pro Gly Gln
1               5                   10                  15
Thr Ala Ser Ile Thr Cys
            20

<210> SEQ ID NO 16
<211> LENGTH: 15
<212> TYPE: PRT
<213> ORGANISM: Homo sapiens
<220> FEATURE:
<223> OTHER INFORMATION: Abet0007

<400> SEQUENCE: 16

Trp Tyr Gln Gln Lys Ser Gly Gln Ser Pro Val Leu Val Ile Tyr
1               5                   10                  15

<210> SEQ ID NO 17
<211> LENGTH: 32
<212> TYPE: PRT
<213> ORGANISM: Homo sapiens
<220> FEATURE:
<223> OTHER INFORMATION: Abet0007

<400> SEQUENCE: 17

Gly Ile Pro Glu Arg Phe Ser Ala Ser Asn Ser Gly His Thr Ala Thr
1               5                   10                  15
Leu Thr Ile Ser Gly Thr Gln Ala Thr Asp Glu Ala Asp Tyr Tyr Cys
            20                  25                  30

<210> SEQ ID NO 18
<211> LENGTH: 10
<212> TYPE: PRT
<213> ORGANISM: Homo sapiens
<220> FEATURE:
<223> OTHER INFORMATION: Abet0007

<400> SEQUENCE: 18

Phe Gly Gly Gly Thr Lys Leu Thr Val Leu
1               5                   10

<210> SEQ ID NO 19
<211> LENGTH: 375
<212> TYPE: DNA
<213> ORGANISM: Homo sapiens
<220> FEATURE:
<223> OTHER INFORMATION: Abet0144-GL

<400> SEQUENCE: 19
gaggtgcagc tgttggagtc tgggggaggc ttggtacagc ctggggggtc cctgagactc      60
tcctgtgcag cctctggatt cacctttagc gtttatacta tgtggtgggt ccgccaggct     120
ccagggaagg ggctggagtg gtctcagtt attggttcta gtggtggtac gacagtttac     180
gcagactccg tgaagggccg gttcaccatc tccagagaca attccaagaa cacgctgtat     240
ctgcaaatga acagcctgag agccgaggac acggccgtgt attactgtgc gagagagtgg     300
atggaccact cccgccccta ctactactac ggtatggacg tctggggggca ggggaccctg     360 gtcaccgtct cctca                                                      375

<210> SEQ ID NO 20
<211> LENGTH: 125

```
<212> TYPE: PRT
<213> ORGANISM: Homo sapiens
<220> FEATURE:
<223> OTHER INFORMATION: Abet0144-GL

<400> SEQUENCE: 20

Glu Val Gln Leu Leu Glu Ser Gly Gly Gly Leu Val Gln Pro Gly Gly
                 5                  10                  15

Ser Leu Arg Leu Ser Cys Ala Ala Ser Gly Phe Thr Phe Ser Val Tyr
             20                  25                  30

Thr Met Trp Trp Val Arg Gln Ala Pro Gly Lys Gly Leu Glu Trp Val
         35                  40                  45

Ser Val Ile Gly Ser Ser Gly Gly Thr Thr Val Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Trp Met Asp His Ser Arg Pro Tyr Tyr Tyr Tyr Gly Met
            100                 105                 110

Asp Val Trp Gly Gln Gly Thr Leu Val Thr Val Ser Ser
        115                 120                 125

<210> SEQ ID NO 21
<211> LENGTH: 5
<212> TYPE: PRT
<213> ORGANISM: Homo sapiens
<220> FEATURE:
<223> OTHER INFORMATION: Abet0144-GL

<400> SEQUENCE: 21

Val Tyr Thr Met Trp
                 5

<210> SEQ ID NO 22
<211> LENGTH: 17
<212> TYPE: PRT
<213> ORGANISM: Homo sapiens
<220> FEATURE:
<223> OTHER INFORMATION: Abet0144-GL

<400> SEQUENCE: 22

Val Ile Gly Ser Ser Gly Gly Thr Thr Val Tyr Ala Asp Ser Val Lys
                 5                  10                  15

Gly

<210> SEQ ID NO 23
<211> LENGTH: 16
<212> TYPE: PRT
<213> ORGANISM: Homo sapiens
<220> FEATURE:
<223> OTHER INFORMATION: Abet0144-GL

<400> SEQUENCE: 23

Glu Trp Met Asp His Ser Arg Pro Tyr Tyr Tyr Tyr Gly Met Asp Val
                 5                  10                  15

<210> SEQ ID NO 24
<211> LENGTH: 30
<212> TYPE: PRT
<213> ORGANISM: Homo sapiens
<220> FEATURE:
<223> OTHER INFORMATION: Abet0144-GL
```

<400> SEQUENCE: 24

Glu Val Gln Leu Leu Glu Ser Gly Gly Gly Leu Val Gln Pro Gly Gly
              5                   10                  15
Ser Leu Arg Leu Ser Cys Ala Ala Ser Gly Phe Thr Phe Ser
         20                  25                  30

<210> SEQ ID NO 25
<211> LENGTH: 14
<212> TYPE: PRT
<213> ORGANISM: Homo sapiens
<220> FEATURE:
<223> OTHER INFORMATION: Abet0144-GL

<400> SEQUENCE: 25

Trp Val Arg Gln Ala Pro Gly Lys Gly Leu Glu Trp Val Ser
              5                   10

<210> SEQ ID NO 26
<211> LENGTH: 32
<212> TYPE: PRT
<213> ORGANISM: Homo sapiens
<220> FEATURE:
<223> OTHER INFORMATION: Abet0144-GL

<400> SEQUENCE: 26

Arg Phe Thr Ile Ser Arg Asp Asn Ser Lys Asn Thr Leu Tyr Leu Gln
              5                   10                  15
Met Asn Ser Leu Arg Ala Glu Asp Thr Ala Val Tyr Tyr Cys Ala Arg
         20                  25                  30

<210> SEQ ID NO 27
<211> LENGTH: 11
<212> TYPE: PRT
<213> ORGANISM: Homo sapiens
<220> FEATURE:
<223> OTHER INFORMATION: Abet0144-GL

<400> SEQUENCE: 27

Trp Gly Gln Gly Thr Leu Val Thr Val Ser Ser
              5                   10

<210> SEQ ID NO 28
<211> LENGTH: 318
<212> TYPE: DNA
<213> ORGANISM: Homo sapiens
<220> FEATURE:
<223> OTHER INFORMATION: Abet0144-GL

<400> SEQUENCE: 28
tcgtacgagt tgactcagcc accctcagtg tccgtgtccc caggacagac ggccagcatc      60
acctgctctg gacataactt ggaagataaa tttgcttcct ggtatcaaca gaagccaggc     120
cagtcccctg tcctggtcat ctatcgagat gacaagcggc cctcagggat ccctgagcga     180
ttctctgcct ccaactctgg gcacactgcc actctgacca tcagcgggac ccaggctatg     240
gatgaggctg actattactg tcaggcgcag gacagtacca ctcgagtgtt cggcggaggg     300
accaagctga ccgtccta                                                   318

<210> SEQ ID NO 29
<211> LENGTH: 106
<212> TYPE: PRT
<213> ORGANISM: Homo sapiens
<220> FEATURE:

<223> OTHER INFORMATION: Abet0144-GL

<400> SEQUENCE: 29

Ser Tyr Glu Leu Thr Gln Pro Pro Ser Val Ser Val Ser Pro Gly Gln
                5                   10                  15

Thr Ala Ser Ile Thr Cys Ser Gly His Asn Leu Glu Asp Lys Phe Ala
            20                  25                  30

Ser Trp Tyr Gln Gln Lys Pro Gly Gln Ser Pro Val Leu Val Ile Tyr
        35                  40                  45

Arg Asp Asp Lys Arg Pro Ser Gly Ile Pro Glu Arg Phe Ser Ala Ser
    50                  55                  60

Asn Ser Gly His Thr Ala Thr Leu Thr Ile Ser Gly Thr Gln Ala Met
65                  70                  75                  80

Asp Glu Ala Asp Tyr Tyr Cys Gln Ala Gln Asp Ser Thr Thr Arg Val
                85                  90                  95

Phe Gly Gly Gly Thr Lys Leu Thr Val Leu
            100                 105

<210> SEQ ID NO 30
<211> LENGTH: 11
<212> TYPE: PRT
<213> ORGANISM: Homo sapiens
<220> FEATURE:
<223> OTHER INFORMATION: Abet0144-GL

<400> SEQUENCE: 30

Ser Gly His Asn Leu Glu Asp Lys Phe Ala Ser
                5                   10

<210> SEQ ID NO 31
<211> LENGTH: 7
<212> TYPE: PRT
<213> ORGANISM: Homo sapiens
<220> FEATURE:
<223> OTHER INFORMATION: Abet0144-GL

<400> SEQUENCE: 31

Arg Asp Asp Lys Arg Pro Ser
                5

<210> SEQ ID NO 32
<211> LENGTH: 9
<212> TYPE: PRT
<213> ORGANISM: Homo sapiens
<220> FEATURE:
<223> OTHER INFORMATION: Abet0144-GL

<400> SEQUENCE: 32

Gln Ala Gln Asp Ser Thr Thr Arg Val
                5

<210> SEQ ID NO 33
<211> LENGTH: 22
<212> TYPE: PRT
<213> ORGANISM: Homo sapiens
<220> FEATURE:
<223> OTHER INFORMATION: Abet0144-GL

<400> SEQUENCE: 33

Ser Tyr Glu Leu Thr Gln Pro Pro Ser Val Ser Val Ser Pro Gly Gln
                5                   10                  15

Thr Ala Ser Ile Thr Cys
            20

<210> SEQ ID NO 34
<211> LENGTH: 15
<212> TYPE: PRT
<213> ORGANISM: Homo sapiens
<220> FEATURE:
<223> OTHER INFORMATION: Abet0144-GL

<400> SEQUENCE: 34

Trp Tyr Gln Gln Lys Pro Gly Gln Ser Pro Val Leu Val Ile Tyr
                 5                  10                  15

<210> SEQ ID NO 35
<211> LENGTH: 32
<212> TYPE: PRT
<213> ORGANISM: Homo sapiens
<220> FEATURE:
<223> OTHER INFORMATION: Abet0144-GL

<400> SEQUENCE: 35

Gly Ile Pro Glu Arg Phe Ser Ala Ser Asn Ser Gly His Thr Ala Thr
                 5                  10                  15

Leu Thr Ile Ser Gly Thr Gln Ala Met Asp Glu Ala Asp Tyr Tyr Cys
             20                  25                  30

<210> SEQ ID NO 36
<211> LENGTH: 10
<212> TYPE: PRT
<213> ORGANISM: Homo sapiens
<220> FEATURE:
<223> OTHER INFORMATION: Abet0144-GL

<400> SEQUENCE: 36

Phe Gly Gly Gly Thr Lys Leu Thr Val Leu
                 5                  10

<210> SEQ ID NO 37
<211> LENGTH: 375
<212> TYPE: DNA
<213> ORGANISM: Homo sapiens
<220> FEATURE:
<223> OTHER INFORMATION: Abet0319

<400> SEQUENCE: 37
gaggtgcagc tgttggagtc tgggggaggc ttggtacagc ctggggggtc cctgagactc      60
tcctgtgcgg cctctgtctc cgtgtacaac aaggacacta tgtggtgggt ccgccaggct     120
ccagggaagg ggctggagtg gtctcagtt attggttcta gtggtggcac gacagtctac     180
gcagactccg tgaagggccg gttcaccatc tccagagaca attccaagaa cacgctgtat     240
ctgcaaatga acagcctgag agccgaggac acggccgtgt attactgtgc gagagagtgg     300
atggaccact cccgccccta ctactactac ggtatggacg tctggggggca ggggaccctg     360 gtcaccgtct cctca                                                      375

<210> SEQ ID NO 38
<211> LENGTH: 125
<212> TYPE: PRT
<213> ORGANISM: Homo sapiens
<220> FEATURE:
<223> OTHER INFORMATION: Abet0319

<400> SEQUENCE: 38

Glu Val Gln Leu Leu Glu Ser Gly Gly Gly Leu Val Gln Pro Gly Gly
                 5                  10                  15

Ser Leu Arg Leu Ser Cys Ala Ala Ser Val Ser Val Tyr Asn Lys Asp
            20                  25                  30

Thr Met Trp Trp Val Arg Gln Ala Pro Gly Lys Gly Leu Glu Trp Val
        35                  40                  45

Ser Val Ile Gly Ser Ser Gly Gly Thr Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Trp Met Asp His Ser Arg Pro Tyr Tyr Tyr Tyr Gly Met
            100                 105                 110

Asp Val Trp Gly Gln Gly Thr Leu Val Thr Val Ser Ser
        115                 120                 125

<210> SEQ ID NO 39
<211> LENGTH: 5
<212> TYPE: PRT
<213> ORGANISM: Homo sapiens
<220> FEATURE:
<223> OTHER INFORMATION: Abet0319

<400> SEQUENCE: 39

Lys Asp Thr Met Trp
            5

<210> SEQ ID NO 40
<211> LENGTH: 17
<212> TYPE: PRT
<213> ORGANISM: Homo sapiens
<220> FEATURE:
<223> OTHER INFORMATION: Abet0319

<400> SEQUENCE: 40

Val Ile Gly Ser Ser Gly Gly Thr Thr Val Tyr Ala Asp Ser Val Lys
                5                   10                  15

Gly

<210> SEQ ID NO 41
<211> LENGTH: 16
<212> TYPE: PRT
<213> ORGANISM: Homo sapiens
<220> FEATURE:
<223> OTHER INFORMATION: Abet0319

<400> SEQUENCE: 41

Glu Trp Met Asp His Ser Arg Pro Tyr Tyr Tyr Tyr Gly Met Asp Val
                5                   10                  15

<210> SEQ ID NO 42
<211> LENGTH: 30
<212> TYPE: PRT
<213> ORGANISM: Homo sapiens
<220> FEATURE:
<223> OTHER INFORMATION: Abet0319

<400> SEQUENCE: 42

Glu Val Gln Leu Leu Glu Ser Gly Gly Gly Leu Val Gln Pro Gly Gly
                5                   10                  15

Ser Leu Arg Leu Ser Cys Ala Ala Ser Val Ser Val Tyr Asn
            20                  25                  30

<210> SEQ ID NO 43
<211> LENGTH: 14
<212> TYPE: PRT
<213> ORGANISM: Homo sapiens
<220> FEATURE:
<223> OTHER INFORMATION: Abet0319

<400> SEQUENCE: 43

Trp Val Arg Gln Ala Pro Gly Lys Gly Leu Glu Trp Val Ser
                5                  10

<210> SEQ ID NO 44
<211> LENGTH: 32
<212> TYPE: PRT
<213> ORGANISM: Homo sapiens
<220> FEATURE:
<223> OTHER INFORMATION: Abet0319

<400> SEQUENCE: 44

Arg Phe Thr Ile Ser Arg Asp Asn Ser Lys Asn Thr Leu Tyr Leu Gln
                5                  10                  15

Met Asn Ser Leu Arg Ala Glu Asp Thr Ala Val Tyr Tyr Cys Ala Arg
            20                  25                  30

<210> SEQ ID NO 45
<211> LENGTH: 11
<212> TYPE: PRT
<213> ORGANISM: Homo sapiens
<220> FEATURE:
<223> OTHER INFORMATION: Abet0319

<400> SEQUENCE: 45

Trp Gly Gln Gly Thr Leu Val Thr Val Ser Ser
                5                  10

<210> SEQ ID NO 46
<211> LENGTH: 318
<212> TYPE: DNA
<213> ORGANISM: Homo sapiens
<220> FEATURE:
<223> OTHER INFORMATION: Abet0319

<400> SEQUENCE: 46
tcgtacgagt tgactcagcc accctcagtg tccgtgtccc caggacagac ggccagcatc      60
acctgctctg gacataacat catggacaag tgggtctctt ggtatcaaca gaagccaggc     120
cggtcccctg ccctggtaat ctatcgagat gacaagcggc cctcagggat ccctgagcga     180
ttctctgcct ccaactctgg gcacactgcc actctgacca tcagcgggac ccaggctacg     240
gatgaggctg actattactg ttcgtcccag gacacggtga ctcgagtgtt cggcggaggg     300
accaagctga ccgtccta                                                    318

<210> SEQ ID NO 47
<211> LENGTH: 106
<212> TYPE: PRT
<213> ORGANISM: Homo sapiens
<220> FEATURE:
<223> OTHER INFORMATION: Abet0319

<400> SEQUENCE: 47

Ser Tyr Glu Leu Thr Gln Pro Pro Ser Val Ser Val Ser Pro Gly Gln
                5                  10                  15

Thr Ala Ser Ile Thr Cys Ser Gly His Asn Ile Met Asp Lys Trp Val
            20                  25                  30

```
Ser Trp Tyr Gln Gln Lys Pro Gly Arg Ser Pro Ala Leu Val Ile Tyr
        35                  40                  45

Arg Asp Asp Lys Arg Pro Ser Gly Ile Pro Glu Arg Phe Ser Ala Ser
 50                  55                  60

Asn Ser Gly His Thr Ala Thr Leu Thr Ile Ser Gly Thr Gln Ala Thr
 65                  70                  75                  80

Asp Glu Ala Asp Tyr Tyr Cys Ser Ser Gln Asp Thr Val Thr Arg Val
                 85                  90                  95

Phe Gly Gly Gly Thr Lys Leu Thr Val Leu
            100                 105

<210> SEQ ID NO 48
<211> LENGTH: 11
<212> TYPE: PRT
<213> ORGANISM: Homo sapiens
<220> FEATURE:
<223> OTHER INFORMATION: Abet0319

<400> SEQUENCE: 48

Ser Gly His Asn Ile Met Asp Lys Trp Val Ser
                 5                  10

<210> SEQ ID NO 49
<211> LENGTH: 7
<212> TYPE: PRT
<213> ORGANISM: Homo sapiens
<220> FEATURE:
<223> OTHER INFORMATION: Abet0319

<400> SEQUENCE: 49

Arg Asp Asp Lys Arg Pro Ser
                 5

<210> SEQ ID NO 50
<211> LENGTH: 9
<212> TYPE: PRT
<213> ORGANISM: Homo sapiens
<220> FEATURE:
<223> OTHER INFORMATION: Abet0319

<400> SEQUENCE: 50

Ser Ser Gln Asp Thr Val Thr Arg Val
                 5

<210> SEQ ID NO 51
<211> LENGTH: 22
<212> TYPE: PRT
<213> ORGANISM: Homo sapiens
<220> FEATURE:
<223> OTHER INFORMATION: Abet0319

<400> SEQUENCE: 51

Ser Tyr Glu Leu Thr Gln Pro Pro Ser Val Ser Val Ser Pro Gly Gln
                 5                  10                  15

Thr Ala Ser Ile Thr Cys
            20

<210> SEQ ID NO 52
<211> LENGTH: 15
<212> TYPE: PRT
<213> ORGANISM: Homo sapiens
<220> FEATURE:
<223> OTHER INFORMATION: Abet0319
```

```
<400> SEQUENCE: 52

Trp Tyr Gln Gln Lys Pro Gly Arg Ser Pro Ala Leu Val Ile Tyr
                 5                  10                  15

<210> SEQ ID NO 53
<211> LENGTH: 32
<212> TYPE: PRT
<213> ORGANISM: Homo sapiens
<220> FEATURE:
<223> OTHER INFORMATION: Abet0319

<400> SEQUENCE: 53

Gly Ile Pro Glu Arg Phe Ser Ala Ser Asn Ser Gly His Thr Ala Thr
                 5                  10                  15

Leu Thr Ile Ser Gly Thr Gln Ala Thr Asp Glu Ala Asp Tyr Tyr Cys
             20                  25                  30

<210> SEQ ID NO 54
<211> LENGTH: 10
<212> TYPE: PRT
<213> ORGANISM: Homo sapiens
<220> FEATURE:
<223> OTHER INFORMATION: Abet0319

<400> SEQUENCE: 54

Phe Gly Gly Gly Thr Lys Leu Thr Val Leu
                 5                  10

<210> SEQ ID NO 55
<211> LENGTH: 375
<212> TYPE: DNA
<213> ORGANISM: Homo sapiens
<220> FEATURE:
<223> OTHER INFORMATION: Abet0321b

<400> SEQUENCE: 55
gaggtgcagc tgttggagtc tgggggaggc ttggtacagc ctgggggtc cctgagactc        60 tcctgtgcag cctctgcgta ccactcgaac cacgacccta tgtggtgggt ccgccaggct      120
ccagggaagg ggctggagtg ggtctcagtt attggttcta gtggtggtac gacagcttac      180
gcagactccg tgaagggccg gttcaccatc tccagagata attccaagaa cacgctgtat      240
ctgcaaatga acagcctgag agccgaggac acggccgtgt attactgtgc gagagagtgg      300
atggaccact cccgccccta ctactactac ggtatggacg tctggggggca ggggaccctg      360 gtcaccgtct cctca                                                       375

<210> SEQ ID NO 56
<211> LENGTH: 125
<212> TYPE: PRT
<213> ORGANISM: Homo sapiens
<220> FEATURE:
<223> OTHER INFORMATION: Abet0321b

<400> SEQUENCE: 56

Glu Val Gln Leu Leu Glu Ser Gly Gly Gly Leu Val Gln Pro Gly Gly
                 5                  10                  15

Ser Leu Arg Leu Ser Cys Ala Ala Ser Ala Tyr His Ser Asn His Asp
             20                  25                  30

Pro Met Trp Trp Val Arg Gln Ala Pro Gly Lys Gly Leu Glu Trp Val
         35                  40                  45

Ser Val Ile Gly Ser Ser Gly Gly Thr Thr Ala Tyr Ala Asp Ser Val
     50                  55                  60
```

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Trp Met Asp His Ser Arg Pro Tyr Tyr Tyr Gly Met
            100                 105                 110

Asp Val Trp Gly Gln Gly Thr Leu Val Thr Val Ser Ser
        115                 120                 125

<210> SEQ ID NO 57
<211> LENGTH: 5
<212> TYPE: PRT
<213> ORGANISM: Homo sapiens
<220> FEATURE:
<223> OTHER INFORMATION: Abet0321b

<400> SEQUENCE: 57

His Asp Pro Met Trp
                5

<210> SEQ ID NO 58
<211> LENGTH: 17
<212> TYPE: PRT
<213> ORGANISM: Homo sapiens
<220> FEATURE:
<223> OTHER INFORMATION: Abet0321b

<400> SEQUENCE: 58

Val Ile Gly Ser Ser Gly Gly Thr Thr Ala Tyr Ala Asp Ser Val Lys
                5                   10                  15

Gly

<210> SEQ ID NO 59
<211> LENGTH: 16
<212> TYPE: PRT
<213> ORGANISM: Homo sapiens
<220> FEATURE:
<223> OTHER INFORMATION: Abet0321b

<400> SEQUENCE: 59

Glu Trp Met Asp His Ser Arg Pro Tyr Tyr Tyr Gly Met Asp Val
                5                   10                  15

<210> SEQ ID NO 60
<211> LENGTH: 30
<212> TYPE: PRT
<213> ORGANISM: Homo sapiens
<220> FEATURE:
<223> OTHER INFORMATION: Abet0321b

<400> SEQUENCE: 60

Glu Val Gln Leu Leu Glu Ser Gly Gly Gly Leu Val Gln Pro Gly Gly
                5                   10                  15

Ser Leu Arg Leu Ser Cys Ala Ala Ser Ala Tyr His Ser Asn
            20                  25                  30

<210> SEQ ID NO 61
<211> LENGTH: 14
<212> TYPE: PRT
<213> ORGANISM: Homo sapiens
<220> FEATURE:
<223> OTHER INFORMATION: Abet0321b

<400> SEQUENCE: 61

Trp Val Arg Gln Ala Pro Gly Lys Gly Leu Glu Trp Val Ser
                5                   10

<210> SEQ ID NO 62
<211> LENGTH: 32
<212> TYPE: PRT
<213> ORGANISM: Homo sapiens
<220> FEATURE:
<223> OTHER INFORMATION: Abet0321b

<400> SEQUENCE: 62

Arg Phe Thr Ile Ser Arg Asp Asn Ser Lys Asn Thr Leu Tyr Leu Gln
                5                   10                  15

Met Asn Ser Leu Arg Ala Glu Asp Thr Ala Val Tyr Tyr Cys Ala Arg
            20                  25                  30

<210> SEQ ID NO 63
<211> LENGTH: 11
<212> TYPE: PRT
<213> ORGANISM: Homo sapiens
<220> FEATURE:
<223> OTHER INFORMATION: Abet0321b

<400> SEQUENCE: 63

Trp Gly Gln Gly Thr Leu Val Thr Val Ser Ser
                5                   10

<210> SEQ ID NO 64
<211> LENGTH: 318
<212> TYPE: DNA
<213> ORGANISM: Homo sapiens
<220> FEATURE:
<223> OTHER INFORMATION: Abet0321b

<400> SEQUENCE: 64
tcgtacgagt tgactcagcc accctcagtg tccgtgtccc caggacagac ggccagcatc      60
acctgctctg gacataactt ggaagataaa tttgcttcct ggtatcaaca gaagccaggc     120
cagtcccctg tcctgatcat ctatcgagat gacaagcggc cctcagggat ccctgagcga     180
ttctctgcct ccaactctgg gcacactgcc actctgacca tcagcgggac ccaggctacg     240
gatgaggctg actattactg ttcgtcccag gacacggtga ctcgagtgtt cggcggaggg     300
accaagctga ccgtccta                                                   318

<210> SEQ ID NO 65
<211> LENGTH: 106
<212> TYPE: PRT
<213> ORGANISM: Homo sapiens
<220> FEATURE:
<223> OTHER INFORMATION: Abet0321b

<400> SEQUENCE: 65

Ser Tyr Glu Leu Thr Gln Pro Pro Ser Val Ser Val Ser Pro Gly Gln
                5                   10                  15

Thr Ala Ser Ile Thr Cys Ser Gly His Asn Leu Glu Asp Lys Phe Ala
            20                  25                  30

Ser Trp Tyr Gln Gln Lys Pro Gly Gln Ser Pro Val Leu Ile Ile Tyr
        35                  40                  45

Arg Asp Asp Lys Arg Pro Ser Gly Ile Pro Glu Arg Phe Ser Ala Ser
    50                  55                  60

Asn Ser Gly His Thr Ala Thr Leu Thr Ile Ser Gly Thr Gln Ala Thr
65                  70                  75                  80

-continued

```
Asp Glu Ala Asp Tyr Tyr Cys Ser Ser Gln Asp Thr Val Thr Arg Val
                85                  90                  95

Phe Gly Gly Gly Thr Lys Leu Thr Val Leu
        100                 105

<210> SEQ ID NO 66
<211> LENGTH: 11
<212> TYPE: PRT
<213> ORGANISM: Homo sapiens
<220> FEATURE:
<223> OTHER INFORMATION: Abet0321b

<400> SEQUENCE: 66

Ser Gly His Asn Leu Glu Asp Lys Phe Ala Ser
                5                   10

<210> SEQ ID NO 67
<211> LENGTH: 7
<212> TYPE: PRT
<213> ORGANISM: Homo sapiens
<220> FEATURE:
<223> OTHER INFORMATION: Abet0321b

<400> SEQUENCE: 67

Arg Asp Asp Lys Arg Pro Ser
                5

<210> SEQ ID NO 68
<211> LENGTH: 9
<212> TYPE: PRT
<213> ORGANISM: Homo sapiens
<220> FEATURE:
<223> OTHER INFORMATION: Abet0321b

<400> SEQUENCE: 68

Ser Ser Gln Asp Thr Val Thr Arg Val
                5

<210> SEQ ID NO 69
<211> LENGTH: 22
<212> TYPE: PRT
<213> ORGANISM: Homo sapiens
<220> FEATURE:
<223> OTHER INFORMATION: Abet0321b

<400> SEQUENCE: 69

Ser Tyr Glu Leu Thr Gln Pro Pro Ser Val Ser Val Ser Pro Gly Gln
                5                   10                  15

Thr Ala Ser Ile Thr Cys
            20

<210> SEQ ID NO 70
<211> LENGTH: 15
<212> TYPE: PRT
<213> ORGANISM: Homo sapiens
<220> FEATURE:
<223> OTHER INFORMATION: Abet0321b

<400> SEQUENCE: 70

Trp Tyr Gln Gln Lys Pro Gly Gln Ser Pro Val Leu Ile Ile Tyr
                5                   10                  15

<210> SEQ ID NO 71
<211> LENGTH: 32
<212> TYPE: PRT
```

<210> SEQ ID NO 71
<211> LENGTH: (not shown, continued)
<212> TYPE: PRT
<213> ORGANISM: Homo sapiens
<220> FEATURE:
<223> OTHER INFORMATION: Abet0321b

<400> SEQUENCE: 71

Gly Ile Pro Glu Arg Phe Ser Ala Ser Asn Ser Gly His Thr Ala Thr
              5                  10                  15
Leu Thr Ile Ser Gly Thr Gln Ala Thr Asp Glu Ala Asp Tyr Tyr Cys
          20                  25                  30

<210> SEQ ID NO 72
<211> LENGTH: 10
<212> TYPE: PRT
<213> ORGANISM: Homo sapiens
<220> FEATURE:
<223> OTHER INFORMATION: Abet0321b

<400> SEQUENCE: 72

Phe Gly Gly Gly Thr Lys Leu Thr Val Leu
              5                  10

<210> SEQ ID NO 73
<211> LENGTH: 375
<212> TYPE: DNA
<213> ORGANISM: Homo sapiens
<220> FEATURE:
<223> OTHER INFORMATION: Abet0322b

<400> SEQUENCE: 73
gaggtgcagc tgttggagtc tgaggaggc ctggtacagc ctgggggtc cctgagactc       60 tcctgtgcag cctctaacga agagttccag tacaaccta tgtggtgggt ccgccaggct     120
ccagggaagg ggctggagtg gtctcagtt attggttcta gtggtggtgc gacagtttac     180
gcagacgccg tgaagggccg gttcaccatc tccagagaca attccgagaa cacgctgtat   240
ctgcaaatga acagcctaag agccgaggac acggccgtgt attactgtgc gagagagtgg   300
atggaccact cccgccccta ctactactac ggtatggacg tctggggca ggggaccctg    360 gtcaccgtct cctca                                                     375

<210> SEQ ID NO 74
<211> LENGTH: 125
<212> TYPE: PRT
<213> ORGANISM: Homo sapiens
<220> FEATURE:
<223> OTHER INFORMATION: Abet0322b

<400> SEQUENCE: 74

Glu Val Gln Leu Leu Glu Ser Gly Gly Gly Leu Val Gln Pro Gly Gly
              5                  10                  15
Ser Leu Arg Leu Ser Cys Ala Ala Ser Asn Glu Glu Phe Gln Tyr Asn
          20                  25                  30
Pro Met Trp Trp Val Arg Gln Ala Pro Gly Lys Gly Leu Glu Trp Val
      35                  40                  45
Ser Val Ile Gly Ser Ser Gly Gly Ala Thr Val Tyr Ala Asp Ala Val
  50                  55                  60
Lys Gly Arg Phe Thr Ile Ser Arg Asp Asn Ser Glu Asn Thr Leu Tyr
65                  70                  75                  80
Leu Gln Met Asn Ser Leu Arg Ala Glu Asp Thr Ala Val Tyr Tyr Cys
              85                  90                  95
Ala Arg Glu Trp Met Asp His Ser Arg Pro Tyr Tyr Tyr Gly Met
          100                 105                 110

Asp Val Trp Gly Gln Gly Thr Leu Val Thr Val Ser Ser
            115                 120                 125

<210> SEQ ID NO 75
<211> LENGTH: 5
<212> TYPE: PRT
<213> ORGANISM: Homo sapiens
<220> FEATURE:
<223> OTHER INFORMATION: Abet0322b

<400> SEQUENCE: 75

Tyr Asn Pro Met Trp
                5

<210> SEQ ID NO 76
<211> LENGTH: 17
<212> TYPE: PRT
<213> ORGANISM: Homo sapiens
<220> FEATURE:
<223> OTHER INFORMATION: Abet0322b

<400> SEQUENCE: 76

Val Ile Gly Ser Ser Gly Gly Ala Thr Val Tyr Ala Asp Ala Val Lys
                5                   10                  15
Gly

<210> SEQ ID NO 77
<211> LENGTH: 16
<212> TYPE: PRT
<213> ORGANISM: Homo sapiens
<220> FEATURE:
<223> OTHER INFORMATION: Abet0322b

<400> SEQUENCE: 77

Glu Trp Met Asp His Ser Arg Pro Tyr Tyr Tyr Tyr Gly Met Asp Val
                5                   10                  15

<210> SEQ ID NO 78
<211> LENGTH: 30
<212> TYPE: PRT
<213> ORGANISM: Homo sapiens
<220> FEATURE:
<223> OTHER INFORMATION: Abet0322b

<400> SEQUENCE: 78

Glu Val Gln Leu Leu Glu Ser Gly Gly Gly Leu Val Gln Pro Gly Gly
                5                   10                  15
Ser Leu Arg Leu Ser Cys Ala Ala Ser Asn Glu Glu Phe Gln
            20                  25                  30

<210> SEQ ID NO 79
<211> LENGTH: 14
<212> TYPE: PRT
<213> ORGANISM: Homo sapiens
<220> FEATURE:
<223> OTHER INFORMATION: Abet0322b

<400> SEQUENCE: 79

Trp Val Arg Gln Ala Pro Gly Lys Gly Leu Glu Trp Val Ser
                5                   10

<210> SEQ ID NO 80
<211> LENGTH: 32
<212> TYPE: PRT
<213> ORGANISM: Homo sapiens
<220> FEATURE:
<223> OTHER INFORMATION: Abet0322b

<400> SEQUENCE: 80

Arg Phe Thr Ile Ser Arg Asp Asn Ser Glu Asn Thr Leu Tyr Leu Gln
                 5                  10                  15
Met Asn Ser Leu Arg Ala Glu Asp Thr Ala Val Tyr Tyr Cys Ala Arg
             20                  25                  30

<210> SEQ ID NO 81
<211> LENGTH: 11
<212> TYPE: PRT
<213> ORGANISM: Homo sapiens
<220> FEATURE:
<223> OTHER INFORMATION: Abet0322b

<400> SEQUENCE: 81

Trp Gly Gln Gly Thr Leu Val Thr Val Ser Ser
                 5                  10

<210> SEQ ID NO 82
<211> LENGTH: 318
<212> TYPE: DNA
<213> ORGANISM: Homo sapiens
<220> FEATURE:
<223> OTHER INFORMATION: Abet0322b

<400> SEQUENCE: 82
tcgtacgagt tgactcagcc accctcagtg tccgtgtccc caggacagac ggccagcatc      60
acctgctctg gacataactt gggagataaa tttgcttcct ggtatcaaca gaagccaggc     120
cagtcccctg tcctggtcat ctatcgagat gacaagcggc cctcagagat ccctgagcga     180
ttctctgcct ccaactctgg gcacactgcc actctgacca tcagcgggac ccaggctacg     240
gatgaggctg actattactg ttcgtcccag gacacggtga ctcgagtgtt cggcggaggg     300
accaagctga ccgtcctg                                                   318

<210> SEQ ID NO 83
<211> LENGTH: 106
<212> TYPE: PRT
<213> ORGANISM: Homo sapiens
<220> FEATURE:
<223> OTHER INFORMATION: Abet0322b

<400> SEQUENCE: 83

Ser Tyr Glu Leu Thr Gln Pro Pro Ser Val Ser Val Ser Pro Gly Gln
                 5                  10                  15
Thr Ala Ser Ile Thr Cys Ser Gly His Asn Leu Gly Asp Lys Phe Ala
             20                  25                  30
Ser Trp Tyr Gln Gln Lys Pro Gly Gln Ser Pro Val Leu Val Ile Tyr
         35                  40                  45
Arg Asp Asp Lys Arg Pro Ser Glu Ile Pro Glu Arg Phe Ser Ala Ser
     50                  55                  60
Asn Ser Gly His Thr Ala Thr Leu Thr Ile Ser Gly Thr Gln Ala Thr
 65                  70                  75                  80
Asp Glu Ala Asp Tyr Tyr Cys Ser Ser Gln Asp Thr Val Thr Arg Val
                 85                  90                  95
Phe Gly Gly Gly Thr Lys Leu Thr Val Leu
                100                 105

<210> SEQ ID NO 84

```
<211> LENGTH: 11
<212> TYPE: PRT
<213> ORGANISM: Homo sapiens
<220> FEATURE:
<223> OTHER INFORMATION: Abet0322b

<400> SEQUENCE: 84

Ser Gly His Asn Leu Gly Asp Lys Phe Ala Ser
                5                  10

<210> SEQ ID NO 85
<211> LENGTH: 7
<212> TYPE: PRT
<213> ORGANISM: Homo sapiens
<220> FEATURE:
<223> OTHER INFORMATION: Abet0322b

<400> SEQUENCE: 85

Arg Asp Asp Lys Arg Pro Ser
                5

<210> SEQ ID NO 86
<211> LENGTH: 9
<212> TYPE: PRT
<213> ORGANISM: Homo sapiens
<220> FEATURE:
<223> OTHER INFORMATION: Abet0322b

<400> SEQUENCE: 86

Ser Ser Gln Asp Thr Val Thr Arg Val
                5

<210> SEQ ID NO 87
<211> LENGTH: 22
<212> TYPE: PRT
<213> ORGANISM: Homo sapiens
<220> FEATURE:
<223> OTHER INFORMATION: Abet0322b

<400> SEQUENCE: 87

Ser Tyr Glu Leu Thr Gln Pro Pro Ser Val Ser Val Ser Pro Gly Gln
                5                  10                  15

Thr Ala Ser Ile Thr Cys
            20

<210> SEQ ID NO 88
<211> LENGTH: 15
<212> TYPE: PRT
<213> ORGANISM: Homo sapiens
<220> FEATURE:
<223> OTHER INFORMATION: Abet0322b

<400> SEQUENCE: 88

Trp Tyr Gln Gln Lys Pro Gly Gln Ser Pro Val Leu Val Ile Tyr
                5                  10                  15

<210> SEQ ID NO 89
<211> LENGTH: 32
<212> TYPE: PRT
<213> ORGANISM: Homo sapiens
<220> FEATURE:
<223> OTHER INFORMATION: Abet0322b

<400> SEQUENCE: 89

Glu Ile Pro Glu Arg Phe Ser Ala Ser Asn Ser Gly His Thr Ala Thr
                5                  10                  15
```

Leu Thr Ile Ser Gly Thr Gln Ala Thr Asp Glu Ala Asp Tyr Tyr Cys
                20                  25                  30

<210> SEQ ID NO 90
<211> LENGTH: 10
<212> TYPE: PRT
<213> ORGANISM: Homo sapiens
<220> FEATURE:
<223> OTHER INFORMATION: Abet0322b

<400> SEQUENCE: 90

Phe Gly Gly Gly Thr Lys Leu Thr Val Leu
                 5                  10

<210> SEQ ID NO 91
<211> LENGTH: 375
<212> TYPE: DNA
<213> ORGANISM: Homo sapiens
<220> FEATURE:
<223> OTHER INFORMATION: Abet0323b

<400> SEQUENCE: 91
gaggtgcagc tgttggagtc tgggggaggc ttggtacagc ctgggggtc cctgagactc      60 tcctgtgcag cctctaccag cacgttccag aagacacta tgtggtgggt ccgccaggct    120
ccagggaagg ggctggagtg ggtctcagtt attggtccca acccgaagaa caacgcctac   180
gcagactccg tgaagggccg gttcaccatc tccagagaca attccaagaa cacgctgtat   240
ctgcaaatga acagcctgag agccgaggac acggccgtgt attactgtgc gagagagtgg   300
atggaccact cccgccccta ctactactac ggtatggacg tctgggggca ggggaccctg   360
gtcaccgtct cctca                                                    375

<210> SEQ ID NO 92
<211> LENGTH: 125
<212> TYPE: PRT
<213> ORGANISM: Homo sapiens
<220> FEATURE:
<223> OTHER INFORMATION: Abet0323b

<400> SEQUENCE: 92

Glu Val Gln Leu Leu Glu Ser Gly Gly Gly Leu Val Gln Pro Gly Gly
                 5                  10                  15

Ser Leu Arg Leu Ser Cys Ala Ala Ser Thr Ser Thr Phe Gln Glu Asp
                20                  25                  30

Thr Met Trp Trp Val Arg Gln Ala Pro Gly Lys Gly Leu Glu Trp Val
            35                  40                  45

Ser Val Ile Gly Pro Asn Pro Lys Asn Asn Ala Tyr Ala Asp Ser Val
        50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Trp Met Asp His Ser Arg Pro Tyr Tyr Tyr Gly Met
            100                 105                 110

Asp Val Trp Gly Gln Gly Thr Leu Val Thr Val Ser Ser
        115                 120                 125

<210> SEQ ID NO 93
<211> LENGTH: 5
<212> TYPE: PRT
<213> ORGANISM: Homo sapiens

```
<220> FEATURE:
<223> OTHER INFORMATION: Abet0323b

<400> SEQUENCE: 93

Glu Asp Thr Met Trp
                5

<210> SEQ ID NO 94
<211> LENGTH: 17
<212> TYPE: PRT
<213> ORGANISM: Homo sapiens
<220> FEATURE:
<223> OTHER INFORMATION: Abet0323b

<400> SEQUENCE: 94

Val Ile Gly Pro Asn Pro Lys Asn Asn Ala Tyr Ala Asp Ser Val Lys
                5                   10                  15

Gly

<210> SEQ ID NO 95
<211> LENGTH: 16
<212> TYPE: PRT
<213> ORGANISM: Homo sapiens
<220> FEATURE:
<223> OTHER INFORMATION: Abet0323b

<400> SEQUENCE: 95

Glu Trp Met Asp His Ser Arg Pro Tyr Tyr Tyr Tyr Gly Met Asp Val
                5                   10                  15

<210> SEQ ID NO 96
<211> LENGTH: 30
<212> TYPE: PRT
<213> ORGANISM: Homo sapiens
<220> FEATURE:
<223> OTHER INFORMATION: Abet0323b

<400> SEQUENCE: 96

Glu Val Gln Leu Leu Glu Ser Gly Gly Gly Leu Val Gln Pro Gly Gly
                5                   10                  15

Ser Leu Arg Leu Ser Cys Ala Ala Ser Thr Ser Thr Phe Gln
            20                  25                  30

<210> SEQ ID NO 97
<211> LENGTH: 14
<212> TYPE: PRT
<213> ORGANISM: Homo sapiens
<220> FEATURE:
<223> OTHER INFORMATION: Abet0323b

<400> SEQUENCE: 97

Trp Val Arg Gln Ala Pro Gly Lys Gly Leu Glu Trp Val Ser
                5                   10

<210> SEQ ID NO 98
<211> LENGTH: 32
<212> TYPE: PRT
<213> ORGANISM: Homo sapiens
<220> FEATURE:
<223> OTHER INFORMATION: Abet0323b

<400> SEQUENCE: 98

Arg Phe Thr Ile Ser Arg Asp Asn Ser Lys Asn Thr Leu Tyr Leu Gln
                5                   10                  15

Met Asn Ser Leu Arg Ala Glu Asp Thr Ala Val Tyr Tyr Cys Ala Arg
```

<210> SEQ ID NO 99
<211> LENGTH: 11
<212> TYPE: PRT
<213> ORGANISM: Homo sapiens
<220> FEATURE:
<223> OTHER INFORMATION: Abet0323b

<400> SEQUENCE: 99

Trp Gly Gln Gly Thr Leu Val Thr Val Ser Ser
                5                  10

<210> SEQ ID NO 100
<211> LENGTH: 318
<212> TYPE: DNA
<213> ORGANISM: Homo sapiens
<220> FEATURE:
<223> OTHER INFORMATION: Abet0323b

<400> SEQUENCE: 100
tcgtacgagt tgactcagcc accctcagta tccgtgtccc caggacagac ggccagcatc      60
acctgctctg gacataactt ggaagataaa tttgcttcct ggtatcaaca gaagccaggc     120
cagtcccctg tcctggtcat ctatcgagat gacaagcggc cctctggggt ccctgagcga     180
ttctctgcct ccaactctgg gcacactgcc actctgacca tcagcgggac ccaggctacg     240
gatgaggctg actattactg ttcgtcccag gacacggtga ctcgagtgtt cggcggaggg     300
accaagctga tcgtccta                                                   318

<210> SEQ ID NO 101
<211> LENGTH: 106
<212> TYPE: PRT
<213> ORGANISM: Homo sapiens
<220> FEATURE:
<223> OTHER INFORMATION: Abet0323b

<400> SEQUENCE: 101

Ser Tyr Glu Leu Thr Gln Pro Pro Ser Val Ser Val Ser Pro Gly Gln
                5                  10                  15

Thr Ala Ser Ile Thr Cys Ser Gly His Asn Leu Glu Asp Lys Phe Ala
            20                  25                  30

Ser Trp Tyr Gln Gln Lys Pro Gly Gln Ser Pro Val Leu Val Ile Tyr
        35                  40                  45

Arg Asp Asp Lys Arg Pro Ser Gly Val Pro Glu Arg Phe Ser Ala Ser
50                  55                  60

Asn Ser Gly His Thr Ala Thr Leu Thr Ile Ser Gly Thr Gln Ala Thr
65                  70                  75                  80

Asp Glu Ala Asp Tyr Tyr Cys Ser Ser Gln Asp Thr Val Thr Arg Val
                85                  90                  95

Phe Gly Gly Gly Thr Lys Leu Ile Val Leu
            100                 105

<210> SEQ ID NO 102
<211> LENGTH: 11
<212> TYPE: PRT
<213> ORGANISM: Homo sapiens
<220> FEATURE:
<223> OTHER INFORMATION: Abet0323b

<400> SEQUENCE: 102

Ser Gly His Asn Leu Glu Asp Lys Phe Ala Ser 5                   10

<210> SEQ ID NO 103
<211> LENGTH: 7
<212> TYPE: PRT
<213> ORGANISM: Homo sapiens
<220> FEATURE:
<223> OTHER INFORMATION: Abet0323b

<400> SEQUENCE: 103

Arg Asp Asp Lys Arg Pro Ser
                5

<210> SEQ ID NO 104
<211> LENGTH: 9
<212> TYPE: PRT
<213> ORGANISM: Homo sapiens
<220> FEATURE:
<223> OTHER INFORMATION: Abet0323b

<400> SEQUENCE: 104

Ser Ser Gln Asp Thr Val Thr Arg Val
                5

<210> SEQ ID NO 105
<211> LENGTH: 22
<212> TYPE: PRT
<213> ORGANISM: Homo sapiens
<220> FEATURE:
<223> OTHER INFORMATION: Abet0323b

<400> SEQUENCE: 105

Ser Tyr Glu Leu Thr Gln Pro Pro Ser Val Ser Val Ser Pro Gly Gln
                5                   10                  15

Thr Ala Ser Ile Thr Cys
            20

<210> SEQ ID NO 106
<211> LENGTH: 15
<212> TYPE: PRT
<213> ORGANISM: Homo sapiens
<220> FEATURE:
<223> OTHER INFORMATION: Abet0323b

<400> SEQUENCE: 106

Trp Tyr Gln Gln Lys Pro Gly Gln Ser Pro Val Leu Val Ile Tyr
                5                   10                  15

<210> SEQ ID NO 107
<211> LENGTH: 32
<212> TYPE: PRT
<213> ORGANISM: Homo sapiens
<220> FEATURE:
<223> OTHER INFORMATION: Abet0323b

<400> SEQUENCE: 107

Gly Val Pro Glu Arg Phe Ser Ala Ser Asn Ser Gly His Thr Ala Thr
                5                   10                  15

Leu Thr Ile Ser Gly Thr Gln Ala Thr Asp Glu Ala Asp Tyr Tyr Cys
            20                  25                  30

<210> SEQ ID NO 108
<211> LENGTH: 10
<212> TYPE: PRT
<213> ORGANISM: Homo sapiens
<220> FEATURE:

<223> OTHER INFORMATION: Abet0323b

<400> SEQUENCE: 108

Phe Gly Gly Gly Thr Lys Leu Ile Val Leu
                5                   10

<210> SEQ ID NO 109
<211> LENGTH: 375
<212> TYPE: DNA
<213> ORGANISM: Homo sapiens
<220> FEATURE:
<223> OTHER INFORMATION: Abet0328

<400> SEQUENCE: 109

```
gaggtgcagc tgttggagtc tgggggaggc ttggtacagc ctgggggtc cctgagactc      60
tcctgtgcag cctccagaga cccttcaag gcggacacta tgtggtgggt ccgccaggct     120
ccaaggaaga ggctggagtg ggtctcagtt attggtgccc acaccaccaa cagcgcgtac    180
gcagactccg tgaagggccg gttcaccatc tccagagaca attccaagaa cacgctgtat    240
ctgcaaatga acagcctgag agccgaggac acggccgtgt attactgtgc gagagagtgg    300
atggaccgct cccgccccta ctactactac ggtatggacg tctggggca ggggaccctg    360
gtcaccgtct cctca                                                    375
```

<210> SEQ ID NO 110
<211> LENGTH: 125
<212> TYPE: PRT
<213> ORGANISM: Homo sapiens
<220> FEATURE:
<223> OTHER INFORMATION: Abet0328

<400> SEQUENCE: 110

Glu Val Gln Leu Leu Glu Ser Gly Gly Gly Leu Val Gln Pro Gly Gly
                5                   10                  15

Ser Leu Arg Leu Ser Cys Ala Ala Ser Arg Asp Pro Phe Lys Ala Asp
            20                  25                  30

Thr Met Trp Trp Val Arg Gln Ala Pro Arg Lys Arg Leu Glu Trp Val
        35                  40                  45

Ser Val Ile Gly Ala His Thr Thr Asn Ser Ala Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Trp Met Asp Arg Ser Arg Pro Tyr Tyr Tyr Gly Met
            100                 105                 110

Asp Val Trp Gly Gln Gly Thr Leu Val Thr Val Ser Ser
        115                 120                 125

<210> SEQ ID NO 111
<211> LENGTH: 5
<212> TYPE: PRT
<213> ORGANISM: Homo sapiens
<220> FEATURE:
<223> OTHER INFORMATION: Abet0328

<400> SEQUENCE: 111

Ala Asp Thr Met Trp
                5

-continued

```
<210> SEQ ID NO 112
<211> LENGTH: 17
<212> TYPE: PRT
<213> ORGANISM: Homo sapiens
<220> FEATURE:
<223> OTHER INFORMATION: Abet0328

<400> SEQUENCE: 112

Val Ile Gly Ala His Thr Thr Asn Ser Ala Tyr Ala Asp Ser Val Lys
                  5                  10                  15
Gly

<210> SEQ ID NO 113
<211> LENGTH: 16
<212> TYPE: PRT
<213> ORGANISM: Homo sapiens
<220> FEATURE:
<223> OTHER INFORMATION: Abet0328

<400> SEQUENCE: 113

Glu Trp Met Asp Arg Ser Arg Pro Tyr Tyr Tyr Gly Met Asp Val
                  5                  10                  15

<210> SEQ ID NO 114
<211> LENGTH: 30
<212> TYPE: PRT
<213> ORGANISM: Homo sapiens
<220> FEATURE:
<223> OTHER INFORMATION: Abet0328

<400> SEQUENCE: 114

Glu Val Gln Leu Leu Glu Ser Gly Gly Gly Leu Val Gln Pro Gly Gly
                  5                  10                  15
Ser Leu Arg Leu Ser Cys Ala Ala Ser Arg Asp Pro Phe Lys
             20                  25                  30

<210> SEQ ID NO 115
<211> LENGTH: 14
<212> TYPE: PRT
<213> ORGANISM: Homo sapiens
<220> FEATURE:
<223> OTHER INFORMATION: Abet0328

<400> SEQUENCE: 115

Trp Val Arg Gln Ala Pro Arg Lys Arg Leu Glu Trp Val Ser
                  5                  10

<210> SEQ ID NO 116
<211> LENGTH: 32
<212> TYPE: PRT
<213> ORGANISM: Homo sapiens
<220> FEATURE:
<223> OTHER INFORMATION: Abet0328

<400> SEQUENCE: 116

Arg Phe Thr Ile Ser Arg Asp Asn Ser Lys Asn Thr Leu Tyr Leu Gln
                  5                  10                  15
Met Asn Ser Leu Arg Ala Glu Asp Thr Ala Val Tyr Tyr Cys Ala Arg
             20                  25                  30

<210> SEQ ID NO 117
<211> LENGTH: 11
<212> TYPE: PRT
<213> ORGANISM: Homo sapiens
<220> FEATURE:
<223> OTHER INFORMATION: Abet0328
```

<400> SEQUENCE: 117

Trp Gly Gln Gly Thr Leu Val Thr Val Ser Ser
                5                   10

<210> SEQ ID NO 118
<211> LENGTH: 318
<212> TYPE: DNA
<213> ORGANISM: Homo sapiens
<220> FEATURE:
<223> OTHER INFORMATION: Abet0328

<400> SEQUENCE: 118
tcgtacgagt tgactcagcc accctcagtg tccgtgtccc caggacagac ggtcagcatc      60
acctgctctg gacgtaactt ggaagataaa tttgcttcct ggtatcaaca gaagccaggc     120
cagtcccctg tcctggtcat ctatcgagat gacaagcggc cctcagggt ccctgagcga     180 ttctctgcct ccaactccgg gcacactgcc actctgacca tcagcgggac ccaggctacg     240
gatgaggctg actattactg ttcgtcccag gacacggtga ctcgagtgtt cggcggaggg     300
accaagctga ccgtccta                                                   318

<210> SEQ ID NO 119
<211> LENGTH: 106
<212> TYPE: PRT
<213> ORGANISM: Homo sapiens
<220> FEATURE:
<223> OTHER INFORMATION: Abet0328

<400> SEQUENCE: 119

Ser Tyr Glu Leu Thr Gln Pro Pro Ser Val Ser Val Ser Pro Gly Gln
                5                   10                  15

Thr Val Ser Ile Thr Cys Ser Gly Arg Asn Leu Glu Asp Lys Phe Ala
            20                  25                  30

Ser Trp Tyr Gln Gln Lys Pro Gly Gln Ser Pro Val Leu Val Ile Tyr
        35                  40                  45

Arg Asp Asp Lys Arg Pro Ser Gly Val Pro Glu Arg Phe Ser Ala Ser
    50                  55                  60

Asn Ser Gly His Thr Ala Thr Leu Thr Ile Ser Gly Thr Gln Ala Thr
65                  70                  75                  80

Asp Glu Ala Asp Tyr Tyr Cys Ser Ser Gln Asp Thr Val Thr Arg Val
                85                  90                  95

Phe Gly Gly Gly Thr Lys Leu Thr Val Leu
            100                 105

<210> SEQ ID NO 120
<211> LENGTH: 11
<212> TYPE: PRT
<213> ORGANISM: Homo sapiens
<220> FEATURE:
<223> OTHER INFORMATION: Abet0328

<400> SEQUENCE: 120

Ser Gly Arg Asn Leu Glu Asp Lys Phe Ala Ser
                5                   10

<210> SEQ ID NO 121
<211> LENGTH: 7
<212> TYPE: PRT
<213> ORGANISM: Homo sapiens
<220> FEATURE:
<223> OTHER INFORMATION: Abet0328

<400> SEQUENCE: 121

Arg Asp Asp Lys Arg Pro Ser
            5

<210> SEQ ID NO 122
<211> LENGTH: 9
<212> TYPE: PRT
<213> ORGANISM: Homo sapiens
<220> FEATURE:
<223> OTHER INFORMATION: Abet0328

<400> SEQUENCE: 122

Ser Ser Gln Asp Thr Val Thr Arg Val
            5

<210> SEQ ID NO 123
<211> LENGTH: 22
<212> TYPE: PRT
<213> ORGANISM: Homo sapiens
<220> FEATURE:
<223> OTHER INFORMATION: Abet0328

<400> SEQUENCE: 123

Ser Tyr Glu Leu Thr Gln Pro Pro Ser Val Ser Val Ser Pro Gly Gln
            5                   10                  15

Thr Val Ser Ile Thr Cys
            20

<210> SEQ ID NO 124
<211> LENGTH: 15
<212> TYPE: PRT
<213> ORGANISM: Homo sapiens
<220> FEATURE:
<223> OTHER INFORMATION: Abet0328

<400> SEQUENCE: 124

Trp Tyr Gln Gln Lys Pro Gly Gln Ser Pro Val Leu Val Ile Tyr
            5                   10                  15

<210> SEQ ID NO 125
<211> LENGTH: 32
<212> TYPE: PRT
<213> ORGANISM: Homo sapiens
<220> FEATURE:
<223> OTHER INFORMATION: Abet0328

<400> SEQUENCE: 125

Gly Val Pro Glu Arg Phe Ser Ala Ser Asn Ser Gly His Thr Ala Thr
            5                   10                  15

Leu Thr Ile Ser Gly Thr Gln Ala Thr Asp Glu Ala Asp Tyr Tyr Cys
            20                  25                  30

<210> SEQ ID NO 126
<211> LENGTH: 10
<212> TYPE: PRT
<213> ORGANISM: Homo sapiens
<220> FEATURE:
<223> OTHER INFORMATION: Abet0328

<400> SEQUENCE: 126

Phe Gly Gly Gly Thr Lys Leu Thr Val Leu
            5                   10

<210> SEQ ID NO 127

-continued

<211> LENGTH: 375
<212> TYPE: DNA
<213> ORGANISM: Homo sapiens
<220> FEATURE:
<223> OTHER INFORMATION: Abet0329

<400> SEQUENCE: 127
gaggtgcagc tgttggagtc tgggggaggc ttggtacagc ctgggggtc cctgagactc      60 tcctgtgcag cctctacgtt taacctcaag cgcgagacta tgtggtgggt ccgccaggct    120
ccagggaagg ggctggagtg ggtctccgtt attggttccc accaggagcg cacgagctac    180
gcagactccg tgaagggccg gttcaccatc tccagagaca attccaagaa cacgctgtat    240
ctgcaaatga acagcctgag agccgaggac acggccgtgt attactgtgc gagagagtgg    300
atggaccact cccgccccta ctactactac ggtatggacg tctggggggca ggggaccctg    360 gtcaccgtct cctca                                                    375

<210> SEQ ID NO 128
<211> LENGTH: 125
<212> TYPE: PRT
<213> ORGANISM: Homo sapiens
<220> FEATURE:
<223> OTHER INFORMATION: Abet0329

<400> SEQUENCE: 128

Glu Val Gln Leu Leu Glu Ser Gly Gly Gly Leu Val Gln Pro Gly Gly
                 5                  10                  15

Ser Leu Arg Leu Ser Cys Ala Ala Ser Thr Phe Asn Leu Lys Arg Glu
            20                  25                  30

Thr Met Trp Trp Val Arg Gln Ala Pro Gly Lys Gly Leu Glu Trp Val
        35                  40                  45

Ser Val Ile Gly Ser His Gln Glu Arg Thr Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Trp Met Asp His Ser Arg Pro Tyr Tyr Tyr Tyr Gly Met
            100                 105                 110

Asp Val Trp Gly Gln Gly Thr Leu Val Thr Val Ser Ser
        115                 120                 125

<210> SEQ ID NO 129
<211> LENGTH: 5
<212> TYPE: PRT
<213> ORGANISM: Homo sapiens
<220> FEATURE:
<223> OTHER INFORMATION: Abet0329

<400> SEQUENCE: 129

Arg Glu Thr Met Trp
                 5

<210> SEQ ID NO 130
<211> LENGTH: 17
<212> TYPE: PRT
<213> ORGANISM: Homo sapiens
<220> FEATURE:
<223> OTHER INFORMATION: Abet0329

<400> SEQUENCE: 130

Val Ile Gly Ser His Gln Glu Arg Thr Ser Tyr Ala Asp Ser Val Lys
                5                   10                  15
Gly

<210> SEQ ID NO 131
<211> LENGTH: 16
<212> TYPE: PRT
<213> ORGANISM: Homo sapiens
<220> FEATURE:
<223> OTHER INFORMATION: Abet0329

<400> SEQUENCE: 131

Glu Trp Met Asp His Ser Arg Pro Tyr Tyr Tyr Gly Met Asp Val
                5                   10                  15

<210> SEQ ID NO 132
<211> LENGTH: 30
<212> TYPE: PRT
<213> ORGANISM: Homo sapiens
<220> FEATURE:
<223> OTHER INFORMATION: Abet0329

<400> SEQUENCE: 132

Glu Val Gln Leu Leu Glu Ser Gly Gly Gly Leu Val Gln Pro Gly Gly
                5                   10                  15

Ser Leu Arg Leu Ser Cys Ala Ala Ser Thr Phe Asn Leu Lys
            20                  25                  30

<210> SEQ ID NO 133
<211> LENGTH: 14
<212> TYPE: PRT
<213> ORGANISM: Homo sapiens
<220> FEATURE:
<223> OTHER INFORMATION: Abet0329

<400> SEQUENCE: 133

Trp Val Arg Gln Ala Pro Gly Lys Gly Leu Glu Trp Val Ser
                5                   10

<210> SEQ ID NO 134
<211> LENGTH: 32
<212> TYPE: PRT
<213> ORGANISM: Homo sapiens
<220> FEATURE:
<223> OTHER INFORMATION: Abet0329

<400> SEQUENCE: 134

Arg Phe Thr Ile Ser Arg Asp Asn Ser Lys Asn Thr Leu Tyr Leu Gln
                5                   10                  15

Met Asn Ser Leu Arg Ala Glu Asp Thr Ala Val Tyr Tyr Cys Ala Arg
            20                  25                  30

<210> SEQ ID NO 135
<211> LENGTH: 11
<212> TYPE: PRT
<213> ORGANISM: Homo sapiens
<220> FEATURE:
<223> OTHER INFORMATION: Abet0329

<400> SEQUENCE: 135

Trp Gly Gln Gly Thr Leu Val Thr Val Ser Ser
                5                   10

<210> SEQ ID NO 136
<211> LENGTH: 318

-continued

<212> TYPE: DNA
<213> ORGANISM: Homo sapiens
<220> FEATURE:
<223> OTHER INFORMATION: Abet0329

<400> SEQUENCE: 136

```
tcgtacgagt tgactcagcc accctcagtg tccgtgtccc caggacagac ggccagcatc    60
acctgctctg gacataacgt gagcgacaag tggatgacgt ggtatcagca gaagccaggc   120
cagtcccctg tcctggtcat ctatcgagat gacaagcggc cctcaggat  ccctgagcga   180
ttctctgcct ccaactctgg gcacactgcc actctgacca tcagcgggac ccaagctacg   240
gatgaggctg actattactg ttcgtcccag gacacggtga ctcgagtgtt cggcggaggg   300
accaagctga ccgtccta                                                 318
```

<210> SEQ ID NO 137
<211> LENGTH: 106
<212> TYPE: PRT
<213> ORGANISM: Homo sapiens
<220> FEATURE:
<223> OTHER INFORMATION: Abet0329

<400> SEQUENCE: 137

Ser Tyr Glu Leu Thr Gln Pro Pro Ser Val Ser Val Ser Pro Gly Gln
 1               5                  10                  15

Thr Ala Ser Ile Thr Cys Ser Gly His Asn Val Ser Asp Lys Trp Met
             20                  25                  30

Thr Trp Tyr Gln Gln Lys Pro Gly Gln Ser Pro Val Leu Val Ile Tyr
         35                  40                  45

Arg Asp Asp Lys Arg Pro Ser Gly Ile Pro Glu Arg Phe Ser Ala Ser
     50                  55                  60

Asn Ser Gly His Thr Ala Thr Leu Thr Ile Ser Gly Thr Gln Ala Thr
 65                  70                  75                  80

Asp Glu Ala Asp Tyr Tyr Cys Ser Ser Gln Asp Thr Val Thr Arg Val
                 85                  90                  95

Phe Gly Gly Gly Thr Lys Leu Thr Val Leu
            100                 105

<210> SEQ ID NO 138
<211> LENGTH: 11
<212> TYPE: PRT
<213> ORGANISM: Homo sapiens
<220> FEATURE:
<223> OTHER INFORMATION: Abet0329

<400> SEQUENCE: 138

Ser Gly His Asn Val Ser Asp Lys Trp Met Thr
 1               5                  10

<210> SEQ ID NO 139
<211> LENGTH: 7
<212> TYPE: PRT
<213> ORGANISM: Homo sapiens
<220> FEATURE:
<223> OTHER INFORMATION: Abet0329

<400> SEQUENCE: 139

Arg Asp Asp Lys Arg Pro Ser
 1               5

<210> SEQ ID NO 140
<211> LENGTH: 9

```
<212> TYPE: PRT
<213> ORGANISM: Homo sapiens
<220> FEATURE:
<223> OTHER INFORMATION: Abet0329

<400> SEQUENCE: 140

Ser Ser Gln Asp Thr Val Thr Arg Val
                 5

<210> SEQ ID NO 141
<211> LENGTH: 22
<212> TYPE: PRT
<213> ORGANISM: Homo sapiens
<220> FEATURE:
<223> OTHER INFORMATION: Abet0329

<400> SEQUENCE: 141

Ser Tyr Glu Leu Thr Gln Pro Pro Ser Val Ser Val Ser Pro Gly Gln
                 5                  10                  15

Thr Ala Ser Ile Thr Cys
             20

<210> SEQ ID NO 142
<211> LENGTH: 15
<212> TYPE: PRT
<213> ORGANISM: Homo sapiens
<220> FEATURE:
<223> OTHER INFORMATION: Abet0329

<400> SEQUENCE: 142

Trp Tyr Gln Gln Lys Pro Gly Gln Ser Pro Val Leu Val Ile Tyr
                 5                  10                  15

<210> SEQ ID NO 143
<211> LENGTH: 32
<212> TYPE: PRT
<213> ORGANISM: Homo sapiens
<220> FEATURE:
<223> OTHER INFORMATION: Abet0329

<400> SEQUENCE: 143

Gly Ile Pro Glu Arg Phe Ser Ala Ser Asn Ser Gly His Thr Ala Thr
                 5                  10                  15

Leu Thr Ile Ser Gly Thr Gln Ala Thr Asp Glu Ala Asp Tyr Tyr Cys
             20                  25                  30

<210> SEQ ID NO 144
<211> LENGTH: 10
<212> TYPE: PRT
<213> ORGANISM: Homo sapiens
<220> FEATURE:
<223> OTHER INFORMATION: Abet0329

<400> SEQUENCE: 144

Phe Gly Gly Gly Thr Lys Leu Thr Val Leu
                 5                  10

<210> SEQ ID NO 145
<211> LENGTH: 375
<212> TYPE: DNA
<213> ORGANISM: Homo sapiens
<220> FEATURE:
<223> OTHER INFORMATION: Abet0332

<400> SEQUENCE: 145
gaggtgcagc tgttggagtc tgggggaggc ttggtacagc ctggggagtc cctgagactc      60
```

-continued

```
tcctgtgcag cctcttccga ctcctggcac accgacatta tgtggtgggt ccgccaggct    120
ccagggaaga ggctggagtg ggtctcagtt attggtaact cgaacaagaa gatcgcctac    180
gcagactccg tgaagggccg gttcaccatc tccagagaca attccaagaa cacgctgtat    240
ctgcaaatga acagcctgag agccgaggac acggccgtgt attactgtgc gagagagtgg    300
atggaccact cccgccccta ctactactac ggtatggacg tctggggca ggggaccctg    360 gtcaccgtct catca                                                     375
```

<210> SEQ ID NO 146
<211> LENGTH: 125
<212> TYPE: PRT
<213> ORGANISM: Homo sapiens
<220> FEATURE:
<223> OTHER INFORMATION: Abet0332

<400> SEQUENCE: 146

Glu Val Gln Leu Leu Glu Ser Gly Gly Gly Leu Val Gln Pro Gly Glu
 1               5                  10                  15

Ser Leu Arg Leu Ser Cys Ala Ala Ser Ser Asp Ser Trp His Thr Asp
            20                  25                  30

Ile Met Trp Trp Val Arg Gln Ala Pro Gly Lys Arg Leu Glu Trp Val
        35                  40                  45

Ser Val Ile Gly Asn Ser Asn Lys Lys Ile Ala Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Trp Met Asp His Ser Arg Pro Tyr Tyr Tyr Gly Met
            100                 105                 110

Asp Val Trp Gly Gln Gly Thr Leu Val Thr Val Ser Ser
        115                 120                 125

<210> SEQ ID NO 147
<211> LENGTH: 5
<212> TYPE: PRT
<213> ORGANISM: Homo sapiens
<220> FEATURE:
<223> OTHER INFORMATION: Abet0332

<400> SEQUENCE: 147

Thr Asp Ile Met Trp
             5

<210> SEQ ID NO 148
<211> LENGTH: 17
<212> TYPE: PRT
<213> ORGANISM: Homo sapiens
<220> FEATURE:
<223> OTHER INFORMATION: Abet0332

<400> SEQUENCE: 148

Val Ile Gly Asn Ser Asn Lys Lys Ile Ala Tyr Ala Asp Ser Val Lys
 1               5                  10                  15

Gly

<210> SEQ ID NO 149
<211> LENGTH: 16
<212> TYPE: PRT

```
<213> ORGANISM: Homo sapiens
<220> FEATURE:
<223> OTHER INFORMATION: Abet0332

<400> SEQUENCE: 149

Glu Trp Met Asp His Ser Arg Pro Tyr Tyr Tyr Tyr Gly Met Asp Val
                5                  10                  15

<210> SEQ ID NO 150
<211> LENGTH: 30
<212> TYPE: PRT
<213> ORGANISM: Homo sapiens
<220> FEATURE:
<223> OTHER INFORMATION: Abet0332

<400> SEQUENCE: 150

Glu Val Gln Leu Leu Glu Ser Gly Gly Gly Leu Val Gln Pro Gly Glu
                5                  10                  15

Ser Leu Arg Leu Ser Cys Ala Ala Ser Ser Asp Ser Trp His
            20                  25                  30

<210> SEQ ID NO 151
<211> LENGTH: 14
<212> TYPE: PRT
<213> ORGANISM: Homo sapiens
<220> FEATURE:
<223> OTHER INFORMATION: Abet0332

<400> SEQUENCE: 151

Trp Val Arg Gln Ala Pro Gly Lys Arg Leu Glu Trp Val Ser
                5                  10

<210> SEQ ID NO 152
<211> LENGTH: 32
<212> TYPE: PRT
<213> ORGANISM: Homo sapiens
<220> FEATURE:
<223> OTHER INFORMATION: Abet0332

<400> SEQUENCE: 152

Arg Phe Thr Ile Ser Arg Asp Asn Ser Lys Asn Thr Leu Tyr Leu Gln
                5                  10                  15

Met Asn Ser Leu Arg Ala Glu Asp Thr Ala Val Tyr Tyr Cys Ala Arg
            20                  25                  30

<210> SEQ ID NO 153
<211> LENGTH: 11
<212> TYPE: PRT
<213> ORGANISM: Homo sapiens
<220> FEATURE:
<223> OTHER INFORMATION: Abet0332

<400> SEQUENCE: 153

Trp Gly Gln Gly Thr Leu Val Thr Val Ser Ser
                5                  10

<210> SEQ ID NO 154
<211> LENGTH: 318
<212> TYPE: DNA
<213> ORGANISM: Homo sapiens
<220> FEATURE:
<223> OTHER INFORMATION: Abet0332

<400> SEQUENCE: 154
tcgtacgagt tgactcagcc accctcagtg tccgtgtccc cagggcagac ggccagcatc    60
```

-continued

```
acctgctctg gacataacat cggcgcgaag tgggtgagct ggtatcaaca gaagccaggc    120
cagtcaccta tcctggtcat ctatcgagat gacaagcggc cctcagggat ccctgagcga    180
ttctctgcct ccaactctgg gcacactgcc actctgacca tcagcgggac ccaggctacg    240
gatgaggctg actattactg tcaggcgcag ggccaggtga ccaggtcgtt cggcggaggg    300
accaagctga ccgtccta                                                  318
```

<210> SEQ ID NO 155
<211> LENGTH: 106
<212> TYPE: PRT
<213> ORGANISM: Homo sapiens
<220> FEATURE:
<223> OTHER INFORMATION: Abet0332

<400> SEQUENCE: 155

Ser Tyr Glu Leu Thr Gln Pro Pro Ser Val Ser Val Ser Pro Gly Gln
1               5                   10                  15

Thr Ala Ser Ile Thr Cys Ser Gly His Asn Ile Gly Ala Lys Trp Val
            20                  25                  30

Ser Trp Tyr Gln Gln Lys Pro Gly Gln Ser Pro Ile Leu Val Ile Tyr
        35                  40                  45

Arg Asp Asp Lys Arg Pro Ser Gly Ile Pro Glu Arg Phe Ser Ala Ser
    50                  55                  60

Asn Ser Gly His Thr Ala Thr Leu Thr Ile Ser Gly Thr Gln Ala Thr
65                  70                  75                  80

Asp Glu Ala Asp Tyr Tyr Cys Gln Ala Gln Gly Gln Val Thr Arg Ser
                85                  90                  95

Phe Gly Gly Gly Thr Lys Leu Thr Val Leu
            100                 105

<210> SEQ ID NO 156
<211> LENGTH: 11
<212> TYPE: PRT
<213> ORGANISM: Homo sapiens
<220> FEATURE:
<223> OTHER INFORMATION: Abet0332

<400> SEQUENCE: 156

Ser Gly His Asn Ile Gly Ala Lys Trp Val Ser
1               5                   10

<210> SEQ ID NO 157
<211> LENGTH: 7
<212> TYPE: PRT
<213> ORGANISM: Homo sapiens
<220> FEATURE:
<223> OTHER INFORMATION: Abet0332

<400> SEQUENCE: 157

Arg Asp Asp Lys Arg Pro Ser
1               5

<210> SEQ ID NO 158
<211> LENGTH: 9
<212> TYPE: PRT
<213> ORGANISM: Homo sapiens
<220> FEATURE:
<223> OTHER INFORMATION: Abet0332

<400> SEQUENCE: 158

Gln Ala Gln Gly Gln Val Thr Arg Ser
1               5

```
<210> SEQ ID NO 159
<211> LENGTH: 22
<212> TYPE: PRT
<213> ORGANISM: Homo sapiens
<220> FEATURE:
<223> OTHER INFORMATION: Abet0332

<400> SEQUENCE: 159

Ser Tyr Glu Leu Thr Gln Pro Pro Ser Val Ser Val Ser Pro Gly Gln
                 5                  10                  15

Thr Ala Ser Ile Thr Cys
            20

<210> SEQ ID NO 160
<211> LENGTH: 15
<212> TYPE: PRT
<213> ORGANISM: Homo sapiens
<220> FEATURE:
<223> OTHER INFORMATION: Abet0332

<400> SEQUENCE: 160

Trp Tyr Gln Gln Lys Pro Gly Gln Ser Pro Ile Leu Val Ile Tyr
                 5                  10                  15

<210> SEQ ID NO 161
<211> LENGTH: 32
<212> TYPE: PRT
<213> ORGANISM: Homo sapiens
<220> FEATURE:
<223> OTHER INFORMATION: Abet0332

<400> SEQUENCE: 161

Gly Ile Pro Glu Arg Phe Ser Ala Ser Asn Ser Gly His Thr Ala Thr
                 5                  10                  15

Leu Thr Ile Ser Gly Thr Gln Ala Thr Asp Glu Ala Asp Tyr Tyr Cys
            20                  25                  30

<210> SEQ ID NO 162
<211> LENGTH: 10
<212> TYPE: PRT
<213> ORGANISM: Homo sapiens
<220> FEATURE:
<223> OTHER INFORMATION: Abet0332

<400> SEQUENCE: 162

Phe Gly Gly Gly Thr Lys Leu Thr Val Leu
                 5                  10

<210> SEQ ID NO 163
<211> LENGTH: 375
<212> TYPE: DNA
<213> ORGANISM: Homo sapiens
<220> FEATURE:
<223> OTHER INFORMATION: Abet0342

<400> SEQUENCE: 163
gaggtgcagc tgttggagtc tgggggaggc ttggtacagc ctgggggtc cctgagactc     60 tcctgtgcag cctctggatt cgactttgc aggtccgtca tgtggtgggt ccgccaggct   120
ccagggaagg ggctggagtg ggtctcagtt attggtgccc agacccagaa caaggcgtac   180
gcagactccg tgaagggccg gttcaccatc tccagagaca attccaagaa cacgctgtat   240
ctgcaaatga acagcctgag agccgaggac acggccgtgt attactgtgc gagagagtgg   300
```

```
atggaccact cccgcccta ctactactac ggtatggacg tctgggggca ggggaccctg      360
gtcaccgtct cctca                                                      375
```

<210> SEQ ID NO 164
<211> LENGTH: 125
<212> TYPE: PRT
<213> ORGANISM: Homo sapiens
<220> FEATURE:
<223> OTHER INFORMATION: Abet0342

<400> SEQUENCE: 164

Glu Val Gln Leu Leu Glu Ser Gly Gly Gly Leu Val Gln Pro Gly Gly
                 5                  10                  15

Ser Leu Arg Leu Ser Cys Ala Ala Ser Gly Phe Asp Phe Arg Arg Ser
            20                  25                  30

Val Met Trp Trp Val Arg Gln Ala Pro Gly Lys Gly Leu Glu Trp Val
        35                  40                  45

Ser Val Ile Gly Ala Gln Thr Gln Asn Lys Ala Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Trp Met Asp His Ser Arg Pro Tyr Tyr Tyr Gly Met
            100                 105                 110

Asp Val Trp Gly Gln Gly Thr Leu Val Thr Val Ser Ser
        115                 120                 125

<210> SEQ ID NO 165
<211> LENGTH: 5
<212> TYPE: PRT
<213> ORGANISM: Homo sapiens
<220> FEATURE:
<223> OTHER INFORMATION: Abet0342

<400> SEQUENCE: 165

Arg Ser Val Met Trp
                 5

<210> SEQ ID NO 166
<211> LENGTH: 17
<212> TYPE: PRT
<213> ORGANISM: Homo sapiens
<220> FEATURE:
<223> OTHER INFORMATION: Abet0342

<400> SEQUENCE: 166

Val Ile Gly Ala Gln Thr Gln Asn Lys Ala Tyr Ala Asp Ser Val Lys
                 5                  10                  15

Gly

<210> SEQ ID NO 167
<211> LENGTH: 16
<212> TYPE: PRT
<213> ORGANISM: Homo sapiens
<220> FEATURE:
<223> OTHER INFORMATION: Abet0342

<400> SEQUENCE: 167

Glu Trp Met Asp His Ser Arg Pro Tyr Tyr Tyr Gly Met Asp Val
                 5                  10                  15

<210> SEQ ID NO 168
<211> LENGTH: 30
<212> TYPE: PRT
<213> ORGANISM: Homo sapiens
<220> FEATURE:
<223> OTHER INFORMATION: Abet0342

<400> SEQUENCE: 168

Glu Val Gln Leu Leu Glu Ser Gly Gly Gly Leu Val Gln Pro Gly Gly
                 5                   10                  15
Ser Leu Arg Leu Ser Cys Ala Ala Ser Gly Phe Asp Phe Arg
            20                  25                  30

<210> SEQ ID NO 169
<211> LENGTH: 14
<212> TYPE: PRT
<213> ORGANISM: Homo sapiens
<220> FEATURE:
<223> OTHER INFORMATION: Abet0342

<400> SEQUENCE: 169

Trp Val Arg Gln Ala Pro Gly Lys Gly Leu Glu Trp Val Ser
                 5                   10

<210> SEQ ID NO 170
<211> LENGTH: 32
<212> TYPE: PRT
<213> ORGANISM: Homo sapiens
<220> FEATURE:
<223> OTHER INFORMATION: Abet0342

<400> SEQUENCE: 170

Arg Phe Thr Ile Ser Arg Asp Asn Ser Lys Asn Thr Leu Tyr Leu Gln
                 5                   10                  15
Met Asn Ser Leu Arg Ala Glu Asp Thr Ala Val Tyr Tyr Cys Ala Arg
            20                  25                  30

<210> SEQ ID NO 171
<211> LENGTH: 11
<212> TYPE: PRT
<213> ORGANISM: Homo sapiens
<220> FEATURE:
<223> OTHER INFORMATION: Abet0342

<400> SEQUENCE: 171

Trp Gly Gln Gly Thr Leu Val Thr Val Ser Ser
                 5                   10

<210> SEQ ID NO 172
<211> LENGTH: 318
<212> TYPE: DNA
<213> ORGANISM: Homo sapiens
<220> FEATURE:
<223> OTHER INFORMATION: Abet0342

<400> SEQUENCE: 172
tcgtacgagt tgactcagcc accctcagtg tccgtgtccc caggacagac ggccagcatc        60
acctgctctg gacataactt ggaagataaa tttgcttcct ggtatcaaca gaagccaggc       120
cagtcccccg tcctggtcat ctatcgggat gacaagcggc cctcagggat ccctgagcga       180
ttctctgcct ccaactctgg ggacactgcc actctgacca tcagcgggac ccaggctatg       240
gatgaggctg actattactg tcaggcgcag gacagtacca ctcgagtgtt cggcggaggg       300
actaagctga ccgtccta                                                     318

<210> SEQ ID NO 173
<211> LENGTH: 106
<212> TYPE: PRT
<213> ORGANISM: Homo sapiens
<220> FEATURE:
<223> OTHER INFORMATION: Abet0342

<400> SEQUENCE: 173

Ser Tyr Glu Leu Thr Gln Pro Pro Ser Val Ser Val Ser Pro Gly Gln
                  5                  10                  15
Thr Ala Ser Ile Thr Cys Ser Gly His Asn Leu Glu Asp Lys Phe Ala
             20                  25                  30
Ser Trp Tyr Gln Gln Lys Pro Gly Gln Ser Pro Val Leu Val Ile Tyr
         35                  40                  45
Arg Asp Asp Lys Arg Pro Ser Gly Ile Pro Glu Arg Phe Ser Ala Ser
     50                  55                  60
Asn Ser Gly Asp Thr Ala Thr Leu Thr Ile Ser Gly Thr Gln Ala Met
 65                  70                  75                  80
Asp Glu Ala Asp Tyr Tyr Cys Gln Ala Gln Asp Ser Thr Thr Arg Val
                 85                  90                  95
Phe Gly Gly Gly Thr Lys Leu Thr Val Leu
            100                 105

<210> SEQ ID NO 174
<211> LENGTH: 11
<212> TYPE: PRT
<213> ORGANISM: Homo sapiens
<220> FEATURE:
<223> OTHER INFORMATION: Abet0342

<400> SEQUENCE: 174

Ser Gly His Asn Leu Glu Asp Lys Phe Ala Ser
                  5                  10

<210> SEQ ID NO 175
<211> LENGTH: 7
<212> TYPE: PRT
<213> ORGANISM: Homo sapiens
<220> FEATURE:
<223> OTHER INFORMATION: Abet0342

<400> SEQUENCE: 175

Arg Asp Asp Lys Arg Pro Ser
                  5

<210> SEQ ID NO 176
<211> LENGTH: 9
<212> TYPE: PRT
<213> ORGANISM: Homo sapiens
<220> FEATURE:
<223> OTHER INFORMATION: Abet0342

<400> SEQUENCE: 176

Gln Ala Gln Asp Ser Thr Thr Arg Val
                  5

<210> SEQ ID NO 177
<211> LENGTH: 22
<212> TYPE: PRT
<213> ORGANISM: Homo sapiens
<220> FEATURE:
<223> OTHER INFORMATION: Abet0342

-continued

<400> SEQUENCE: 177

Ser Tyr Glu Leu Thr Gln Pro Pro Ser Val Ser Val Ser Pro Gly Gln
                5                   10                  15

Thr Ala Ser Ile Thr Cys
            20

<210> SEQ ID NO 178
<211> LENGTH: 15
<212> TYPE: PRT
<213> ORGANISM: Homo sapiens
<220> FEATURE:
<223> OTHER INFORMATION: Abet0342

<400> SEQUENCE: 178

Trp Tyr Gln Gln Lys Pro Gly Gln Ser Pro Val Leu Val Ile Tyr
                5                   10                  15

<210> SEQ ID NO 179
<211> LENGTH: 32
<212> TYPE: PRT
<213> ORGANISM: Homo sapiens
<220> FEATURE:
<223> OTHER INFORMATION: Abet0342

<400> SEQUENCE: 179

Gly Ile Pro Glu Arg Phe Ser Ala Ser Asn Ser Gly Asp Thr Ala Thr
                5                   10                  15

Leu Thr Ile Ser Gly Thr Gln Ala Met Asp Glu Ala Asp Tyr Tyr Cys
            20                  25                  30

<210> SEQ ID NO 180
<211> LENGTH: 10
<212> TYPE: PRT
<213> ORGANISM: Homo sapiens
<220> FEATURE:
<223> OTHER INFORMATION: Abet0342

<400> SEQUENCE: 180

Phe Gly Gly Gly Thr Lys Leu Thr Val Leu
                5                   10

<210> SEQ ID NO 181
<211> LENGTH: 375
<212> TYPE: DNA
<213> ORGANISM: Homo sapiens
<220> FEATURE:
<223> OTHER INFORMATION: Abet0343

<400> SEQUENCE: 181
gaggtgcagc tgttggagtc tgggggaggc ttggtacagc ctggggggtc cctgagactc      60
tcctgtgcag cctctggatt caactttaac caccaggtga tgtggtgggt ccgccaggct     120
ccagggaagg ggctggagtg ggtctcagtt attggtaaga ccaacgagaa catcgcctac     180
gcagactccg tgaagggccg gttcaccatc tccagagaca attccaagaa cacgctgtat     240
ctgcaaatga acagcctgag agccgaggac acggccgtgt attactgtgc gagagagtgg     300
atggaccact ctcgccccta ctactactac ggtatggacg tctggggggca ggggaccctg     360 gtcaccgtct cctca                                                     375

<210> SEQ ID NO 182
<211> LENGTH: 125
<212> TYPE: PRT
<213> ORGANISM: Homo sapiens
<220> FEATURE:
<223> OTHER INFORMATION: Abet0343

<400> SEQUENCE: 182

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asn Phe Asn His Gln
            20                  25                  30

Val Met Trp Trp Val Arg Gln Ala Pro Gly Lys Gly Leu Glu Trp Val
        35                  40                  45

Ser Val Ile Gly Lys Thr Asn Glu Asn Ile Ala Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Trp Met Asp His Ser Arg Pro Tyr Tyr Tyr Gly Met
            100                 105                 110

Asp Val Trp Gly Gln Gly Thr Leu Val Thr Val Ser Ser
        115                 120                 125

<210> SEQ ID NO 183
<211> LENGTH: 5
<212> TYPE: PRT
<213> ORGANISM: Homo sapiens
<220> FEATURE:
<223> OTHER INFORMATION: Abet0343

<400> SEQUENCE: 183

His Gln Val Met Trp
1               5

<210> SEQ ID NO 184
<211> LENGTH: 17
<212> TYPE: PRT
<213> ORGANISM: Homo sapiens
<220> FEATURE:
<223> OTHER INFORMATION: Abet0343

<400> SEQUENCE: 184

Val Ile Gly Lys Thr Asn Glu Asn Ile Ala Tyr Ala Asp Ser Val Lys
1               5                   10                  15

Gly

<210> SEQ ID NO 185
<211> LENGTH: 16
<212> TYPE: PRT
<213> ORGANISM: Homo sapiens
<220> FEATURE:
<223> OTHER INFORMATION: Abet0343

<400> SEQUENCE: 185

Glu Trp Met Asp His Ser Arg Pro Tyr Tyr Tyr Gly Met Asp Val
1               5                   10                  15

<210> SEQ ID NO 186
<211> LENGTH: 30
<212> TYPE: PRT
<213> ORGANISM: Homo sapiens
<220> FEATURE:
<223> OTHER INFORMATION: Abet0343

<400> SEQUENCE: 186

Glu Val Gln Leu Leu Glu Ser Gly Gly Gly Leu Val Gln Pro Gly Gly
            5                   10                  15

Ser Leu Arg Leu Ser Cys Ala Ala Ser Gly Phe Asn Phe Asn
            20                  25                  30

<210> SEQ ID NO 187
<211> LENGTH: 14
<212> TYPE: PRT
<213> ORGANISM: Homo sapiens
<220> FEATURE:
<223> OTHER INFORMATION: Abet0343

<400> SEQUENCE: 187

Trp Val Arg Gln Ala Pro Gly Lys Gly Leu Glu Trp Val Ser
            5                   10

<210> SEQ ID NO 188
<211> LENGTH: 32
<212> TYPE: PRT
<213> ORGANISM: Homo sapiens
<220> FEATURE:
<223> OTHER INFORMATION: Abet0343

<400> SEQUENCE: 188

Arg Phe Thr Ile Ser Arg Asp Asn Ser Lys Asn Thr Leu Tyr Leu Gln
            5                   10                  15

Met Asn Ser Leu Arg Ala Glu Asp Thr Ala Val Tyr Tyr Cys Ala Arg
            20                  25                  30

<210> SEQ ID NO 189
<211> LENGTH: 11
<212> TYPE: PRT
<213> ORGANISM: Homo sapiens
<220> FEATURE:
<223> OTHER INFORMATION: Abet0343

<400> SEQUENCE: 189

Trp Gly Gln Gly Thr Leu Val Thr Val Ser Ser
            5                   10

<210> SEQ ID NO 190
<211> LENGTH: 318
<212> TYPE: DNA
<213> ORGANISM: Homo sapiens
<220> FEATURE:
<223> OTHER INFORMATION: Abet0343

<400> SEQUENCE: 190
cagagcgtct tgactcagcc accctcagtg tccgtgtccc caggacagac ggccagcatc      60
acctgctctg gacataactt ggaagataaa tttgcttcct ggtatcaaca gaagtcaggc     120
cagtcccctg tcctggtcat ctatcgagat gacaagcggc cctcagggat ccctgagcga     180
ttctctgcct ccaactctgg gcacactgcc actctgacca tcagcgggac ccaggctacg     240
gatgaggctg actattactg ttcgtcccag gacacggtga ctcgagtgtt cggcggaggg     300
accaagctga ccgtccta                                                    318

<210> SEQ ID NO 191
<211> LENGTH: 106
<212> TYPE: PRT
<213> ORGANISM: Homo sapiens
<220> FEATURE:
<223> OTHER INFORMATION: Abet0343

<400> SEQUENCE: 191

Gln Ser Val Leu Thr Gln Pro Pro Ser Val Ser Val Ser Pro Gly Gln
1               5                   10                  15

Thr Ala Ser Ile Thr Cys Ser Gly His Asn Leu Glu Asp Lys Phe Ala
            20                  25                  30

Ser Trp Tyr Gln Gln Lys Ser Gly Gln Ser Pro Val Leu Val Ile Tyr
        35                  40                  45

Arg Asp Asp Lys Arg Pro Ser Gly Ile Pro Glu Arg Phe Ser Ala Ser
50                  55                  60

Asn Ser Gly His Thr Ala Thr Leu Thr Ile Ser Gly Thr Gln Ala Thr
65                  70                  75                  80

Asp Glu Ala Asp Tyr Tyr Cys Ser Ser Gln Asp Thr Val Thr Arg Val
            85                  90                  95

Phe Gly Gly Gly Thr Lys Leu Thr Val Leu
            100                 105

<210> SEQ ID NO 192
<211> LENGTH: 11
<212> TYPE: PRT
<213> ORGANISM: Homo sapiens
<220> FEATURE:
<223> OTHER INFORMATION: Abet0343

<400> SEQUENCE: 192

Ser Gly His Asn Leu Glu Asp Lys Phe Ala Ser
1               5                   10

<210> SEQ ID NO 193
<211> LENGTH: 7
<212> TYPE: PRT
<213> ORGANISM: Homo sapiens
<220> FEATURE:
<223> OTHER INFORMATION: Abet0343

<400> SEQUENCE: 193

Arg Asp Asp Lys Arg Pro Ser
1               5

<210> SEQ ID NO 194
<211> LENGTH: 9
<212> TYPE: PRT
<213> ORGANISM: Homo sapiens
<220> FEATURE:
<223> OTHER INFORMATION: Abet0343

<400> SEQUENCE: 194

Ser Ser Gln Asp Thr Val Thr Arg Val
1               5

<210> SEQ ID NO 195
<211> LENGTH: 22
<212> TYPE: PRT
<213> ORGANISM: Homo sapiens
<220> FEATURE:
<223> OTHER INFORMATION: Abet0343

<400> SEQUENCE: 195

Gln Ser Val Leu Thr Gln Pro Pro Ser Val Ser Val Ser Pro Gly Gln
1               5                   10                  15

Thr Ala Ser Ile Thr Cys
            20

<210> SEQ ID NO 196
<211> LENGTH: 15
<212> TYPE: PRT
<213> ORGANISM: Homo sapiens
<220> FEATURE:
<223> OTHER INFORMATION: Abet0343

<400> SEQUENCE: 196

Trp Tyr Gln Gln Lys Ser Gly Gln Ser Pro Val Leu Val Ile Tyr
1               5                   10                  15

<210> SEQ ID NO 197
<211> LENGTH: 32
<212> TYPE: PRT
<213> ORGANISM: Homo sapiens
<220> FEATURE:
<223> OTHER INFORMATION: Abet0343

<400> SEQUENCE: 197

Gly Ile Pro Glu Arg Phe Ser Ala Ser Asn Ser Gly His Thr Ala Thr
1               5                   10                  15

Leu Thr Ile Ser Gly Thr Gln Ala Thr Asp Glu Ala Asp Tyr Tyr Cys
            20                  25                  30

<210> SEQ ID NO 198
<211> LENGTH: 10
<212> TYPE: PRT
<213> ORGANISM: Homo sapiens
<220> FEATURE:
<223> OTHER INFORMATION: Abet0343

<400> SEQUENCE: 198

Phe Gly Gly Gly Thr Lys Leu Thr Val Leu
1               5                   10

<210> SEQ ID NO 199
<211> LENGTH: 375
<212> TYPE: DNA
<213> ORGANISM: Homo sapiens
<220> FEATURE:
<223> OTHER INFORMATION: Abet0344

<400> SEQUENCE: 199

```
gaggtgcagc tattggagtc tgggggaggc ttggtacagc ctggggggtc cctgagtctc     60
tcctgtgcag cctctggatt cacctttagc gtttatacta tgtggtgggt ccgccaggct    120
ccagggaagg ggctggagtg ggtctcagtt attggtggga acgagacccg gaaggcctac    180
gcagactccg tgaagggccg gttcaccatc tccaggagac attccaagaa caggctgtat    240
ctgcaaatga acagcctgag agccgaggac acggccgtgt attactgtgc gagagagtgg    300
atggaccact cccgccccta ctactactac ggtatggacg tctggggggca ggggaccctg    360
gtcaccgtct cctca                                                     375
```

<210> SEQ ID NO 200
<211> LENGTH: 125
<212> TYPE: PRT
<213> ORGANISM: Homo sapiens
<220> FEATURE:
<223> OTHER INFORMATION: Abet0344

<400> SEQUENCE: 200

Glu Val Gln Leu Leu Glu Ser Gly Gly Gly Leu Val Gln Pro Gly Gly
1               5                   10                  15

Ser Leu Ser Leu Ser Cys Ala Ala Ser Gly Phe Thr Phe Ser Val Tyr

```
                20                  25                  30
Thr Met Trp Trp Val Arg Gln Ala Pro Gly Lys Gly Leu Glu Trp Val
                35                  40                  45

Ser Val Ile Gly Gly Asn Glu Thr Arg Lys Ala Tyr Ala Asp Ser Val
                50                  55                  60

Lys Gly Arg Phe Thr Ile Ser Arg Asp Asn Ser Lys Asn Arg Leu Tyr
 65                  70                  75                  80

Leu Gln Met Asn Ser Leu Arg Ala Glu Asp Thr Ala Val Tyr Tyr Cys
                85                  90                  95

Ala Arg Glu Trp Met Asp His Ser Arg Pro Tyr Tyr Tyr Tyr Gly Met
                100                 105                 110

Asp Val Trp Gly Gln Gly Thr Leu Val Thr Val Ser Ser
                115                 120                 125

<210> SEQ ID NO 201
<211> LENGTH: 5
<212> TYPE: PRT
<213> ORGANISM: Homo sapiens
<220> FEATURE:
<223> OTHER INFORMATION: Abet0344

<400> SEQUENCE: 201

Val Tyr Thr Met Trp
                5

<210> SEQ ID NO 202
<211> LENGTH: 17
<212> TYPE: PRT
<213> ORGANISM: Homo sapiens
<220> FEATURE:
<223> OTHER INFORMATION: Abet0344

<400> SEQUENCE: 202

Val Ile Gly Gly Asn Glu Thr Arg Lys Ala Tyr Ala Asp Ser Val Lys
                 5                  10                  15

Gly

<210> SEQ ID NO 203
<211> LENGTH: 16
<212> TYPE: PRT
<213> ORGANISM: Homo sapiens
<220> FEATURE:
<223> OTHER INFORMATION: Abet0344

<400> SEQUENCE: 203

Glu Trp Met Asp His Ser Arg Pro Tyr Tyr Tyr Tyr Gly Met Asp Val
                 5                  10                  15

<210> SEQ ID NO 204
<211> LENGTH: 30
<212> TYPE: PRT
<213> ORGANISM: Homo sapiens
<220> FEATURE:
<223> OTHER INFORMATION: Abet0344

<400> SEQUENCE: 204

Glu Val Gln Leu Leu Glu Ser Gly Gly Gly Leu Val Gln Pro Gly Gly
                 5                  10                  15

Ser Leu Ser Leu Ser Cys Ala Ala Ser Gly Phe Thr Phe Ser
                20                  25                  30

<210> SEQ ID NO 205
```

```
<211> LENGTH: 14
<212> TYPE: PRT
<213> ORGANISM: Homo sapiens
<220> FEATURE:
<223> OTHER INFORMATION: Abet0344

<400> SEQUENCE: 205

Trp Val Arg Gln Ala Pro Gly Lys Gly Leu Glu Trp Val Ser
                5                   10

<210> SEQ ID NO 206
<211> LENGTH: 32
<212> TYPE: PRT
<213> ORGANISM: Homo sapiens
<220> FEATURE:
<223> OTHER INFORMATION: Abet0344

<400> SEQUENCE: 206

Arg Phe Thr Ile Ser Arg Asp Asn Ser Lys Asn Arg Leu Tyr Leu Gln
                5                   10                  15
Met Asn Ser Leu Arg Ala Glu Asp Thr Ala Val Tyr Tyr Cys Ala Arg
            20                  25                  30

<210> SEQ ID NO 207
<211> LENGTH: 11
<212> TYPE: PRT
<213> ORGANISM: Homo sapiens
<220> FEATURE:
<223> OTHER INFORMATION: Abet0344

<400> SEQUENCE: 207

Trp Gly Gln Gly Thr Leu Val Thr Val Ser Ser
                5                   10

<210> SEQ ID NO 208
<211> LENGTH: 318
<212> TYPE: DNA
<213> ORGANISM: Homo sapiens
<220> FEATURE:
<223> OTHER INFORMATION: Abet0344

<400> SEQUENCE: 208
cagagcgtct tgactcagcc acccccagtg tccgtgtccc caggacagac ggccagcatc    60
acctgctctg gacataactt ggaagataaa tttgcttcct ggtatcaaca gaagtcaggc   120
cagtccctg tcctggtcat ctatcgagat gacaagcggc cctcagggat ccctgagcga   180
ttctctgcct ccaactctgg gcacactgcc actctgacca tcagcgggac ccaggctacg   240
gatgaggctg actattactg tgcgacccag gacaacttca ctcgagtgtt cggcggaggc   300
accaagctga ccgtccta                                                 318

<210> SEQ ID NO 209
<211> LENGTH: 106
<212> TYPE: PRT
<213> ORGANISM: Homo sapiens
<220> FEATURE:
<223> OTHER INFORMATION: Abet0344

<400> SEQUENCE: 209

Gln Ser Val Leu Thr Gln Pro Pro Ser Val Ser Val Ser Pro Gly Gln
                5                   10                  15
Thr Ala Ser Ile Thr Cys Ser Gly His Asn Leu Glu Asp Lys Phe Ala
            20                  25                  30
Ser Trp Tyr Gln Gln Lys Ser Gly Gln Ser Pro Val Leu Val Ile Tyr
```

```
                35                  40                  45
Arg Asp Asp Lys Arg Pro Ser Gly Ile Pro Glu Arg Phe Ser Ala Ser
 50                  55                  60

Asn Ser Gly His Thr Ala Thr Leu Thr Ile Ser Gly Thr Gln Ala Thr
 65                  70                  75                  80

Asp Glu Ala Asp Tyr Tyr Cys Ala Thr Gln Asp Asn Phe Thr Arg Val
                 85                  90                  95

Phe Gly Gly Gly Thr Lys Leu Thr Val Leu
            100                 105
```

<210> SEQ ID NO 210
<211> LENGTH: 11
<212> TYPE: PRT
<213> ORGANISM: Homo sapiens
<220> FEATURE:
<223> OTHER INFORMATION: Abet0344

<400> SEQUENCE: 210

```
Ser Gly His Asn Leu Glu Asp Lys Phe Ala Ser
                  5                  10
```

<210> SEQ ID NO 211
<211> LENGTH: 7
<212> TYPE: PRT
<213> ORGANISM: Homo sapiens
<220> FEATURE:
<223> OTHER INFORMATION: Abet0344

<400> SEQUENCE: 211

```
Arg Asp Asp Lys Arg Pro Ser
                  5
```

<210> SEQ ID NO 212
<211> LENGTH: 9
<212> TYPE: PRT
<213> ORGANISM: Homo sapiens
<220> FEATURE:
<223> OTHER INFORMATION: Abet0344

<400> SEQUENCE: 212

```
Ala Thr Gln Asp Asn Phe Thr Arg Val
                  5
```

<210> SEQ ID NO 213
<211> LENGTH: 22
<212> TYPE: PRT
<213> ORGANISM: Homo sapiens
<220> FEATURE:
<223> OTHER INFORMATION: Abet0344

<400> SEQUENCE: 213

```
Gln Ser Val Leu Thr Gln Pro Pro Ser Val Ser Val Ser Pro Gly Gln
                  5                  10                  15

Thr Ala Ser Ile Thr Cys
            20
```

<210> SEQ ID NO 214
<211> LENGTH: 15
<212> TYPE: PRT
<213> ORGANISM: Homo sapiens
<220> FEATURE:
<223> OTHER INFORMATION: Abet0344

<400> SEQUENCE: 214

```
Trp Tyr Gln Gln Lys Ser Gly Gln Ser Pro Val Leu Val Ile Tyr
              5                  10                  15
```

<210> SEQ ID NO 215
<211> LENGTH: 32
<212> TYPE: PRT
<213> ORGANISM: Homo sapiens
<220> FEATURE:
<223> OTHER INFORMATION: Abet0344

<400> SEQUENCE: 215

```
Gly Ile Pro Glu Arg Phe Ser Ala Ser Asn Ser Gly His Thr Ala Thr
              5                  10                  15

Leu Thr Ile Ser Gly Thr Gln Ala Thr Asp Glu Ala Asp Tyr Tyr Cys
          20                  25                  30
```

<210> SEQ ID NO 216
<211> LENGTH: 10
<212> TYPE: PRT
<213> ORGANISM: Homo sapiens
<220> FEATURE:
<223> OTHER INFORMATION: Abet0344

<400> SEQUENCE: 216

```
Phe Gly Gly Gly Thr Lys Leu Thr Val Leu
              5                  10
```

<210> SEQ ID NO 217
<211> LENGTH: 375
<212> TYPE: DNA
<213> ORGANISM: Homo sapiens
<220> FEATURE:
<223> OTHER INFORMATION: Abet0368

<400> SEQUENCE: 217

```
gaggtgcagc tgttggagtc tgggggaggc ttagtacagc cggggggtc  cctgagactc      60 tcctgtgcag cctctggatt cgactttggg ccgagcccta tgtggtgggt ccgccaggct     120
ccagggaagg ggctggagtg ggtctcagtt attggtaagg acacccagaa cagcacgtac     180
gcagactccg tgaagggccg gttcaccatc tccagagaca attccaagga cacgctgtat     240
ctgcaaatga acagcctgaa agccgaggac acggccgtgt attactgtgc gagagagtgg     300
atggaccact cccgccccta ctactactac ggtatggacg tctggggca  ggggaccctg     360 gtcaccgtct cctca                                                     375
```

<210> SEQ ID NO 218
<211> LENGTH: 125
<212> TYPE: PRT
<213> ORGANISM: Homo sapiens
<220> FEATURE:
<223> OTHER INFORMATION: Abet0368

<400> SEQUENCE: 218

```
Glu Val Gln Leu Leu Glu Ser Gly Gly Gly Leu Val Gln Pro Gly Gly
              5                  10                  15

Ser Leu Arg Leu Ser Cys Ala Ala Ser Gly Phe Asp Phe Gly Pro Ser
          20                  25                  30

Pro Met Trp Trp Val Arg Gln Ala Pro Gly Lys Gly Leu Glu Trp Val
      35                  40                  45

Ser Val Ile Gly Lys Asp Thr Gln Asn Ser Thr Tyr Ala Asp Ser Val
  50                  55                  60

Lys Gly Arg Phe Thr Ile Ser Arg Asp Asn Ser Lys Asp Thr Leu Tyr
```

```
                65                  70                  75                  80
Leu Gln Met Asn Ser Leu Lys Ala Glu Asp Thr Ala Val Tyr Tyr Cys
                85                  90                  95
Ala Arg Glu Trp Met Asp His Ser Arg Pro Tyr Tyr Tyr Gly Met
               100                 105                 110
Asp Val Trp Gly Gln Gly Thr Leu Val Thr Val Ser Ser
               115                 120                 125

<210> SEQ ID NO 219
<211> LENGTH: 5
<212> TYPE: PRT
<213> ORGANISM: Homo sapiens
<220> FEATURE:
<223> OTHER INFORMATION: Abet0368

<400> SEQUENCE: 219

Pro Ser Pro Met Trp
                5

<210> SEQ ID NO 220
<211> LENGTH: 17
<212> TYPE: PRT
<213> ORGANISM: Homo sapiens
<220> FEATURE:
<223> OTHER INFORMATION: Abet0368

<400> SEQUENCE: 220

Val Ile Gly Lys Asp Thr Gln Asn Ser Thr Tyr Ala Asp Ser Val Lys
                5                  10                  15
Gly

<210> SEQ ID NO 221
<211> LENGTH: 16
<212> TYPE: PRT
<213> ORGANISM: Homo sapiens
<220> FEATURE:
<223> OTHER INFORMATION: Abet0368

<400> SEQUENCE: 221

Glu Trp Met Asp His Ser Arg Pro Tyr Tyr Tyr Gly Met Asp Val
                5                  10                  15

<210> SEQ ID NO 222
<211> LENGTH: 30
<212> TYPE: PRT
<213> ORGANISM: Homo sapiens
<220> FEATURE:
<223> OTHER INFORMATION: Abet0368

<400> SEQUENCE: 222

Glu Val Gln Leu Leu Glu Ser Gly Gly Gly Leu Val Gln Pro Gly Gly
                5                  10                  15
Ser Leu Arg Leu Ser Cys Ala Ala Ser Gly Phe Asp Phe Gly
               20                  25                  30

<210> SEQ ID NO 223
<211> LENGTH: 14
<212> TYPE: PRT
<213> ORGANISM: Homo sapiens
<220> FEATURE:
<223> OTHER INFORMATION: Abet0368

<400> SEQUENCE: 223

Trp Val Arg Gln Ala Pro Gly Lys Gly Leu Glu Trp Val Ser
```

<210> SEQ ID NO 224
<211> LENGTH: 32
<212> TYPE: PRT
<213> ORGANISM: Homo sapiens
<220> FEATURE:
<223> OTHER INFORMATION: Abet0368

<400> SEQUENCE: 224

Arg Phe Thr Ile Ser Arg Asp Asn Ser Lys Asp Thr Leu Tyr Leu Gln
                 5                  10                  15
Met Asn Ser Leu Lys Ala Glu Asp Thr Ala Val Tyr Tyr Cys Ala Arg
            20                  25                  30

<210> SEQ ID NO 225
<211> LENGTH: 11
<212> TYPE: PRT
<213> ORGANISM: Homo sapiens
<220> FEATURE:
<223> OTHER INFORMATION: Abet0368

<400> SEQUENCE: 225

Trp Gly Gln Gly Thr Leu Val Thr Val Ser Ser
                 5                  10

<210> SEQ ID NO 226
<211> LENGTH: 318
<212> TYPE: DNA
<213> ORGANISM: Homo sapiens
<220> FEATURE:
<223> OTHER INFORMATION: Abet0368

<400> SEQUENCE: 226
tcgtacgagt tgactcagcc accctcagtg tccgtgtccc caggacagac ggccagcatc      60
acctgctctg gacataactt ggaagataaa tttacttcct ggtatcaaca gaagtcaggc     120
cagtcccctg tcctggtcat ctatcgagat gacaagcggc cctcagggat ccctgagcga     180
ttctctgcct ccaactctgg gcacactgcc actctgacca tcagcggggc ccaggctacg     240
gatgaggctg actattactg ttcgtcccag gacacggtga ctcgagtgtt cggcggaggg     300
accaagctga ccgtccta                                                   318

<210> SEQ ID NO 227
<211> LENGTH: 106
<212> TYPE: PRT
<213> ORGANISM: Homo sapiens
<220> FEATURE:
<223> OTHER INFORMATION: Abet0368

<400> SEQUENCE: 227

Ser Tyr Glu Leu Thr Gln Pro Pro Ser Val Ser Val Ser Pro Gly Gln
                 5                  10                  15
Thr Ala Ser Ile Thr Cys Ser Gly His Asn Leu Glu Asp Lys Phe Thr
            20                  25                  30
Ser Trp Tyr Gln Gln Lys Ser Gly Gln Ser Pro Val Leu Val Ile Tyr
        35                  40                  45
Arg Asp Asp Lys Arg Pro Ser Gly Ile Pro Glu Arg Phe Ser Ala Ser
    50                  55                  60
Asn Ser Gly His Thr Ala Thr Leu Thr Ile Ser Gly Ala Gln Ala Thr
65                  70                  75                  80
Asp Glu Ala Asp Tyr Tyr Cys Ser Ser Gln Asp Thr Val Thr Arg Val

```
                      85                  90                  95

Phe Gly Gly Gly Thr Lys Leu Thr Val Leu
            100                 105

<210> SEQ ID NO 228
<211> LENGTH: 11
<212> TYPE: PRT
<213> ORGANISM: Homo sapiens
<220> FEATURE:
<223> OTHER INFORMATION: Abet0368

<400> SEQUENCE: 228

Ser Gly His Asn Leu Glu Asp Lys Phe Thr Ser
                  5                  10

<210> SEQ ID NO 229
<211> LENGTH: 7
<212> TYPE: PRT
<213> ORGANISM: Homo sapiens
<220> FEATURE:
<223> OTHER INFORMATION: Abet0368

<400> SEQUENCE: 229

Arg Asp Asp Lys Arg Pro Ser
                  5

<210> SEQ ID NO 230
<211> LENGTH: 9
<212> TYPE: PRT
<213> ORGANISM: Homo sapiens
<220> FEATURE:
<223> OTHER INFORMATION: Abet0368

<400> SEQUENCE: 230

Ser Ser Gln Asp Thr Val Thr Arg Val
                  5

<210> SEQ ID NO 231
<211> LENGTH: 22
<212> TYPE: PRT
<213> ORGANISM: Homo sapiens
<220> FEATURE:
<223> OTHER INFORMATION: Abet0368

<400> SEQUENCE: 231

Ser Tyr Glu Leu Thr Gln Pro Pro Ser Val Ser Val Ser Pro Gly Gln
                  5                  10                  15

Thr Ala Ser Ile Thr Cys
            20

<210> SEQ ID NO 232
<211> LENGTH: 15
<212> TYPE: PRT
<213> ORGANISM: Homo sapiens
<220> FEATURE:
<223> OTHER INFORMATION: Abet0368

<400> SEQUENCE: 232

Trp Tyr Gln Gln Lys Ser Gly Gln Ser Pro Val Leu Val Ile Tyr
                  5                  10                  15

<210> SEQ ID NO 233
<211> LENGTH: 32
<212> TYPE: PRT
<213> ORGANISM: Homo sapiens
<220> FEATURE:
```

<223> OTHER INFORMATION: Abet0368

<400> SEQUENCE: 233

Gly Ile Pro Glu Arg Phe Ser Ala Ser Asn Ser Gly His Thr Ala Thr
 1               5                  10                  15
Leu Thr Ile Ser Gly Ala Gln Thr Asp Glu Ala Asp Tyr Tyr Cys
             20                  25                  30

<210> SEQ ID NO 234
<211> LENGTH: 10
<212> TYPE: PRT
<213> ORGANISM: Homo sapiens
<220> FEATURE:
<223> OTHER INFORMATION: Abet0368

<400> SEQUENCE: 234

Phe Gly Gly Gly Thr Lys Leu Thr Val Leu
 1               5                  10

<210> SEQ ID NO 235
<211> LENGTH: 375
<212> TYPE: DNA
<213> ORGANISM: Homo sapiens
<220> FEATURE:
<223> OTHER INFORMATION: Abet0369

<400> SEQUENCE: 235

```
gaggtgcagc tgttggagtc tgggggaggc tggtacagc ctgggggtc cctgagactc       60
tcctgtgcag cctcttcgtt ccagatctcg aagaacacta tgtggtgggt ccgccgggct      120
ccagggaagg gctggagtg gtctcagtt attggtaagg acgagacccg cttcaactac       180
gcagactccg tgaagggccg gttcaccatc tccagacaa attccaagaa cacctgtat      240
ctgcaaatga acagcctgag agccgaggac acggccgtgt attactgtgc gagagagtgg    300
atggaccact cccgccccta ctactactac ggtatggacg tctggggca ggggaccctg      360
gtcaccgtct cctca                                                     375
```

<210> SEQ ID NO 236
<211> LENGTH: 125
<212> TYPE: PRT
<213> ORGANISM: Homo sapiens
<220> FEATURE:
<223> OTHER INFORMATION: Abet0369

<400> SEQUENCE: 236

Glu Val Gln Leu Leu Glu Ser Gly Gly Gly Leu Val Gln Pro Gly Gly
 1               5                  10                  15
Ser Leu Arg Leu Ser Cys Ala Ala Ser Ser Phe Gln Ile Ser Lys Asn
             20                  25                  30
Thr Met Trp Trp Val Arg Arg Ala Pro Gly Lys Gly Leu Glu Trp Val
         35                  40                  45
Ser Val Ile Gly Lys Asp Glu Thr Arg Phe Asn Tyr Ala Asp Ser Val
     50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Glu Trp Met Asp His Ser Arg Pro Tyr Tyr Tyr Tyr Gly Met
            100                 105                 110
Asp Val Trp Gly Gln Gly Thr Leu Val Thr Val Ser Ser
        115                 120                 125

<210> SEQ ID NO 237
<211> LENGTH: 5
<212> TYPE: PRT
<213> ORGANISM: Homo sapiens
<220> FEATURE:
<223> OTHER INFORMATION: Abet0369

<400> SEQUENCE: 237

Lys Asn Thr Met Trp
                5

<210> SEQ ID NO 238
<211> LENGTH: 17
<212> TYPE: PRT
<213> ORGANISM: Homo sapiens
<220> FEATURE:
<223> OTHER INFORMATION: Abet0369

<400> SEQUENCE: 238

Val Ile Gly Lys Asp Glu Thr Arg Phe Asn Tyr Ala Asp Ser Val Lys
                5                   10                  15
Gly

<210> SEQ ID NO 239
<211> LENGTH: 16
<212> TYPE: PRT
<213> ORGANISM: Homo sapiens
<220> FEATURE:
<223> OTHER INFORMATION: Abet0369

<400> SEQUENCE: 239

Glu Trp Met Asp His Ser Arg Pro Tyr Tyr Tyr Tyr Gly Met Asp Val
                5                   10                  15

<210> SEQ ID NO 240
<211> LENGTH: 30
<212> TYPE: PRT
<213> ORGANISM: Homo sapiens
<220> FEATURE:
<223> OTHER INFORMATION: Abet0369

<400> SEQUENCE: 240

Glu Val Gln Leu Leu Glu Ser Gly Gly Gly Leu Val Gln Pro Gly Gly
                5                   10                  15
Ser Leu Arg Leu Ser Cys Ala Ala Ser Ser Phe Gln Ile Ser
            20                  25                  30

<210> SEQ ID NO 241
<211> LENGTH: 14
<212> TYPE: PRT
<213> ORGANISM: Homo sapiens
<220> FEATURE:
<223> OTHER INFORMATION: Abet0369

<400> SEQUENCE: 241

Trp Val Arg Arg Ala Pro Gly Lys Gly Leu Glu Trp Val Ser
                5                   10

<210> SEQ ID NO 242
<211> LENGTH: 32
<212> TYPE: PRT
<213> ORGANISM: Homo sapiens
<220> FEATURE:
<223> OTHER INFORMATION: Abet0369

<400> SEQUENCE: 242

Arg Phe Thr Ile Ser Arg Asp Asn Ser Lys Asn Thr Leu Tyr Leu Gln
                5                   10                  15

Met Asn Ser Leu Arg Ala Glu Asp Thr Ala Val Tyr Tyr Cys Ala Arg
            20                  25                  30

<210> SEQ ID NO 243
<211> LENGTH: 11
<212> TYPE: PRT
<213> ORGANISM: Homo sapiens
<220> FEATURE:
<223> OTHER INFORMATION: Abet0369

<400> SEQUENCE: 243

Trp Gly Gln Gly Thr Leu Val Thr Val Ser Ser
                5                   10

<210> SEQ ID NO 244
<211> LENGTH: 318
<212> TYPE: DNA
<213> ORGANISM: Homo sapiens
<220> FEATURE:
<223> OTHER INFORMATION: Abet0369

<400> SEQUENCE: 244
tcgtacgggt tgactcagcc accctcagtg tccgtgtccc caggacagac ggccagcatc     60
acctgctctg gacgtaacat cggggacagc tgggtcgcgt ggtatcaaca gaagccaggc    120
cagtcccctg tcctggtcat ctatcgagat gacaagcggc cctcagggat ccctgagcga    180
ttctctgcct ccaactctgg gcacactgcc actctgacca tcagcgggac ccaggctacg    240
gatgaggctg actattactg ttcgtcccag gacacggtga ctcgagtgtt cggcggaggg    300
accaagctga ccgtccta                                                   318

<210> SEQ ID NO 245
<211> LENGTH: 106
<212> TYPE: PRT
<213> ORGANISM: Homo sapiens
<220> FEATURE:
<223> OTHER INFORMATION: Abet0369

<400> SEQUENCE: 245

Ser Tyr Gly Leu Thr Gln Pro Pro Ser Val Ser Val Ser Pro Gly Gln
                5                   10                  15

Thr Ala Ser Ile Thr Cys Ser Gly Arg Asn Ile Gly Asp Ser Trp Val
            20                  25                  30

Ala Trp Tyr Gln Gln Lys Pro Gly Gln Ser Pro Val Leu Val Ile Tyr
        35                  40                  45

Arg Asp Asp Lys Arg Pro Ser Gly Ile Pro Glu Arg Phe Ser Ala Ser
    50                  55                  60

Asn Ser Gly His Thr Ala Thr Leu Thr Ile Ser Gly Thr Gln Ala Thr
65                  70                  75                  80

Asp Glu Ala Asp Tyr Tyr Cys Ser Ser Gln Asp Thr Val Thr Arg Val
                85                  90                  95

Phe Gly Gly Gly Thr Lys Leu Thr Val Leu
                100                 105

<210> SEQ ID NO 246
<211> LENGTH: 11
<212> TYPE: PRT

<213> ORGANISM: Homo sapiens
<220> FEATURE:
<223> OTHER INFORMATION: Abet0369

<400> SEQUENCE: 246

Ser Gly Arg Asn Ile Gly Asp Ser Trp Val Ala
                5                   10

<210> SEQ ID NO 247
<211> LENGTH: 7
<212> TYPE: PRT
<213> ORGANISM: Homo sapiens
<220> FEATURE:
<223> OTHER INFORMATION: Abet0369

<400> SEQUENCE: 247

Arg Asp Asp Lys Arg Pro Ser
                5

<210> SEQ ID NO 248
<211> LENGTH: 9
<212> TYPE: PRT
<213> ORGANISM: Homo sapiens
<220> FEATURE:
<223> OTHER INFORMATION: Abet0369

<400> SEQUENCE: 248

Ser Ser Gln Asp Thr Val Thr Arg Val
                5

<210> SEQ ID NO 249
<211> LENGTH: 22
<212> TYPE: PRT
<213> ORGANISM: Homo sapiens
<220> FEATURE:
<223> OTHER INFORMATION: Abet0369

<400> SEQUENCE: 249

Ser Tyr Gly Leu Thr Gln Pro Pro Ser Val Ser Val Ser Pro Gly Gln
                5                   10                  15

Thr Ala Ser Ile Thr Cys
            20

<210> SEQ ID NO 250
<211> LENGTH: 15
<212> TYPE: PRT
<213> ORGANISM: Homo sapiens
<220> FEATURE:
<223> OTHER INFORMATION: Abet0369

<400> SEQUENCE: 250

Trp Tyr Gln Gln Lys Pro Gly Gln Ser Pro Val Leu Val Ile Tyr
                5                   10                  15

<210> SEQ ID NO 251
<211> LENGTH: 32
<212> TYPE: PRT
<213> ORGANISM: Homo sapiens
<220> FEATURE:
<223> OTHER INFORMATION: Abet0369

<400> SEQUENCE: 251

Gly Ile Pro Glu Arg Phe Ser Ala Ser Asn Ser Gly His Thr Ala Thr
                5                   10                  15

Leu Thr Ile Ser Gly Thr Gln Ala Thr Asp Glu Ala Asp Tyr Tyr Cys
            20                  25                  30

<210> SEQ ID NO 252
<211> LENGTH: 10
<212> TYPE: PRT
<213> ORGANISM: Homo sapiens
<220> FEATURE:
<223> OTHER INFORMATION: Abet0369

<400> SEQUENCE: 252

Phe Gly Gly Gly Thr Lys Leu Thr Val Leu
                 5                  10

<210> SEQ ID NO 253
<211> LENGTH: 375
<212> TYPE: DNA
<213> ORGANISM: Homo sapiens
<220> FEATURE:
<223> OTHER INFORMATION: Abet0370

<400> SEQUENCE: 253
gaggtgcagc tgttggagtc tgggggaggc ttggtacagc ctgggggtc cctgagactc      60 tcctgtgcag cctctggatt ccactttccc atgagcgcca tgtggtgggt ccgccaggct    120
ccagggaagg ggctggagtg gtctcagtc attggtgaga ccccggagag gcaggcctac    180
gcagactccg tgaagggccg gttcaccatc tccagagaca attccaagag cacgctgtat    240
ctgcaaatga acagcctgag agccgaggac acggccgtgt attactgtgc gagagagtgg    300
atggaccact cccgccccta ctactactac ggtatggacg tctggggca ggggaccctg    360 gtcaccgtct cctca                                                      375

<210> SEQ ID NO 254
<211> LENGTH: 125
<212> TYPE: PRT
<213> ORGANISM: Homo sapiens
<220> FEATURE:
<223> OTHER INFORMATION: Abet0370

<400> SEQUENCE: 254

Glu Val Gln Leu Leu Glu Ser Gly Gly Gly Leu Val Gln Pro Gly Gly
                 5                  10                  15

Ser Leu Arg Leu Ser Cys Ala Ala Ser Gly Phe His Phe Pro Met Ser
             20                  25                  30

Ala Met Trp Trp Val Arg Gln Ala Pro Gly Lys Gly Leu Glu Trp Val
         35                  40                  45

Ser Val Ile Gly Glu Thr Pro Glu Arg Gln Ala Tyr Ala Asp Ser Val
     50                  55                  60

Lys Gly Arg Phe Thr Ile Ser Arg Asp Asn Ser Lys Ser Thr Leu Tyr
65                  70                  75                  80

Leu Gln Met Asn Ser Leu Arg Ala Glu Asp Thr Ala Val Tyr Tyr Cys
                 85                  90                  95

Ala Arg Glu Trp Met Asp His Ser Arg Pro Tyr Tyr Tyr Gly Met
            100                 105                 110

Asp Val Trp Gly Gln Gly Thr Leu Val Thr Val Ser Ser
        115                 120                 125

<210> SEQ ID NO 255
<211> LENGTH: 5
<212> TYPE: PRT
<213> ORGANISM: Homo sapiens
<220> FEATURE:
<223> OTHER INFORMATION: Abet0370

<400> SEQUENCE: 255

Met Ser Ala Met Trp
                5

<210> SEQ ID NO 256
<211> LENGTH: 17
<212> TYPE: PRT
<213> ORGANISM: Homo sapiens
<220> FEATURE:
<223> OTHER INFORMATION: Abet0370

<400> SEQUENCE: 256

Val Ile Gly Glu Thr Pro Glu Arg Gln Ala Tyr Ala Asp Ser Val Lys
                5                   10                  15

Gly

<210> SEQ ID NO 257
<211> LENGTH: 16
<212> TYPE: PRT
<213> ORGANISM: Homo sapiens
<220> FEATURE:
<223> OTHER INFORMATION: Abet0370

<400> SEQUENCE: 257

Glu Trp Met Asp His Ser Arg Pro Tyr Tyr Tyr Tyr Gly Met Asp Val
                5                   10                  15

<210> SEQ ID NO 258
<211> LENGTH: 30
<212> TYPE: PRT
<213> ORGANISM: Homo sapiens
<220> FEATURE:
<223> OTHER INFORMATION: Abet0370

<400> SEQUENCE: 258

Glu Val Gln Leu Leu Glu Ser Gly Gly Gly Leu Val Gln Pro Gly Gly
                5                   10                  15

Ser Leu Arg Leu Ser Cys Ala Ala Ser Gly Phe His Phe Pro
        20                  25                  30

<210> SEQ ID NO 259
<211> LENGTH: 14
<212> TYPE: PRT
<213> ORGANISM: Homo sapiens
<220> FEATURE:
<223> OTHER INFORMATION: Abet0370

<400> SEQUENCE: 259

Trp Val Arg Gln Ala Pro Gly Lys Gly Leu Glu Trp Val Ser
                5                   10

<210> SEQ ID NO 260
<211> LENGTH: 32
<212> TYPE: PRT
<213> ORGANISM: Homo sapiens
<220> FEATURE:
<223> OTHER INFORMATION: Abet0370

<400> SEQUENCE: 260

Arg Phe Thr Ile Ser Arg Asp Asn Ser Lys Ser Thr Leu Tyr Leu Gln
                5                   10                  15

Met Asn Ser Leu Arg Ala Glu Asp Thr Ala Val Tyr Tyr Cys Ala Arg
        20                  25                  30

<210> SEQ ID NO 261
<211> LENGTH: 11
<212> TYPE: PRT
<213> ORGANISM: Homo sapiens
<220> FEATURE:
<223> OTHER INFORMATION: Abet0370

<400> SEQUENCE: 261

Trp Gly Gln Gly Thr Leu Val Thr Val Ser Ser
                5                   10

<210> SEQ ID NO 262
<211> LENGTH: 318
<212> TYPE: DNA
<213> ORGANISM: Homo sapiens
<220> FEATURE:
<223> OTHER INFORMATION: Abet0370

<400> SEQUENCE: 262
tcgtacgagt tgactcagcc accctcagtg tccgtgtccc caggacagac ggccagcatc     60
acctgcacga ccccgcactt caacagcaaa tttgcttcct ggtatcaaca gaagccgggc    120
cagtcccctg tcctggtcat ctatcgagat gacaagcggc cctcagggat ccctgagcga    180
ttctctgcct ccaactctgg gcacactgcc actctgacca tcagcgggac ccaggctatg    240
gatgaggctg actattactg tcaggcgcag gatagtacca ctcgagtgtt cggcggaggg    300
accaggctga ccgtccta                                                  318

<210> SEQ ID NO 263
<211> LENGTH: 106
<212> TYPE: PRT
<213> ORGANISM: Homo sapiens
<220> FEATURE:
<223> OTHER INFORMATION: Abet0370

<400> SEQUENCE: 263

Ser Tyr Glu Leu Thr Gln Pro Pro Ser Val Ser Val Ser Pro Gly Gln
                5                   10                  15

Thr Ala Ser Ile Thr Cys Thr Thr Pro His Phe Asn Ser Lys Phe Ala
            20                  25                  30

Ser Trp Tyr Gln Gln Lys Pro Gly Gln Ser Pro Val Leu Val Ile Tyr
        35                  40                  45

Arg Asp Asp Lys Arg Pro Ser Gly Ile Pro Glu Arg Phe Ser Ala Ser
    50                  55                  60

Asn Ser Gly His Thr Ala Thr Leu Thr Ile Ser Gly Thr Gln Ala Met
65                  70                  75                  80

Asp Glu Ala Asp Tyr Tyr Cys Gln Ala Gln Asp Ser Thr Thr Arg Val
                85                  90                  95

Phe Gly Gly Gly Thr Arg Leu Thr Val Leu
            100                 105

<210> SEQ ID NO 264
<211> LENGTH: 11
<212> TYPE: PRT
<213> ORGANISM: Homo sapiens
<220> FEATURE:
<223> OTHER INFORMATION: Abet0370

<400> SEQUENCE: 264

Thr Thr Pro His Phe Asn Ser Lys Phe Ala Ser
                5                   10

```
<210> SEQ ID NO 265
<211> LENGTH: 7
<212> TYPE: PRT
<213> ORGANISM: Homo sapiens
<220> FEATURE:
<223> OTHER INFORMATION: Abet0370

<400> SEQUENCE: 265

Arg Asp Asp Lys Arg Pro Ser
                5

<210> SEQ ID NO 266
<211> LENGTH: 9
<212> TYPE: PRT
<213> ORGANISM: Homo sapiens
<220> FEATURE:
<223> OTHER INFORMATION: Abet0370

<400> SEQUENCE: 266

Gln Ala Gln Asp Ser Thr Thr Arg Val
                5

<210> SEQ ID NO 267
<211> LENGTH: 22
<212> TYPE: PRT
<213> ORGANISM: Homo sapiens
<220> FEATURE:
<223> OTHER INFORMATION: Abet0370

<400> SEQUENCE: 267

Ser Tyr Glu Leu Thr Gln Pro Pro Ser Val Ser Val Ser Pro Gly Gln
                5                   10                  15

Thr Ala Ser Ile Thr Cys
            20

<210> SEQ ID NO 268
<211> LENGTH: 15
<212> TYPE: PRT
<213> ORGANISM: Homo sapiens
<220> FEATURE:
<223> OTHER INFORMATION: Abet0370

<400> SEQUENCE: 268

Trp Tyr Gln Gln Lys Pro Gly Gln Ser Pro Val Leu Val Ile Tyr
                5                   10                  15

<210> SEQ ID NO 269
<211> LENGTH: 32
<212> TYPE: PRT
<213> ORGANISM: Homo sapiens
<220> FEATURE:
<223> OTHER INFORMATION: Abet0370

<400> SEQUENCE: 269

Gly Ile Pro Glu Arg Phe Ser Ala Ser Asn Ser Gly His Thr Ala Thr
                5                   10                  15

Leu Thr Ile Ser Gly Thr Gln Ala Met Asp Glu Ala Asp Tyr Tyr Cys
            20                  25                  30

<210> SEQ ID NO 270
<211> LENGTH: 10
<212> TYPE: PRT
<213> ORGANISM: Homo sapiens
<220> FEATURE:
<223> OTHER INFORMATION: Abet0370
```

<400> SEQUENCE: 270

Phe Gly Gly Gly Thr Arg Leu Thr Val Leu
              5                   10

<210> SEQ ID NO 271
<211> LENGTH: 375
<212> TYPE: DNA
<213> ORGANISM: Homo sapiens
<220> FEATURE:
<223> OTHER INFORMATION: Abet0371

<400> SEQUENCE: 271
gaggtgcagc tgtcggagtc tgggggaggc ttggtacagc ctgggggtc cctgagactc      60 tcctgtgcag cctctcacga cgccttcccc ttcgacacta tgtggtgggt ccgccaggct    120
ccagggaagg gctggagtg gtctcagtt attggttcta gtggtggtac gacagtttac     180
gcagactccg tgaagggccg gttcaccgtt tccagagaca attccaagaa cacgctgtat    240
ctgcaaatga acagcctgag agccgaggac acggccgtgt attactgtgc gagagagtgg    300
atggaccact cccgccccta ctactactac ggtatggacg tctgggggca ggggaccctg    360
gtcaccgtct cctca                                                     375

<210> SEQ ID NO 272
<211> LENGTH: 125
<212> TYPE: PRT
<213> ORGANISM: Homo sapiens
<220> FEATURE:
<223> OTHER INFORMATION: Abet0371

<400> SEQUENCE: 272

Glu Val Gln Leu Ser Glu Ser Gly Gly Gly Leu Val Gln Pro Gly Gly
              5                   10                  15

Ser Leu Arg Leu Ser Cys Ala Ala Ser His Asp Ala Phe Pro Phe Asp
         20                  25                  30

Thr Met Trp Trp Val Arg Gln Ala Pro Gly Lys Gly Leu Glu Trp Val
     35                  40                  45

Ser Val Ile Gly Ser Ser Gly Gly Thr Thr Val Tyr Ala Asp Ser Val
 50                  55                  60

Lys Gly Arg Phe Thr Val Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                 85                  90                  95

Ala Arg Glu Trp Met Asp His Ser Arg Pro Tyr Tyr Tyr Gly Met
            100                 105                 110

Asp Val Trp Gly Gln Gly Thr Leu Val Thr Val Ser Ser
        115                 120                 125

<210> SEQ ID NO 273
<211> LENGTH: 5
<212> TYPE: PRT
<213> ORGANISM: Homo sapiens
<220> FEATURE:
<223> OTHER INFORMATION: Abet0371

<400> SEQUENCE: 273

Phe Asp Thr Met Trp
              5

<210> SEQ ID NO 274
<211> LENGTH: 17

```
<212> TYPE: PRT
<213> ORGANISM: Homo sapiens
<220> FEATURE:
<223> OTHER INFORMATION: Abet0371

<400> SEQUENCE: 274

Val Ile Gly Ser Ser Gly Gly Thr Thr Val Tyr Ala Asp Ser Val Lys
                 5                  10                  15
Gly

<210> SEQ ID NO 275
<211> LENGTH: 16
<212> TYPE: PRT
<213> ORGANISM: Homo sapiens
<220> FEATURE:
<223> OTHER INFORMATION: Abet0371

<400> SEQUENCE: 275

Glu Trp Met Asp His Ser Arg Pro Tyr Tyr Tyr Gly Met Asp Val
                 5                  10                  15

<210> SEQ ID NO 276
<211> LENGTH: 30
<212> TYPE: PRT
<213> ORGANISM: Homo sapiens
<220> FEATURE:
<223> OTHER INFORMATION: Abet0371

<400> SEQUENCE: 276

Glu Val Gln Leu Ser Glu Ser Gly Gly Gly Leu Val Gln Pro Gly Gly
                 5                  10                  15

Ser Leu Arg Leu Ser Cys Ala Ala Ser His Asp Ala Phe Pro
         20                  25                  30

<210> SEQ ID NO 277
<211> LENGTH: 14
<212> TYPE: PRT
<213> ORGANISM: Homo sapiens
<220> FEATURE:
<223> OTHER INFORMATION: Abet0371

<400> SEQUENCE: 277

Trp Val Arg Gln Ala Pro Gly Lys Gly Leu Glu Trp Val Ser
                 5                  10

<210> SEQ ID NO 278
<211> LENGTH: 32
<212> TYPE: PRT
<213> ORGANISM: Homo sapiens
<220> FEATURE:
<223> OTHER INFORMATION: Abet0371

<400> SEQUENCE: 278

Arg Phe Thr Val Ser Arg Asp Asn Ser Lys Asn Thr Leu Tyr Leu Gln
                 5                  10                  15

Met Asn Ser Leu Arg Ala Glu Asp Thr Ala Val Tyr Tyr Cys Ala Arg
         20                  25                  30

<210> SEQ ID NO 279
<211> LENGTH: 11
<212> TYPE: PRT
<213> ORGANISM: Homo sapiens
<220> FEATURE:
<223> OTHER INFORMATION: Abet0371

<400> SEQUENCE: 279
```

```
Trp Gly Gln Gly Thr Leu Val Thr Val Ser Ser
                5                  10

<210> SEQ ID NO 280
<211> LENGTH: 318
<212> TYPE: DNA
<213> ORGANISM: Homo sapiens
<220> FEATURE:
<223> OTHER INFORMATION: Abet0371

<400> SEQUENCE: 280
tcgtacgagt tgactcagcc accctcagtg tccgtgtccc caggacagac ggccagcatc    60
acctgctccg gacataacat ctcgtcgagc tgggtctcct ggtatcaaca gaagccaggc   120
cagtcccctg tcctggtcat ctatcgagat gacaagcggc cctcagggat ccctgagcga   180
ttctctgcct ccaactctgg gcacactgcc actctgacca tcagcgggac ccaggctacg   240
gatgaggctg actattactg ttcgtcccag gacacggtga ctcgagtctt cggcggaggg   300
accaagctga ccgtccta                                                 318

<210> SEQ ID NO 281
<211> LENGTH: 106
<212> TYPE: PRT
<213> ORGANISM: Homo sapiens
<220> FEATURE:
<223> OTHER INFORMATION: Abet0371

<400> SEQUENCE: 281

Ser Tyr Glu Leu Thr Gln Pro Pro Ser Val Ser Val Ser Pro Gly Gln
                5                  10                  15

Thr Ala Ser Ile Thr Cys Ser Gly His Asn Ile Ser Ser Ser Trp Val
            20                  25                  30

Ser Trp Tyr Gln Gln Lys Pro Gly Gln Ser Pro Val Leu Val Ile Tyr
        35                  40                  45

Arg Asp Asp Lys Arg Pro Ser Gly Ile Pro Glu Arg Phe Ser Ala Ser
    50                  55                  60

Asn Ser Gly His Thr Ala Thr Leu Thr Ile Ser Gly Thr Gln Ala Thr
65                  70                  75                  80

Asp Glu Ala Asp Tyr Tyr Cys Ser Ser Gln Asp Thr Val Thr Arg Val
                85                  90                  95

Phe Gly Gly Gly Thr Lys Leu Thr Val Leu
            100                 105

<210> SEQ ID NO 282
<211> LENGTH: 11
<212> TYPE: PRT
<213> ORGANISM: Homo sapiens
<220> FEATURE:
<223> OTHER INFORMATION: Abet0371

<400> SEQUENCE: 282

Ser Gly His Asn Ile Ser Ser Ser Trp Val Ser
                5                  10

<210> SEQ ID NO 283
<211> LENGTH: 7
<212> TYPE: PRT
<213> ORGANISM: Homo sapiens
<220> FEATURE:
<223> OTHER INFORMATION: Abet0371

<400> SEQUENCE: 283
```

Arg Asp Asp Lys Arg Pro Ser
            5

<210> SEQ ID NO 284
<211> LENGTH: 9
<212> TYPE: PRT
<213> ORGANISM: Homo sapiens
<220> FEATURE:
<223> OTHER INFORMATION: Abet0371

<400> SEQUENCE: 284

Ser Ser Gln Asp Thr Val Thr Arg Val
            5

<210> SEQ ID NO 285
<211> LENGTH: 22
<212> TYPE: PRT
<213> ORGANISM: Homo sapiens
<220> FEATURE:
<223> OTHER INFORMATION: Abet0371

<400> SEQUENCE: 285

Ser Tyr Glu Leu Thr Gln Pro Pro Ser Val Ser Val Ser Pro Gly Gln
            5                   10                  15

Thr Ala Ser Ile Thr Cys
            20

<210> SEQ ID NO 286
<211> LENGTH: 15
<212> TYPE: PRT
<213> ORGANISM: Homo sapiens
<220> FEATURE:
<223> OTHER INFORMATION: Abet0371

<400> SEQUENCE: 286

Trp Tyr Gln Gln Lys Pro Gly Gln Ser Pro Val Leu Val Ile Tyr
            5                   10                  15

<210> SEQ ID NO 287
<211> LENGTH: 32
<212> TYPE: PRT
<213> ORGANISM: Homo sapiens
<220> FEATURE:
<223> OTHER INFORMATION: Abet0371

<400> SEQUENCE: 287

Gly Ile Pro Glu Arg Phe Ser Ala Ser Asn Ser Gly His Thr Ala Thr
            5                   10                  15

Leu Thr Ile Ser Gly Thr Gln Ala Thr Asp Glu Ala Asp Tyr Tyr Cys
            20                  25                  30

<210> SEQ ID NO 288
<211> LENGTH: 10
<212> TYPE: PRT
<213> ORGANISM: Homo sapiens
<220> FEATURE:
<223> OTHER INFORMATION: Abet0371

<400> SEQUENCE: 288

Phe Gly Gly Gly Thr Lys Leu Thr Val Leu
            5                   10

<210> SEQ ID NO 289
<211> LENGTH: 375
<212> TYPE: DNA

-continued

<213> ORGANISM: Homo sapiens
<220> FEATURE:
<223> OTHER INFORMATION: Abet0372

<400> SEQUENCE: 289
gaggtgcagc tgttggagtc tgggggggc ttggtacagc ctgggggtc cctgagactc      60 tcctgtgcag cctctagcga catgttcaac atcgagacca tgtggtgggt ccgccaggct    120
ccagggaagg ggctggagtg ggtctcagtt attggtaagg ggatgaacaa cgtctcgtac    180
gcagactccg tgaagggccg gttcaccatc tccagagaca attccaagaa cacgctgtat    240
ctgcaaatga acagcctgag agccgaggac acggccgtgt attactgtgc gagagagtgg    300
atggaccact cccgccccta ctactactac ggtatggacg tctggggggca ggggaccctg    360 gtcaccgtct cctca                                                     375

<210> SEQ ID NO 290
<211> LENGTH: 125
<212> TYPE: PRT
<213> ORGANISM: Homo sapiens
<220> FEATURE:
<223> OTHER INFORMATION: Abet0372

<400> SEQUENCE: 290

Glu Val Gln Leu Leu Glu Ser Gly Gly Gly Leu Val Gln Pro Gly Gly
1               5                   10                  15

Ser Leu Arg Leu Ser Cys Ala Ala Ser Ser Asp Met Phe Asn Ile Glu
            20                  25                  30

Thr Met Trp Trp Val Arg Gln Ala Pro Gly Lys Gly Leu Glu Trp Val
        35                  40                  45

Ser Val Ile Gly Lys Gly Met Asn Asn Val Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Trp Met Asp His Ser Arg Pro Tyr Tyr Tyr Gly Met
            100                 105                 110

Asp Val Trp Gly Gln Gly Thr Leu Val Thr Val Ser Ser
        115                 120                 125

<210> SEQ ID NO 291
<211> LENGTH: 5
<212> TYPE: PRT
<213> ORGANISM: Homo sapiens
<220> FEATURE:
<223> OTHER INFORMATION: Abet0372

<400> SEQUENCE: 291

Ile Glu Thr Met Trp
1               5

<210> SEQ ID NO 292
<211> LENGTH: 17
<212> TYPE: PRT
<213> ORGANISM: Homo sapiens
<220> FEATURE:
<223> OTHER INFORMATION: Abet0372

<400> SEQUENCE: 292

Val Ile Gly Lys Gly Met Asn Asn Val Ser Tyr Ala Asp Ser Val Lys
1               5                   10                  15

Gly

<210> SEQ ID NO 293
<211> LENGTH: 16
<212> TYPE: PRT
<213> ORGANISM: Homo sapiens
<220> FEATURE:
<223> OTHER INFORMATION: Abet0372

<400> SEQUENCE: 293

Glu Trp Met Asp His Ser Arg Pro Tyr Tyr Tyr Gly Met Asp Val
                 5                  10                  15

<210> SEQ ID NO 294
<211> LENGTH: 30
<212> TYPE: PRT
<213> ORGANISM: Homo sapiens
<220> FEATURE:
<223> OTHER INFORMATION: Abet0372

<400> SEQUENCE: 294

Glu Val Gln Leu Leu Glu Ser Gly Gly Gly Leu Val Gln Pro Gly Gly
                 5                  10                  15

Ser Leu Arg Leu Ser Cys Ala Ala Ser Ser Asp Met Phe Asn
             20                  25                  30

<210> SEQ ID NO 295
<211> LENGTH: 14
<212> TYPE: PRT
<213> ORGANISM: Homo sapiens
<220> FEATURE:
<223> OTHER INFORMATION: Abet0372

<400> SEQUENCE: 295

Trp Val Arg Gln Ala Pro Gly Lys Gly Leu Glu Trp Val Ser
                 5                  10

<210> SEQ ID NO 296
<211> LENGTH: 32
<212> TYPE: PRT
<213> ORGANISM: Homo sapiens
<220> FEATURE:
<223> OTHER INFORMATION: Abet0372

<400> SEQUENCE: 296

Arg Phe Thr Ile Ser Arg Asp Asn Ser Lys Asn Thr Leu Tyr Leu Gln
                 5                  10                  15

Met Asn Ser Leu Arg Ala Glu Asp Thr Ala Val Tyr Tyr Cys Ala Arg
             20                  25                  30

<210> SEQ ID NO 297
<211> LENGTH: 11
<212> TYPE: PRT
<213> ORGANISM: Homo sapiens
<220> FEATURE:
<223> OTHER INFORMATION: Abet0372

<400> SEQUENCE: 297

Trp Gly Gln Gly Thr Leu Val Thr Val Ser Ser
                 5                  10

<210> SEQ ID NO 298
<211> LENGTH: 318
<212> TYPE: DNA
<213> ORGANISM: Homo sapiens
<220> FEATURE:
<223> OTHER INFORMATION: Abet0372

<400> SEQUENCE: 298

```
tcgtacgagt tgactcagcc accctcagtg tccgtgtccc caggacagac ggccagcatc    60
acctgctctg gacataactt ggaagataaa tttgcttcct ggtatcaaca gaagccaggc   120 cagtccctg  tcctggtcat ctatcgagat gacaagcggc cctcagggat ccctgagcga   180
ttctctgcct ccaactctgg gcacactgcc actctgacca ttagcgggac ccaggctacg   240
gatgaggctg attattactg ttcgtcccag gacacggtga ctcgagtgtt cggcggaggg   300
accaagctga ccgtccta                                                 318
```

<210> SEQ ID NO 299
<211> LENGTH: 106
<212> TYPE: PRT
<213> ORGANISM: Homo sapiens
<220> FEATURE:
<223> OTHER INFORMATION: Abet0372

<400> SEQUENCE: 299

Ser Tyr Glu Leu Thr Gln Pro Pro Ser Val Ser Val Ser Pro Gly Gln
1               5                   10                  15

Thr Ala Ser Ile Thr Cys Ser Gly His Asn Leu Glu Asp Lys Phe Ala
            20                  25                  30

Ser Trp Tyr Gln Gln Lys Pro Gly Gln Ser Pro Val Leu Val Ile Tyr
        35                  40                  45

Arg Asp Asp Lys Arg Pro Ser Gly Ile Pro Glu Arg Phe Ser Ala Ser
    50                  55                  60

Asn Ser Gly His Thr Ala Thr Leu Thr Ile Ser Gly Thr Gln Ala Thr
65                  70                  75                  80

Asp Glu Ala Asp Tyr Tyr Cys Ser Ser Gln Asp Thr Val Thr Arg Val
                85                  90                  95

Phe Gly Gly Gly Thr Lys Leu Thr Val Leu
            100                 105

<210> SEQ ID NO 300
<211> LENGTH: 11
<212> TYPE: PRT
<213> ORGANISM: Homo sapiens
<220> FEATURE:
<223> OTHER INFORMATION: Abet0372

<400> SEQUENCE: 300

Ser Gly His Asn Leu Glu Asp Lys Phe Ala Ser
1               5                   10

<210> SEQ ID NO 301
<211> LENGTH: 7
<212> TYPE: PRT
<213> ORGANISM: Homo sapiens
<220> FEATURE:
<223> OTHER INFORMATION: Abet0372

<400> SEQUENCE: 301

Arg Asp Asp Lys Arg Pro Ser
1               5

<210> SEQ ID NO 302
<211> LENGTH: 9
<212> TYPE: PRT
<213> ORGANISM: Homo sapiens

```
<220> FEATURE:
<223> OTHER INFORMATION: Abet0372

<400> SEQUENCE: 302

Ser Ser Gln Asp Thr Val Thr Arg Val
                5

<210> SEQ ID NO 303
<211> LENGTH: 22
<212> TYPE: PRT
<213> ORGANISM: Homo sapiens
<220> FEATURE:
<223> OTHER INFORMATION: Abet0372

<400> SEQUENCE: 303

Ser Tyr Glu Leu Thr Gln Pro Pro Ser Val Ser Val Ser Pro Gly Gln
                5                   10                  15

Thr Ala Ser Ile Thr Cys
            20

<210> SEQ ID NO 304
<211> LENGTH: 15
<212> TYPE: PRT
<213> ORGANISM: Homo sapiens
<220> FEATURE:
<223> OTHER INFORMATION: Abet0372

<400> SEQUENCE: 304

Trp Tyr Gln Gln Lys Pro Gly Gln Ser Pro Val Leu Val Ile Tyr
                5                   10                  15

<210> SEQ ID NO 305
<211> LENGTH: 32
<212> TYPE: PRT
<213> ORGANISM: Homo sapiens
<220> FEATURE:
<223> OTHER INFORMATION: Abet0372

<400> SEQUENCE: 305

Gly Ile Pro Glu Arg Phe Ser Ala Ser Asn Ser Gly His Thr Ala Thr
                5                   10                  15

Leu Thr Ile Ser Gly Thr Gln Ala Thr Asp Glu Ala Asp Tyr Tyr Cys
            20                  25                  30

<210> SEQ ID NO 306
<211> LENGTH: 10
<212> TYPE: PRT
<213> ORGANISM: Homo sapiens
<220> FEATURE:
<223> OTHER INFORMATION: Abet0372

<400> SEQUENCE: 306

Phe Gly Gly Gly Thr Lys Leu Thr Val Leu
                5                   10

<210> SEQ ID NO 307
<211> LENGTH: 375
<212> TYPE: DNA
<213> ORGANISM: Homo sapiens
<220> FEATURE:
<223> OTHER INFORMATION: Abet0373

<400> SEQUENCE: 307
gaggtgcagc tgttggagtc tgggggaggc ttggtacagc ctggggggtc cctgagactc      60
tcctgtgtag cctccggatt cgactttgag cggtccgtca tgtggtgggt ccgccaggct     120
```

-continued

```
ccagggaaga ggctggagtg ggtctcagtt attggtagcg ggaagaccaa catcacctac    180
gcagactccg tgaagggccg gtttaccatc tccagagaca attccaagaa cacgctgtat    240
ctgcaaatga acagcctgag agccgaggac acggccgtgt attactgtgc gagagagtgg    300
atggaccact cccgccccta ctactactac ggtatggacg tctggggggca ggggaccctg    360 gtcaccgtct cctca                                                     375
```

```
<210> SEQ ID NO 308
<211> LENGTH: 125
<212> TYPE: PRT
<213> ORGANISM: Homo sapiens
<220> FEATURE:
<223> OTHER INFORMATION: Abet0373

<400> SEQUENCE: 308
```

Glu Val Gln Leu Leu Glu Ser Gly Gly Gly Leu Val Gln Pro Gly Gly
 1               5                  10                  15

Ser Leu Arg Leu Ser Cys Val Ala Ser Gly Phe Asp Phe Glu Arg Ser
            20                  25                  30

Val Met Trp Trp Val Arg Gln Ala Pro Gly Lys Arg Leu Glu Trp Val
        35                  40                  45

Ser Val Ile Gly Ser Gly Lys Thr Asn Ile Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Trp Met Asp His Ser Arg Pro Tyr Tyr Tyr Tyr Gly Met
            100                 105                 110

Asp Val Trp Gly Gln Gly Thr Leu Val Thr Val Ser Ser
        115                 120                 125

```
<210> SEQ ID NO 309
<211> LENGTH: 5
<212> TYPE: PRT
<213> ORGANISM: Homo sapiens
<220> FEATURE:
<223> OTHER INFORMATION: Abet0373

<400> SEQUENCE: 309
```

Arg Ser Val Met Trp
 1               5

```
<210> SEQ ID NO 310
<211> LENGTH: 17
<212> TYPE: PRT
<213> ORGANISM: Homo sapiens
<220> FEATURE:
<223> OTHER INFORMATION: Abet0373

<400> SEQUENCE: 310
```

Val Ile Gly Ser Gly Lys Thr Asn Ile Thr Tyr Ala Asp Ser Val Lys
 1               5                  10                  15

Gly

```
<210> SEQ ID NO 311
<211> LENGTH: 16
<212> TYPE: PRT
<213> ORGANISM: Homo sapiens
<220> FEATURE:
```

<223> OTHER INFORMATION: Abet0373

<400> SEQUENCE: 311

Glu Trp Met Asp His Ser Arg Pro Tyr Tyr Tyr Gly Met Asp Val
                5                   10                  15

<210> SEQ ID NO 312
<211> LENGTH: 30
<212> TYPE: PRT
<213> ORGANISM: Homo sapiens
<220> FEATURE:
<223> OTHER INFORMATION: Abet0373

<400> SEQUENCE: 312

Glu Val Gln Leu Leu Glu Ser Gly Gly Gly Leu Val Gln Pro Gly Gly
                5                   10                  15

Ser Leu Arg Leu Ser Cys Val Ala Ser Gly Phe Asp Phe Glu
            20                  25                  30

<210> SEQ ID NO 313
<211> LENGTH: 14
<212> TYPE: PRT
<213> ORGANISM: Homo sapiens
<220> FEATURE:
<223> OTHER INFORMATION: Abet0373

<400> SEQUENCE: 313

Trp Val Arg Gln Ala Pro Gly Lys Arg Leu Glu Trp Val Ser
                5                   10

<210> SEQ ID NO 314
<211> LENGTH: 32
<212> TYPE: PRT
<213> ORGANISM: Homo sapiens
<220> FEATURE:
<223> OTHER INFORMATION: Abet0373

<400> SEQUENCE: 314

Arg Phe Thr Ile Ser Arg Asp Asn Ser Lys Asn Thr Leu Tyr Leu Gln
                5                   10                  15

Met Asn Ser Leu Arg Ala Glu Asp Thr Ala Val Tyr Tyr Cys Ala Arg
            20                  25                  30

<210> SEQ ID NO 315
<211> LENGTH: 11
<212> TYPE: PRT
<213> ORGANISM: Homo sapiens
<220> FEATURE:
<223> OTHER INFORMATION: Abet0373

<400> SEQUENCE: 315

Trp Gly Gln Gly Thr Leu Val Thr Val Ser Ser
                5                   10

<210> SEQ ID NO 316
<211> LENGTH: 318
<212> TYPE: DNA
<213> ORGANISM: Homo sapiens
<220> FEATURE:
<223> OTHER INFORMATION: Abet0373

<400> SEQUENCE: 316
tcgtacgagt tgactcagcc acccctcagtg tccgtgtccc cagggcagac ggccagcatc    60
acctgctctg gtcataactt ggaggataaa tttgcttcct ggtatcaaca gaagccaggc   120

```
cagtcccccg tcctggtcat ctatcgagat gacaagcggc cctcagagat ccctgagcga    180
ttctctgcct ccaactctgg gcacaccgcc actctgacca tcagcgggac ccaggctacg    240
gatgaggctg actattactg ttcgtcccag gacacggtga ctcgagtgtt cggcggaggg    300
accaagctga ccgtccta                                                  318
```

<210> SEQ ID NO 317
<211> LENGTH: 106
<212> TYPE: PRT
<213> ORGANISM: Homo sapiens
<220> FEATURE:
<223> OTHER INFORMATION: Abet0373

<400> SEQUENCE: 317

Ser Tyr Glu Leu Thr Gln Pro Pro Ser Val Ser Val Ser Pro Gly Gln
 1               5                  10                  15

Thr Ala Ser Ile Thr Cys Ser Gly His Asn Leu Glu Asp Lys Phe Ala
             20                  25                  30

Ser Trp Tyr Gln Gln Lys Pro Gly Gln Ser Pro Val Leu Val Ile Tyr
         35                  40                  45

Arg Asp Asp Lys Arg Pro Ser Glu Ile Pro Glu Arg Phe Ser Ala Ser
 50                  55                  60

Asn Ser Gly His Thr Ala Thr Leu Thr Ile Ser Gly Thr Gln Ala Thr
 65                  70                  75                  80

Asp Glu Ala Asp Tyr Tyr Cys Ser Ser Gln Asp Thr Val Thr Arg Val
                 85                  90                  95

Phe Gly Gly Gly Thr Lys Leu Thr Val Leu
            100                 105

<210> SEQ ID NO 318
<211> LENGTH: 11
<212> TYPE: PRT
<213> ORGANISM: Homo sapiens
<220> FEATURE:
<223> OTHER INFORMATION: Abet0373

<400> SEQUENCE: 318

Ser Gly His Asn Leu Glu Asp Lys Phe Ala Ser
 1               5                  10

<210> SEQ ID NO 319
<211> LENGTH: 7
<212> TYPE: PRT
<213> ORGANISM: Homo sapiens
<220> FEATURE:
<223> OTHER INFORMATION: Abet0373

<400> SEQUENCE: 319

Arg Asp Asp Lys Arg Pro Ser
 1               5

<210> SEQ ID NO 320
<211> LENGTH: 9
<212> TYPE: PRT
<213> ORGANISM: Homo sapiens
<220> FEATURE:
<223> OTHER INFORMATION: Abet0373

<400> SEQUENCE: 320

Ser Ser Gln Asp Thr Val Thr Arg Val
 1               5

-continued

```
<210> SEQ ID NO 321
<211> LENGTH: 22
<212> TYPE: PRT
<213> ORGANISM: Homo sapiens
<220> FEATURE:
<223> OTHER INFORMATION: Abet0373

<400> SEQUENCE: 321

Ser Tyr Glu Leu Thr Gln Pro Pro Ser Val Ser Val Ser Pro Gly Gln
                5                  10                  15

Thr Ala Ser Ile Thr Cys
            20

<210> SEQ ID NO 322
<211> LENGTH: 15
<212> TYPE: PRT
<213> ORGANISM: Homo sapiens
<220> FEATURE:
<223> OTHER INFORMATION: Abet0373

<400> SEQUENCE: 322

Trp Tyr Gln Gln Lys Pro Gly Gln Ser Pro Val Leu Val Ile Tyr
                5                  10                  15

<210> SEQ ID NO 323
<211> LENGTH: 32
<212> TYPE: PRT
<213> ORGANISM: Homo sapiens
<220> FEATURE:
<223> OTHER INFORMATION: Abet0373

<400> SEQUENCE: 323

Glu Ile Pro Glu Arg Phe Ser Ala Ser Asn Ser Gly His Thr Ala Thr
                5                  10                  15

Leu Thr Ile Ser Gly Thr Gln Ala Thr Asp Glu Ala Asp Tyr Tyr Cys
            20                  25                  30

<210> SEQ ID NO 324
<211> LENGTH: 10
<212> TYPE: PRT
<213> ORGANISM: Homo sapiens
<220> FEATURE:
<223> OTHER INFORMATION: Abet0373

<400> SEQUENCE: 324

Phe Gly Gly Gly Thr Lys Leu Thr Val Leu
                5                  10

<210> SEQ ID NO 325
<211> LENGTH: 375
<212> TYPE: DNA
<213> ORGANISM: Homo sapiens
<220> FEATURE:
<223> OTHER INFORMATION: Abet0374

<400> SEQUENCE: 325
gaggtgcagc tgttggagtc tgggggaggc ttggtacagc ctggggggtc cctgagactc      60
tcctgtgcag cctctggatt ccagtttaag gacacgccca tgtggtgggt ccgccaggct     120
ccagggaagg ggctagagtg ggtctcagtt attggtgacc agaaccacaa gaaggcctac     180
gcagactccg tgaagggccg gttcaccatc tccagagaca attccaagaa cacgctgtat     240
ctgcaaatga acagcctgag agccgaggac acggccgtgt attactgtgc gagagagtgg     300
atggaccact cccgccccta ctactactac ggtatggacg cctgggggca ggggaccctg     360
```
gtcaccgtct cctca                                                    375

<210> SEQ ID NO 326
<211> LENGTH: 125
<212> TYPE: PRT
<213> ORGANISM: Homo sapiens
<220> FEATURE:
<223> OTHER INFORMATION: Abet0374

<400> SEQUENCE: 326

Glu Val Gln Leu Leu Glu Ser Gly Gly Gly Leu Val Gln Pro Gly Gly
                5                   10                  15

Ser Leu Arg Leu Ser Cys Ala Ala Ser Gly Phe Gln Phe Lys Asp Thr
            20                  25                  30

Pro Met Trp Trp Val Arg Gln Ala Pro Gly Lys Gly Leu Glu Trp Val
        35                  40                  45

Ser Val Ile Gly Asp Gln Asn His Lys Lys Ala Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Trp Met Asp His Ser Arg Pro Tyr Tyr Tyr Gly Met
            100                 105                 110

Asp Ala Trp Gly Gln Gly Thr Leu Val Thr Val Ser Ser
        115                 120                 125

<210> SEQ ID NO 327
<211> LENGTH: 5
<212> TYPE: PRT
<213> ORGANISM: Homo sapiens
<220> FEATURE:
<223> OTHER INFORMATION: Abet0374

<400> SEQUENCE: 327

Asp Thr Pro Met Trp
                5

<210> SEQ ID NO 328
<211> LENGTH: 17
<212> TYPE: PRT
<213> ORGANISM: Homo sapiens
<220> FEATURE:
<223> OTHER INFORMATION: Abet0374

<400> SEQUENCE: 328

Val Ile Gly Asp Gln Asn His Lys Lys Ala Tyr Ala Asp Ser Val Lys
                5                   10                  15

Gly

<210> SEQ ID NO 329
<211> LENGTH: 16
<212> TYPE: PRT
<213> ORGANISM: Homo sapiens
<220> FEATURE:
<223> OTHER INFORMATION: Abet0374

<400> SEQUENCE: 329

Glu Trp Met Asp His Ser Arg Pro Tyr Tyr Tyr Gly Met Asp Ala
                5                   10                  15

<210> SEQ ID NO 330

```
<211> LENGTH: 30
<212> TYPE: PRT
<213> ORGANISM: Homo sapiens
<220> FEATURE:
<223> OTHER INFORMATION: Abet0374

<400> SEQUENCE: 330

Glu Val Gln Leu Leu Glu Ser Gly Gly Gly Leu Val Gln Pro Gly Gly
 1               5                  10                  15
Ser Leu Arg Leu Ser Cys Ala Ala Ser Gly Phe Gln Phe Lys
            20                  25                  30

<210> SEQ ID NO 331
<211> LENGTH: 14
<212> TYPE: PRT
<213> ORGANISM: Homo sapiens
<220> FEATURE:
<223> OTHER INFORMATION: Abet0374

<400> SEQUENCE: 331

Trp Val Arg Gln Ala Pro Gly Lys Gly Leu Glu Trp Val Ser
 1               5                  10

<210> SEQ ID NO 332
<211> LENGTH: 32
<212> TYPE: PRT
<213> ORGANISM: Homo sapiens
<220> FEATURE:
<223> OTHER INFORMATION: Abet0374

<400> SEQUENCE: 332

Arg Phe Thr Ile Ser Arg Asp Asn Ser Lys Asn Thr Leu Tyr Leu Gln
 1               5                  10                  15
Met Asn Ser Leu Arg Ala Glu Asp Thr Ala Val Tyr Tyr Cys Ala Arg
            20                  25                  30

<210> SEQ ID NO 333
<211> LENGTH: 11
<212> TYPE: PRT
<213> ORGANISM: Homo sapiens
<220> FEATURE:
<223> OTHER INFORMATION: Abet0374

<400> SEQUENCE: 333

Trp Gly Gln Gly Thr Leu Val Thr Val Ser Ser
 1               5                  10

<210> SEQ ID NO 334
<211> LENGTH: 318
<212> TYPE: DNA
<213> ORGANISM: Homo sapiens
<220> FEATURE:
<223> OTHER INFORMATION: Abet0374

<400> SEQUENCE: 334
tcgtacgagt tgactcagcc accctcagtg tccgtgaccc caggacagac ggccagcatc      60
acctgctctg gacataactt gggaggtaaa tttgcttcct ggtatcaaca gaagccaggc     120
cagtcccctg tcctggtcat ctatcgagat gacaagcggc cctcaggat cccctgagcga     180 ttctctgcct ccaactttgg gcacactgcc actctgacca tcagcgggac ccaggctacg     240
gatgaggctg actattactg ttcgtcccag gacacggtga ctcgagtgtt cggcggaggg     300
accaagctga ccgtccta                                                   318
```

<210> SEQ ID NO 335
<211> LENGTH: 106
<212> TYPE: PRT
<213> ORGANISM: Homo sapiens
<220> FEATURE:
<223> OTHER INFORMATION: Abet0374

<400> SEQUENCE: 335

Ser Tyr Glu Leu Thr Gln Pro Pro Ser Val Ser Val Thr Pro Gly Gln
                 5                  10                  15

Thr Ala Ser Ile Thr Cys Ser Gly His Asn Leu Gly Gly Lys Phe Ala
             20                  25                  30

Ser Trp Tyr Gln Gln Lys Pro Gly Gln Ser Pro Val Leu Val Ile Tyr
         35                  40                  45

Arg Asp Asp Lys Arg Pro Ser Gly Ile Pro Glu Arg Phe Ser Ala Ser
     50                  55                  60

Asn Phe Gly His Thr Ala Thr Leu Thr Ile Ser Gly Thr Gln Ala Thr
 65                  70                  75                  80

Asp Glu Ala Asp Tyr Tyr Cys Ser Ser Gln Asp Thr Val Thr Arg Val
                 85                  90                  95

Phe Gly Gly Gly Thr Lys Leu Thr Val Leu
            100                 105

<210> SEQ ID NO 336
<211> LENGTH: 11
<212> TYPE: PRT
<213> ORGANISM: Homo sapiens
<220> FEATURE:
<223> OTHER INFORMATION: Abet0374

<400> SEQUENCE: 336

Ser Gly His Asn Leu Gly Gly Lys Phe Ala Ser
                 5                  10

<210> SEQ ID NO 337
<211> LENGTH: 7
<212> TYPE: PRT
<213> ORGANISM: Homo sapiens
<220> FEATURE:
<223> OTHER INFORMATION: Abet0374

<400> SEQUENCE: 337

Arg Asp Asp Lys Arg Pro Ser
                 5

<210> SEQ ID NO 338
<211> LENGTH: 9
<212> TYPE: PRT
<213> ORGANISM: Homo sapiens
<220> FEATURE:
<223> OTHER INFORMATION: Abet0374

<400> SEQUENCE: 338

Ser Ser Gln Asp Thr Val Thr Arg Val
                 5

<210> SEQ ID NO 339
<211> LENGTH: 22
<212> TYPE: PRT
<213> ORGANISM: Homo sapiens
<220> FEATURE:
<223> OTHER INFORMATION: Abet0374

<400> SEQUENCE: 339

-continued

Ser Tyr Glu Leu Thr Gln Pro Pro Ser Val Ser Val Thr Pro Gly Gln
　　　　　　　　　5　　　　　　　　　　　10　　　　　　　　　　15

Thr Ala Ser Ile Thr Cys
　　　　　　20

<210> SEQ ID NO 340
<211> LENGTH: 15
<212> TYPE: PRT
<213> ORGANISM: Homo sapiens
<220> FEATURE:
<223> OTHER INFORMATION: Abet0374

<400> SEQUENCE: 340

Trp Tyr Gln Gln Lys Pro Gly Gln Ser Pro Val Leu Val Ile Tyr
　　　　　　　　　5　　　　　　　　　　　10　　　　　　　　　　15

<210> SEQ ID NO 341
<211> LENGTH: 32
<212> TYPE: PRT
<213> ORGANISM: Homo sapiens
<220> FEATURE:
<223> OTHER INFORMATION: Abet0374

<400> SEQUENCE: 341

Gly Ile Pro Glu Arg Phe Ser Ala Ser Asn Phe Gly His Thr Ala Thr
　　　　　　　　　5　　　　　　　　　　　10　　　　　　　　　　15

Leu Thr Ile Ser Gly Thr Gln Ala Thr Asp Glu Ala Asp Tyr Tyr Cys
　　　　　　20　　　　　　　　　　　25　　　　　　　　　　　30

<210> SEQ ID NO 342
<211> LENGTH: 10
<212> TYPE: PRT
<213> ORGANISM: Homo sapiens
<220> FEATURE:
<223> OTHER INFORMATION: Abet0374

<400> SEQUENCE: 342

Phe Gly Gly Gly Thr Lys Leu Thr Val Leu
　　　　　　　　　5　　　　　　　　　　　10

<210> SEQ ID NO 343
<211> LENGTH: 375
<212> TYPE: DNA
<213> ORGANISM: Homo sapiens
<220> FEATURE:
<223> OTHER INFORMATION: Abet0377

<400> SEQUENCE: 343
gaggtgcagc tgttggagtc tgggggaggc ttggtacagc ctgggggtc cctgagactc　　60 tcctgtgcag cctctggatt caactttaac gagcagaccc tctggtgggt ccgccaagcc　120 ccagggaaag gctggagtg gtctcagtt attggtgtgg ggaccaagaa catcgcctac　180 gcagacaccg tgaagggccg gttcaccatc tccagagaca attccaagaa cacgctgtat　240 ctgcaaatga acagcctgag agccgaggac acggccgtgt attactgtgc gagagagtgg　300 atggaccact cccgccccta ctactactac ggtatggacg tctggggaca ggggaccctg　360 gtcaccgtct cctca　　　　　　　　　　　　　　　　　　　　　　375

<210> SEQ ID NO 344
<211> LENGTH: 125
<212> TYPE: PRT
<213> ORGANISM: Homo sapiens
<220> FEATURE:
<223> OTHER INFORMATION: Abet0377

-continued

<400> SEQUENCE: 344

Glu Val Gln Leu Leu Glu Ser Gly Gly Gly Leu Val Gln Pro Gly Gly
                 5                  10                  15
Ser Leu Arg Leu Ser Cys Ala Ala Ser Gly Phe Asn Phe Asn Glu Gln
             20                  25                  30
Thr Leu Trp Trp Val Arg Gln Ala Pro Gly Lys Gly Leu Glu Trp Val
         35                  40                  45
Ser Val Ile Gly Val Gly Thr Lys Asn Ile Ala Tyr Ala Asp Thr Val
     50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Glu Trp Met Asp His Ser Arg Pro Tyr Tyr Tyr Gly Met
            100                 105                 110
Asp Val Trp Gly Gln Gly Thr Leu Val Thr Val Ser Ser
        115                 120                 125

<210> SEQ ID NO 345
<211> LENGTH: 5
<212> TYPE: PRT
<213> ORGANISM: Homo sapiens
<220> FEATURE:
<223> OTHER INFORMATION: Abet0377

<400> SEQUENCE: 345

Glu Gln Thr Leu Trp
                 5

<210> SEQ ID NO 346
<211> LENGTH: 17
<212> TYPE: PRT
<213> ORGANISM: Homo sapiens
<220> FEATURE:
<223> OTHER INFORMATION: Abet0377

<400> SEQUENCE: 346

Val Ile Gly Val Gly Thr Lys Asn Ile Ala Tyr Ala Asp Thr Val Lys
                 5                  10                  15
Gly

<210> SEQ ID NO 347
<211> LENGTH: 16
<212> TYPE: PRT
<213> ORGANISM: Homo sapiens
<220> FEATURE:
<223> OTHER INFORMATION: Abet0377

<400> SEQUENCE: 347

Glu Trp Met Asp His Ser Arg Pro Tyr Tyr Tyr Gly Met Asp Val
                 5                  10                  15

<210> SEQ ID NO 348
<211> LENGTH: 30
<212> TYPE: PRT
<213> ORGANISM: Homo sapiens
<220> FEATURE:
<223> OTHER INFORMATION: Abet0377

<400> SEQUENCE: 348

Glu Val Gln Leu Leu Glu Ser Gly Gly Gly Leu Val Gln Pro Gly Gly 5                   10                  15

Ser Leu Arg Leu Ser Cys Ala Ala Ser Gly Phe Asn Phe Asn
            20                  25                  30

<210> SEQ ID NO 349
<211> LENGTH: 14
<212> TYPE: PRT
<213> ORGANISM: Homo sapiens
<220> FEATURE:
<223> OTHER INFORMATION: Abet0377

<400> SEQUENCE: 349

Trp Val Arg Gln Ala Pro Gly Lys Gly Leu Glu Trp Val Ser
                5                   10

<210> SEQ ID NO 350
<211> LENGTH: 32
<212> TYPE: PRT
<213> ORGANISM: Homo sapiens
<220> FEATURE:
<223> OTHER INFORMATION: Abet0377

<400> SEQUENCE: 350

Arg Phe Thr Ile Ser Arg Asp Asn Ser Lys Asn Thr Leu Tyr Leu Gln
                5                   10                  15

Met Asn Ser Leu Arg Ala Glu Asp Thr Ala Val Tyr Tyr Cys Ala Arg
            20                  25                  30

<210> SEQ ID NO 351
<211> LENGTH: 11
<212> TYPE: PRT
<213> ORGANISM: Homo sapiens
<220> FEATURE:
<223> OTHER INFORMATION: Abet0377

<400> SEQUENCE: 351

Trp Gly Gln Gly Thr Leu Val Thr Val Ser Ser
                5                   10

<210> SEQ ID NO 352
<211> LENGTH: 318
<212> TYPE: DNA
<213> ORGANISM: Homo sapiens
<220> FEATURE:
<223> OTHER INFORMATION: Abet0377

<400> SEQUENCE: 352
tcgtacgagt tgactcagcc accctcagtg tccgtgtccc caggacagac ggccagcatc      60
acctgctctg gacataacac cgagcacaag tggatctcgt ggtatcaaca gaagccaggc     120
cagtcccctg tcctggtcat ctatcgagat gacaagcggc cctcagggat ccctgagcga     180
ttctctgcca ccaactctgg gcacactgcc actctgacca tcagcgggac ccaggctacg     240
gatgaggctg actattactg ttcgtcccag gacacggtga ctcgagtgtt cggcggaggg     300
accaagctga ccgtccta                                                   318

<210> SEQ ID NO 353
<211> LENGTH: 106
<212> TYPE: PRT
<213> ORGANISM: Homo sapiens
<220> FEATURE:
<223> OTHER INFORMATION: Abet0377

<400> SEQUENCE: 353

```
Ser Tyr Glu Leu Thr Gln Pro Pro Ser Val Ser Val Ser Pro Gly Gln
             5                  10                  15

Thr Ala Ser Ile Thr Cys Ser Gly His Asn Thr Glu His Lys Trp Ile
         20                  25                  30

Ser Trp Tyr Gln Gln Lys Pro Gly Gln Ser Pro Val Leu Val Ile Tyr
         35                  40                  45

Arg Asp Asp Lys Arg Pro Ser Gly Ile Pro Glu Arg Phe Ser Ala Thr
 50                  55                  60

Asn Ser Gly His Thr Ala Thr Leu Thr Ile Ser Gly Thr Gln Ala Thr
 65                  70                  75                  80

Asp Glu Ala Asp Tyr Tyr Cys Ser Ser Gln Asp Thr Val Thr Arg Val
                 85                  90                  95

Phe Gly Gly Gly Thr Lys Leu Thr Val Leu
                100                 105
```

<210> SEQ ID NO 354
<211> LENGTH: 11
<212> TYPE: PRT
<213> ORGANISM: Homo sapiens
<220> FEATURE:
<223> OTHER INFORMATION: Abet0377

<400> SEQUENCE: 354

```
Ser Gly His Asn Thr Glu His Lys Trp Ile Ser
             5                  10
```

<210> SEQ ID NO 355
<211> LENGTH: 7
<212> TYPE: PRT
<213> ORGANISM: Homo sapiens
<220> FEATURE:
<223> OTHER INFORMATION: Abet0377

<400> SEQUENCE: 355

```
Arg Asp Asp Lys Arg Pro Ser
             5
```

<210> SEQ ID NO 356
<211> LENGTH: 9
<212> TYPE: PRT
<213> ORGANISM: Homo sapiens
<220> FEATURE:
<223> OTHER INFORMATION: Abet0377

<400> SEQUENCE: 356

```
Ser Ser Gln Asp Thr Val Thr Arg Val
             5
```

<210> SEQ ID NO 357
<211> LENGTH: 22
<212> TYPE: PRT
<213> ORGANISM: Homo sapiens
<220> FEATURE:
<223> OTHER INFORMATION: Abet0377

<400> SEQUENCE: 357

```
Ser Tyr Glu Leu Thr Gln Pro Pro Ser Val Ser Val Ser Pro Gly Gln
             5                  10                  15

Thr Ala Ser Ile Thr Cys
         20
```

<210> SEQ ID NO 358
<211> LENGTH: 15

```
<212> TYPE: PRT
<213> ORGANISM: Homo sapiens
<220> FEATURE:
<223> OTHER INFORMATION: Abet0377

<400> SEQUENCE: 358

Trp Tyr Gln Gln Lys Pro Gly Gln Ser Pro Val Leu Val Ile Tyr
                 5                  10                  15

<210> SEQ ID NO 359
<211> LENGTH: 32
<212> TYPE: PRT
<213> ORGANISM: Homo sapiens
<220> FEATURE:
<223> OTHER INFORMATION: Abet0377

<400> SEQUENCE: 359

Gly Ile Pro Glu Arg Phe Ser Ala Thr Asn Ser Gly His Thr Ala Thr
                 5                  10                  15

Leu Thr Ile Ser Gly Thr Gln Ala Thr Asp Glu Ala Asp Tyr Tyr Cys
             20                  25                  30

<210> SEQ ID NO 360
<211> LENGTH: 10
<212> TYPE: PRT
<213> ORGANISM: Homo sapiens
<220> FEATURE:
<223> OTHER INFORMATION: Abet0377

<400> SEQUENCE: 360

Phe Gly Gly Gly Thr Lys Leu Thr Val Leu
                 5                  10

<210> SEQ ID NO 361
<211> LENGTH: 375
<212> TYPE: DNA
<213> ORGANISM: Homo sapiens
<220> FEATURE:
<223> OTHER INFORMATION: Abet0378

<400> SEQUENCE: 361
gaggtgcagc tgttggagtc tgggggaggc ttggtacagc ctggggggtc cctgagactc        60
tcctgtgcag cctctggatt ccccttttgag accgacatca tgtggtgggt ccgccaggct      120
ccagggaagg ggctggagtg gtctcagtt attggtacca caccgacaa cgtcgcctac         180 gcagactccg tgaagggccg gttcaccatc tccagagaca attccaagaa cacgctgtat       240
ctgcaaatga acagcctgag agccgaggac acggccgtgt attactgtgc gagagagtgg       300
atggaccact cccgccccta ctactactac ggtatggacg tctggggca ggggaccctg        360 gtcaccgtct cctca                                                        375

<210> SEQ ID NO 362
<211> LENGTH: 125
<212> TYPE: PRT
<213> ORGANISM: Homo sapiens
<220> FEATURE:
<223> OTHER INFORMATION: Abet0378

<400> SEQUENCE: 362

Glu Val Gln Leu Leu Glu Ser Gly Gly Gly Leu Val Gln Pro Gly Gly
                 5                  10                  15

Ser Leu Arg Leu Ser Cys Ala Ala Ser Gly Phe Pro Phe Glu Thr Asp
             20                  25                  30
```

```
Ile Met Trp Trp Val Arg Gln Ala Pro Gly Lys Gly Leu Glu Trp Val
         35                  40                  45

Ser Val Ile Gly Thr Asn Thr Asp Asn Val Ala Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Trp Met Asp His Ser Arg Pro Tyr Tyr Tyr Gly Met
             100                 105                 110

Asp Val Trp Gly Gln Gly Thr Leu Val Thr Val Ser Ser
         115                 120                 125
```

<210> SEQ ID NO 363
<211> LENGTH: 5
<212> TYPE: PRT
<213> ORGANISM: Homo sapiens
<220> FEATURE:
<223> OTHER INFORMATION: Abet0378

<400> SEQUENCE: 363

```
Thr Asp Ile Met Trp
             5
```

<210> SEQ ID NO 364
<211> LENGTH: 17
<212> TYPE: PRT
<213> ORGANISM: Homo sapiens
<220> FEATURE:
<223> OTHER INFORMATION: Abet0378

<400> SEQUENCE: 364

```
Val Ile Gly Thr Asn Thr Asp Asn Val Ala Tyr Ala Asp Ser Val Lys
                 5                  10                  15

Gly
```

<210> SEQ ID NO 365
<211> LENGTH: 16
<212> TYPE: PRT
<213> ORGANISM: Homo sapiens
<220> FEATURE:
<223> OTHER INFORMATION: Abet0378

<400> SEQUENCE: 365

```
Glu Trp Met Asp His Ser Arg Pro Tyr Tyr Tyr Gly Met Asp Val
                 5                  10                  15
```

<210> SEQ ID NO 366
<211> LENGTH: 30
<212> TYPE: PRT
<213> ORGANISM: Homo sapiens
<220> FEATURE:
<223> OTHER INFORMATION: Abet0378

<400> SEQUENCE: 366

```
Glu Val Gln Leu Leu Glu Ser Gly Gly Gly Leu Val Gln Pro Gly Gly
                 5                  10                  15

Ser Leu Arg Leu Ser Cys Ala Ala Ser Gly Phe Pro Phe Glu
             20                  25                  30
```

<210> SEQ ID NO 367
<211> LENGTH: 14
<212> TYPE: PRT

```
<213> ORGANISM: Homo sapiens
<220> FEATURE:
<223> OTHER INFORMATION: Abet0378

<400> SEQUENCE: 367

Trp Val Arg Gln Ala Pro Gly Lys Gly Leu Glu Trp Val Ser
                5                   10

<210> SEQ ID NO 368
<211> LENGTH: 32
<212> TYPE: PRT
<213> ORGANISM: Homo sapiens
<220> FEATURE:
<223> OTHER INFORMATION: Abet0378

<400> SEQUENCE: 368

Arg Phe Thr Ile Ser Arg Asp Asn Ser Lys Asn Thr Leu Tyr Leu Gln
                5                   10                  15
Met Asn Ser Leu Arg Ala Glu Asp Thr Ala Val Tyr Tyr Cys Ala Arg
            20                  25                  30

<210> SEQ ID NO 369
<211> LENGTH: 11
<212> TYPE: PRT
<213> ORGANISM: Homo sapiens
<220> FEATURE:
<223> OTHER INFORMATION: Abet0378

<400> SEQUENCE: 369

Trp Gly Gln Gly Thr Leu Val Thr Val Ser Ser
                5                   10

<210> SEQ ID NO 370
<211> LENGTH: 318
<212> TYPE: DNA
<213> ORGANISM: Homo sapiens
<220> FEATURE:
<223> OTHER INFORMATION: Abet0378

<400> SEQUENCE: 370
tcgtacgagt tgacccagcc accctcagtg tccgtgtccc caggacagac ggccagcatc        60
acctgctctg gacataactt ggaagataaa tttgcttcct ggtatcaaca gaagccaggc       120
cagtcccctg tcctggtcat ctatcgagat gacaagcggc cctcaggat  ccctgagcga       180 ttctctgcct ccaactctgg gcacactgcc actctgacca tcagcgggac ccaggctacg       240
gatgaggctg actattactg ctcgtcctag gacacggtga ctcgggtgtt cggcggaggg       300
accaagctga ccgtcccta                                                    318

<210> SEQ ID NO 371
<211> LENGTH: 89
<212> TYPE: PRT
<213> ORGANISM: Homo sapiens
<220> FEATURE:
<223> OTHER INFORMATION: Amino acids 1-89 of Abet0378 VL protein
      sequence

<400> SEQUENCE: 371

Ser Tyr Glu Leu Thr Gln Pro Pro Ser Val Ser Val Pro Gly Gln
                5                   10                  15
Thr Ala Ser Ile Thr Cys Ser Gly His Asn Leu Glu Asp Lys Phe Ala
            20                  25                  30
Ser Trp Tyr Gln Gln Lys Pro Gly Gln Ser Pro Val Leu Val Ile Tyr
        35                  40                  45
```

```
Arg Asp Asp Lys Arg Pro Ser Gly Ile Pro Glu Arg Phe Ser Ala Ser
 50                  55                  60

Asn Ser Gly His Thr Ala Thr Leu Thr Ile Ser Gly Thr Gln Ala Thr
 65                  70                  75                  80

Asp Glu Ala Asp Tyr Tyr Cys Ser Ser
                 85

<210> SEQ ID NO 372
<211> LENGTH: 11
<212> TYPE: PRT
<213> ORGANISM: Homo sapiens
<220> FEATURE:
<223> OTHER INFORMATION: Abet0378

<400> SEQUENCE: 372

Ser Gly His Asn Leu Glu Asp Lys Phe Ala Ser
                 5                  10

<210> SEQ ID NO 373
<211> LENGTH: 7
<212> TYPE: PRT
<213> ORGANISM: Homo sapiens
<220> FEATURE:
<223> OTHER INFORMATION: Abet0378

<400> SEQUENCE: 373

Arg Asp Asp Lys Arg Pro Ser
                 5

<210> SEQ ID NO 374
<211> LENGTH: 6
<212> TYPE: PRT
<213> ORGANISM: Homo sapiens
<220> FEATURE:
<223> OTHER INFORMATION: Amino acids 4-9 of Abet0378 light chain CDR3
      protein sequence

<400> SEQUENCE: 374

Asp Thr Val Thr Arg Val
                 5

<210> SEQ ID NO 375
<211> LENGTH: 22
<212> TYPE: PRT
<213> ORGANISM: Homo sapiens
<220> FEATURE:
<223> OTHER INFORMATION: Abet0378

<400> SEQUENCE: 375

Ser Tyr Glu Leu Thr Gln Pro Pro Ser Val Ser Val Ser Pro Gly Gln
                 5                  10                  15

Thr Ala Ser Ile Thr Cys
             20

<210> SEQ ID NO 376
<211> LENGTH: 15
<212> TYPE: PRT
<213> ORGANISM: Homo sapiens
<220> FEATURE:
<223> OTHER INFORMATION: Abet0378

<400> SEQUENCE: 376

Trp Tyr Gln Gln Lys Pro Gly Gln Ser Pro Val Leu Val Ile Tyr
                 5                  10                  15
```

<210> SEQ ID NO 377
<211> LENGTH: 32
<212> TYPE: PRT
<213> ORGANISM: Homo sapiens
<220> FEATURE:
<223> OTHER INFORMATION: Abet0378

<400> SEQUENCE: 377

Gly Ile Pro Glu Arg Phe Ser Ala Ser Asn Ser Gly His Thr Ala Thr
                5                   10                  15

Leu Thr Ile Ser Gly Thr Gln Ala Thr Asp Glu Ala Asp Tyr Tyr Cys
            20                  25                  30

<210> SEQ ID NO 378
<211> LENGTH: 10
<212> TYPE: PRT
<213> ORGANISM: Homo sapiens
<220> FEATURE:
<223> OTHER INFORMATION: Abet0378

<400> SEQUENCE: 378

Phe Gly Gly Gly Thr Lys Leu Thr Val Leu
                5                   10

<210> SEQ ID NO 379
<211> LENGTH: 375
<212> TYPE: DNA
<213> ORGANISM: Homo sapiens
<220> FEATURE:
<223> OTHER INFORMATION: Abet0379

<400> SEQUENCE: 379
gaggtgcagc tgttggagtc tgggggaggc ttggtacagc ctggggggtc cctgagactc      60
tcctgtgcag cctctggatt cgactttgcc gagacgcctt tgtggtgggt ccgccaggct     120
ccagggagag gctggagtg gtctcagtt attggtagca accagaacaa gaccgcctac      180
gcagactccg tgaagggccg gttcaccatc tccagagaca attccaagga cacgctgtat     240
ctgcaaatga acagcctgag agccgaggac acggccgtgt attactgtgc gagagagtgg     300
atggaccact cccgccccta ctactactac ggtatggacg tctggggca ggggaccctg      360 gtcaccgtct cctca                                                     375

<210> SEQ ID NO 380
<211> LENGTH: 125
<212> TYPE: PRT
<213> ORGANISM: Homo sapiens
<220> FEATURE:
<223> OTHER INFORMATION: Abet0379

<400> SEQUENCE: 380

Glu Val Gln Leu Leu Glu Ser Gly Gly Gly Leu Val Gln Pro Gly Gly
                5                   10                  15

Ser Leu Arg Leu Ser Cys Ala Ala Ser Gly Phe Asp Phe Ala Glu Thr
            20                  25                  30

Pro Leu Trp Trp Val Arg Gln Ala Pro Gly Glu Arg Leu Glu Trp Val
        35                  40                  45

Ser Val Ile Gly Ser Asn Gln Asn Lys Thr Ala Tyr Ala Asp Ser Val
    50                  55                  60

Lys Gly Arg Phe Thr Ile Ser Arg Asp Asn Ser Lys Asp Thr Leu Tyr
65                  70                  75                  80

Leu Gln Met Asn Ser Leu Arg Ala Glu Asp Thr Ala Val Tyr Tyr Cys

```
                    85                  90                  95

Ala Arg Glu Trp Met Asp His Ser Arg Pro Tyr Tyr Tyr Gly Met
                100                 105                 110

Asp Val Trp Gly Gln Gly Thr Leu Val Thr Val Ser Ser
            115                 120                 125

<210> SEQ ID NO 381
<211> LENGTH: 5
<212> TYPE: PRT
<213> ORGANISM: Homo sapiens
<220> FEATURE:
<223> OTHER INFORMATION: Abet0379

<400> SEQUENCE: 381

Glu Thr Pro Leu Trp
                5

<210> SEQ ID NO 382
<211> LENGTH: 17
<212> TYPE: PRT
<213> ORGANISM: Homo sapiens
<220> FEATURE:
<223> OTHER INFORMATION: Abet0379

<400> SEQUENCE: 382

Val Ile Gly Ser Asn Gln Asn Lys Thr Ala Tyr Ala Asp Ser Val Lys
                5                   10                  15

Gly

<210> SEQ ID NO 383
<211> LENGTH: 16
<212> TYPE: PRT
<213> ORGANISM: Homo sapiens
<220> FEATURE:
<223> OTHER INFORMATION: Abet0379

<400> SEQUENCE: 383

Glu Trp Met Asp His Ser Arg Pro Tyr Tyr Tyr Gly Met Asp Val
                5                   10                  15

<210> SEQ ID NO 384
<211> LENGTH: 30
<212> TYPE: PRT
<213> ORGANISM: Homo sapiens
<220> FEATURE:
<223> OTHER INFORMATION: Abet0379

<400> SEQUENCE: 384

Glu Val Gln Leu Leu Glu Ser Gly Gly Gly Leu Val Gln Pro Gly Gly
                5                   10                  15

Ser Leu Arg Leu Ser Cys Ala Ala Ser Gly Phe Asp Phe Ala
            20                  25                  30

<210> SEQ ID NO 385
<211> LENGTH: 14
<212> TYPE: PRT
<213> ORGANISM: Homo sapiens
<220> FEATURE:
<223> OTHER INFORMATION: Abet0379

<400> SEQUENCE: 385

Trp Val Arg Gln Ala Pro Gly Glu Arg Leu Glu Trp Val Ser
                5                   10
```

```
<210> SEQ ID NO 386
<211> LENGTH: 32
<212> TYPE: PRT
<213> ORGANISM: Homo sapiens
<220> FEATURE:
<223> OTHER INFORMATION: Abet0379

<400> SEQUENCE: 386
```

Arg Phe Thr Ile Ser Arg Asp Asn Ser Lys Asp Thr Leu Tyr Leu Gln
 1               5                  10                  15

Met Asn Ser Leu Arg Ala Glu Asp Thr Ala Val Tyr Tyr Cys Ala Arg
             20                  25                  30

```
<210> SEQ ID NO 387
<211> LENGTH: 11
<212> TYPE: PRT
<213> ORGANISM: Homo sapiens
<220> FEATURE:
<223> OTHER INFORMATION: Abet0379

<400> SEQUENCE: 387
```

Trp Gly Gln Gly Thr Leu Val Thr Val Ser Ser
 1               5                  10

```
<210> SEQ ID NO 388
<211> LENGTH: 318
<212> TYPE: DNA
<213> ORGANISM: Homo sapiens
<220> FEATURE:
<223> OTHER INFORMATION: Abet0379

<400> SEQUENCE: 388
```
cagagcgtct tgactcagcc accctcagtg tccgtgtccc caggacagac ggccagcatc    60
acctgctctg gacataactt ggaagataaa tttgcttcct ggtatcaaca gaagtcaggc   120 cagtccctg tcctggtcat ctatcgagat gacaagcggc cctcagggat ccctgagcga   180
ttctctgcct ccaactccgg gcacactgcc actctgacca tcagcgggac ccaggctacg   240
gatggggctg actattactg tgcgacccag gacaacttca ctcgagtgtt cggcggaggg   300
accaagctga ccgtccta                                                 318

```
<210> SEQ ID NO 389
<211> LENGTH: 106
<212> TYPE: PRT
<213> ORGANISM: Homo sapiens
<220> FEATURE:
<223> OTHER INFORMATION: Abet0379

<400> SEQUENCE: 389
```

Gln Ser Val Leu Thr Gln Pro Pro Ser Val Ser Val Ser Pro Gly Gln
 1               5                  10                  15

Thr Ala Ser Ile Thr Cys Ser Gly His Asn Leu Glu Asp Lys Phe Ala
             20                  25                  30

Ser Trp Tyr Gln Gln Lys Ser Gly Gln Ser Pro Val Leu Val Ile Tyr
         35                  40                  45

Arg Asp Asp Lys Arg Pro Ser Gly Ile Pro Glu Arg Phe Ser Ala Ser
     50                  55                  60

Asn Ser Gly His Thr Ala Thr Leu Thr Ile Ser Gly Thr Gln Ala Thr
 65                  70                  75                  80

Asp Gly Ala Asp Tyr Tyr Cys Ala Thr Gln Asp Asn Phe Thr Arg Val
                 85                  90                  95

Phe Gly Gly Gly Thr Lys Leu Thr Val Leu
            100                 105

-continued

```
                100                 105

<210> SEQ ID NO 390
<211> LENGTH: 11
<212> TYPE: PRT
<213> ORGANISM: Homo sapiens
<220> FEATURE:
<223> OTHER INFORMATION: Abet0379

<400> SEQUENCE: 390

Ser Gly His Asn Leu Glu Asp Lys Phe Ala Ser
                  5                  10

<210> SEQ ID NO 391
<211> LENGTH: 7
<212> TYPE: PRT
<213> ORGANISM: Homo sapiens
<220> FEATURE:
<223> OTHER INFORMATION: Abet0379

<400> SEQUENCE: 391

Arg Asp Asp Lys Arg Pro Ser
                  5

<210> SEQ ID NO 392
<211> LENGTH: 9
<212> TYPE: PRT
<213> ORGANISM: Homo sapiens
<220> FEATURE:
<223> OTHER INFORMATION: Abet0379

<400> SEQUENCE: 392

Ala Thr Gln Asp Asn Phe Thr Arg Val
                  5

<210> SEQ ID NO 393
<211> LENGTH: 22
<212> TYPE: PRT
<213> ORGANISM: Homo sapiens
<220> FEATURE:
<223> OTHER INFORMATION: Abet0379

<400> SEQUENCE: 393

Gln Ser Val Leu Thr Gln Pro Pro Ser Val Ser Val Ser Pro Gly Gln
                  5                  10                  15

Thr Ala Ser Ile Thr Cys
            20

<210> SEQ ID NO 394
<211> LENGTH: 15
<212> TYPE: PRT
<213> ORGANISM: Homo sapiens
<220> FEATURE:
<223> OTHER INFORMATION: Abet0379

<400> SEQUENCE: 394

Trp Tyr Gln Gln Lys Ser Gly Gln Ser Pro Val Leu Val Ile Tyr
                  5                  10                  15

<210> SEQ ID NO 395
<211> LENGTH: 32
<212> TYPE: PRT
<213> ORGANISM: Homo sapiens
<220> FEATURE:
<223> OTHER INFORMATION: Abet0379

<400> SEQUENCE: 395
```

```
Gly Ile Pro Glu Arg Phe Ser Ala Ser Asn Ser Gly His Thr Ala Thr
                5                   10                  15

Leu Thr Ile Ser Gly Thr Gln Ala Thr Asp Gly Ala Asp Tyr Tyr Cys
            20                  25                  30

<210> SEQ ID NO 396
<211> LENGTH: 10
<212> TYPE: PRT
<213> ORGANISM: Homo sapiens
<220> FEATURE:
<223> OTHER INFORMATION: Abet0379

<400> SEQUENCE: 396

Phe Gly Gly Gly Thr Lys Leu Thr Val Leu
                5                   10

<210> SEQ ID NO 397
<211> LENGTH: 375
<212> TYPE: DNA
<213> ORGANISM: Homo sapiens
<220> FEATURE:
<223> OTHER INFORMATION: Abet0380

<400> SEQUENCE: 397
gaggtgcagc tgttggagtc tgggggaggc ttggtacagc ctggggggtc cctgagactc      60
tcctgtgcag cctctatggg caacttcaac taccagacta tgtggtgggt ccgccaggct     120
ccagggaggg ggctggagtg ggtctcagtt attggtaaga ccaacgagaa catcgcctac     180
gcagactccg tgaagggccg gttcaccatc tccagagaca attccaagaa cacgctgtat     240
ctgcaaatga acagcctgag agccgaggac acggccgtgt attactgtgc gagagagtgg     300
atggaccact cccgccccta ctactactac ggtatggacg tctgggggca ggggaccctg     360
gtcaccgtct cctca                                                     375

<210> SEQ ID NO 398
<211> LENGTH: 125
<212> TYPE: PRT
<213> ORGANISM: Homo sapiens
<220> FEATURE:
<223> OTHER INFORMATION: Abet0380

<400> SEQUENCE: 398

Glu Val Gln Leu Leu Glu Ser Gly Gly Gly Leu Val Gln Pro Gly Gly
                5                   10                  15

Ser Leu Arg Leu Ser Cys Ala Ala Ser Met Gly Asn Phe Asn Tyr Gln
            20                  25                  30

Thr Met Trp Trp Val Arg Gln Ala Pro Gly Arg Gly Leu Glu Trp Val
        35                  40                  45

Ser Val Ile Gly Lys Thr Asn Glu Asn Ile Ala Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Trp Met Asp His Ser Arg Pro Tyr Tyr Tyr Tyr Gly Met
            100                 105                 110

Asp Val Trp Gly Gln Gly Thr Leu Val Thr Val Ser Ser
        115                 120                 125
```

```
<210> SEQ ID NO 399
<211> LENGTH: 5
<212> TYPE: PRT
<213> ORGANISM: Homo sapiens
<220> FEATURE:
<223> OTHER INFORMATION: Abet0380

<400> SEQUENCE: 399

Tyr Gln Thr Met Trp
                5

<210> SEQ ID NO 400
<211> LENGTH: 17
<212> TYPE: PRT
<213> ORGANISM: Homo sapiens
<220> FEATURE:
<223> OTHER INFORMATION: Abet0380

<400> SEQUENCE: 400

Val Ile Gly Lys Thr Asn Glu Asn Ile Ala Tyr Ala Asp Ser Val Lys
                5                   10                  15

Gly

<210> SEQ ID NO 401
<211> LENGTH: 16
<212> TYPE: PRT
<213> ORGANISM: Homo sapiens
<220> FEATURE:
<223> OTHER INFORMATION: Abet0380

<400> SEQUENCE: 401

Glu Trp Met Asp His Ser Arg Pro Tyr Tyr Tyr Tyr Gly Met Asp Val
                5                   10                  15

<210> SEQ ID NO 402
<211> LENGTH: 30
<212> TYPE: PRT
<213> ORGANISM: Homo sapiens
<220> FEATURE:
<223> OTHER INFORMATION: Abet0380

<400> SEQUENCE: 402

Glu Val Gln Leu Leu Glu Ser Gly Gly Gly Leu Val Gln Pro Gly Gly
                5                   10                  15

Ser Leu Arg Leu Ser Cys Ala Ala Ser Met Gly Asn Phe Asn
            20                  25                  30

<210> SEQ ID NO 403
<211> LENGTH: 14
<212> TYPE: PRT
<213> ORGANISM: Homo sapiens
<220> FEATURE:
<223> OTHER INFORMATION: Abet0380

<400> SEQUENCE: 403

Trp Val Arg Gln Ala Pro Gly Arg Gly Leu Glu Trp Val Ser
                5                   10

<210> SEQ ID NO 404
<211> LENGTH: 32
<212> TYPE: PRT
<213> ORGANISM: Homo sapiens
<220> FEATURE:
<223> OTHER INFORMATION: Abet0380

<400> SEQUENCE: 404
```

```
Arg Phe Thr Ile Ser Arg Asp Asn Ser Lys Asn Thr Leu Tyr Leu Gln
            5                   10                  15

Met Asn Ser Leu Arg Ala Glu Asp Thr Ala Val Tyr Tyr Cys Ala Arg
            20                  25                  30

<210> SEQ ID NO 405
<211> LENGTH: 11
<212> TYPE: PRT
<213> ORGANISM: Homo sapiens
<220> FEATURE:
<223> OTHER INFORMATION: Abet0380

<400> SEQUENCE: 405

Trp Gly Gln Gly Thr Leu Val Thr Val Ser Ser
            5                   10

<210> SEQ ID NO 406
<211> LENGTH: 318
<212> TYPE: DNA
<213> ORGANISM: Homo sapiens
<220> FEATURE:
<223> OTHER INFORMATION: Abet0380

<400> SEQUENCE: 406
tcgtacgagt tgactcagcc accctcagtg tccgtgtccc caggacagac ggccagcatc    60
acctgctctg gacataactt ggaagataaa tttgcttcct ggtatcaaca gaagccaggc   120
cagtcccctg tcctggtcat ctatcgagat gacaagcggc cctcagggat ccctgagcga   180
ttctctgcct ccaactctgg gcacactgcc actctgacca tcagcgggac ccaggctacg   240
gatgaggctg actattactg ttcgtcccag gacacggtga ctcgagtgtt cggcggaggg   300
accaagctga ccgtccta                                                  318

<210> SEQ ID NO 407
<211> LENGTH: 106
<212> TYPE: PRT
<213> ORGANISM: Homo sapiens
<220> FEATURE:
<223> OTHER INFORMATION: Abet0380

<400> SEQUENCE: 407

Ser Tyr Glu Leu Thr Gln Pro Pro Ser Val Ser Val Ser Pro Gly Gln
            5                   10                  15

Thr Ala Ser Ile Thr Cys Ser Gly His Asn Leu Glu Asp Lys Phe Ala
            20                  25                  30

Ser Trp Tyr Gln Gln Lys Pro Gly Gln Ser Pro Val Leu Val Ile Tyr
            35                  40                  45

Arg Asp Asp Lys Arg Pro Ser Gly Ile Pro Glu Arg Phe Ser Ala Ser
        50                  55                  60

Asn Ser Gly His Thr Ala Thr Leu Thr Ile Ser Gly Thr Gln Ala Thr
65                  70                  75                  80

Asp Glu Ala Asp Tyr Tyr Cys Ser Ser Gln Asp Thr Val Thr Arg Val
            85                  90                  95

Phe Gly Gly Gly Thr Lys Leu Thr Val Leu
            100                 105

<210> SEQ ID NO 408
<211> LENGTH: 11
<212> TYPE: PRT
<213> ORGANISM: Homo sapiens
<220> FEATURE:
<223> OTHER INFORMATION: Abet0380
```

```
<400> SEQUENCE: 408

Ser Gly His Asn Leu Glu Asp Lys Phe Ala Ser
                5                  10

<210> SEQ ID NO 409
<211> LENGTH: 7
<212> TYPE: PRT
<213> ORGANISM: Homo sapiens
<220> FEATURE:
<223> OTHER INFORMATION: Abet0380

<400> SEQUENCE: 409

Arg Asp Asp Lys Arg Pro Ser
                5

<210> SEQ ID NO 410
<211> LENGTH: 9
<212> TYPE: PRT
<213> ORGANISM: Homo sapiens
<220> FEATURE:
<223> OTHER INFORMATION: Abet0380

<400> SEQUENCE: 410

Ser Ser Gln Asp Thr Val Thr Arg Val
                5

<210> SEQ ID NO 411
<211> LENGTH: 22
<212> TYPE: PRT
<213> ORGANISM: Homo sapiens
<220> FEATURE:
<223> OTHER INFORMATION: Abet0380

<400> SEQUENCE: 411

Ser Tyr Glu Leu Thr Gln Pro Pro Ser Val Ser Val Ser Pro Gly Gln
                5                  10                  15

Thr Ala Ser Ile Thr Cys
            20

<210> SEQ ID NO 412
<211> LENGTH: 15
<212> TYPE: PRT
<213> ORGANISM: Homo sapiens
<220> FEATURE:
<223> OTHER INFORMATION: Abet0380

<400> SEQUENCE: 412

Trp Tyr Gln Gln Lys Pro Gly Gln Ser Pro Val Leu Val Ile Tyr
                5                  10                  15

<210> SEQ ID NO 413
<211> LENGTH: 32
<212> TYPE: PRT
<213> ORGANISM: Homo sapiens
<220> FEATURE:
<223> OTHER INFORMATION: Abet0380

<400> SEQUENCE: 413

Gly Ile Pro Glu Arg Phe Ser Ala Ser Asn Ser Gly His Thr Ala Thr
                5                  10                  15

Leu Thr Ile Ser Gly Thr Gln Ala Thr Asp Glu Ala Asp Tyr Tyr Cys
            20                  25                  30

<210> SEQ ID NO 414
```

<210> SEQ ID NO 414
<211> LENGTH: 10
<212> TYPE: PRT
<213> ORGANISM: Homo sapiens
<220> FEATURE:
<223> OTHER INFORMATION: Abet0380

<400> SEQUENCE: 414

Phe Gly Gly Gly Thr Lys Leu Thr Val Leu
                5                   10

<210> SEQ ID NO 415
<211> LENGTH: 375
<212> TYPE: DNA
<213> ORGANISM: Homo sapiens
<220> FEATURE:
<223> OTHER INFORMATION: Abet0381

<400> SEQUENCE: 415
gaggtgcagc tgttggagtc tgggggaggc ttggtacagc ctgggggtc cttgagactc      60 tcctgtgcag cctcttcccc gtcgttcccg cgggagacca tgtggtgggt ccgccaggct    120
ccagggaagg ggcttgagtg ggtctcagtt attggtaccc agccgaaccg cttgacgtac    180
gcagactccg tgaagggccg gttcaccatc tccagagaca attccaagaa cacgctgtat    240
ctgcaaatga acagcctgag agccgaggac acggccgtgt attactgtgc gagagagtgg    300
atggaccact cccgccccta ctactactac ggtatagacg tctggggca ggggaccctg     360 gtcaccgtct cccca                                                    375

<210> SEQ ID NO 416
<211> LENGTH: 125
<212> TYPE: PRT
<213> ORGANISM: Homo sapiens
<220> FEATURE:
<223> OTHER INFORMATION: Abet0381

<400> SEQUENCE: 416

Glu Val Gln Leu Leu Glu Ser Gly Gly Gly Leu Val Gln Pro Gly Gly
                5                   10                  15

Ser Leu Arg Leu Ser Cys Ala Ala Ser Ser Pro Ser Phe Pro Arg Glu
            20                  25                  30

Thr Met Trp Trp Val Arg Gln Ala Pro Gly Lys Gly Leu Glu Trp Val
        35                  40                  45

Ser Val Ile Gly Thr Gln Pro Asn Arg Leu Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Trp Met Asp His Ser Arg Pro Tyr Tyr Tyr Tyr Gly Ile
            100                 105                 110

Asp Val Trp Gly Gln Gly Thr Leu Val Thr Val Ser Pro
        115                 120                 125

<210> SEQ ID NO 417
<211> LENGTH: 5
<212> TYPE: PRT
<213> ORGANISM: Homo sapiens
<220> FEATURE:
<223> OTHER INFORMATION: Abet0381

<400> SEQUENCE: 417

Arg Glu Thr Met Trp
                5

<210> SEQ ID NO 418
<211> LENGTH: 17
<212> TYPE: PRT
<213> ORGANISM: Homo sapiens
<220> FEATURE:
<223> OTHER INFORMATION: Abet0381

<400> SEQUENCE: 418

Val Ile Gly Thr Gln Pro Asn Arg Leu Thr Tyr Ala Asp Ser Val Lys
                5                   10                  15
Gly

<210> SEQ ID NO 419
<211> LENGTH: 16
<212> TYPE: PRT
<213> ORGANISM: Homo sapiens
<220> FEATURE:
<223> OTHER INFORMATION: Abet0381

<400> SEQUENCE: 419

Glu Trp Met Asp His Ser Arg Pro Tyr Tyr Tyr Gly Ile Asp Val
                5                   10                  15

<210> SEQ ID NO 420
<211> LENGTH: 30
<212> TYPE: PRT
<213> ORGANISM: Homo sapiens
<220> FEATURE:
<223> OTHER INFORMATION: Abet0381

<400> SEQUENCE: 420

Glu Val Gln Leu Leu Glu Ser Gly Gly Gly Leu Val Gln Pro Gly Gly
                5                   10                  15
Ser Leu Arg Leu Ser Cys Ala Ala Ser Ser Pro Ser Phe Pro
            20                  25                  30

<210> SEQ ID NO 421
<211> LENGTH: 14
<212> TYPE: PRT
<213> ORGANISM: Homo sapiens
<220> FEATURE:
<223> OTHER INFORMATION: Abet0381

<400> SEQUENCE: 421

Trp Val Arg Gln Ala Pro Gly Lys Gly Leu Glu Trp Val Ser
                5                   10

<210> SEQ ID NO 422
<211> LENGTH: 32
<212> TYPE: PRT
<213> ORGANISM: Homo sapiens
<220> FEATURE:
<223> OTHER INFORMATION: Abet0381

<400> SEQUENCE: 422

Arg Phe Thr Ile Ser Arg Asp Asn Ser Lys Asn Thr Leu Tyr Leu Gln
                5                   10                  15
Met Asn Ser Leu Arg Ala Glu Asp Thr Ala Val Tyr Tyr Cys Ala Arg
            20                  25                  30

<210> SEQ ID NO 423
<211> LENGTH: 11

```
<212> TYPE: PRT
<213> ORGANISM: Homo sapiens
<220> FEATURE:
<223> OTHER INFORMATION: Abet0381

<400> SEQUENCE: 423

Trp Gly Gln Gly Thr Leu Val Thr Val Ser Pro
                5                   10

<210> SEQ ID NO 424
<211> LENGTH: 318
<212> TYPE: DNA
<213> ORGANISM: Homo sapiens
<220> FEATURE:
<223> OTHER INFORMATION: Abet0381

<400> SEQUENCE: 424
tcgtacgagt tgactcagcc accctcagtg tccgcgtccc caggacagac ggccagcatc      60
acctgctctg gacataactt ggaagataaa tttgtttcct ggtatcaaca gaagccaggc     120
cagtcccctg tcctggtcat ctatcgagat gacaagcgac cctcagggat ccctgagcga     180
ttctctgcct ccaactctgg gcacactgcc actctgacca tcagcgggac ccaggctacg     240
gatgaggcta actattactg ttcgtcccag gacacggtga ctcgagcgtt cggcggaggg     300
accaagctga ccgtccta                                                   318

<210> SEQ ID NO 425
<211> LENGTH: 106
<212> TYPE: PRT
<213> ORGANISM: Homo sapiens
<220> FEATURE:
<223> OTHER INFORMATION: Abet0381

<400> SEQUENCE: 425

Ser Tyr Glu Leu Thr Gln Pro Pro Ser Val Ser Ala Ser Pro Gly Gln
                5                   10                  15

Thr Ala Ser Ile Thr Cys Ser Gly His Asn Leu Glu Asp Lys Phe Val
            20                  25                  30

Ser Trp Tyr Gln Gln Lys Pro Gly Gln Ser Pro Val Leu Val Ile Tyr
        35                  40                  45

Arg Asp Asp Lys Arg Pro Ser Gly Ile Pro Glu Arg Phe Ser Ala Ser
    50                  55                  60

Asn Ser Gly His Thr Ala Thr Leu Thr Ile Ser Gly Thr Gln Ala Thr
65                  70                  75                  80

Asp Glu Ala Asn Tyr Tyr Cys Ser Ser Gln Asp Thr Val Thr Arg Ala
                85                  90                  95

Phe Gly Gly Gly Thr Lys Leu Thr Val Leu
            100                 105

<210> SEQ ID NO 426
<211> LENGTH: 11
<212> TYPE: PRT
<213> ORGANISM: Homo sapiens
<220> FEATURE:
<223> OTHER INFORMATION: Abet0381

<400> SEQUENCE: 426

Ser Gly His Asn Leu Glu Asp Lys Phe Val Ser
                5                   10

<210> SEQ ID NO 427
<211> LENGTH: 7
```

```
<212> TYPE: PRT
<213> ORGANISM: Homo sapiens
<220> FEATURE:
<223> OTHER INFORMATION: Abet0381

<400> SEQUENCE: 427

Arg Asp Asp Lys Arg Pro Ser
                5

<210> SEQ ID NO 428
<211> LENGTH: 9
<212> TYPE: PRT
<213> ORGANISM: Homo sapiens
<220> FEATURE:
<223> OTHER INFORMATION: Abet0381

<400> SEQUENCE: 428

Ser Ser Gln Asp Thr Val Thr Arg Ala
                5

<210> SEQ ID NO 429
<211> LENGTH: 22
<212> TYPE: PRT
<213> ORGANISM: Homo sapiens
<220> FEATURE:
<223> OTHER INFORMATION: Abet0381

<400> SEQUENCE: 429

Ser Tyr Glu Leu Thr Gln Pro Pro Ser Val Ser Ala Ser Pro Gly Gln
                5                   10                  15

Thr Ala Ser Ile Thr Cys
            20

<210> SEQ ID NO 430
<211> LENGTH: 15
<212> TYPE: PRT
<213> ORGANISM: Homo sapiens
<220> FEATURE:
<223> OTHER INFORMATION: Abet0381

<400> SEQUENCE: 430

Trp Tyr Gln Gln Lys Pro Gly Gln Ser Pro Val Leu Val Ile Tyr
                5                   10                  15

<210> SEQ ID NO 431
<211> LENGTH: 32
<212> TYPE: PRT
<213> ORGANISM: Homo sapiens
<220> FEATURE:
<223> OTHER INFORMATION: Abet0381

<400> SEQUENCE: 431

Gly Ile Pro Glu Arg Phe Ser Ala Ser Asn Ser Gly His Thr Ala Thr
                5                   10                  15

Leu Thr Ile Ser Gly Thr Gln Ala Thr Asp Glu Ala Asn Tyr Tyr Cys
            20                  25                  30

<210> SEQ ID NO 432
<211> LENGTH: 10
<212> TYPE: PRT
<213> ORGANISM: Homo sapiens
<220> FEATURE:
<223> OTHER INFORMATION: Abet0381

<400> SEQUENCE: 432

Phe Gly Gly Gly Thr Lys Leu Thr Val Leu
```

<210> SEQ ID NO 433
<211> LENGTH: 375
<212> TYPE: DNA
<213> ORGANISM: Homo sapiens
<220> FEATURE:
<223> OTHER INFORMATION: Abet0382

<400> SEQUENCE: 433

```
gaggtgcagc tgttggagtc tgggggaggc ttggtacagc ctggggggtc cctgaggctc    60
tcctgtgcag cctctggatt ccactttacc aactccatca tgtggtgggt ccgccaggct   120
ccagggaagg ggctggagtg ggtctcagtt attggtagcg aggcgcaccg cgtcacgtac   180
gcagactccg tgaagggccg gttcaccatc tccagagaca attccaagaa cacgctgtat   240
ctgcaaatga acagcctgag agccgaggac acggccgtgt attactgtgc gagagagtgg   300
atggaccact cccgccccta ctactactac ggtatggacg tctggggggca ggggaccctg   360
gtcaccgtct cctca                                                    375
```

<210> SEQ ID NO 434
<211> LENGTH: 125
<212> TYPE: PRT
<213> ORGANISM: Homo sapiens
<220> FEATURE:
<223> OTHER INFORMATION: Abet0382

<400> SEQUENCE: 434

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe His Phe Thr Asn Ser
            20                  25                  30

Ile Met Trp Trp Val Arg Gln Ala Pro Gly Lys Gly Leu Glu Trp Val
        35                  40                  45

Ser Val Ile Gly Ser Glu Ala His Arg Val Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Trp Met Asp His Ser Arg Pro Tyr Tyr Tyr Tyr Gly Met
            100                 105                 110

Asp Val Trp Gly Gln Gly Thr Leu Val Thr Val Ser Ser
        115                 120                 125

<210> SEQ ID NO 435
<211> LENGTH: 5
<212> TYPE: PRT
<213> ORGANISM: Homo sapiens
<220> FEATURE:
<223> OTHER INFORMATION: Abet0382

<400> SEQUENCE: 435

Asn Ser Ile Met Trp
1               5

<210> SEQ ID NO 436
<211> LENGTH: 17
<212> TYPE: PRT
<213> ORGANISM: Homo sapiens
<220> FEATURE:

<223> OTHER INFORMATION: Abet0382

<400> SEQUENCE: 436

Val Ile Gly Ser Glu Ala His Arg Val Thr Tyr Ala Asp Ser Val Lys
                5                   10                  15
Gly

<210> SEQ ID NO 437
<211> LENGTH: 16
<212> TYPE: PRT
<213> ORGANISM: Homo sapiens
<220> FEATURE:
<223> OTHER INFORMATION: Abet0382

<400> SEQUENCE: 437

Glu Trp Met Asp His Ser Arg Pro Tyr Tyr Tyr Tyr Gly Met Asp Val
                5                   10                  15

<210> SEQ ID NO 438
<211> LENGTH: 30
<212> TYPE: PRT
<213> ORGANISM: Homo sapiens
<220> FEATURE:
<223> OTHER INFORMATION: Abet0382

<400> SEQUENCE: 438

Glu Val Gln Leu Leu Glu Ser Gly Gly Gly Leu Val Gln Pro Gly Gly
                5                   10                  15

Ser Leu Arg Leu Ser Cys Ala Ala Ser Gly Phe His Phe Thr
            20                  25                  30

<210> SEQ ID NO 439
<211> LENGTH: 14
<212> TYPE: PRT
<213> ORGANISM: Homo sapiens
<220> FEATURE:
<223> OTHER INFORMATION: Abet0382

<400> SEQUENCE: 439

Trp Val Arg Gln Ala Pro Gly Lys Gly Leu Glu Trp Val Ser
                5                   10

<210> SEQ ID NO 440
<211> LENGTH: 32
<212> TYPE: PRT
<213> ORGANISM: Homo sapiens
<220> FEATURE:
<223> OTHER INFORMATION: Abet0382

<400> SEQUENCE: 440

Arg Phe Thr Ile Ser Arg Asp Asn Ser Lys Asn Thr Leu Tyr Leu Gln
                5                   10                  15

Met Asn Ser Leu Arg Ala Glu Asp Thr Ala Val Tyr Tyr Cys Ala Arg
            20                  25                  30

<210> SEQ ID NO 441
<211> LENGTH: 11
<212> TYPE: PRT
<213> ORGANISM: Homo sapiens
<220> FEATURE:
<223> OTHER INFORMATION: Abet0382

<400> SEQUENCE: 441

Trp Gly Gln Gly Thr Leu Val Thr Val Ser Ser
                5                   10

<210> SEQ ID NO 442
<211> LENGTH: 318
<212> TYPE: DNA
<213> ORGANISM: Homo sapiens
<220> FEATURE:
<223> OTHER INFORMATION: Abet0382

<400> SEQUENCE: 442

```
tcgtacgagt tgattcagcc accctcagtg tccgtgtccc caggacagac agccagcatc    60
acctgctctg gacataactt ggaagataaa tttgcttcct ggtatcaaca gaagccaggc   120
cagtcccctg tcctggtcat ctatcgagat gacaagcggc cctcagggat ccctgagcga   180
ttctctgcca ccaactctgg gcacactgcc actctgacca tcagcgggac ccaggctacg   240
gatgaggctg actattactg ttcgtcccag gactcggtga ctcgagtgtt cggcggaggg   300
accaagctga ccgtccta                                                 318
```

<210> SEQ ID NO 443
<211> LENGTH: 106
<212> TYPE: PRT
<213> ORGANISM: Homo sapiens
<220> FEATURE:
<223> OTHER INFORMATION: Abet0382

<400> SEQUENCE: 443

Ser Tyr Glu Leu Ile Gln Pro Pro Ser Val Ser Val Ser Pro Gly Gln
                 5                  10                  15

Thr Ala Ser Ile Thr Cys Ser Gly His Asn Leu Glu Asp Lys Phe Ala
             20                  25                  30

Ser Trp Tyr Gln Gln Lys Pro Gly Gln Ser Pro Val Leu Val Ile Tyr
         35                  40                  45

Arg Asp Asp Lys Arg Pro Ser Gly Ile Pro Glu Arg Phe Ser Ala Thr
     50                  55                  60

Asn Ser Gly His Thr Ala Thr Leu Thr Ile Ser Gly Thr Gln Ala Thr
 65                  70                  75                  80

Asp Glu Ala Asp Tyr Tyr Cys Ser Ser Gln Asp Ser Val Thr Arg Val
                 85                  90                  95

Phe Gly Gly Gly Thr Lys Leu Thr Val Leu
            100                 105

<210> SEQ ID NO 444
<211> LENGTH: 11
<212> TYPE: PRT
<213> ORGANISM: Homo sapiens
<220> FEATURE:
<223> OTHER INFORMATION: Abet0382

<400> SEQUENCE: 444

Ser Gly His Asn Leu Glu Asp Lys Phe Ala Ser
                 5                  10

<210> SEQ ID NO 445
<211> LENGTH: 7
<212> TYPE: PRT
<213> ORGANISM: Homo sapiens
<220> FEATURE:
<223> OTHER INFORMATION: Abet0382

<400> SEQUENCE: 445

Arg Asp Asp Lys Arg Pro Ser
                 5

```
<210> SEQ ID NO 446
<211> LENGTH: 9
<212> TYPE: PRT
<213> ORGANISM: Homo sapiens
<220> FEATURE:
<223> OTHER INFORMATION: Abet0382

<400> SEQUENCE: 446

Ser Ser Gln Asp Ser Val Thr Arg Val
                5

<210> SEQ ID NO 447
<211> LENGTH: 22
<212> TYPE: PRT
<213> ORGANISM: Homo sapiens
<220> FEATURE:
<223> OTHER INFORMATION: Abet0382

<400> SEQUENCE: 447

Ser Tyr Glu Leu Ile Gln Pro Pro Ser Val Ser Val Ser Pro Gly Gln
                5                   10                  15

Thr Ala Ser Ile Thr Cys
            20

<210> SEQ ID NO 448
<211> LENGTH: 15
<212> TYPE: PRT
<213> ORGANISM: Homo sapiens
<220> FEATURE:
<223> OTHER INFORMATION: Abet0382

<400> SEQUENCE: 448

Trp Tyr Gln Gln Lys Pro Gly Gln Ser Pro Val Leu Val Ile Tyr
                5                   10                  15

<210> SEQ ID NO 449
<211> LENGTH: 32
<212> TYPE: PRT
<213> ORGANISM: Homo sapiens
<220> FEATURE:
<223> OTHER INFORMATION: Abet0382

<400> SEQUENCE: 449

Gly Ile Pro Glu Arg Phe Ser Ala Thr Asn Ser Gly His Thr Ala Thr
                5                   10                  15

Leu Thr Ile Ser Gly Thr Gln Ala Thr Asp Glu Ala Asp Tyr Tyr Cys
            20                  25                  30

<210> SEQ ID NO 450
<211> LENGTH: 10
<212> TYPE: PRT
<213> ORGANISM: Homo sapiens
<220> FEATURE:
<223> OTHER INFORMATION: Abet0382

<400> SEQUENCE: 450

Phe Gly Gly Gly Thr Lys Leu Thr Val Leu
                5                   10

<210> SEQ ID NO 451
<211> LENGTH: 375
<212> TYPE: DNA
<213> ORGANISM: Homo sapiens
<220> FEATURE:
<223> OTHER INFORMATION: Abet0383
```

<400> SEQUENCE: 451

```
gaggtgcagc tgttggagtc cgggggaggc ttggtacagc ctggggggtc cctgaaactc      60
tcctgtgcag cctctggatt cacgtttgac tggtacccga tgtggtgggt ccgccaggct     120
ccagggaaga ggctggagtg gatctcagtt attggtgcgg acaacgccaa gatcgcctac     180
gcagactccg tgaagggccg gtttaccatc tccagagaca attccaagaa cacgctgtat     240
ctgcaaatga acagcctgag agccgaggac acggccgtgt attactgtgc gagagagtgg     300
atgggccact cccgccccta ctactactac ggtatggacg tctggggggca ggggaccccg     360
gtcaccgtct cctca                                                     375
```

<210> SEQ ID NO 452
<211> LENGTH: 125
<212> TYPE: PRT
<213> ORGANISM: Homo sapiens
<220> FEATURE:
<223> OTHER INFORMATION: Abet0383

<400> SEQUENCE: 452

```
Glu Val Gln Leu Leu Glu Ser Gly Gly Gly Leu Val Gln Pro Gly Gly
                5                   10                  15
Ser Leu Lys Leu Ser Cys Ala Ala Ser Gly Phe Thr Phe Asp Trp Tyr
            20                  25                  30
Pro Met Trp Trp Val Arg Gln Ala Pro Gly Lys Arg Leu Glu Trp Ile
        35                  40                  45
Ser Val Ile Gly Ala Asp Asn Ala Lys Ile Ala Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Glu Trp Met Gly His Ser Arg Pro Tyr Tyr Tyr Gly Met
            100                 105                 110
Asp Val Trp Gly Gln Gly Thr Pro Val Thr Val Ser Ser
        115                 120                 125
```

<210> SEQ ID NO 453
<211> LENGTH: 5
<212> TYPE: PRT
<213> ORGANISM: Homo sapiens
<220> FEATURE:
<223> OTHER INFORMATION: Abet0383

<400> SEQUENCE: 453

```
Trp Tyr Pro Met Trp
                5
```

<210> SEQ ID NO 454
<211> LENGTH: 17
<212> TYPE: PRT
<213> ORGANISM: Homo sapiens
<220> FEATURE:
<223> OTHER INFORMATION: Abet0383

<400> SEQUENCE: 454

```
Val Ile Gly Ala Asp Asn Ala Lys Ile Ala Tyr Ala Asp Ser Val Lys
                5                   10                  15
Gly
```

<210> SEQ ID NO 455
<211> LENGTH: 16
<212> TYPE: PRT
<213> ORGANISM: Homo sapiens
<220> FEATURE:
<223> OTHER INFORMATION: Abet0383

<400> SEQUENCE: 455

Glu Trp Met Gly His Ser Arg Pro Tyr Tyr Tyr Gly Met Asp Val
                5                   10                  15

<210> SEQ ID NO 456
<211> LENGTH: 30
<212> TYPE: PRT
<213> ORGANISM: Homo sapiens
<220> FEATURE:
<223> OTHER INFORMATION: Abet0383

<400> SEQUENCE: 456

Glu Val Gln Leu Leu Glu Ser Gly Gly Gly Leu Val Gln Pro Gly Gly
                5                   10                  15

Ser Leu Lys Leu Ser Cys Ala Ala Ser Gly Phe Thr Phe Asp
            20                  25                  30

<210> SEQ ID NO 457
<211> LENGTH: 14
<212> TYPE: PRT
<213> ORGANISM: Homo sapiens
<220> FEATURE:
<223> OTHER INFORMATION: Abet0383

<400> SEQUENCE: 457

Trp Val Arg Gln Ala Pro Gly Lys Arg Leu Glu Trp Ile Ser
                5                   10

<210> SEQ ID NO 458
<211> LENGTH: 32
<212> TYPE: PRT
<213> ORGANISM: Homo sapiens
<220> FEATURE:
<223> OTHER INFORMATION: Abet0383

<400> SEQUENCE: 458

Arg Phe Thr Ile Ser Arg Asp Asn Ser Lys Asn Thr Leu Tyr Leu Gln
                5                   10                  15

Met Asn Ser Leu Arg Ala Glu Asp Thr Ala Val Tyr Tyr Cys Ala Arg
            20                  25                  30

<210> SEQ ID NO 459
<211> LENGTH: 11
<212> TYPE: PRT
<213> ORGANISM: Homo sapiens
<220> FEATURE:
<223> OTHER INFORMATION: Abet0383

<400> SEQUENCE: 459

Trp Gly Gln Gly Thr Pro Val Thr Val Ser Ser
                5                   10

<210> SEQ ID NO 460
<211> LENGTH: 318
<212> TYPE: DNA
<213> ORGANISM: Homo sapiens
<220> FEATURE:
<223> OTHER INFORMATION: Abet0383

-continued

<400> SEQUENCE: 460

```
tcgtacgagt tgactcagcc accctcagta tccgtgtccc caggacagac ggccagcatc    60
acctgctctg gacataactt gggagataaa tttgcttcct ggtatcaaca gaagccaggc   120
cagtcccctg tcctggtcat ctatcgagat gacaagcggc cctcaggat cccctgagcga   180
ttctctgcct ccaactctgg gcacactgcc actctgacca ttagcgggac ccaggctacg   240
gatgaggctg actattactg ttcgtcccag gacacggtga ctcgagtgtt cggcggaggg   300
accaagctga ccgtcctg                                                 318
```

<210> SEQ ID NO 461
<211> LENGTH: 106
<212> TYPE: PRT
<213> ORGANISM: Homo sapiens
<220> FEATURE:
<223> OTHER INFORMATION: Abet0383

<400> SEQUENCE: 461

Ser Tyr Glu Leu Thr Gln Pro Pro Ser Val Ser Val Ser Pro Gly Gln
1               5                   10                  15
Thr Ala Ser Ile Thr Cys Ser Gly His Asn Leu Gly Asp Lys Phe Ala
            20                  25                  30
Ser Trp Tyr Gln Gln Lys Pro Gly Gln Ser Pro Val Leu Val Ile Tyr
        35                  40                  45
Arg Asp Asp Lys Arg Pro Ser Gly Ile Pro Glu Arg Phe Ser Ala Ser
    50                  55                  60
Asn Ser Gly His Thr Ala Thr Leu Thr Ile Ser Gly Thr Gln Ala Thr
65                  70                  75                  80
Asp Glu Ala Asp Tyr Tyr Cys Ser Ser Gln Asp Thr Val Thr Arg Val
                85                  90                  95
Phe Gly Gly Gly Thr Lys Leu Thr Val Leu
            100                 105

<210> SEQ ID NO 462
<211> LENGTH: 11
<212> TYPE: PRT
<213> ORGANISM: Homo sapiens
<220> FEATURE:
<223> OTHER INFORMATION: Abet0383

<400> SEQUENCE: 462

Ser Gly His Asn Leu Gly Asp Lys Phe Ala Ser
1               5                   10

<210> SEQ ID NO 463
<211> LENGTH: 7
<212> TYPE: PRT
<213> ORGANISM: Homo sapiens
<220> FEATURE:
<223> OTHER INFORMATION: Abet0383

<400> SEQUENCE: 463

Arg Asp Asp Lys Arg Pro Ser
1               5

<210> SEQ ID NO 464
<211> LENGTH: 9
<212> TYPE: PRT
<213> ORGANISM: Homo sapiens
<220> FEATURE:
<223> OTHER INFORMATION: Abet0383

-continued

<400> SEQUENCE: 464

Ser Ser Gln Asp Thr Val Thr Arg Val
              5

<210> SEQ ID NO 465
<211> LENGTH: 22
<212> TYPE: PRT
<213> ORGANISM: Homo sapiens
<220> FEATURE:
<223> OTHER INFORMATION: Abet0383

<400> SEQUENCE: 465

Ser Tyr Glu Leu Thr Gln Pro Pro Ser Val Ser Val Ser Pro Gly Gln
              5                  10                  15

Thr Ala Ser Ile Thr Cys
            20

<210> SEQ ID NO 466
<211> LENGTH: 15
<212> TYPE: PRT
<213> ORGANISM: Homo sapiens
<220> FEATURE:
<223> OTHER INFORMATION: Abet0383

<400> SEQUENCE: 466

Trp Tyr Gln Gln Lys Pro Gly Gln Ser Pro Val Leu Val Ile Tyr
              5                  10                  15

<210> SEQ ID NO 467
<211> LENGTH: 32
<212> TYPE: PRT
<213> ORGANISM: Homo sapiens
<220> FEATURE:
<223> OTHER INFORMATION: Abet0383

<400> SEQUENCE: 467

Gly Ile Pro Glu Arg Phe Ser Ala Ser Asn Ser Gly His Thr Ala Thr
              5                  10                  15

Leu Thr Ile Ser Gly Thr Gln Ala Thr Asp Glu Ala Asp Tyr Tyr Cys
            20                  25                  30

<210> SEQ ID NO 468
<211> LENGTH: 10
<212> TYPE: PRT
<213> ORGANISM: Homo sapiens
<220> FEATURE:
<223> OTHER INFORMATION: Abet0383

<400> SEQUENCE: 468

Phe Gly Gly Gly Thr Lys Leu Thr Val Leu
              5                  10

<210> SEQ ID NO 469
<211> LENGTH: 375
<212> TYPE: DNA
<213> ORGANISM: Homo sapiens
<220> FEATURE:
<223> OTHER INFORMATION: Abet0343-GL

<400> SEQUENCE: 469
gaggtgcagc tgttggagtc tgggggaggc ttggtacagc ctggggggtc cctgagactc      60
tcctgtgcag cctctggatt caactttaac caccaggtga tgtggtgggt ccgccaggct     120
ccagggaagg ggctggagtg ggtctcagtt attggtaaga ccaacgagaa catcgcctac    180

```
gcagactccg tgaagggccg gttcaccatc tccagagaca attccaagaa cacgctgtat    240
ctgcaaatga acagcctgag agccgaggac acggccgtgt attactgtgc gagagagtgg    300
atggaccact ctcgccccta ctactactac ggtatggacg tctgggggca ggggaccctg    360
gtcaccgtct cctca                                                    375
```

```
<210> SEQ ID NO 470
<211> LENGTH: 125
<212> TYPE: PRT
<213> ORGANISM: Homo sapiens
<220> FEATURE:
<223> OTHER INFORMATION: Abet0343-GL

<400> SEQUENCE: 470
```

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Asn Phe Asn His Gln
             20                  25                  30

Val Met Trp Trp Val Arg Gln Ala Pro Gly Lys Gly Leu Glu Trp Val
         35                  40                  45

Ser Val Ile Gly Lys Thr Asn Glu Asn Ile Ala Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Trp Met Asp His Ser Arg Pro Tyr Tyr Tyr Tyr Gly Met
            100                 105                 110

Asp Val Trp Gly Gln Gly Thr Leu Val Thr Val Ser Ser
        115                 120                 125

```
<210> SEQ ID NO 471
<211> LENGTH: 5
<212> TYPE: PRT
<213> ORGANISM: Homo sapiens
<220> FEATURE:
<223> OTHER INFORMATION: Abet0343-GL

<400> SEQUENCE: 471
```

His Gln Val Met Trp
  1               5

```
<210> SEQ ID NO 472
<211> LENGTH: 17
<212> TYPE: PRT
<213> ORGANISM: Homo sapiens
<220> FEATURE:
<223> OTHER INFORMATION: Abet0343-GL

<400> SEQUENCE: 472
```

Val Ile Gly Lys Thr Asn Glu Asn Ile Ala Tyr Ala Asp Ser Val Lys
  1               5                  10                  15

Gly

```
<210> SEQ ID NO 473
<211> LENGTH: 16
<212> TYPE: PRT
<213> ORGANISM: Homo sapiens
<220> FEATURE:
<223> OTHER INFORMATION: Abet0343-GL

<400> SEQUENCE: 473
```

```
Glu Trp Met Asp His Ser Arg Pro Tyr Tyr Tyr Gly Met Asp Val
                 5                  10                  15
```

```
<210> SEQ ID NO 474
<211> LENGTH: 30
<212> TYPE: PRT
<213> ORGANISM: Homo sapiens
<220> FEATURE:
<223> OTHER INFORMATION: Abet0343-GL
```

<400> SEQUENCE: 474

```
Glu Val Gln Leu Leu Glu Ser Gly Gly Gly Leu Val Gln Pro Gly Gly
                 5                  10                  15

Ser Leu Arg Leu Ser Cys Ala Ala Ser Gly Phe Asn Phe Asn
         20                  25                  30
```

```
<210> SEQ ID NO 475
<211> LENGTH: 14
<212> TYPE: PRT
<213> ORGANISM: Homo sapiens
<220> FEATURE:
<223> OTHER INFORMATION: Abet0343-GL
```

<400> SEQUENCE: 475

```
Trp Val Arg Gln Ala Pro Gly Lys Gly Leu Glu Trp Val Ser
                 5                  10
```

```
<210> SEQ ID NO 476
<211> LENGTH: 32
<212> TYPE: PRT
<213> ORGANISM: Homo sapiens
<220> FEATURE:
<223> OTHER INFORMATION: Abet0343-GL
```

<400> SEQUENCE: 476

```
Arg Phe Thr Ile Ser Arg Asp Asn Ser Lys Asn Thr Leu Tyr Leu Gln
                 5                  10                  15

Met Asn Ser Leu Arg Ala Glu Asp Thr Ala Val Tyr Tyr Cys Ala Arg
         20                  25                  30
```

```
<210> SEQ ID NO 477
<211> LENGTH: 11
<212> TYPE: PRT
<213> ORGANISM: Homo sapiens
<220> FEATURE:
<223> OTHER INFORMATION: Abet0343-GL
```

<400> SEQUENCE: 477

```
Trp Gly Gln Gly Thr Leu Val Thr Val Ser Ser
                 5                  10
```

```
<210> SEQ ID NO 478
<211> LENGTH: 318
<212> TYPE: DNA
<213> ORGANISM: Homo sapiens
<220> FEATURE:
<223> OTHER INFORMATION: Abet0343-GL
```

<400> SEQUENCE: 478

```
tcgtacgagt tgactcagcc accctcagtg tccgtgtccc caggacagac ggccagcatc    60
acctgctctg gacataactt ggaagataaa tttgcttcct ggtatcaaca gaagccaggc   120
cagtcccctg tcctggtcat ctatcgagat gacaagcggc cctcagggat ccctgagcga   180
ttctctgcct ccaactctgg gcacactgcc actctgacca tcagcgggac ccaggctatg   240
```

```
gatgaggctg actattactg ttcgtcccag gacacggtga ctcgagtgtt cggcggaggg    300
accaagctga ccgtccta                                                  318
```

<210> SEQ ID NO 479
<211> LENGTH: 106
<212> TYPE: PRT
<213> ORGANISM: Homo sapiens
<220> FEATURE:
<223> OTHER INFORMATION: Abet0343-GL

<400> SEQUENCE: 479

```
Ser Tyr Glu Leu Thr Gln Pro Pro Ser Val Ser Val Ser Pro Gly Gln
                5                  10                  15

Thr Ala Ser Ile Thr Cys Ser Gly His Asn Leu Glu Asp Lys Phe Ala
            20                  25                  30

Ser Trp Tyr Gln Gln Lys Pro Gly Gln Ser Pro Val Leu Val Ile Tyr
        35                  40                  45

Arg Asp Asp Lys Arg Pro Ser Gly Ile Pro Glu Arg Phe Ser Ala Ser
    50                  55                  60

Asn Ser Gly His Thr Ala Thr Leu Thr Ile Ser Gly Thr Gln Ala Met
65                  70                  75                  80

Asp Glu Ala Asp Tyr Tyr Cys Ser Ser Gln Asp Thr Val Thr Arg Val
                85                  90                  95

Phe Gly Gly Gly Thr Lys Leu Thr Val Leu
            100                 105
```

<210> SEQ ID NO 480
<211> LENGTH: 11
<212> TYPE: PRT
<213> ORGANISM: Homo sapiens
<220> FEATURE:
<223> OTHER INFORMATION: Abet0343-GL

<400> SEQUENCE: 480

```
Ser Gly His Asn Leu Glu Asp Lys Phe Ala Ser
                5                  10
```

<210> SEQ ID NO 481
<211> LENGTH: 7
<212> TYPE: PRT
<213> ORGANISM: Homo sapiens
<220> FEATURE:
<223> OTHER INFORMATION: Abet0343-GL

<400> SEQUENCE: 481

```
Arg Asp Asp Lys Arg Pro Ser
                5
```

<210> SEQ ID NO 482
<211> LENGTH: 9
<212> TYPE: PRT
<213> ORGANISM: Homo sapiens
<220> FEATURE:
<223> OTHER INFORMATION: Abet0343-GL

<400> SEQUENCE: 482

```
Ser Ser Gln Asp Thr Val Thr Arg Val
                5
```

<210> SEQ ID NO 483
<211> LENGTH: 22
<212> TYPE: PRT

```
<213> ORGANISM: Homo sapiens
<220> FEATURE:
<223> OTHER INFORMATION: Abet0343-GL

<400> SEQUENCE: 483

Ser Tyr Glu Leu Thr Gln Pro Pro Ser Val Ser Val Ser Pro Gly Gln
              5                  10                  15
Thr Ala Ser Ile Thr Cys
             20

<210> SEQ ID NO 484
<211> LENGTH: 15
<212> TYPE: PRT
<213> ORGANISM: Homo sapiens
<220> FEATURE:
<223> OTHER INFORMATION: Abet0343-GL

<400> SEQUENCE: 484

Trp Tyr Gln Gln Lys Pro Gly Gln Ser Pro Val Leu Val Ile Tyr
              5                  10                  15

<210> SEQ ID NO 485
<211> LENGTH: 32
<212> TYPE: PRT
<213> ORGANISM: Homo sapiens
<220> FEATURE:
<223> OTHER INFORMATION: Abet0343-GL

<400> SEQUENCE: 485

Gly Ile Pro Glu Arg Phe Ser Ala Ser Asn Ser Gly His Thr Ala Thr
              5                  10                  15
Leu Thr Ile Ser Gly Thr Gln Ala Met Asp Glu Ala Asp Tyr Tyr Cys
             20                  25                  30

<210> SEQ ID NO 486
<211> LENGTH: 10
<212> TYPE: PRT
<213> ORGANISM: Homo sapiens
<220> FEATURE:
<223> OTHER INFORMATION: Abet0343-GL

<400> SEQUENCE: 486

Phe Gly Gly Gly Thr Lys Leu Thr Val Leu
              5                  10

<210> SEQ ID NO 487
<211> LENGTH: 375
<212> TYPE: DNA
<213> ORGANISM: Homo sapiens
<220> FEATURE:
<223> OTHER INFORMATION: Abet0369-GL

<400> SEQUENCE: 487
gaggtgcagc tgttggagtc tgggggaggc ttggtacagc ctggggggtc cctgagactc      60
tcctgtgcag cctcttcgtt ccagatctcg aagaacacta tgtggtgggt ccgccaggct     120
ccagggaagg ggctggagtg ggtctcagtt attggtaagg acgagacccg cttcaactac     180
gcagactccg tgaagggccg gttcaccatc tccagagaca attccaagaa cacgctgtat     240
ctgcaaatga acagcctgag agccgaggac acggccgtgt attactgtgc gagagagtgg     300
atgaccactc ccgccccta ctactactac ggtatggacg tctggggca ggggaccctg      360 gtcaccgtct cctca                                                      375
```

```
<210> SEQ ID NO 488
<211> LENGTH: 125
<212> TYPE: PRT
<213> ORGANISM: Homo sapiens
<220> FEATURE:
<223> OTHER INFORMATION: Abet0369-GL

<400> SEQUENCE: 488

Glu Val Gln Leu Leu Glu Ser Gly Gly Gly Leu Val Gln Pro Gly Gly
                 5                  10                  15

Ser Leu Arg Leu Ser Cys Ala Ala Ser Ser Phe Gln Ile Ser Lys Asn
             20                  25                  30

Thr Met Trp Trp Val Arg Gln Ala Pro Gly Lys Gly Leu Glu Trp Val
         35                  40                  45

Ser Val Ile Gly Lys Asp Glu Thr Arg Phe Asn Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Trp Met Asp His Ser Arg Pro Tyr Tyr Tyr Tyr Gly Met
            100                 105                 110

Asp Val Trp Gly Gln Gly Thr Leu Val Thr Val Ser Ser
        115                 120                 125

<210> SEQ ID NO 489
<211> LENGTH: 5
<212> TYPE: PRT
<213> ORGANISM: Homo sapiens
<220> FEATURE:
<223> OTHER INFORMATION: Abet0369-GL

<400> SEQUENCE: 489

Lys Asn Thr Met Trp
                 5

<210> SEQ ID NO 490
<211> LENGTH: 17
<212> TYPE: PRT
<213> ORGANISM: Homo sapiens
<220> FEATURE:
<223> OTHER INFORMATION: Abet0369-GL

<400> SEQUENCE: 490

Val Ile Gly Lys Asp Glu Thr Arg Phe Asn Tyr Ala Asp Ser Val Lys
                 5                  10                  15

Gly

<210> SEQ ID NO 491
<211> LENGTH: 16
<212> TYPE: PRT
<213> ORGANISM: Homo sapiens
<220> FEATURE:
<223> OTHER INFORMATION: Abet0369-GL

<400> SEQUENCE: 491

Glu Trp Met Asp His Ser Arg Pro Tyr Tyr Tyr Tyr Gly Met Asp Val
                 5                  10                  15

<210> SEQ ID NO 492
<211> LENGTH: 30
<212> TYPE: PRT
<213> ORGANISM: Homo sapiens
```

```
<220> FEATURE:
<223> OTHER INFORMATION: Abet0369-GL

<400> SEQUENCE: 492

Glu Val Gln Leu Leu Glu Ser Gly Gly Gly Leu Val Gln Pro Gly Gly
 1               5                  10                  15

Ser Leu Arg Leu Ser Cys Ala Ala Ser Ser Phe Gln Ile Ser
            20                  25                  30

<210> SEQ ID NO 493
<211> LENGTH: 14
<212> TYPE: PRT
<213> ORGANISM: Homo sapiens
<220> FEATURE:
<223> OTHER INFORMATION: Abet0369-GL

<400> SEQUENCE: 493

Trp Val Arg Gln Ala Pro Gly Lys Gly Leu Glu Trp Val Ser
 1               5                  10

<210> SEQ ID NO 494
<211> LENGTH: 32
<212> TYPE: PRT
<213> ORGANISM: Homo sapiens
<220> FEATURE:
<223> OTHER INFORMATION: Abet0369-GL

<400> SEQUENCE: 494

Arg Phe Thr Ile Ser Arg Asp Asn Ser Lys Asn Thr Leu Tyr Leu Gln
 1               5                  10                  15

Met Asn Ser Leu Arg Ala Glu Asp Thr Ala Val Tyr Tyr Cys Ala Arg
            20                  25                  30

<210> SEQ ID NO 495
<211> LENGTH: 11
<212> TYPE: PRT
<213> ORGANISM: Homo sapiens
<220> FEATURE:
<223> OTHER INFORMATION: Abet0369-GL

<400> SEQUENCE: 495

Trp Gly Gln Gly Thr Leu Val Thr Val Ser Ser
 1               5                  10

<210> SEQ ID NO 496
<211> LENGTH: 318
<212> TYPE: DNA
<213> ORGANISM: Homo sapiens
<220> FEATURE:
<223> OTHER INFORMATION: Abet0369-GL

<400> SEQUENCE: 496
tcgtacgagt tgactcagcc accctcagtg tccgtgtccc caggacagac ggccagcatc      60
acctgctctg gacgtaacat cggggacagc tgggtcgcgt ggtatcaaca gaagccaggc     120
cagtcccctg tcctggtcat ctatcgagat gacaagcggc cctcagggat ccctgagcga     180
ttctctgcct ccaactctgg gcacactgcc actctgacca tcagcgggac ccaggctatg     240
gatgaggctg actattactg ttcgtccag gacacggtga ctcgagtgtt cggcggaggg     300
accaagctga ccgtccta                                                   318

<210> SEQ ID NO 497
<211> LENGTH: 106
<212> TYPE: PRT
```

-continued

```
<213> ORGANISM: Homo sapiens
<220> FEATURE:
<223> OTHER INFORMATION: Abet0369-GL

<400> SEQUENCE: 497

Ser Tyr Glu Leu Thr Gln Pro Pro Ser Val Ser Val Ser Pro Gly Gln
                 5                   10                  15

Thr Ala Ser Ile Thr Cys Ser Gly Arg Asn Ile Gly Asp Ser Trp Val
             20                  25                  30

Ala Trp Tyr Gln Gln Lys Pro Gly Gln Ser Pro Val Leu Val Ile Tyr
         35                  40                  45

Arg Asp Asp Lys Arg Pro Ser Gly Ile Pro Glu Arg Phe Ser Ala Ser
 50                  55                  60

Asn Ser Gly His Thr Ala Thr Leu Thr Ile Ser Gly Thr Gln Ala Met
 65                  70                  75                  80

Asp Glu Ala Asp Tyr Tyr Cys Ser Ser Gln Asp Thr Val Thr Arg Val
                 85                  90                  95

Phe Gly Gly Gly Thr Lys Leu Thr Val Leu
            100                 105

<210> SEQ ID NO 498
<211> LENGTH: 11
<212> TYPE: PRT
<213> ORGANISM: Homo sapiens
<220> FEATURE:
<223> OTHER INFORMATION: Abet0369-GL

<400> SEQUENCE: 498

Ser Gly Arg Asn Ile Gly Asp Ser Trp Val Ala
                 5                  10

<210> SEQ ID NO 499
<211> LENGTH: 7
<212> TYPE: PRT
<213> ORGANISM: Homo sapiens
<220> FEATURE:
<223> OTHER INFORMATION: Abet0369-GL

<400> SEQUENCE: 499

Arg Asp Asp Lys Arg Pro Ser
                 5

<210> SEQ ID NO 500
<211> LENGTH: 9
<212> TYPE: PRT
<213> ORGANISM: Homo sapiens
<220> FEATURE:
<223> OTHER INFORMATION: Abet0369-GL

<400> SEQUENCE: 500

Ser Ser Gln Asp Thr Val Thr Arg Val
                 5

<210> SEQ ID NO 501
<211> LENGTH: 22
<212> TYPE: PRT
<213> ORGANISM: Homo sapiens
<220> FEATURE:
<223> OTHER INFORMATION: Abet0369-GL

<400> SEQUENCE: 501

Ser Tyr Glu Leu Thr Gln Pro Pro Ser Val Ser Val Ser Pro Gly Gln
                 5                  10                  15
```

Thr Ala Ser Ile Thr Cys
            20

<210> SEQ ID NO 502
<211> LENGTH: 15
<212> TYPE: PRT
<213> ORGANISM: Homo sapiens
<220> FEATURE:
<223> OTHER INFORMATION: Abet0369-GL

<400> SEQUENCE: 502

Trp Tyr Gln Gln Lys Pro Gly Gln Ser Pro Val Leu Val Ile Tyr
1               5                   10                  15

<210> SEQ ID NO 503
<211> LENGTH: 32
<212> TYPE: PRT
<213> ORGANISM: Homo sapiens
<220> FEATURE:
<223> OTHER INFORMATION: Abet0369-GL

<400> SEQUENCE: 503

Gly Ile Pro Glu Arg Phe Ser Ala Ser Asn Ser Gly His Thr Ala Thr
1               5                   10                  15

Leu Thr Ile Ser Gly Thr Gln Ala Met Asp Glu Ala Asp Tyr Tyr Cys
            20                  25                  30

<210> SEQ ID NO 504
<211> LENGTH: 10
<212> TYPE: PRT
<213> ORGANISM: Homo sapiens
<220> FEATURE:
<223> OTHER INFORMATION: Abet0369-GL

<400> SEQUENCE: 504

Phe Gly Gly Gly Thr Lys Leu Thr Val Leu
1               5                   10

<210> SEQ ID NO 505
<211> LENGTH: 375
<212> TYPE: DNA
<213> ORGANISM: Homo sapiens
<220> FEATURE:
<223> OTHER INFORMATION: Abet0377-GL

<400> SEQUENCE: 505
gaggtgcagc tgttggagtc tgggggaggc ttggtacagc ctgggggtc cctgagactc      60 tcctgtgcag cctctggatt caactttaac gagcagaccc tctggtgggt ccgccaagcc    120
ccagggaaag gctggagtg gtctcagtt attggtgtgg ggaccaagaa catcgcctac      180
gcagacaccg tgaagggccg gttcaccatc tccagagaca attccaagaa cacgctgtat    240
ctgcaaatga acagcctgag agccgaggac acggccgtgt attactgtgc gagagagtgg    300
atggaccact cccgccccta ctactactac ggtatggacg tctggggaca ggggaccctg    360
gtcaccgtct cctca                                                    375

<210> SEQ ID NO 506
<211> LENGTH: 125
<212> TYPE: PRT
<213> ORGANISM: Homo sapiens
<220> FEATURE:
<223> OTHER INFORMATION: Abet0377-GL

<400> SEQUENCE: 506

Glu Val Gln Leu Leu Glu Ser Gly Gly Gly Leu Val Gln Pro Gly Gly
                 5                  10                  15

Ser Leu Arg Leu Ser Cys Ala Ala Ser Gly Phe Asn Phe Asn Glu Gln
             20                  25                  30

Thr Leu Trp Trp Val Arg Gln Ala Pro Gly Lys Gly Leu Glu Trp Val
         35                  40                  45

Ser Val Ile Gly Val Gly Thr Lys Asn Ile Ala Tyr Ala Asp Thr Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Trp Met Asp His Ser Arg Pro Tyr Tyr Tyr Gly Met
            100                 105                 110

Asp Val Trp Gly Gln Gly Thr Leu Val Thr Val Ser Ser
            115                 120                 125

<210> SEQ ID NO 507
<211> LENGTH: 5
<212> TYPE: PRT
<213> ORGANISM: Homo sapiens
<220> FEATURE:
<223> OTHER INFORMATION: Abet0377-GL

<400> SEQUENCE: 507

Glu Gln Thr Leu Trp
              5

<210> SEQ ID NO 508
<211> LENGTH: 17
<212> TYPE: PRT
<213> ORGANISM: Homo sapiens
<220> FEATURE:
<223> OTHER INFORMATION: Abet0377-GL

<400> SEQUENCE: 508

Val Ile Gly Val Gly Thr Lys Asn Ile Ala Tyr Ala Asp Thr Val Lys
                 5                  10                  15

Gly

<210> SEQ ID NO 509
<211> LENGTH: 16
<212> TYPE: PRT
<213> ORGANISM: Homo sapiens
<220> FEATURE:
<223> OTHER INFORMATION: Abet0377-GL

<400> SEQUENCE: 509

Glu Trp Met Asp His Ser Arg Pro Tyr Tyr Tyr Gly Met Asp Val
                 5                  10                  15

<210> SEQ ID NO 510
<211> LENGTH: 30
<212> TYPE: PRT
<213> ORGANISM: Homo sapiens
<220> FEATURE:
<223> OTHER INFORMATION: Abet0377-GL

<400> SEQUENCE: 510

Glu Val Gln Leu Leu Glu Ser Gly Gly Gly Leu Val Gln Pro Gly Gly
                 5                  10                  15

Ser Leu Arg Leu Ser Cys Ala Ala Ser Gly Phe Asn Phe Asn

<210> SEQ ID NO 511
<211> LENGTH: 14
<212> TYPE: PRT
<213> ORGANISM: Homo sapiens
<220> FEATURE:
<223> OTHER INFORMATION: Abet0377-GL

<400> SEQUENCE: 511

Trp Val Arg Gln Ala Pro Gly Lys Gly Leu Glu Trp Val Ser
                5                  10

<210> SEQ ID NO 512
<211> LENGTH: 32
<212> TYPE: PRT
<213> ORGANISM: Homo sapiens
<220> FEATURE:
<223> OTHER INFORMATION: Abet0377-GL

<400> SEQUENCE: 512

Arg Phe Thr Ile Ser Arg Asp Asn Ser Lys Asn Thr Leu Tyr Leu Gln
                5                  10                  15
Met Asn Ser Leu Arg Ala Glu Asp Thr Ala Val Tyr Tyr Cys Ala Arg
            20                  25                  30

<210> SEQ ID NO 513
<211> LENGTH: 11
<212> TYPE: PRT
<213> ORGANISM: Homo sapiens
<220> FEATURE:
<223> OTHER INFORMATION: Abet0377-GL

<400> SEQUENCE: 513

Trp Gly Gln Gly Thr Leu Val Thr Val Ser Ser
                5                  10

<210> SEQ ID NO 514
<211> LENGTH: 318
<212> TYPE: DNA
<213> ORGANISM: Homo sapiens
<220> FEATURE:
<223> OTHER INFORMATION: Abet0377-GL

<400> SEQUENCE: 514
tcgtacgagt tgactcagcc accctcagtg tccgtgtccc caggacagac ggccagcatc      60
acctgctctg gacataacac cgagcacaag tggatctcgt ggtatcaaca gaagccaggc     120
cagtccctg tcctggtcat ctatcgagat gacaagcggc cctcagggat ccctgagcga     180
ttctctgcct ccaactctgg gcacactgcc actctgacca tcagcgggac ccaggctatg     240
gatgaggctg actattactg ttcgtcccag gacacggtga ctcgagtgtt cggcggaggg     300
accaagctga ccgtccta                                                  318

<210> SEQ ID NO 515
<211> LENGTH: 106
<212> TYPE: PRT
<213> ORGANISM: Homo sapiens
<220> FEATURE:
<223> OTHER INFORMATION: Abet0377-GL

<400> SEQUENCE: 515

Ser Tyr Glu Leu Thr Gln Pro Pro Ser Val Ser Val Pro Gly Gln
                5                  10                  15

Thr Ala Ser Ile Thr Cys Ser Gly His Asn Thr Glu His Lys Trp Ile
            20                  25                  30

Ser Trp Tyr Gln Gln Lys Pro Gly Gln Ser Pro Val Leu Val Ile Tyr
        35                  40                  45

Arg Asp Asp Lys Arg Pro Ser Gly Ile Pro Glu Arg Phe Ser Ala Ser
    50                  55                  60

Asn Ser Gly His Thr Ala Thr Leu Thr Ile Ser Gly Thr Gln Ala Met
65                  70                  75                  80

Asp Glu Ala Asp Tyr Tyr Cys Ser Ser Gln Asp Thr Val Thr Arg Val
                85                  90                  95

Phe Gly Gly Gly Thr Lys Leu Thr Val Leu
            100                 105

<210> SEQ ID NO 516
<211> LENGTH: 11
<212> TYPE: PRT
<213> ORGANISM: Homo sapiens
<220> FEATURE:
<223> OTHER INFORMATION: Abet0377-GL

<400> SEQUENCE: 516

Ser Gly His Asn Thr Glu His Lys Trp Ile Ser
            5                   10

<210> SEQ ID NO 517
<211> LENGTH: 7
<212> TYPE: PRT
<213> ORGANISM: Homo sapiens
<220> FEATURE:
<223> OTHER INFORMATION: Abet0377-GL

<400> SEQUENCE: 517

Arg Asp Asp Lys Arg Pro Ser
            5

<210> SEQ ID NO 518
<211> LENGTH: 9
<212> TYPE: PRT
<213> ORGANISM: Homo sapiens
<220> FEATURE:
<223> OTHER INFORMATION: Abet0377-GL

<400> SEQUENCE: 518

Ser Ser Gln Asp Thr Val Thr Arg Val
            5

<210> SEQ ID NO 519
<211> LENGTH: 22
<212> TYPE: PRT
<213> ORGANISM: Homo sapiens
<220> FEATURE:
<223> OTHER INFORMATION: Abet0377-GL

<400> SEQUENCE: 519

Ser Tyr Glu Leu Thr Gln Pro Pro Ser Val Ser Val Ser Pro Gly Gln
            5                   10                  15

Thr Ala Ser Ile Thr Cys
            20

<210> SEQ ID NO 520
<211> LENGTH: 15
<212> TYPE: PRT
<213> ORGANISM: Homo sapiens
<220> FEATURE:

<223> OTHER INFORMATION: Abet0377-GL

<400> SEQUENCE: 520

Trp Tyr Gln Gln Lys Pro Gly Gln Ser Pro Val Leu Val Ile Tyr
                5                   10                  15

<210> SEQ ID NO 521
<211> LENGTH: 32
<212> TYPE: PRT
<213> ORGANISM: Homo sapiens
<220> FEATURE:
<223> OTHER INFORMATION: Abet0377-GL

<400> SEQUENCE: 521

Gly Ile Pro Glu Arg Phe Ser Ala Ser Asn Ser Gly His Thr Ala Thr
                5                   10                  15

Leu Thr Ile Ser Gly Thr Gln Ala Met Asp Glu Ala Asp Tyr Tyr Cys
            20                  25                  30

<210> SEQ ID NO 522
<211> LENGTH: 10
<212> TYPE: PRT
<213> ORGANISM: Homo sapiens
<220> FEATURE:
<223> OTHER INFORMATION: Abet0377-GL

<400> SEQUENCE: 522

Phe Gly Gly Gly Thr Lys Leu Thr Val Leu
                5                   10

<210> SEQ ID NO 523
<211> LENGTH: 375
<212> TYPE: DNA
<213> ORGANISM: Homo sapiens
<220> FEATURE:
<223> OTHER INFORMATION: Abet0380-GL

<400> SEQUENCE: 523
gaggtgcagc tgttggagtc tgggggaggc ttggtacagc ctggggggtc cctgagactc      60
tcctgtgcag cctctatggg caacttcaac taccagacta tgtggtgggt ccgccaggct     120
ccagggaagg ggctggagtg ggtctcagtt attggtaaga ccaacgagaa catcgcctac     180
gcagactccg tgaagggccg gttcaccatc tccagagaca attccaagaa cacgctgtat     240
ctgcaaatga acagcctgag agccgaggac acggccgtgt attactgtgc gagagagtgg     300
atggaccact cccgccccta ctactactac ggtatggacg tctggggcca ggggaccctg     360
gtcaccgtct cctca                                                     375

<210> SEQ ID NO 524
<211> LENGTH: 125
<212> TYPE: PRT
<213> ORGANISM: Homo sapiens
<220> FEATURE:
<223> OTHER INFORMATION: Abet0380-GL

<400> SEQUENCE: 524

Glu Val Gln Leu Leu Glu Ser Gly Gly Gly Leu Val Gln Pro Gly Gly
                5                   10                  15

Ser Leu Arg Leu Ser Cys Ala Ala Ser Met Gly Asn Phe Asn Tyr Gln
            20                  25                  30

Thr Met Trp Trp Val Arg Gln Ala Pro Gly Lys Gly Leu Glu Trp Val
        35                  40                  45

-continued

```
Ser Val Ile Gly Lys Thr Asn Glu Asn Ile Ala Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Glu Trp Met Asp His Ser Arg Pro Tyr Tyr Tyr Gly Met
            100                 105                 110
Asp Val Trp Gly Gln Gly Thr Leu Val Thr Val Ser Ser
            115                 120                 125

<210> SEQ ID NO 525
<211> LENGTH: 5
<212> TYPE: PRT
<213> ORGANISM: Homo sapiens
<220> FEATURE:
<223> OTHER INFORMATION: Abet0380-GL

<400> SEQUENCE: 525

Tyr Gln Thr Met Trp
              5

<210> SEQ ID NO 526
<211> LENGTH: 17
<212> TYPE: PRT
<213> ORGANISM: Homo sapiens
<220> FEATURE:
<223> OTHER INFORMATION: Abet0380-GL

<400> SEQUENCE: 526

Val Ile Gly Lys Thr Asn Glu Asn Ile Ala Tyr Ala Asp Ser Val Lys
                  5                  10                  15
Gly

<210> SEQ ID NO 527
<211> LENGTH: 16
<212> TYPE: PRT
<213> ORGANISM: Homo sapiens
<220> FEATURE:
<223> OTHER INFORMATION: Abet0380-GL

<400> SEQUENCE: 527

Glu Trp Met Asp His Ser Arg Pro Tyr Tyr Tyr Gly Met Asp Val
              5                  10                  15

<210> SEQ ID NO 528
<211> LENGTH: 30
<212> TYPE: PRT
<213> ORGANISM: Homo sapiens
<220> FEATURE:
<223> OTHER INFORMATION: Abet0380-GL

<400> SEQUENCE: 528

Glu Val Gln Leu Leu Glu Ser Gly Gly Gly Leu Val Gln Pro Gly Gly
                  5                  10                  15
Ser Leu Arg Leu Ser Cys Ala Ala Ser Met Gly Asn Phe Asn
             20                  25                  30

<210> SEQ ID NO 529
<211> LENGTH: 14
<212> TYPE: PRT
<213> ORGANISM: Homo sapiens
<220> FEATURE:
<223> OTHER INFORMATION: Abet0380-GL
```

<400> SEQUENCE: 529

Trp Val Arg Gln Ala Pro Gly Lys Gly Leu Glu Trp Val Ser
            5                   10

<210> SEQ ID NO 530
<211> LENGTH: 32
<212> TYPE: PRT
<213> ORGANISM: Homo sapiens
<220> FEATURE:
<223> OTHER INFORMATION: Abet0380-GL

<400> SEQUENCE: 530

Arg Phe Thr Ile Ser Arg Asp Asn Ser Lys Asn Thr Leu Tyr Leu Gln
            5                   10                  15

Met Asn Ser Leu Arg Ala Glu Asp Thr Ala Val Tyr Tyr Cys Ala Arg
        20                  25                  30

<210> SEQ ID NO 531
<211> LENGTH: 11
<212> TYPE: PRT
<213> ORGANISM: Homo sapiens
<220> FEATURE:
<223> OTHER INFORMATION: Abet0380-GL

<400> SEQUENCE: 531

Trp Gly Gln Gly Thr Leu Val Thr Val Ser Ser
            5                   10

<210> SEQ ID NO 532
<211> LENGTH: 318
<212> TYPE: DNA
<213> ORGANISM: Homo sapiens
<220> FEATURE:
<223> OTHER INFORMATION: Abet0380-GL

<400> SEQUENCE: 532
tcgtacgagt tgactcagcc accctcagtg tccgtgtccc caggacagac ggccagcatc      60
acctgctctg gacataactt ggaagataaa tttgcttcct ggtatcaaca gaagccaggc     120
cagtcccctg tcctggtcat ctatcgagat gacaagcggc cctcagggat ccctgagcga     180
ttctctgcct ccaactctgg gcacactgcc actctgacca tcagcgggac ccaggctatg     240
gatgaggctg actattactg ttcgtcccag gacacggtga ctcgagtgtt cggcggaggg     300
accaagctga ccgtccta                                                  318

<210> SEQ ID NO 533
<211> LENGTH: 106
<212> TYPE: PRT
<213> ORGANISM: Homo sapiens
<220> FEATURE:
<223> OTHER INFORMATION: Abet0380-GL

<400> SEQUENCE: 533

Ser Tyr Glu Leu Thr Gln Pro Pro Ser Val Ser Val Ser Pro Gly Gln
            5                   10                  15

Thr Ala Ser Ile Thr Cys Ser Gly His Asn Leu Glu Asp Lys Phe Ala
        20                  25                  30

Ser Trp Tyr Gln Gln Lys Pro Gly Gln Ser Pro Val Leu Val Ile Tyr
        35                  40                  45

Arg Asp Asp Lys Arg Pro Ser Gly Ile Pro Glu Arg Phe Ser Ala Ser
    50                  55                  60

```
Asn Ser Gly His Thr Ala Thr Leu Thr Ile Ser Gly Thr Gln Ala Met
 65                  70                  75                  80

Asp Glu Ala Asp Tyr Tyr Cys Ser Ser Gln Asp Thr Val Thr Arg Val
                 85                  90                  95

Phe Gly Gly Gly Thr Lys Leu Thr Val Leu
            100                 105

<210> SEQ ID NO 534
<211> LENGTH: 11
<212> TYPE: PRT
<213> ORGANISM: Homo sapiens
<220> FEATURE:
<223> OTHER INFORMATION: Abet0380-GL

<400> SEQUENCE: 534

Ser Gly His Asn Leu Glu Asp Lys Phe Ala Ser
              5                  10

<210> SEQ ID NO 535
<211> LENGTH: 7
<212> TYPE: PRT
<213> ORGANISM: Homo sapiens
<220> FEATURE:
<223> OTHER INFORMATION: Abet0380-GL

<400> SEQUENCE: 535

Arg Asp Asp Lys Arg Pro Ser
              5

<210> SEQ ID NO 536
<211> LENGTH: 9
<212> TYPE: PRT
<213> ORGANISM: Homo sapiens
<220> FEATURE:
<223> OTHER INFORMATION: Abet0380-GL

<400> SEQUENCE: 536

Ser Ser Gln Asp Thr Val Thr Arg Val
              5

<210> SEQ ID NO 537
<211> LENGTH: 22
<212> TYPE: PRT
<213> ORGANISM: Homo sapiens
<220> FEATURE:
<223> OTHER INFORMATION: Abet0380-GL

<400> SEQUENCE: 537

Ser Tyr Glu Leu Thr Gln Pro Pro Ser Val Ser Val Ser Pro Gly Gln
              5                  10                  15

Thr Ala Ser Ile Thr Cys
             20

<210> SEQ ID NO 538
<211> LENGTH: 15
<212> TYPE: PRT
<213> ORGANISM: Homo sapiens
<220> FEATURE:
<223> OTHER INFORMATION: Abet0380-GL

<400> SEQUENCE: 538

Trp Tyr Gln Gln Lys Pro Gly Gln Ser Pro Val Leu Val Ile Tyr
              5                  10                  15

<210> SEQ ID NO 539
```

<211> LENGTH: 32
<212> TYPE: PRT
<213> ORGANISM: Homo sapiens
<220> FEATURE:
<223> OTHER INFORMATION: Abet0380-GL

<400> SEQUENCE: 539

Gly Ile Pro Glu Arg Phe Ser Ala Ser Asn Ser Gly His Thr Ala Thr
            5                   10                  15
Leu Thr Ile Ser Gly Thr Gln Ala Met Asp Glu Ala Asp Tyr Tyr Cys
        20                  25                  30

<210> SEQ ID NO 540
<211> LENGTH: 10
<212> TYPE: PRT
<213> ORGANISM: Homo sapiens
<220> FEATURE:
<223> OTHER INFORMATION: Abet0380-GL

<400> SEQUENCE: 540

Phe Gly Gly Gly Thr Lys Leu Thr Val Leu
            5                   10

<210> SEQ ID NO 541
<211> LENGTH: 375
<212> TYPE: DNA
<213> ORGANISM: Homo sapiens
<220> FEATURE:
<223> OTHER INFORMATION: Abet0382-GL

<400> SEQUENCE: 541
gaggtgcagc tgttggagtc tgggggaggc ttggtacagc ctggggggtc cctgaggctc      60
tcctgtgcag cctctggatt ccactttacc aactccatca gtggtgggt ccgccaggct      120
ccagggaagg ggctggagtg gtctcagtt attggtagcg aggcgcaccg cgtcacgtac      180
gcagactccg tgaagggccg gttcaccatc tccagagaca attccaagaa cacgctgtat      240
ctgcaaatga acagcctgag agccgaggac acggccgtgt attactgtgc gagagagtgg      300
atggaccact cccgccccta ctactactac ggtatggacg tctggggca ggggaccctg      360
gtcaccgtct cctca                                                      375

<210> SEQ ID NO 542
<211> LENGTH: 125
<212> TYPE: PRT
<213> ORGANISM: Homo sapiens
<220> FEATURE:
<223> OTHER INFORMATION: Abet0382-GL

<400> SEQUENCE: 542

Glu Val Gln Leu Leu Glu Ser Gly Gly Gly Leu Val Gln Pro Gly Gly
            5                   10                  15
Ser Leu Arg Leu Ser Cys Ala Ala Ser Gly Phe His Phe Thr Asn Ser
        20                  25                  30
Ile Met Trp Trp Val Arg Gln Ala Pro Gly Lys Gly Leu Glu Trp Val
    35                  40                  45
Ser Val Ile Gly Ser Glu Ala His Arg Val Thr Tyr Ala Asp Ser Val
50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
            85                  90                  95

Ala Arg Glu Trp Met Asp His Ser Arg Pro Tyr Tyr Tyr Gly Met
            100                 105                 110

Asp Val Trp Gly Gln Gly Thr Leu Val Thr Val Ser Ser
        115                 120                 125

<210> SEQ ID NO 543
<211> LENGTH: 5
<212> TYPE: PRT
<213> ORGANISM: Homo sapiens
<220> FEATURE:
<223> OTHER INFORMATION: Abet0382-GL

<400> SEQUENCE: 543

Asn Ser Ile Met Trp
              5

<210> SEQ ID NO 544
<211> LENGTH: 17
<212> TYPE: PRT
<213> ORGANISM: Homo sapiens
<220> FEATURE:
<223> OTHER INFORMATION: Abet0382-GL

<400> SEQUENCE: 544

Val Ile Gly Ser Glu Ala His Arg Val Thr Tyr Ala Asp Ser Val Lys
              5                   10                  15

Gly

<210> SEQ ID NO 545
<211> LENGTH: 16
<212> TYPE: PRT
<213> ORGANISM: Homo sapiens
<220> FEATURE:
<223> OTHER INFORMATION: Abet0382-GL

<400> SEQUENCE: 545

Glu Trp Met Asp His Ser Arg Pro Tyr Tyr Tyr Gly Met Asp Val
              5                   10                  15

<210> SEQ ID NO 546
<211> LENGTH: 30
<212> TYPE: PRT
<213> ORGANISM: Homo sapiens
<220> FEATURE:
<223> OTHER INFORMATION: Abet0382-GL

<400> SEQUENCE: 546

Glu Val Gln Leu Leu Glu Ser Gly Gly Gly Leu Val Gln Pro Gly Gly
              5                   10                  15

Ser Leu Arg Leu Ser Cys Ala Ala Ser Gly Phe His Phe Thr
         20                  25                  30

<210> SEQ ID NO 547
<211> LENGTH: 14
<212> TYPE: PRT
<213> ORGANISM: Homo sapiens
<220> FEATURE:
<223> OTHER INFORMATION: Abet0382-GL

<400> SEQUENCE: 547

Trp Val Arg Gln Ala Pro Gly Lys Gly Leu Glu Trp Val Ser
              5                   10

<210> SEQ ID NO 548
<211> LENGTH: 32

```
<212> TYPE: PRT
<213> ORGANISM: Homo sapiens
<220> FEATURE:
<223> OTHER INFORMATION: Abet0382-GL

<400> SEQUENCE: 548

Arg Phe Thr Ile Ser Arg Asp Asn Ser Lys Asn Thr Leu Tyr Leu Gln
                 5                  10                  15
Met Asn Ser Leu Arg Ala Glu Asp Thr Ala Val Tyr Tyr Cys Ala Arg
             20                  25                  30

<210> SEQ ID NO 549
<211> LENGTH: 11
<212> TYPE: PRT
<213> ORGANISM: Homo sapiens
<220> FEATURE:
<223> OTHER INFORMATION: Abet0382-GL

<400> SEQUENCE: 549

Trp Gly Gln Gly Thr Leu Val Thr Val Ser Ser
                 5                  10

<210> SEQ ID NO 550
<211> LENGTH: 318
<212> TYPE: DNA
<213> ORGANISM: Homo sapiens
<220> FEATURE:
<223> OTHER INFORMATION: Abet0382-GL

<400> SEQUENCE: 550
tcgtacgagt tgactcagcc accctcagtg tccgtgtccc caggacagac ggccagcatc        60
acctgctctg gacataactt ggaagataaa tttgcttcct ggtatcaaca gaagccaggc       120
cagtcccctg tcctggtcat ctatcgagat gacaagcggc cctcagggat ccctgagcga       180
ttctctgcct ccaactctgg gcacactgcc actctgacca tcagcgggac ccaggctatg       240
gatgaggctg actattactg ttcgtcccag gacacggtga ctcgagtgtt cggcggaggg       300
accaagctga ccgtccta                                                    318

<210> SEQ ID NO 551
<211> LENGTH: 106
<212> TYPE: PRT
<213> ORGANISM: Homo sapiens
<220> FEATURE:
<223> OTHER INFORMATION: Abet0382-GL

<400> SEQUENCE: 551

Ser Tyr Glu Leu Thr Gln Pro Pro Ser Val Ser Val Ser Pro Gly Gln
                 5                  10                  15
Thr Ala Ser Ile Thr Cys Ser Gly His Asn Leu Glu Asp Lys Phe Ala
             20                  25                  30
Ser Trp Tyr Gln Gln Lys Pro Gly Gln Ser Pro Val Leu Val Ile Tyr
         35                  40                  45
Arg Asp Asp Lys Arg Pro Ser Gly Ile Pro Glu Arg Phe Ser Ala Ser
     50                  55                  60
Asn Ser Gly His Thr Ala Thr Leu Thr Ile Ser Gly Thr Gln Ala Met
65                  70                  75                  80
Asp Glu Ala Asp Tyr Tyr Cys Ser Ser Gln Asp Thr Val Thr Arg Val
                 85                  90                  95
Phe Gly Gly Gly Thr Lys Leu Thr Val Leu
                100                 105
```

<210> SEQ ID NO 552
<211> LENGTH: 11
<212> TYPE: PRT
<213> ORGANISM: Homo sapiens
<220> FEATURE:
<223> OTHER INFORMATION: Abet0382-GL

<400> SEQUENCE: 552

Ser Gly His Asn Leu Glu Asp Lys Phe Ala Ser
                5                   10

<210> SEQ ID NO 553
<211> LENGTH: 7
<212> TYPE: PRT
<213> ORGANISM: Homo sapiens
<220> FEATURE:
<223> OTHER INFORMATION: Abet0382-GL

<400> SEQUENCE: 553

Arg Asp Asp Lys Arg Pro Ser
                5

<210> SEQ ID NO 554
<211> LENGTH: 9
<212> TYPE: PRT
<213> ORGANISM: Homo sapiens
<220> FEATURE:
<223> OTHER INFORMATION: Abet0382-GL

<400> SEQUENCE: 554

Ser Ser Gln Asp Thr Val Thr Arg Val
                5

<210> SEQ ID NO 555
<211> LENGTH: 22
<212> TYPE: PRT
<213> ORGANISM: Homo sapiens
<220> FEATURE:
<223> OTHER INFORMATION: Abet0382-GL

<400> SEQUENCE: 555

Ser Tyr Glu Leu Thr Gln Pro Pro Ser Val Ser Val Ser Pro Gly Gln
                5                   10                  15

Thr Ala Ser Ile Thr Cys
            20

<210> SEQ ID NO 556
<211> LENGTH: 15
<212> TYPE: PRT
<213> ORGANISM: Homo sapiens
<220> FEATURE:
<223> OTHER INFORMATION: Abet0382-GL

<400> SEQUENCE: 556

Trp Tyr Gln Gln Lys Pro Gly Gln Ser Pro Val Leu Val Ile Tyr
                5                   10                  15

<210> SEQ ID NO 557
<211> LENGTH: 32
<212> TYPE: PRT
<213> ORGANISM: Homo sapiens
<220> FEATURE:
<223> OTHER INFORMATION: Abet0382-GL

<400> SEQUENCE: 557

Gly Ile Pro Glu Arg Phe Ser Ala Ser Asn Ser Gly His Thr Ala Thr

```
                    5                   10                  15

Leu Thr Ile Ser Gly Thr Gln Ala Met Asp Glu Ala Asp Tyr Tyr Cys
                20                  25                  30

<210> SEQ ID NO 558
<211> LENGTH: 10
<212> TYPE: PRT
<213> ORGANISM: Homo sapiens
<220> FEATURE:
<223> OTHER INFORMATION: Abet0382-GL

<400> SEQUENCE: 558

Phe Gly Gly Gly Thr Lys Leu Thr Val Leu
                5                   10

<210> SEQ ID NO 559
<211> LENGTH: 42
<212> TYPE: PRT
<213> ORGANISM: Homo sapiens

<400> SEQUENCE: 559

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
                20                  25                  30

Gly Leu Met Val Gly Gly Val Val Ile Ala
                35                  40

<210> SEQ ID NO 560
<211> LENGTH: 42
<212> TYPE: PRT
<213> ORGANISM: Homo sapiens

<400> SEQUENCE: 560

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
                20                  25                  30

Gly Leu Met Val Gly Gly Val Val Ile Ala
                35                  40

<210> SEQ ID NO 561
<211> LENGTH: 40
<212> TYPE: PRT
<213> ORGANISM: Homo sapiens

<400> SEQUENCE: 561

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
                20                  25                  30

Gly Leu Met Val Gly Gly Val Val
                35                  40

<210> SEQ ID NO 562
<211> LENGTH: 40
<212> TYPE: PRT
<213> ORGANISM: Homo sapiens

<400> SEQUENCE: 562

Asp Ala Glu Phe Arg His Asp Ser Gly Tyr Glu Val His His Gln Lys
1               5                   10                  15
```

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 563
<211> LENGTH: 42
<212> TYPE: PRT
<213> ORGANISM: Mus musculus

<400> SEQUENCE: 563

Asp Ala Glu Phe Gly His Asp Ser Gly Phe Glu Val Arg His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 564
<211> LENGTH: 42
<212> TYPE: PRT
<213> ORGANISM: Mus musculus

<400> SEQUENCE: 564

Asp Ala Glu Phe Gly His Asp Ser Gly Phe Glu Val Arg His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 565
<211> LENGTH: 42
<212> TYPE: PRT
<213> ORGANISM: Mus musculus

<400> SEQUENCE: 565

Asp Ala Glu Phe Gly His Asp Ser Gly Phe Glu Val Arg His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 566
<211> LENGTH: 40
<212> TYPE: PRT
<213> ORGANISM: Mus musculus

<400> SEQUENCE: 566

Asp Ala Glu Phe Gly His Asp Ser Gly Phe Glu Val Arg His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 567
<211> LENGTH: 40
<212> TYPE: PRT

<213> ORGANISM: Mus musculus

<400> SEQUENCE: 567

Asp Ala Glu Phe Gly His Asp Ser Gly Phe Glu Val Arg His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 568
<211> LENGTH: 42
<212> TYPE: PRT
<213> ORGANISM: Artificial sequence
<220> FEATURE:
<223> OTHER INFORMATION: Biotinylated Scrambled Amyloid Beta 1-42
      peptide

<400> SEQUENCE: 568

Ala Ile Ala Glu Gly Asp Ser His Val Leu Lys Glu Gly Ala Tyr Met
1               5                   10                  15

Glu Ile Phe Asp Val Gln Gly His Val Phe Gly Gly Leu Ile Phe Arg
            20                  25                  30

Val Val Asp Leu Gly Ser His Asn Val Ala
        35                  40

<210> SEQ ID NO 569
<211> LENGTH: 43
<212> TYPE: PRT
<213> ORGANISM: Homo sapiens

<400> SEQUENCE: 569

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala Thr
        35                  40

<210> SEQ ID NO 570
<211> LENGTH: 17
<212> TYPE: PRT
<213> ORGANISM: Homo sapiens

<400> SEQUENCE: 570

Lys Lys Lys Gly Ala Ile Ile Gly Leu Met Val Gly Gly Val Val Ile
1               5                   10                  15

Ala

<210> SEQ ID NO 571
<211> LENGTH: 15
<212> TYPE: PRT
<213> ORGANISM: Homo sapiens

<400> SEQUENCE: 571

Lys Lys Lys Gly Ala Ile Ile Gly Leu Met Val Gly Gly Val Val
1               5                   10                  15

<210> SEQ ID NO 572
<211> LENGTH: 16
<212> TYPE: PRT
<213> ORGANISM: Homo sapiens

<400> SEQUENCE: 572

Asp Ala Glu Phe Arg His Asp Ser Gly Tyr Glu Val His His Gln Lys
1               5                   10                  15

<210> SEQ ID NO 573
<211> LENGTH: 12
<212> TYPE: PRT
<213> ORGANISM: Homo sapiens

<400> SEQUENCE: 573

Glu Val Arg His Gln Lys Leu Val Phe Phe Ala Glu
1               5                   10

<210> SEQ ID NO 574
<211> LENGTH: 17
<212> TYPE: PRT
<213> ORGANISM: Homo sapiens

<400> SEQUENCE: 574

Val Arg His Gln Lys Leu Val Phe Phe Ala Glu Asp Val Gly Ser Asn
1               5                   10                  15

Lys

<210> SEQ ID NO 575
<211> LENGTH: 26
<212> TYPE: PRT
<213> ORGANISM: Homo sapiens

<400> SEQUENCE: 575

Leu Val Phe Phe Ala Glu Asp Val Gly Ser Asn Lys Gly Ala Ile Ile
1               5                   10                  15

Gly Leu Met Val Gly Gly Val Val Ile Ala
            20                  25

<210> SEQ ID NO 576
<211> LENGTH: 32
<212> TYPE: PRT
<213> ORGANISM: Homo sapiens

<400> SEQUENCE: 576

Glu Val Arg His Gln Lys Leu Val Phe Phe Ala Glu Asp Val Gly Ser
1               5                   10                  15

Asn Lys Gly Ala Ile Ile Gly Leu Met Val Gly Gly Val Val Ile Ala
            20                  25                  30

<210> SEQ ID NO 577
<211> LENGTH: 40
<212> TYPE: PRT
<213> ORGANISM: Homo sapiens

<400> SEQUENCE: 577

Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Val Gly Gly Val Val Ile Ala
                35                  40

<210> SEQ ID NO 578
<211> LENGTH: 16
<212> TYPE: PRT

```
<213> ORGANISM: Homo sapiens
<220> FEATURE:
<223> OTHER INFORMATION: Amino acids 91-106 of Abet0378 VL protein
      sequence

<400> SEQUENCE: 578

Asp Thr Val Thr Arg Val Phe Gly Gly Gly Thr Lys Leu Thr Val Leu
1               5                   10                  15
```

ANTIBODIES TO AMYLOID BETA

CROSS-REFERENCE TO RELATED APPLICATIONS

This application is a continuation of U.S. application Ser. No. 16/864,439, filed May 1, 2020 (pending), which is a continuation of U.S. application Ser. No. 15/793,510, filed Oct. 25, 2017 (now U.S. Pat. No. 10,662,239), which is a continuation of U.S. application Ser. No. 14/435,520, filed on Apr. 14, 2015 (now U.S. Pat. No. 9,834,598), which is a U.S. National Stage application of International Application No. PCT/EP2013/071567, filed on Oct. 15, 2013 (expired), said International Application No. PCT/EP2013/071567 claims benefit under 35 U.S.C. § 119(e) of the U.S. Provisional Application No. 61/713,996, filed on Oct. 15, 2012. The disclosures of each of the foregoing applications are hereby incorporated by reference herein in their entireties.

REFERENCE TO THE SEQUENCE LISTING

This application incorporates by reference a Sequence Listing submitted with this application as text file entitled, 1848081_0002_094_304_Sequence_Listing, created on Feb. 10, 2022, and having a size of 211,084 bytes.

FIELD OF THE INVENTION

This invention relates to antibodies that bind to human amyloid beta 1-42 peptide and N-terminal truncates thereof, collectively referred to as Aβn-42 peptides, wherein n is 1 to 29. It relates to antibodies that are selective in binding to amyloid beta n-42 peptide over amyloid beta 1-40 peptide. The invention also relates to use of anti-Aβn-42 antibodies for treating conditions associated with amyloidosis, including Alzheimer's disease.

BACKGROUND

Alzheimer's disease (AD) is characterised by worsening cognitive impairment, affecting memory, that debilitates the patient's social and occupational functioning. The degenerative disease causes loss of nerve cells within the brain, which brings about cognitive difficulties with language and higher functioning, such as judgement, planning, organisation and reasoning, which can lead eventually to personality changes. The end stages of the disease are characterised by a complete loss of independent functioning.

Histologically, AD (sporadic and familial) is defined by the presence of intracellular neurofibrillary tangles (NFT's) and extracellular plaques. Plaques are aggregations of amyloid β peptide (Aβ) derived from the aberrant cleavage of the amyloid precursor protein (APP), a transmembrane protein found in neurons and astrocytes in the brain. Aβ deposits are also found in the blood vessels of AD patients.

Cholinergic neurons are particularly vulnerable in AD, and the consequent neurotransmitter decline affects other neurotransmitter systems. Other symptoms of the disease include oxidative stress, inflammation and neuronal apoptosis (programmed cell death). In the AD patient, extensive neuronal cell death leads to cognitive decline and the eventual death of the patient. (Younkin, 1995; Borchelt et al., 1996; Selkoe, 1999).

Current treatments are symptomatic only and are seen as minimally effective with minor improvements in symptoms for a limited duration of time. However, overproduction or changes in Aβ levels are believed to be key events in the pathogenesis of sporadic and early onset AD. For this reason, Aβ has become a major target for the development of drugs designed to reduce its formation (Vassar et al., 1999), or to activate mechanisms that accelerate its clearance from brain.

The amyloid cascade hypothesis proposes that production of the Aβ peptide adversely affects neuron function, thereby, leading neuron death and dementia in AD. Aβ is produced from the amyloid precursor protein (APP) which is cleaved sequentially by secretases to generate species of different lengths. The main plaque component is the 42 amino acid isoform of Aβ1-42 which is involved in the formation of neurotoxic oligomers and plaque formation in AD pathogenesis. A number of isoforms of Aβ including Aβ1-42, pGluAβ3-42, Aβ-42 and 4-42 predominate in the AD brain, of which Aβ1-42 and Aβ4-42 are the main forms in the hippocampus and cortex of familial and sporadic AD (Portelius et al., 2010).

Aβ ending at residue 42 is a minor component of the Aβ species produced by processing of APP. Other forms include Aβ1-40 and N-terminal truncates Aβn-40. However, Aβ ending at residue 42 is most prone to aggregate and drives the deposition into amyloid plaques. In addition to being more prone to aggregate, the Aβ1-42 peptide forms soluble low-n polymers (or oligomers) that have been shown to be toxic to neurons in culture. Unlike the larger conspicuous fibril deposits, oligomers are not detected in typical pathology assays. Oligomers having similar properties have been isolated from AD brains and these are more closely associated to disease progression than the plaques (Younkin, 1998; Walsh et al., 2005a; Walsh et al., 2005b).

Experimentally generated oligomers applied to brain slices or injected in vivo cause failure of hippocampal long-term potentiation (LTP) which is a form of synaptic information storage well known as a paradigm for memory mechanisms (Lambert et al., 1998; Walsh et al., 2002; Wang et al., 2002). Soluble oligomers have been involved in the physical degeneration of synapses (Mucke et al., 2000). Reversal of memory failure by antibodies in mouse models has confirmed the emerging concept that oligomers have a major role to play in synaptic failure.

Genetic evidence suggests that increased amounts of Aβ1-42 and N-terminal truncates thereof (Aβn-42) are produced in many, if not all, genetic conditions that cause familial AD (Borchelt et al., 1996; Duff et al., 1996; Scheuner et al., 1996; Citron et al., 1998), pointing to the possibility that amyloid formation may be caused either by increased generation of Aβn-42 or decreased degradation, or both (Glabe, 2000). In particular, familial AD causing genetic mutations in the APP gene and/or in the gene encoding the γ-secretase complex component presenilin increased the production of Aβ1-42 relative to Aβ1-40. It has also been proposed that the absolute quantity of peptides produced within the brain might be less important than the ratio of Aβ peptides (reflected in a changed Aβ1-42 to Aβ1-40 ratio) for the generation of toxic Aβ species (De Strooper, 2007; Kuperstein et al., 2010). In addition, animal models of amyloid deposition, both mice and *Drosophila*, suggest that Aβ1-42 is required for the formation of amyloid deposits (Greeve et al., 2004; Iijima et al., 2004; McGowan et al., 2005).

Results from a vaccination study in 2000 suggested possible new treatment strategies for AD. The PDAPP transgenic mouse, which overexpresses mutant human APP (in which the amino acid at position 717 is phenylalanine instead of the normal valine), progressively develops many of the neuropathological hallmarks of AD in an age- and brain region-dependent manner. Transgenic animals were immunised with Aβ1-42 peptide either before the onset of AD-type neuropathologies (at 6 weeks of age) or at an older age (11 months), when Aβ deposition and several of the subsequent neuropathological changes were well established. Immunisation of the young animals essentially prevented the development of plaque formation, neuritic dystrophy and astrogliosis. Treatment of the older animals also markedly reduced the extent and progression of these AD-like neuropathologies. It was shown that Aβ1-42 immunisation resulted in the generation of anti-Aβ antibodies and that Aβ-immunoreactive monocytic/microglial cells appear in the region of remaining plaques (Schenk et al., 1999; Schenk et al., 2000). However, the active immunisation approach when applied to humans resulted in several cases of meningoencephalitis, most likely due to a T-cell response, and was discontinued although the initial results on efficacy were promising (Orgogozo et al., 2003; Gilman et al., 2005; Pride et al., 2008).

Following this, several passive vaccination strategies were investigated. The peripheral administration of antibodies against Aβ was sufficient to reduce amyloid burden (Bard et al., 2000). Despite relatively modest antibody serum levels achieved in these experiments, the passively administered antibodies were able to cross the blood-brain barrier and enter the central nervous system, decorate plaques and induce clearance of pre-existing amyloid. In a comparison between an Aβ1-40-specific antibody, an Aβ1-42-specific antibody and an antibody directed against residues 1-16 of Aβ, all antibodies were shown to reduce Aβ accumulation in mouse brain (Levites et al., 2006).

More recently, it has been suggested that CNS penetration is the most likely route to effective Aβ clearance for passively administered antibodies (Golde et al., 2009). However, in addition to the antibodies being able to cross the blood-brain barrier, the sink hypothesis was proposed as a possible mechanism of action.

The sink hypothesis states that Aβ can be removed from CNS indirectly by lowering the concentration of the peptide in the plasma. In the experiments describing this, an antibody that binds the Aβ in the plasma and thereby sequesters Aβ from the CNS was used. This was accomplished because the antibody prevents influx of Aβ from the plasma to CNS and/or changes the equilibrium between the plasma and CNS due to a lowering of the free Aβ concentration in plasma (DeMattos et al., 2001). Amyloid binding agents unrelated to antibodies have also been shown to be effective in removing Aβ from CNS through binding in plasma. Two Aβ binding agents, gelsolin and GM1, which sequester plasma Aβ were shown to reduce or prevent brain amyloidosis (Matsuoka et al., 2003).

Regarding safety, one pathogenic feature in AD is cerebral amyloid angiopathy (CAA) where there is a replacement of vascular smooth muscle cells with Aβ, mainly Aβ1-40, in the walls of cerebral arteries (Weller et al., 2003). Treating AD patients with pan-Aβ antibodies has been shown to lead to microhemorrhages reflecting the removal of Aβ from the vessel wall (Wilcock et al., 2009) which could be detrimental to patients. One way to circumvent this has been to generate de-glycosylated antibodies which may reduce the clearance mechanisms contributing to microhemorrhages and/or reduce the rate by which Aβ is cleared from the vascular deposits, preventing saturation of efflux pathways (Wilcock et al., 2006).

Targeting the n-42β peptide species with an Aβ42 specific antibody would target the species which is the key peptide composite in the AD brain and the driver of plaque formation. An antibody with a primary specificity for n-42 monomer and low n oligomer species would not only deplete these species, but could also prevent the build-up of other oligomeric species shown to be toxic to neurons.

SUMMARY OF THE INVENTION

This invention relates to fully human antibodies that are specific for Aβ 1-42 and N-terminal truncates thereof and bind to an epitope between amino acids 29-42 of the Aβ42 peptide. Antibodies according to this invention may be used for the preventative and/or therapeutic treatment of conditions associated with beta amyloid such as AD, including mild cognitive impairment (MCI) due to AD, and Down's syndrome.

The invention concerns the use of fully human antibodies to suppress isoforms of Aβ peptide (n-42) in plasma, brain and cerebrospinal fluid (CSF) to prevent accumulation or reverse the deposition of Aβ n-42 isoforms within the brain and cerebrovasculature and to improve cognition.

Described herein is the production of fully human antibodies to the Aβ n-42 peptides, which recognise monomer and low n oligomeric forms (up to and including pentamer) of Aβ n-42 and are epitope mapped to a region encompassing amino acids 17-42 on the Aβ42 peptide, more specifically to a region encompassing amino acids 29 to 42 on the Aβ42 peptide.

Antibodies in accordance with the invention are specific for Aβ n-42 species (wherein n is an integer in the range of from 1 to 29) and thus can be expected to selectively reduce the key driver of AD progression. Antibodies in accordance with the invention are effective in binding Aβ42 (not Aβ40) in human plasma, brain and cerebrospinal fluid (CSF) leading to increased clearance of Aβ n-42 isoforms from the brain. Antibodies in accordance with the invention are also effective in reducing the binding of Aβ42 soluble aggregates to neurons and thus the portion of the antibody that enters the brain will have an effect on the health of the neurons.

Described herein are potent, high affinity antibodies, including an antibody with a KD of 320 pM for monomer. Such high affinity may enable effective suppression of Aβ n-42 to levels enabling AD disease prevention and modification.

The levels of soluble Aβ42 and Aβ40 species can be detected in the brain, CSF and blood with standardised assays using antibodies directed against epitopes on the Aβ peptide. As shown in a rat PK:PD described herein, a dose-dependent suppression of free Aβ42 was observed in the CSF of rats post peripheral administration of antibody. Also demonstrated is a dose-dependent increase in total Aβ42 in the brain of rats with negligible effect on Aβ40 peptide.

Thus, described herein are antibodies that have the capacity to penetrate the brain (0.1% of total peripheral administration in the CSF) and specifically suppress the key toxic species Aβ42 (not Aβ40) in the CSF.

The specificity and mechanism of action of antibodies according to the invention may enable both the prophylactic and therapeutic treatment of a number of diseases linked to a build-up of amyloid which accumulates within organs in the body including different stages of the AD disease process: prodromal, mild and moderate AD, Down's syndrome as well as macular degeneration.

Antibodies according to the invention may have the capacity to reverse cognitive decline, treat cognitive decline and prevent cognitive decline in subjects diagnosed with prodromal, mild to moderate AD and Down's Syndrome.

Accordingly, a first aspect of the invention relates to binding members for human Aβ1-42, especially antibody molecules.

Binding members, e.g. antibody molecules, according to the invention may have any or all of the following properties:

Binding to soluble monomeric human Aβ1-42 and/or oligomeric Aβ1-42;

Selectivity in binding Aβ1-42 over Aβ1-40. They may show no binding to Aβ1-40, or binding may be negligible. For example, antibody molecules according to the invention may bind monomeric Aβ1-42 with a dissociation constant ($K_D$) of 500 pM or less. They may not bind Aβ1-40, or may bind Aβ1-40 with a $K_D$ greater than 1 mM;

Binding to human Aβ17-42. Accordingly, the antibody molecule may recognise an epitope between amino acids 17-42 of the Aβ1-42 peptide, more specifically the antibody molecule may recognise an epitope between amino acids 29-42 of the Aβ1-42 peptide;

Binding to soluble monomeric human 3pyro-42 (pyroglutamate 3) and 11pyro-42 (pyroglutamate 11)

Binding to human Aβ1-43; and

Cross-reactivity with murine Aβ1-42.

A binding member may comprise a set of HCDRs and/or a set of LCDRs of an antibody molecule as described herein. Examples of antibody molecules according to the invention comprise a VH domain containing a set of HCDRs (HCDR1, HCDR2 and HCDR3) and a VL domain containing a set of LCDRs (LCDR1, LCDR2 and LCDR3), where the HCDRs and LCDRs are the HCDRs and LCDRs respectively of any of the antibodies Abet0380, Abet0007, Abet0144, Abet0319, Abet0321b, Abet0322b, Abet0323b, Abet0328, Abet0329, Abet0332, Abet0342, Abet0343, Abet0344, Abet0368, Abet0369, Abet0370, Abet0371, Abet0372, Abet0373, Abet0374, Abet0377, Abet0378, Abet0379, Abet0381, Abet0382 and Abet0383, or a GL version thereof, whose sequences are shown in the appended sequence listing. Correspondence between the antibody molecules and the sequence identifiers in the sequence listing is indicated in Table 16.

An antibody molecule for human Aβ1-42 may comprise
  (i) a VH domain comprising a set of HCDRs: HCDR1, HCDR2 and HCDR3, interspersed with framework regions, wherein the amino acid sequences of the set of HCDRs are as shown in Table 16 for any of antibodies Abet0380, Abet0007, Abet0144, Abet0319, Abet0321b, Abet0322b, Abet0323b, Abet0328, Abet0329, Abet0332, Abet0342, Abet0343, Abet0344, Abet0368, Abet0369, Abet0370, Abet0371, Abet0372, Abet0373, Abet0374, Abet0377, Abet0378, Abet0379, Abet0381, Abet0382 and Abet0383 or a GL version thereof,
  or may comprise that set of HCDRs with one or two amino acid mutations; and
  (ii) a VL domain comprising a set of LCDRs: LCDR1, LCDR2 and LCDR3, interspersed with framework regions, wherein the amino acid sequences of the set of LCDRs are as shown in Table 16 for any of antibodies Abet0380, Abet0007, Abet0144, Abet0319, Abet0321b, Abet0322b, Abet0323b, Abet0328, Abet0329, Abet0332, Abet0342, Abet0343, Abet0344, Abet0368, Abet0369, Abet0370, Abet0371, Abet0372, Abet0373, Abet0374, Abet0377, Abet0378, Abet0379, Abet0381, Abet0382 and Abet0383, or a GL version thereof,
  or may comprise that set of LCDRs with one or two amino acid mutations.

An antibody molecule according to the invention may comprise
  (i) a VH domain comprising the Abet0380 or Abet0380 GL set of HCDRs, wherein the amino acid sequences of the Abet0380 HCDRs are
  HCDR1 SEQ ID NO: 525,
  HCDR2 SEQ ID NO: 526, and
  HCDR3 SEQ ID NO: 527,
  or may comprise the Abet0380 or Abet0380 GL set of HCDRs with one or two amino acid mutations, and
  (ii) a VL domain comprising the Abet0380 or Abet0380 GL set of LCDRs, wherein the amino acid sequences of the Abet0380 LCDRs are
  LCDR1 SEQ ID NO: 534
  LCDR2 SEQ ID NO: 535, and
  LCDR3 SEQ ID NO: 536,
  or may comprise the Abet0380 or Abet0380 GL set of LCDRs with one or two amino acid mutations.

The antibody molecule may comprise
  (i) a VH domain comprising a set of HCDRs: HCDR1, HCDR2 and HCDR3, interspersed with framework regions, wherein the amino acid sequences of the HCDRs are
  HCDR1 SEQ ID NO: 525,
  HCDR2 SEQ ID NO: 526, and
  HCDR3 SEQ ID NO: 527,
  or may comprise that set of HCDRs with one or more amino acid substitutions, wherein the one or more substitutions are selected from those shown in Table 12 or Table 14; and
  (ii) a VL domain comprising a set of LCDRs: LCDR1, LCDR2 and LCDR3, interspersed with framework regions, wherein the amino acid sequences of the LCDRs are
  LCDR1 SEQ ID NO: 534
  LCDR2 SEQ ID NO: 535, and
  LCDR3 SEQ ID NO: 536,
  or may comprise that set of LCDRs with one or more amino acid substitutions, wherein the one or more substitutions are selected from those shown in Table 13 or Table 15.

The VH domain of the antibody molecule may comprise a FW1 region in which the amino acid residues at Kabat positions 26-30 are selected from those shown in Table 14.

The VH domain of the antibody molecule may comprise heavy chain framework regions FW1, FW2, FW3 and FW4, wherein the amino acid sequences of the heavy chain framework regions are
  FW1 SEQ ID NO: 528
  FW2 SEQ ID NO: 529
  FW3 SEQ ID NO: 530, and
  FW4 SEQ ID NO: 531
  or wherein FW1 comprises SEQ ID NO: 528 with one or more amino acid substitutions, wherein the one or more substitutions in FW1 are selected from those shown in Table 12 or Table 14.

The VL domain of the antibody molecule may comprise light chain framework regions FW1, FW2, FW3 and FW4, wherein the amino acid sequences of the light chain framework regions are
  FW1 SEQ ID NO: 537
  FW2 SEQ ID NO: 538
  FW3 SEQ ID NO: 539, and
  FW4 SEQ ID NO: 540.

An antibody molecule according to the invention may comprise
(i) a VH domain amino acid sequence as shown in Table 16 for any of Abet0380, Abet0343, Abet0369, Abet0377 and Abet0382, or a GL version thereof, or may comprise that amino acid sequence with one or two amino acid mutations; and
(ii) a VL domain amino acid sequence as shown in Table 16 for any of Abet0380, Abet0343, Abet0369, Abet0377 and Abet0382, or a GL version thereof, or may comprise that amino acid sequence with one or two amino acid mutations.

An antibody molecule according to the invention may comprise a VH domain having an amino acid sequence at least 85% identical to SEQ ID NO: 524 and a VL domain having an amino acid sequence at least 85% identical to SEQ ID NO: 533, wherein in the VH domain:
amino acid 26 is M, G or S;
amino acid 27 is G, F or D;
amino acid 28 is N, T, D or H,
amino acid 29 is F
amino acid 30 is N, S, K, or P;
amino acid 31 is Y, V, R, E, or T;
amino acid 32 is Q, Y, D, S, or E;
amino acid 33 is T, P, I, or V;
amino acid 34 is M;
amino acid 35 is W;
amino acid 50 is V;
amino acid 51 is I;
amino acid 52 is G;
amino acid 52a is K, S, or A;
amino acid 53 is T, S, N, D, G, or Q;
amino acid 54 is N, G, T, or P;
amino acid 55 is E, G, N, K, or T;
amino acid 56 is N, T, R, or K;
amino acid 57 is I, T, K, or V;
amino acid 58 is A, V, or T;
amino acid 59 is Y;
amino acid 60 is A;
amino acid 61 is D;
amino acid 62 is S;
amino acid 63 is V;
amino acid 64 is K;
amino acid 65 is G;
amino acid 95 is E;
amino acid 96 is W;
amino acid 97 is M
amino acid 98 is D;
amino acid 99 is H;
amino acid 100 is S;
amino acid 100a is R;
amino acid 100b is P;
amino acid 100c is Y;
amino acid 100d is Y;
amino acid 100e is Y;
amino acid 100f is Y;
amino acid 100g is G;
amino acid 100h is M;
amino acid 101 is D;
amino acid 102 is V;
and wherein in the VL domain:
amino acid 24 is S;
amino acid 25 is G;
amino acid 26 is H;
amino acid 27 is N;
amino acid 28 is L, or I;
amino acid 29 is E, or G;
amino acid 30 is D;
amino acid 31 is K;
amino acid 32 is F, or W;
amino acid 33 is A, or V;
amino acid 34 is S;
amino acid 50 is R;
amino acid 51 is D;
amino acid 52 is D;
amino acid 53 is K;
amino acid 54 is R;
amino acid 55 is P;
amino acid 56 is S;
amino acid 89 is S, or Q;
amino acid 90 is S, or A;
amino acid 91 is Q;
amino acid 92 is D;
amino acid 93 is T, or S;
amino acid 94 is V, or T;
amino acid 95 is T;
amino acid 96 is R;
amino acid 97 is V.

An antibody molecule according to the invention may comprise a VH domain having an amino acid sequence at least 85% identical to SEQ ID NO: 524 and a VL domain having an amino acid sequence at least 85% identical to SEQ ID NO: 533, wherein in the VH domain:
amino acid 26 is M, G, S, V, A, N, T, or H;
amino acid 27 is G, F, S, Y, E, D, or P;
amino acid 28 is N, Q, H, V, E, T, A, S, D, M, or P;
amino acid 29 is F, I, Y, S, L, or W;
amino acid 30 is N, S, T, Q, K, H, R, G, P, E, K, A, or D;
amino acid 31 is Y, H, K, E, N, T, R, V, P, M, F, I, D, or W;
amino acid 32 is Q, Y, D, N, S, E, or T;
amino acid 33 is T, P, I, or V;
amino acid 34 is M, or L;
amino acid 35 is W;
amino acid 50 is V;
amino acid 51 is I;
amino acid 52 is G;
amino acid 52a is K, S, P, A, N, G, E, D, V, or T;
amino acid 53 is T, S, N, H, Q, D, G, or E;
amino acid 54 is N, G, P, T, Q, E, M, K, or A;
amino acid 55 is E, G, K, N, Q, T, H, D, or A;
amino acid 56 is N, T, A, R, or K;
amino acid 57 is I, T, N, S, K, F, Q, V, or L;
amino acid 58 is A, V, S, T, or N;
amino acid 59 is Y;
amino acid 60 is A;
amino acid 61 is D;
amino acid 62 is S, A, or T;
amino acid 63 is V;
amino acid 64 is K;
amino acid 65 is G;
amino acid 95 is E;
amino acid 96 is W;
amino acid 97 is M
amino acid 98 is D, or G;
amino acid 99 is H, or R;
amino acid 100 is S;
amino acid 100a is R;
amino acid 100b is P;
amino acid 100c is Y;
amino acid 100d is Y;
amino acid 100e is Y;
amino acid 100f is Y;
amino acid 100g is G;

amino acid 100h is M, or I;
amino acid 101 is D;
amino acid 102 is V, or A;
and wherein in the VL domain:
amino acid 24 is S, or T;
amino acid 25 is G, or T;
amino acid 26 is H, R, or P;
amino acid 27 is N, or H;
amino acid 28 is L, I, V, F, or T;
amino acid 29 is E, M, G, S, or N;
amino acid 30 is D, A, S, G, or H;
amino acid 31 is K, or S;
amino acid 32 is F, or W;
amino acid 33 is A, V, M, T, or I;
amino acid 34 is S, T, or A;
amino acid 50 is R;
amino acid 51 is D;
amino acid 52 is D;
amino acid 53 is K;
amino acid 54 is R;
amino acid 55 is P;
amino acid 56 is S;
amino acid 89 is S, Q, or A;
amino acid 90 is S, A, or T;
amino acid 91 is Q
amino acid 92 is D, or G;
amino acid 93 is T, Q, S, N, or K;
amino acid 94 is V, T, or F;
amino acid 95 is T;
amino acid 96 is R;
amino acid 97 is V, S, or A.

An antibody molecule according to the invention may comprise:
(i) a VH domain having an amino acid sequence at least 90% identical to a VH domain amino acid sequence shown in Table 16 for any of Abet0380, Abet0343, Abet0369, Abet0377 and Abet0382, or a GL version thereof; and
(ii) a VL domain having an amino acid sequence at least 90% identical to a VL domain amino acid sequence shown in Table 16 for any of Abet0380, Abet0343, Abet0369, Abet0377 and Abet0382, or a GL version thereof.

The antibody molecule may comprise a VH domain and a VL domain at least 90% identical with the VH domain and VL domain, respectively, of any of Abet0380, Abet0343, Abet0369, Abet0377 and Abet0382, or a GL version thereof.

The indicated percentage identity of the VH and/or VL domain may be at least 95%, at least 98% or at least 99%.

The antibody molecule may comprise the VH domain and VL domain of any of Abet0380, Abet0343, Abet0369, Abet0377 and Abet0382 or a GL version thereof.

For example, the antibody molecule may comprise the Abet0380-GL VH domain amino acid sequence SEQ ID NO: 524 and the Abet0380-GL VL domain amino acid sequence SEQ ID NO: 533.

An antibody molecule according to the invention may be one that competes for binding to Aβ1-42 with:
(i) an antibody molecule comprising a VH domain amino acid sequence SEQ ID NO: 524 and a VL domain amino acid sequence SEQ ID NO: 533,
(ii) an antibody molecule encoded by nucleic acid deposited under accession number NCIMB 41890, 41891 or 41892.

An antibody molecule may comprise a VH domain and a VL domain encoded by:
(i) the Abet0380-GL nucleic acid sequence deposited under accession number 41890;
(ii) the Abet0144-GL nucleic acid sequence deposited under accession number 41891; or
(ii) the Abet0377-GL nucleic acid sequence deposited under accession number 41892.

The antibody molecule may comprise a VH domain and a VL domain comprising the HCDRs and LCDRs, respectively, of a deposited antibody mentioned above. The antibody molecule may be the antibody encoded by the deposited nucleic acid mentioned above.

Also described herein are nucleic acid molecules encoding binding members according to the invention, host cells containing the nucleic acid, and methods of producing the binding members by expressing the nucleic acid and recovering the binding member.

Further aspects of the invention relate to compositions comprising an antibody molecule according to any of the preceding claims, and one or more additional components, such as a pharmaceutically acceptable excipient, and to such compositions for medical use. Compositions comprising binding members according to the present invention may be provided for use in a method of treatment of the human or animal body.

Binding members described herein may be used in methods of diagnosis or treatment in human or animal subjects, e.g. humans. Binding members of the invention may be used to decrease levels of Aβ1-42 in an individual and/or to reduce amyloidosis. Binding members may be used to reduce amyloidosis and to treat, reduce or prevent conditions associated with amyloidosis. Conditions and diseases that may be treated include Alzheimer's disease, such as prodomal, mild or moderate AD. AD treated by the invention may be familial or sporadic AD. The invention may be used to prevent, reduce or reverse mild cognitive impairment (MCI) associated with AD. Cognition may be improved, and/or cognitive decline may be lessened, in AD patients or Down's syndrome patients. The invention may also be used to treat or prevent macular degeneration, which is linked with amyloid beta (Ding et al. PNAS 108(28): E279-287 2011).

Accordingly, in a further aspect, the invention provides a method of reducing amyloidosis, treating Alzheimer's disease, improving cognition or reducing cognitive decline in Alzheimer's disease or Down's syndrome, and/or treating macular degeneration in an individual, comprising administering a binding member of the invention to the individual.

These and other aspects of the invention are described in more detail below.

- ✱— Abeta 1-42
- ✦--- Abeta 1-43
- ▼ Abeta 1-16
- ◆ Abeta 12-28
- ✲⋯ Abeta 17-42
- ✱- Abeta Pyro-3-42
- ✱- Abeta Pyro 11-42
- ◇ Vehicle 1 (DMSO)
- − Vehicle 2 (NH4OH)

The x-axis shows the concentration of Abeta peptide in log M, the y-axis shows % specific binding. Inhibition of Abet0380-GL IgG1-TM: N-terminal Biotin Abeta 1-42 binding was observed with Abeta 1-42, Abeta 1-43, Abeta 17-42, Abeta Pyro-3-42 & Abeta Pyro-11-42 with $IC_{50}$ values ranging from 10- to 10-molar for this group. No inhibition of Abet0380-GL IgG1-TM: N-terminal Biotin Abeta 1-42 binding was observed with Abeta 1-16 or Abeta 12-28.

Figure 19:
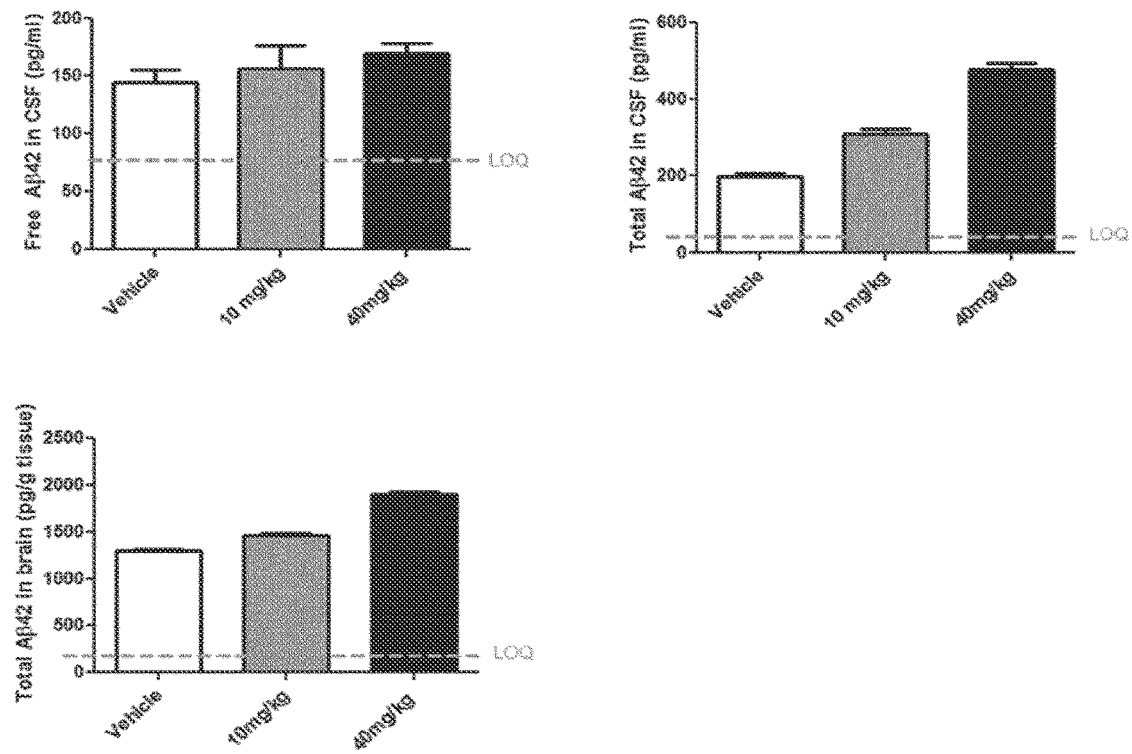

FIG. 19 shows the ability of antibody Abet0144-GL to sequester amyloid beta 1-42 in a normal rat PK-PD study. The x-axis shows vehicle or concentration of Abet0144-GL (10 mg/kg, or 40 mg/kg), the y-axis shows the concentration of total amyloid beta 1-42 in CSF in μg/ml. Free amyloid beta 1-42 in CSF was not significantly altered by either 10 or 40 mg/kg of Abet0144-GL (5 and 18% increase respectively when compared with vehicle). Total amyloid beta 1-42 in CSF was significantly increased by 38% at 10 mg/kg, and by 139% at 40 mg/kg. Total amyloid beta 1-42 in brain tissue was also significantly increased, by 16% and 50% at 10 and 40 mg/kg respectively. Data from this study in normal rats, demonstrate that Abet0144-GL had no significant effect on free amyloid beta 1-42 levels in CSF, whilst increasing total amyloid beta 1-42 levels in both CSF and brain.

DETAILED DESCRIPTION

By binding isoforms of Aβ peptide 1-42 and N-terminal truncates thereof (n-42) in plasma, brain and cerebrospinal fluid (CSF), a binding member according to the present invention may prevent accumulation or reverse the deposition of Aβ n-42 isoforms within the brain and cerebrovasculature. Binding members according to the present invention may bind and precipitate soluble Aβ1-42 in blood plasma and/or in cerebrospinal fluid (CSF), thereby reducing the concentration of Aβ1-42 in the serum and/or CSF, respectively. This represents a therapeutic approach for Alzheimer's disease and other conditions associated with amyloidosis.

Binding members are specific for the target epitope within Aβ17-42, more specifically within Aβ29-42, and bind this target epitope with high affinity relative to non-target epitopes, for example epitopes from Aβ1-40, thereby targeting the main toxic species linked with amyloid plaque formation. For example, a binding member may display a binding affinity for Aβ1-42 which is at least 10-fold, at least 100-fold, at least 1000-fold or at least 10,000-fold greater than for Aβ1-40. Thus, the binding member is selective for binding Aβ1-42 over Aβ1-40. As noted above, the binding member may bind Aβ1-42 with a dissociation constant ($K_D$) of 500 pM or less. Preferably, it shows no significant binding to Aβ1-40. Affinity and binding can be determined using surface plasmon resonance using monomeric Aβ peptide, as described in the Examples.

Binding to Aβ can also be measured in a homogenous time resolved fluorescence (HTRF™) assay, to determine whether the antibody is able to compete for binding to Aβ with a reference antibody molecule to the Aβ peptide, as described in the Examples.

An HTRF™ assay is a homogeneous assay technology that utilises fluorescence resonance energy transfer between a donor and acceptor fluorophore that are in close proximity. Such assays can be used to measure macromolecular interactions by directly or indirectly coupling one of the molecules of interest to a donor fluorophore, europium (Eu3+) cryptate, and coupling the other molecule of interest to an acceptor fluorophore XL665, (a stable cross linked allophycocyanin). Excitation of the cryptate molecule (at 337 nm) results in fluorescence emission at 620 nm. The energy from this emission can be transferred to XL665 in close proximity to the cryptate, resulting in the emission of a specific long-lived fluorescence (at 665 nm) from the XL665. The specific signals of both the donor (at 620 nm) and the acceptor (at 665 nm) are measured, allowing the calculation of a 665/620 nm ratio that compensates for the presence of coloured compounds in the assay.

A binding member according to the invention may compete for binding to Aβ1-42 and thus inhibit binding of the reference antibody in an HTFR™ competition assay with Aβ1-42, but not with Aβ1-40. A binding member may show at least 70%, at least 75%, at least 80%, at least 85% or at least 90% inhibition of Abet0144GL for binding to Aβ1-42 in an HTRF™ assay.

Potency of inhibition of binding may be expressed as an $IC_{50}$ value, in nM unless otherwise stated. In functional assays, $IC_{50}$ is the concentration of an antibody molecule that reduces a biological response by 50% of its maximum. In ligand-binding studies, $IC_{50}$ is the concentration that reduces receptor binding by 50% of maximal specific binding level. $IC_{50}$ may be calculated by plotting % of maximal biological response as a function of the log of the binding member concentration, and using a software program, such as Prism (GraphPad) or Origin (Origin Labs) to fit a sigmoidal function to the data to generate $IC_{50}$ values. Suitable assays for measuring or determining potency are well known in the art.

A binding member may have an $IC_{50}$ of 5 nM or less, e.g. 2 nM or less, e.g. 1 nM or less, in HTRF™ epitope competition assay with Abet0144-GL and Aβ1-42. Abet0144-GL is an antibody molecule having VH domain SEQ ID NO: 20 and VL domain SEQ ID NO: 29. It may be used in the assay in the same format as the antibody molecule to be tested, for example in scFv or IgG, e.g. IgG1 format. Thus, IgG antibody molecules according to the invention may compete with Abet0144-GL IgG for binding to human Aβ1-42 in an HTRF epitope competition assay. Potency in such an assay may be less than 1 nM.

A binding member according to the invention may show specific binding for Aβ1-42 over Aβ1-40, as determined by an HTRF™ competition assay. In such an assay, Aβ1-40 may show no significant inhibition of the binding member binding to the Aβ1-42 peptide, e.g. it may show less than 20%, e.g. less than 10% or less than 5%, inhibition in such an assay, and preferably shows no significant inhibition in such an assay.

Binding members according to the invention recognise an epitope within human Aβ17-42, more specifically within human Aβ29-42 and may also recognise their target epitope in Aβ from other species, e.g. mouse or rat. The potency of a binding member as calculated in an HTRF™ competition assay using Aβ1-42 from a first species (e.g. human) may be compared with potency of the binding member in the same assay using Aβ1-42 from a second species (e.g. mouse Aβ1-42), in order to assess the extent of cross-reactivity of the binding member for Aβ1-42 of the two species. Potency, as determined by IC$_{50}$ measurements, may be within 10-fold or within 100-fold. As noted above, Abet0144GL may be used as reference antibody in the HTRF™ competition assay. Binding members described herein may have a greater potency in a human Aβ1-42 assay than in a non-human Aβ1-42 assay.

A binding member may comprise an antibody molecule having one or more CDRs, e.g. a set of CDRs, within an antibody framework (i.e. an antibody antigen-binding domain). For example, an antibody molecule may comprise an antibody VH and/or VL domain. VH and VL domains of antibody molecules are also provided as part of the invention. As is well-known, VH and VL domains comprise complementarity determining regions, ("CDRs"), and framework regions, ("FWs"). A VH domain comprises a set of HCDRs and a VL domain comprises a set of LCDRs. An antibody molecule may comprise an antibody VH domain comprising a VH CDR1, CDR2 and CDR3 and/or an antibody VL domain comprising a VL CDR1, CDR2 and CDR3. VH or VL domains may further comprise a framework. A VH or VL domain framework typically comprises four framework regions, FW1, FW2, FW3 and FW4, which are interspersed with CDRs in the following structure: FW1-CDR1-FW2-CDR2-FW3-CDR3-FW4.

Examples of antibody VH and VL domains, FWs and CDRs according to aspects of the invention are listed in Tables 5 and 6 and the appended sequence listing that forms part of the present disclosure. All VH and VL sequences, CDR sequences, sets of CDRs, sets of HCDRs and sets of LCDRs disclosed herein, as well as combinations of these elements, represent aspects of the invention. As described herein, a "set of CDRs" comprises CDR1, CDR2 and CDR3. Thus, a set of HCDRs refers to HCDR1, HCDR2 and HCDR3, and a set of LCDRs refers to LCDR1, LCDR2 and LCDR3. Unless otherwise stated, a "set of CDRs" includes HCDRs and LCDRs. Typically antibody molecules of the invention are monoclonal antibodies.

In other embodiments, a binding member may comprise an antigen-binding site within a non-antibody molecule, normally provided by one or more CDRs e.g. a set of CDRs in a non-antibody protein scaffold, as discussed further below.

The isolation of a parent antibody molecule designated Abet0007, followed by directed mutation of CDR3 and selection of an optimised antibody Abet0144, germlined to Abet0144-GL with a set of CDR sequences and framework sequences as shown in Tables 5, 6 and the sequence listing, is described herein. Through an extensive process of further optimisation and recombination of multiple libraries as described in the Examples, a panel of antibody clones was generated from Abet0144GL. These further optimised clones are designated Abet0380, Abet0319, Abet0321b, Abet0322b, Abet0323b, Abet0328, Abet0329, Abet0332, Abet0342, Abet0343, Abet0369, Abet0370, Abet0371, Abet0372, Abet0373, Abet0374, Abet0377, Abet0378, Abet0379, Abet0381, Abet0382 and Abet0383. Their CDR sequences and variable domain sequences are referenced in Tables 5 and 6 and set out in the sequence listing. Germlined VH and VL domain sequences Abet0380GL, Abet0377GL, Abet0343GL, Abet0369GL and Abet0382GL are shown in Table 8 and Table 9.

For example, Tables 5 and 6 show that Abet0380 has a set of CDRs, in which HCDR1 is SEQ ID NO: 525 (Kabat residues 31-35), HCDR2 is SEQ ID NO: 526 (Kabat residues 50-65), HCDR3 is SEQ ID NO: 527 (Kabat residues 95-102), LCDR1 is SEQ ID NO: 534 (Kabat residues 24-34), LCDR2 is SEQ ID NO: 535 (Kabat residues 50-56) and LCDR3 is SEQ ID NO: 536 (Kabat residues 89-97). The other optimised antibody clones are shown in Tables 5 and 6 in a similar way and are also provided as aspects of the invention.

A binding member for human Aβ1-42 in accordance with the invention may comprise one or more CDRs as described herein, e.g. a set of CDRs. The CDR or set of CDRs may be an Abet0380, Abet0319, Abet0321b, Abet0322b, Abet0323b, Abet0328, Abet0329, Abet0332, Abet0342, Abet0343, Abet0369, Abet0370, Abet0371, Abet0372, Abet0373, Abet0374, Abet0377, Abet0378, Abet0379, Abet0381, Abet0382 and Abet0383 set of CDRs, or a germlined version thereof, or may be a variant thereof as described herein.

In some embodiments;
HCDR1 is may be 5 amino acids long, consisting of Kabat residues 31-35;
HCDR2 may be 17 amino acids long, consisting of Kabat residues 50-65;
HCDR3 may be 16 amino acids long, consisting of Kabat residues 95-102;
LCDR1 may be 11 amino acids long, consisting of Kabat residues 24-34;
LCDR2 may be 7 amino acids long, consisting of Kabat residues 50-56; and/or
LCDR3 may be 9 amino acids long, consisting of Kabat residues 89-97.

Binding members may comprise a HCDR1, HCDR2 and/or HCDR3 and/or an LCDR1, LCDR2 and/or LCDR3 of any of the antibodies listed in Tables 5 and 6, e.g., a set of CDRs of any of the antibodies listed in Table 5 or 6. The binding member may comprise a set of VH CDRs of any one of these antibodies. Optionally, it may also comprise a set of VL CDRs of one of these antibodies. The VL CDRs may be from the same or a different antibody as the VH CDRs. A VH domain comprising a set of HCDRs of any of the antibodies listed in Tables 5, and/or a VL domain comprising a set of LCDRs of any of the antibodies listed in Tables 6, are also provided herein.

A binding member may comprise a set of H and/or L CDRs of any of the antibodies listed in Tables 5 and 6 with one or more amino acid mutations, e.g. up to 5, 10 or 15 mutations, within the disclosed set of H and/or L CDRs. A mutation may be an amino acid substitution, deletion or insertion. For example, an antibody molecule of the invention may comprise the set of H and/or L CDRs from any one of Abet0380, Abet0319, Abet0321b, Abet0322b, Abet0323b, Abet0328, Abet0329, Abet0332, Abet0342, Abet0343, Abet0369, Abet0370, Abet0371, Abet0372, Abet0373, Abet0374, Abet0377, Abet0378, Abet0379, Abet0381, Abet0382 and Abet0383, or a germlined version thereof, with one or two amino acid mutations, e.g. substitutions.

For example, the binding member may comprise
a VH domain comprising the Abet0380 or Abet0380GL set of HCDRs, wherein the amino acid sequences of the Abet0380 or Abet0380GL HCDRs are
HCDR1 SEQ ID NO: 525,
HCDR2 SEQ ID NO: 526, and
HCDR3 SEQ ID NO: 527,
or comprising the Abet0380 set of HCDRs with one or two amino acid mutations, and (ii) a VL domain comprising the Abet0380 or Abet0380GL set of LCDRs, wherein the amino acid sequences of the Abet0380 or Abet0380GL LCDRs are
LCDR1 SEQ ID NO: 534
LCDR2 SEQ ID NO: 535, and
LCDR3 SEQ ID NO: 536,
or comprising the Abet0380 or Abet0380GL set of LCDRs with one or two amino acid mutations.

Mutations may potentially be made at any residue within the set of CDRs. In some embodiments, substitutions may be made at the positions substituted in any of Abet0380, Abet0319, Abet0321b, Abet0322b, Abet0323b, Abet0328, Abet0329, Abet0332, Abet0342, Abet0343, Abet0369, Abet0370, Abet0371, Abet0372, Abet0373, Abet0374, Abet0377, Abet0378, Abet0379, Abet0381, Abet0382 and Abet0383 compared with Abet0144GL, or at the positions substituted in any of Abet0319, Abet0321b, Abet0322b, Abet0323b, Abet0328, Abet0329, Abet0332, Abet0342, Abet0343, Abet0369, Abet0370, Abet0371, Abet0372, Abet0373, Abet0374, Abet0377, Abet0378, Abet0379, Abet0381, Abet0382 and Abet0383 compared with Abet0380, or germlined versions thereof, as shown in Tables 5 and 6.

For example, the one or more substitutions may be at one or more of the following Kabat residues:
26, 27, 28, 29 or 30 in VH FW1;
31, 32, 33, 34 or 35 in VH CDR1;
52a, 53, 54, 55, 56, 57, 58 or 62 in VH CDR2;
98, 99, 100h or 102 in VH CDR3;
24, 25, 26, 27, 28, 29, 30, 31, 32, 33, 34 in VL CDR1;
89, 90, 92, 93, 94 or 97 in VL CDR3.

Examples of possible amino acid substitutions at particular Kabat residue positions are shown in Tables 12 and 14 for the VH domain and Tables 13 and 15 for the VL domain.

As described above, a binding member may comprise an antibody molecule having one or more CDRs, e.g. a set of CDRs, within an antibody framework. For example, one or more CDRs or a set of CDRs of an antibody may be grafted into a framework (e.g. human framework) to provide an antibody molecule. The framework regions may be of human germline gene segment sequences. Thus, the framework may be germlined, whereby one or more residues within the framework are changed to match the residues at the equivalent position in the most similar human germline framework. The skilled person can select a germline segment that is closest in sequence to the framework sequence of the antibody before germlining and test the affinity or activity of the antibodies to confirm that germlining does not significantly reduce antigen binding or potency in assays described herein. Human germline gene segment sequences are known to those skilled in the art and can be accessed for example from the VBASE compilation (VBASE, MRC Centre of Protein Engineering, U K, 1997, http//mrc-cpe-.cam.ac.uk).

A binding member as described herein may be an isolated human antibody molecule having a VH domain comprising a set of HCDRs in a human germline framework, e.g. Vh3-23 DP-47. Thus, the VH domain framework regions FW1, FW2 and/or FW3 may comprise framework regions of human germline gene segment Vh3-23 DP-47 and/or may be germlined by mutating framework residues to match the framework residues of this human germline gene segment. FW4 may comprise a framework region of a human germline j segment.

The amino acid sequence of VH FW1 may be SEQ ID NO: 528. VH FW1 contains a series of residues at Kabat positions 26-30 that are believed to contribute to antigen binding and/or to be important for structural conformation of the CDR1 loop. Substitutions may be included in SEQ ID NO: 528, for example to synergise with the selected sequence of HCDR1. The one or more substitutions may optionally be selected from those shown in Table 12 or Table 14.

The amino acid sequence of VH FW2 may be SEQ ID NO: 529. The amino acid sequence of VH FW3 may be SEQ ID NO: 530. The amino acid sequence of VH FW4 may be SEQ ID NO: 531.

Normally the binding member also has a VL domain comprising a set of LCDRs, e.g. in a human germline framework, e.g. V lambda 23-3 DPL-23. Thus, the VL domain framework regions may comprise framework regions FW1, FW2 and/or FW3 of human germline gene segment V lambda 23-3 DPL-23 and/or may be germlined by mutating framework residues to match the framework residues of this human germline gene segment. FW4 may comprise a framework region of a human germline j segment. The amino acid sequence of VL FW1 may be SEQ ID NO: 537. The amino acid sequence of VL FW2 may be SEQ ID NO: 538. The amino acid sequence of VL FW3 may be SEQ ID NO: 539. The amino acid sequence of VL FW4 may be SEQ ID NO: 540.

A germlined VH or VL domain may or may not be germlined at one or more Vernier residues, but is normally not.

For example, an antibody molecule or a VH domain as described herein may comprise the following set of heavy chain framework regions:
FW1 SEQ ID NO: 528;
FW2 SEQ ID NO: 529;
FW3 SEQ ID NO: 530;
FW4 SEQ ID NO: 531;
or may comprise the said set of heavy chain framework regions with 1, 2, 3, 4, 5, 6 or 7 amino acid mutations, e.g. substitutions.

An antibody molecule or a VL domain as described herein may comprise the following set of light chain framework regions:
FW1 SEQ ID NO: 537;
FW2 SEQ ID NO: 538;
FW3 SEQ ID NO: 539;
FW4 SEQ ID NO: 540;
or may comprise the said set of light chain framework regions with 1, 2, 3, 4, 5, or 6 amino acid mutations, e.g. substitutions.

A non-germlined antibody molecule has the same CDRs, but different frameworks, compared to a germlined antibody molecule. Of the antibody sequences shown herein in the appended sequence listing, sequences of Abet0144-GL, Abet0380-GL, Abet0377-GL, Abet0343-GL, Abet0369-GL, and Abet0382-GL are germlined. Germlined antibodies of other antibody molecules whose sequences are disclosed herein may be produced by germlining framework regions of their VH and VL domain sequences, optionally to Vh3-23 DP-47 in the VH domain and V lambda 23-3 DPL-23 in the VL domain.

Typically, a VH domain is paired with a VL domain to provide an antibody antigen-binding site, although as discussed above a VH or VL domain alone may be used to bind antigen. For example, the Abet0380-GL VH domain (SEQ ID NO: 524) may be paired with the Abet0380-GL VL domain (SEQ ID NO:533), so that an antibody antigen-binding site is formed comprising both the Abet0380-GL VH and VL domains. Analogous embodiments are provided for the VH and VL domains of the other antibodies disclosed herein. In other embodiments, the Abet0380-GL VH is paired with a VL domain other than the Abet0380-GL VL. Light-chain promiscuity is well established in the art. Again, analogous embodiments are provided by the invention for the other VH and VL domains disclosed herein. Thus, a VH domain comprising the VH CDRs or the germlined VH domain sequence of any of Abet0319, Abet0321b, Abet0322b, Abet0323b, Abet0328, Abet0329, Abet0332, Abet0342, Abet0343, Abet0369, Abet0370, Abet0371, Abet0372, Abet0373, Abet0374, Abet0377, Abet0378, Abet0379, Abet0380, Abet0381, Abet0382 and Abet0383 may be paired with a VL domain comprising the VL CDRs or germlined VL domain from a different antibody e.g. the VH and VL domains may be from different antibodies selected from Abet0319, Abet0321b, Abet0322b, Abet0323b, Abet0328, Abet0329, Abet0332, Abet0342, Abet0343, Abet0369, Abet0370, Abet0371, Abet0372, Abet0373, Abet0374, Abet0377, Abet0378, Abet0379, Abet0380, Abet0381, Abet0382 and Abet0383.

A binding member may comprise
(i) a VH domain amino acid sequence as shown in Table 16 or in the appended sequence listing for any of Abet0380, Abet0343, Abet0369, Abet0377 and Abet0382, or a germlined version thereof,
or comprising that amino acid sequence with one or two amino acid mutations; and
(ii) a VL domain amino acid sequence as shown in Table 16 or in the appended sequence listing for any of Abet0380, Abet0343, Abet0369, Abet0377 and Abet0382, or a germlined version thereof,
or comprising that amino acid sequence with one or two amino acid mutations.

An antibody molecule may comprise:
(i) a VH domain having an amino acid sequence at least 90%, 95% or 98% identical to a VH domain amino acid sequence shown in Table 16 for any of Abet0380, Abet0343, Abet0369, Abet0377 and Abet0382, or a germlined version thereof; and
(ii) a VL domain having an amino acid sequence at least 90%, 95% or 98% identical to a VL domain amino acid sequence shown in Table 16 for any of Abet0380, Abet0343, Abet0369, Abet0377 and Abet0382, or a germlined version thereof.

It may comprise a VH domain and a VL domain at least 90%, 95% or 98% identical with the VH domain and VL domain, respectively, of any of Abet0380, Abet0343, Abet0369, Abet0377 and Abet0382, or a germlined version thereof.

A binding member may comprise a VH domain and a VL domain in which;
(i) the VH domain amino acid sequence is shown in SEQ ID NO: 524 and the VL domain amino acid sequence is shown in SEQ ID NO: 533.
(ii) the VH domain amino acid sequence has 1, 2, 3, 4, 5, 6, 7, 8, 9 or 10 amino acid substitutions as compared to SEQ ID NO: 524 and the VL domain amino acid sequence has 1, 2, 3, 4, 5, 6, 7, 8, 9 or 10 amino acid substitutions as compared to SEQ ID NO: 533; or
(iii) the VH domain amino acid sequence has at least 80%, at least 85%, at least 90% or at least 95% sequence identity with SEQ ID NO: 524 and the VL domain amino acid sequence has at least 80%, at least 85%, at least 90% or at least 95% sequence identity with SEQ ID NO: 533.

In some embodiments, an antibody molecule may lack antibody constant regions, for example an scFv.

In other embodiments, an antibody molecule may comprise an antibody constant region. An antibody molecule may be a whole antibody such as an IgG, i.e. an IgG1, IgG2, or IgG4, or may be an antibody fragment or derivative as described below. Antibody molecules can also have other formats, e.g. IgG1 with YTE (Dall'Acqua et al. (2002) J. Immunology, 169: 5171-5180; Dall'Acqua et al. (2006) J Biol. Chem. 281(33):23514-24) and/or TM mutations (Oganesyan et al. (2008) Acta Cryst D64:700-4) in the Fc region.

The invention provides a binding member of the present invention with a variant Fc region, wherein the variant comprises a phenylalanine (F) residue at position 234, a phenylalanine (F) residue or a glutamic acid (E) residue at position 235 and a serine (S) residue at position 331, as numbered by the EU index as set forth in Kabat. Such mutation combinations are hereinafter referred to as the triple mutant (TM).

A binding member as described herein may comprise a CDR, VH domain, VL domain, antibody-antigen binding site or antibody molecule which is encoded by the nucleic acid sequences and/or the vector of any of:
(i) deposit accession number NCIMB 41889 (Abet0007);
(ii) deposit accession number NCIMB 41890 (Abet0380-GL);
(iii) deposit accession number NCIMB 41891 (Abet0144-GL);
(iv) deposit accession number NCIMB 41892 (Abet0377-GL).

A binding member as described herein may be produced or producible from the nucleic acid, vector or cell line of deposit accession number NCIMB 41889, 41890, 41891 or 41892. For example, a binding member may be produced by expression of the nucleic acid or vector of the cell line of deposit accession number NCIMB 41890. The nucleic acid or vector may be expressed any convenient expression system. Alternatively, the binding member may be expressed by the cell line of deposit accession number NCIMB 41889, 41890, 41891 or 41892.

Aspects of the invention also provide nucleic acid encoding the VH and/or VL domains, which is contained in the cell line of accession number 41889, 41890, 41891 or 41892; a vector comprising said nucleic acid, which is contained in the cell line of accession number 41889, 41890, 41891 or 41892; and the cells or cell line of accession number 41889, 41890, 41891 or 41892.

A binding member according to the present invention may comprise an antibody antigen binding site or antibody molecule that competes for binding to human Aβ1-42 with any antibody molecule encoded by nucleic acid deposited under accession number 41889, 41890, 41891 or 41892, or with an antibody molecule that comprises the VH domain and VL domain amino acid sequences of Abet007, Abet0380-GL, Abet0144-GL or Abet0377-GL as set out in the appended sequence listing.

Binding Member

The term binding member describes one member of a pair of molecules that bind one another. The members of a binding pair may be naturally derived or wholly or partially synthetically produced. One member of the pair of molecules has an area on its surface, or a cavity, which binds to and is therefore complementary to a particular spatial and polar organization of the other member of the pair of molecules. Examples of types of binding pairs are antigen-antibody, biotin-avidin, hormone-hormone receptor, receptor-ligand, enzyme-substrate. The present invention is concerned with antigen-antibody type reactions.

A binding member normally comprises a molecule having an antigen-binding site. For example, a binding member may be an antibody molecule or a non-antibody protein that comprises an antigen-binding site.

An antigen binding site may be provided by means of arrangement of CDRs on non-antibody protein scaffolds, such as fibronectin or cytochrome B etc. [Haan & Maggos (2004) BioCentury, 12(5): A1-A6; Koide et al. (1998) Journal of Molecular Biology, 284:1141-1151; Nygren et al. (1997) Current Opinion in Structural Biology, 7: 463-469], or by randomising or mutating amino acid residues of a loop within a protein scaffold to confer binding specificity for a desired target. Scaffolds for engineering novel binding sites in proteins have been reviewed in detail by Nygren et al. [supra]. Protein scaffolds for antibody mimics are disclosed in WO00/34784, which is herein incorporated by reference in its entirety, in which the inventors describe proteins (antibody mimics) that include a fibronectin type III domain having at least one randomised loop. A suitable scaffold into which to graft one or more CDRs, e.g. a set of HCDRs or an HCDR3 and/or LCDR3, may be provided by any domain member of the immunoglobulin gene superfamily. The scaffold may be a human or non-human protein. An advantage of a non-antibody protein scaffold is that it may provide an antigen-binding site in a scaffold molecule that is smaller and/or easier to manufacture than at least some antibody molecules. Small size of a binding member may confer useful physiological properties, such as an ability to enter cells, penetrate deep into tissues or reach targets within other structures, or to bind within protein cavities of the target antigen. Use of antigen binding sites in non-antibody protein scaffolds is reviewed in Wess, 2004 [Wess, L. In: BioCentury, The Bernstein Report on BioBusiness, 12(42), A1-A7, 2004]. Typical are proteins having a stable backbone and one or more variable loops, in which the amino acid sequence of the loop or loops is specifically or randomly mutated to create an antigen-binding site that binds the target antigen. Such proteins include the IgG-binding domains of protein A from *S. aureus*, transferrin, tetranectin, fibronectin (e.g. 10th fibronectin type Ill domain), lipocalins as well as gamma-crystalline and other Affilin™ scaffolds (Scil Proteins). Examples of other approaches include synthetic "Microbodies" based on cyclotides—small proteins having intra-molecular disulphide bonds, Microproteins (Versabodies™, Amunix) and ankyrin repeat proteins (DARPins, Molecular Partners).

In addition to antibody sequences and/or an antigen-binding site, a binding member may comprise other amino acids, e.g. forming a peptide or polypeptide, such as a folded domain, or to impart to the molecule another functional characteristic in addition to ability to bind antigen. Binding members may carry a detectable label, or may be conjugated to a toxin or a targeting moiety or enzyme (e.g. via a peptidyl bond or linker). For example, a binding member may comprise a catalytic site (e.g. in an enzyme domain) as well as an antigen binding site, wherein the antigen binding site binds to the antigen and thus targets the catalytic site to the antigen. The catalytic site may inhibit biological function of the antigen, e.g. by cleavage.

Although, as noted, CDRs can be carried by non-antibody scaffolds, the structure for carrying a CDR, e.g. CDR3, or a set of CDRs of the invention will generally be an antibody heavy or light chain sequence or substantial portion thereof in which the CDR or set of CDRs is located at a location corresponding to the CDR or set of CDRs of naturally occurring VH and VL antibody variable domains encoded by rearranged immunoglobulin genes. The structures and locations of immunoglobulin variable domains may be determined by reference to Kabat, et al., 1987 [Kabat, E. A. et al, Sequences of Proteins of Immunological Interest. $4^{th}$ Edition. US Department of Health and Human Services. 1987] and updates thereof. A number of academic and commercial on-line resources are available to query this database. For example, see Martin, A. C. R. Accessing the Kabat Antibody Sequence Database by Computer PROTEINS: Structure, Function and Genetics, 25 (1996), 130-133 and the associated on-line resource, currently at the web address of http://www.bioinf.org.uk/abs/simkab.html.

By CDR region or CDR, it is intended to indicate the hypervariable regions of the heavy and light chains of the immunoglobulin as defined by Kabat et al. 1991 [Kabat, E. A. et al. (1991) Sequences of Proteins of Immunological Interest, 5th Edition. US Department of Health and Human Services, Public Service, NIH, Washington], and later editions. An antibody typically contains 3 heavy chain CDRs and 3 light chain CDRs. The term CDR or CDRs is used here in order to indicate, according to the case, one of these regions or several, or even the whole, of these regions which contain the majority of the amino acid residues responsible for the binding by affinity of the antibody for the antigen or the epitope which it recognizes.

Among the six short CDR sequences, the third CDR of the heavy chain (HCDR3) has greater size variability (greater diversity essentially due to the mechanisms of arrangement of the genes which give rise to it). It may be as short as 2 amino acids although the longest size known is 26. CDR length may also vary according to the length that can be accommodated by the particular underlying framework. Functionally, HCDR3 plays a role in part in the determination of the specificity of the antibody (Segal et al., PNAS, 71:4298-4302, 1974; Amit et al., Science, 233:747-753, 1986; Chothia et al., J. Mol. Biol., 196:901-917, 1987; Chothia et al., Nature, 342:877-883, 1989; Caton et al., J. Immunol., 144:1965-1968, 199; Sharon et al., PNAS, 87:4814-4817, 1990; Sharon et al., J. Immunol., 144:4863-4869, 1990; and Kabat et al., J. Immunol., 147:1709-1719, 1991).

Antibody Molecule

This describes an immunoglobulin whether natural or partly or wholly synthetically produced. The term also covers any polypeptide or protein comprising an antibody antigen-binding site. It must be understood here that the invention does not relate to the antibodies in natural form, that is to say they are not in their natural environment but that they have been able to be isolated or obtained by purification from natural sources, or else obtained by genetic recombination, or by chemical synthesis, and that they can then contain unnatural amino acids as will be described later. Antibody fragments that comprise an antibody antigen-binding site include, but are not limited to, molecules such as Fab, Fab', Fab'-SH, scFv, Fv, dAb and Fd. Various other antibody molecules including one or more antibody antigen-binding sites have been engineered, including for example $Fab_2$, $Fab_3$, diabodies, triabodies, tetrabodies and minibodies. Antibody molecules and methods for their construction and use are described in Holliger & Hudson, *Nature Biotechnology* 23(9):1126-1136 2005.

It is possible to take monoclonal and other antibodies and use techniques of recombinant DNA technology to produce other antibodies or chimeric molecules that bind the target antigen. Such techniques may involve introducing DNA encoding the immunoglobulin variable region, or the CDRs, of an antibody to the constant regions, or constant regions plus framework regions, of a different immunoglobulin. See, for instance, EP-A-184187, GB 2188638A or EP-A-239400, and a large body of subsequent literature. A hybridoma or other cell producing an antibody may be subject to genetic mutation or other changes, which may or may not alter the binding specificity of antibodies produced.

As antibodies can be modified in a number of ways, the term "antibody molecule" should be construed as covering any binding member or substance having an antibody antigen-binding site with the required specificity and/or binding to antigen. Thus, this term covers antibody fragments and derivatives, including any polypeptide comprising an antibody antigen-binding site, whether natural or wholly or partially synthetic. Chimeric molecules comprising an antibody antigen-binding site, or equivalent, fused to another polypeptide (e.g. derived from another species or belonging to another antibody class or subclass) are therefore included. Cloning and expression of chimeric antibodies are described in EP-A-0120694 and EP-A-0125023, and a large body of subsequent literature.

Further techniques available in the art of antibody engineering have made it possible to isolate human and humanised antibodies. For example, human hybridomas can be made as described by Kontermann & Dubel [Kontermann, R & Dubel, S, *Antibody Engineering*, Springer-Verlag New York, LLC; 2001, ISBN: 3540413545]. Phage display, another established technique for generating binding members has been described in detail in many publications, such as Kontermann & Dubel [supra] and WO92/01047 (discussed further below), and U.S. Pat. Nos. 5,969,108, 5,565,332, 5,733,743, 5,858,657, 5,871,907, 5,872,215, 5,885,793, 5,962,255, 6,140,471, 6,172,197, 6,225,447, 6,291,650, 6,492,160, 6,521,404.

Transgenic mice in which the mouse antibody genes are inactivated and functionally replaced with human antibody genes while leaving intact other components of the mouse immune system, can be used for isolating human antibodies [Mendez, M. et al. (1997) Nature Genet, 15(2): 146-156]. Humanised antibodies can be produced using techniques known in the art such as those disclosed in for example WO91/09967, U.S. Pat. No. 5,585,089, EP592106, US 565,332 and WO93/17105. Further, WO2004/006955 describes methods for humanising antibodies, based on selecting variable region framework sequences from human antibody genes by comparing canonical CDR structure types for CDR sequences of the variable region of a non-human antibody to canonical CDR structure types for corresponding CDRs from a library of human antibody sequences, e.g. germline antibody gene segments. Human antibody variable regions having similar canonical CDR structure types to the non-human CDRs form a subset of member human antibody sequences from which to select human framework sequences. The subset members may be further ranked by amino acid similarity between the human and the non-human CDR sequences. In the method of WO2004/006955, top ranking human sequences are selected to provide the framework sequences for constructing a chimeric antibody that functionally replaces human CDR sequences with the non-human CDR counterparts using the selected subset member human frameworks, thereby providing a humanized antibody of high affinity and low immunogenicity without need for comparing framework sequences between the non-human and human antibodies. Chimeric antibodies made according to the method are also disclosed.

Synthetic antibody molecules may be created by expression from genes generated by means of oligonucleotides synthesized and assembled within suitable expression vectors, for example as described by Knappik et al. [Knappik et al. J. Mol. Biol. (2000) 296, 57-86] or Krebs et al. [Krebs et al. Journal of Immunological Methods 254 2001 67-84].

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment [Ward, E. S. et al., Nature 341, 544-546 (1989); McCafferty et al. (1990) Nature, 348, 552-554; Holt et al. (2003) Trends in Biotechnology 21, 484-490], which consists of a VH or a VL domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site [Bird et al., Science, 242, 423-426, 1988; Huston et al., PNAS USA, 85, 5879-5883, 1988]; (viii) bispecific single chain Fv dimers (PCT/US92/09965) and (ix) "diabodies", multivalent or multispecific fragments constructed by gene fusion (WO94/13804; Holliger, P. et al., Proc. Natl. Acad. Sci. USA 90 6444-6448, 1993). Fv, scFv or diabody molecules may be stabilized by the incorporation of disulphide bridges linking the VH and VL domains [Reiter, Y. et al., Nature Biotech, 14, 1239-1245, 1996]. Minibodies comprising a scFv joined to a CH3 domain may also be made [Hu, S. et al., Cancer Res., 56, 3055-3061, 1996]. Other examples of binding fragments are Fab', which differs from Fab fragments by the addition of a few residues at the carboxyl terminus of the heavy chain CH1 domain, including one or more cysteines from the antibody hinge region, and Fab'-SH, which is a Fab' fragment in which the cysteine residue(s) of the constant domains bear a free thiol group.

Qui et al. [Qui et al., *Nat. Biotechnol.* 25:921-929 2007] described antibody molecules containing just two CDRs linked by a framework region. CDR3 from the VH or VL domain was linked to the CDR1 or CDR2 loop of the other domain. Linkage was through the C terminus of the selected CDR1 or CDR2 to the N terminus of the CDR3, via a FR region. Qui et al. selected the FR region having the fewest hydrophobic patches. The best combination for the antibody tested was found to be VL CDR1 linked by VH FR2 to VH CDR3 (VHCDR1-VHFR2-VLCDR3). At a molecular weight of around 3 kDa, these antibody molecules offer advantages in terms of improved tissue penetration as compared with full immunoglobulins (approx. 150 kDa) or scFv (approx. 28 kDa).

Antibody fragments of the invention can be obtained starting from any of the antibodies listed herein, by methods such as digestion by enzymes e.g. pepsin or papain and/or by cleavage of the disulfide bridges by chemical reduction. In another manner, the antibody fragments comprised in the present invention can be obtained by techniques of genetic recombination likewise well known to the person skilled in the art or else by peptide synthesis by means of, for example, automatic peptide synthesizers, such as those supplied by the company Applied Biosystems, etc., or by nucleic acid synthesis and expression.

Functional antibody fragments according to the present invention include any functional fragment whose half-life is increased by a chemical modification, especially by PEGylation, or by incorporation in a liposome.

A dAb (domain antibody) is a small monomeric antigen-binding fragment of an antibody, namely the variable region of an antibody heavy or light chain. VH dAbs occur naturally in camelids (e.g., camel, llama) and may be produced by immunizing a camelid with a target antigen, isolating antigen-specific B cells and directly cloning dAb genes from individual B cells. dAbs are also producible in cell culture. Their small size, good solubility and temperature stability makes them particularly physiologically useful and suitable for selection and affinity maturation. Camelid VH dAbs are being developed for therapeutic use under the name "Nanobodies™". A binding member of the present invention may be a dAb comprising a VH or VL domain substantially as set out herein, or a VH or VL domain comprising a set of CDRs substantially as set out herein.

Bispecific or bifunctional antibodies form a second generation of monoclonal antibodies in which two different variable regions are combined in the same molecule [Holliger and Bohlen (1999) Cancer and Metastasis Rev. 18: 411-419]. Their use has been demonstrated both in the diagnostic field and in the therapy field from their capacity to recruit new effector functions or to target several molecules on the surface of tumour cells. Where bispecific antibodies are to be used, these may be conventional bispecific antibodies, which can be manufactured in a variety of ways [Holliger, P. and Winter G. Current Opinion Biotechnol 4, 446-449. 1993], e.g., prepared chemically or from hybrid hybridomas, or may be any of the bispecific antibody fragments mentioned above. These antibodies can be obtained by chemical methods [Glennie M J et al., 1987 J. Immunol. 139, 2367-2375; Repp R. et al., 1995 J. Hemat. 377-382] or somatic methods [Staerz U. D. and Bevan M. J. 1986 PNAS 83; Suresh M. R. et al., 1986 Methods Enzymol. 121: 210-228] but likewise and preferentially by genetic engineering techniques which allow the heterodimerization to be forced and thus facilitate the process of purification of the antibody sought [Merchand et al., 1998 Nature Biotech. 16:677-681]. Examples of bispecific antibodies include those of the BiTE™ technology in which the binding domains of two antibodies with different specificity can be used and directly linked via short flexible peptides. This combines two antibodies on a short single polypeptide chain. Diabodies and scFv can be constructed without an Fc region, using only variable domains, potentially reducing the effects of anti-idiotypic reaction.

Bispecific antibodies can be constructed as entire IgG, as bispecific Fab'2, as Fab'PEG, as diabodies or else as bispecific scFv. Further, two bispecific antibodies can be linked using routine methods known in the art to form tetravalent antibodies.

Bispecific diabodies, as opposed to bispecific whole antibodies, may also be particularly useful because they can be readily constructed and expressed in E. coli. Diabodies (and many other polypeptides, such as antibody fragments) of appropriate binding specificities can be readily selected using phage display (WO94/13804) from libraries. If one arm of the diabody is to be kept constant, for instance, with a specificity directed against amyloid beta as described herein, then a library can be made where the other arm is varied and an antibody of appropriate specificity selected. Bispecific whole antibodies may be made by alternative engineering methods as described in Ridgeway et al., 1996 [Ridgeway, J. B. B. et al., Protein Eng., 9, 616-621, 1996].

Various methods are available in the art for obtaining antibodies. The antibodies may be monoclonal antibodies, especially of human, murine, chimeric or humanized origin, which can be obtained according to the standard methods well known to the person skilled in the art.

In general, for the preparation of monoclonal antibodies or their functional fragments, especially of murine origin, it is possible to refer to techniques which are described in particular in the manual "Antibodies" [Harlow and Lane, Antibodies: A Laboratory Manual, Cold Spring Harbor Laboratory, Cold Spring Harbor N.Y., pp. 726, 1988] or to the technique of preparation from hybridomas described by Köhler and Milstein [Köhler and Milstein, Nature, 256:495-497, 1975].

Monoclonal antibodies can be obtained, for example, from an animal cell immunized with human $A\beta 1$-42, or one of its fragments containing the epitope recognized by said monoclonal antibodies, e.g. $A\beta 17$-42. Suitable fragments and peptides or polypeptides comprising them are described herein, and may be used to immunise animals to generate antibodies against $A\beta 1$-42. Said antigen, or one of its fragments, can especially be produced according to the usual working methods, by genetic recombination starting with a nucleic acid sequence contained in the cDNA sequence coding for $A\beta 1$-42 or fragment thereof, by peptide synthesis starting from a sequence of amino acids comprised in the peptide sequence of the $A\beta 1$-42 and/or fragment thereof.

The monoclonal antibodies can, for example, be purified on an affinity column on which human $A\beta 1$-42 or one of its fragments containing the epitope recognized by said monoclonal antibodies, e.g. $A\beta 17$-42, has previously been immobilized. More particularly, the monoclonal antibodies can be purified by chromatography on protein A and/or G, followed or not followed by ion-exchange chromatography aimed at eliminating the residual protein contaminants as well as the DNA and the LPS, in itself, followed or not followed by exclusion chromatography on Sepharose gel in order to eliminate the potential aggregates due to the presence of dimers or of other multimers. In one embodiment, the whole of these techniques can be used simultaneously or successively.

Antigen-Binding Site

This describes the part of a molecule that binds to and is complementary to all or part of the target antigen. In an antibody molecule, it is referred to as the antibody antigen-binding site, and comprises the part of the antibody that binds to and is complementary to all or part of the target antigen. Where an antigen is large, an antibody may only bind to a particular part of the antigen, which part is termed an epitope. An antibody antigen-binding site may be provided by one or more antibody variable domains. An antibody antigen-binding site may comprise an antibody light chain variable region (VL) and an antibody heavy chain variable region (VH).

WO 2006/072620 describes engineering of antigen-binding sites in structural (non-CDR) loops extending between beta strands of immunoglobulin domains. An antigen-binding site may be engineered in a region of an antibody molecule separate from the natural location of the CDRs, e.g. in a framework region of a VH or VL domain, or in an antibody constant domain, e.g., CH1 and/or CH3. An antigen-binding site engineered in a structural region may be additional to, or instead of, an antigen-binding site formed by sets of CDRs of a VH and VL domain. Where multiple antigen-binding sites are present in an antibody molecule, they may bind the same antigen (target antigen), thereby increasing valency of the binding member. Alternatively, multiple antigen-binding sites may bind different antigens (the target antigen and one or more another antigen), and this may be used to add effector functions, prolong half-life or improve in vivo delivery of the antibody molecule.

Isolated

This refers to the state in which binding members of the invention, or nucleic acid encoding such binding members, will generally be in accordance with the present invention.

Thus, binding members, VH and/or VL domains, and encoding nucleic acid molecules and vectors according to the present invention may be provided isolated and/or purified, e.g. from their natural environment, in substantially pure or homogeneous form, or, in the case of nucleic acid, free or substantially free of nucleic acid or genes of origin other than the sequence encoding a polypeptide with the required function. Isolated members and isolated nucleic acid will be free or substantially free of material with which they are naturally associated, such as other polypeptides or nucleic acids with which they are found in their natural environment, or the environment in which they are prepared (e.g. cell culture) when such preparation is by recombinant DNA technology practised in vitro or in vivo. Members and nucleic acid may be formulated with diluents or adjuvants and still for practical purposes be isolated—for example the members will normally be mixed with gelatin or other carriers if used to coat microtitre plates for use in immunoassays, or will be mixed with pharmaceutically acceptable carriers or diluents when used in diagnosis or therapy. Binding members may be glycosylated, either naturally or by systems of heterologous eukaryotic cells (e.g. CHO or NS0 (ECACC 85110503) cells, or they may be (for example if produced by expression in a prokaryotic cell) unglycosylated.

Heterogeneous preparations comprising antibody molecules also form part of the invention. For example, such preparations may be mixtures of antibodies with full-length heavy chains and heavy chains lacking the C-terminal lysine, with various degrees of glycosylation and/or with derivatized amino acids, such as cyclization of an N-terminal glutamic acid to form a pyroglutamic acid residue.

As used herein, the phrase "substantially as set out" refers to the characteristic(s) of the relevant CDRs of the VH or VL domain of binding members described herein will be either identical or highly similar to the specified regions of which the sequence is set out herein. As described herein, the phrase "highly similar" with respect to specified region(s) of one or more variable domains, it is contemplated that 1, 2, 3, 4, 5, 6, 7, 8, 9, 10, 11, 12, 13, 14 or 15 amino acid substitutions may be made in the CDR and/or VH or VL domain.

As noted above, a binding member in accordance with the present invention binds human Aβ1-42. As described herein, binding members of the present invention may be optimised for affinity and/or for potency of inhibition in an HTRF™ competition assay. Generally, potency optimisation involves mutating the sequence of a selected binding member (normally the variable domain sequence of an antibody) to generate a library of binding members, which are then assayed for potency and the more potent binding members are selected. Thus selected "potency-optimised" binding members tend to have a higher potency than the binding member from which the library was generated. Nevertheless, high potency binding members may also be obtained without optimisation, for example a high potency binding member may be obtained directly from an initial screen. Assays and potencies are described in more detail elsewhere herein. The skilled person can thus generate binding members having high potency.

In a further aspect, the present invention provides a method of obtaining one or more binding members able to bind the antigen, the method including bringing into contact a library of binding members according to the invention and said antigen, and selecting one or more binding members of the library able to bind said antigen.

The library may be displayed on particles or molecular complexes, e.g. replicable genetic packages, such as yeast, bacterial or bacteriophage (e.g. T7) particles, viruses, cells or covalent, ribosomal or other in vitro display systems, each particle or molecular complex containing nucleic acid encoding the antibody VH variable domain displayed on it, and optionally also a displayed VL domain if present. Phage display is described in WO92/01047 and e.g. U.S. Pat. Nos. 5,969,108, 5,565,332, 5,733,743, 5,858,657, 5,871,907, 5,872,215, 5,885,793, 5,962,255, 6,140,471, 6,172,197, 6,225,447, 6,291,650, 6,492,160 and 6,521,404, each of which is herein incorporated by reference in their entirety. Ribosome display is described in Hanes J and Plückthun A. (1997) Proc Natl Acad Sci USA. 1997 May 13; 94(10): 4937-42; WO01/75097 and WO2006/072773, each of which is herein incorporated by reference in their entirety.

Following selection of binding members able to bind the antigen and displayed on bacteriophage or other library particles or molecular complexes, nucleic acid may be taken from a bacteriophage or other particle or molecular complex displaying a said selected binding member. Such nucleic acid may be used in subsequent production of a binding member or an antibody VH or VL variable domain by expression from nucleic acid with the sequence of nucleic acid taken from a bacteriophage or other particle or molecular complex displaying a said selected binding member.

An antibody VH variable domain with the amino acid sequence of an antibody VH variable domain of a said selected binding member may be provided in isolated form, as may a binding member comprising such a VH domain.

Ability to bind human Aβ1-42 and Aβ1-40 may be further tested, also ability to compete with, e.g., any of the antibodies as listed herein (e.g. in scFv format and/or IgG format, e.g. IgG2 or IgG1) for binding to human Aβ1-42. Ability to neutralize Aβ1-42 may be tested, as discussed further elsewhere herein.

A binding member may bind human Aβ1-42 with the affinity of any of the antibodies listed in Tables 5 and 6, e.g. scFv, IgG2, IgG1TM or IgG1, or with an affinity that is better. Antibody binding affinities are shown in Table 7. Binding affinity and neutralization potency of different binding members can be compared under appropriate conditions.

Variants of the VH and VL domains and CDRs described herein, including those for which amino acid sequences are set out herein, and which can be employed in binding members for Aβ1-42 can be obtained by means of methods of sequence alteration or mutation and screening for antigen binding members with desired characteristics. Examples of desired characteristics include but are not limited to: increased binding affinity for antigen relative to known antibodies which are specific for the antigen, increased neutralization of an antigen activity relative to known antibodies which are specific for the antigen if the activity is known specified competitive ability with a known antibody or ligand to the antigen at a specific molar ratio, ability to immunoprecipitate complex, ability to bind to a specified epitope: a linear epitope, e.g., peptide sequence identified using peptide-binding scan as described herein, e.g., using peptides screened in linear and/or constrained conformation, or a conformational epitope, formed by non-continuous residues; and ability to modulate a new biological activity of human Aβ1-42. Such methods are also provided herein.

Variants of antibody molecules disclosed herein may be produced and used in the present invention. Following the lead of computational chemistry in applying multivariate data analysis techniques to the structure/property-activity relationships [see for example, Wold, et al. Multivariate data analysis in chemistry. Chemometrics-Mathematics and Statistics in Chemistry (Ed.: B. Kowalski); D. Reidel Publishing Company, Dordrecht, Holland, 1984 (ISBN 90-277-1846-6] quantitative activity-property relationships of antibodies can be derived using well-known mathematical techniques, such as statistical regression, pattern recognition and classification [see for example Norman et al. Applied Regression Analysis. Wiley-Interscience; 3$^{rd}$ edition (April 1998) ISBN: 0471170828; Kandel, Abraham et al. Computer-Assisted Reasoning in Cluster Analysis. Prentice Hall PTR, (May 11, 1995), ISBN: 0133418847; Krzanowski, Wojtek. Principles of Multivariate Analysis: A User's Perspective (Oxford Statistical Science Series, No 22 (Paper)). Oxford University Press; (December 2000), ISBN: 0198507089; Witten, Ian H. et al Data Mining: Practical Machine Learning Tools and Techniques with Java Implementations. Morgan Kaufmann; (Oct. 11, 1999), ISBN: 1558605525; Denison David G. T. (Editor) et t Bayesian Methods for Nonlinear Classification and Regression (Wiley Series in Probability and Statistics). John Wiley & Sons; (July 2002), ISBN: 0471490369; Ghose, Arup K. et t. Combinatorial Library Design and Evaluation Principles, Software, Tools, and Applications in Drug Discovery. ISBN: 0-8247-0487-8]. The properties of antibodies can be derived from empirical and theoretical models (for example, analysis of likely contact residues or calculated physicochemical property) of antibody sequence, functional and three-dimensional structures and these properties can be considered individually and in combination.

An antibody antigen-binding site composed of a VH domain and a VL domain is typically formed by six loops of polypeptide: three from the light chain variable domain (VL) and three from the heavy chain variable domain (VH). Analysis of antibodies of known atomic structure has elucidated relationships between the sequence and three-dimensional structure of antibody combining sites [Chothia C. et al. Journal Molecular Biology (1992) 227, 799-817; Al-Lazikani, et al. Journal Molecular Biology (1997) 273 (4), 927-948]. These relationships imply that, except for the third region (loop) in VH domains, binding site loops have one of a small number of main-chain conformations: canonical structures. The canonical structure formed in a particular loop has been shown to be determined by its size and the presence of certain residues at key sites in both the loop and in framework regions.

This study of sequence-structure relationship can be used for prediction of those residues in an antibody of known sequence, but of an unknown three-dimensional structure, which are important in maintaining the three-dimensional structure of its CDR loops and hence maintain binding specificity. These predictions can be backed up by comparison of the predictions to the output from lead optimization experiments. In a structural approach, a model can be created of the antibody molecule [Chothia, et al. Science, 223, 755-758 (1986)] using any freely available or commercial package, such as WAM [Whitelegg, N. R.u. and Rees, A. R (2000). Prot. Eng., 12, 815-824]. A protein visualisation and analysis software package, such as Insight II (Accelrys, Inc.) or Deep View [Guex, N. and Peitsch, M. C. Electrophoresis (1997) 18, 2714-2723] may then be used to evaluate possible substitutions at each position in the CDR. This information may then be used to make substitutions likely to have a minimal or beneficial effect on activity.

The techniques required to make substitutions within amino acid sequences of CDRs, antibody VH or VL domains and binding members generally are available in the art. Variant sequences may be made, with substitutions that may or may not be predicted to have a minimal or beneficial effect on activity, and tested for ability to bind Aβ1-42 and/or for any other desired property.

Variable domain amino acid sequence variants of any of the VH and VL domains whose sequences are specifically disclosed herein may be employed in accordance with the present invention, as discussed.

As described above, aspects of the invention provide a binding member, such as an antibody molecule, comprising a VH domain that has at least 75%, at least 80%, at least 85%, at least 90%, at least 93%, at least 94%, at least 95%, at least 96%, at least 97%, at least 98% or at least 99% amino acid sequence identity with a VH domain of any of the antibodies listed herein, for which VH domain sequences are shown in the appended sequence listing below; and/or comprising a VL domain that has at least 75%, at least 80%, at least 85%, at least 90%, at least 93%, at least 94%, at least 95%, at least 96%, at least 97%, at least 98% or at least 99% amino acid sequence identity with a VL domain of any of the antibodies listed in Table 11, for which VL domain sequences are shown in the appended sequence listing.

Aspects of the invention provide a binding member, such as an antibody molecule, comprising a VH domain having a set of VH CDRs that have at least 75%, at least 80%, at least 85%, at least 90%, at least 93%, at least 94%, at least 95%, at least 96%, at least 97%, at least 98% or at least 99% amino acid sequence identity with the set of VH CDRs of any of the antibodies listed herein, for which VH CDR sequences are shown herein; and/or comprising a VL domain having a set of VL CDRs that have at that has at least 75%, at least 80%, at least 85%, at least 90%, at least 93%, at least 94%, at least 95%, at least 96%, at least 97%, at least 98% or at least 99% amino acid sequence identity with the set of VL CDRs of any of the antibodies listed herein, for which the VL CDR sequences are shown in herein.

Algorithms that can be used to calculate % identity of two amino acid sequences include e.g. BLAST [Altschul et al. (1990) J. Mol. Biol. 215: 405-410], FASTA [Pearson and Lipman (1988) PNAS USA 85: 2444-2448], or the Smith-Waterman algorithm [Smith and Waterman (1981) J. Mol Biol. 147: 195-197] e.g., employing default parameters.

Particular variable domains may include one or more amino acid sequence mutations (substitution, deletion, and/or insertion of an amino acid residue), and less than about 15 14, 13, 12, 11, 10, 9, 8, 7, 6, 5, 4, 3 or 2.

Mutations may be made in one or more framework regions and/or one or more CDRs. The mutations normally do not result in loss of function, so a binding member comprising a thus-altered amino acid sequence may retain an ability to bind human Aβ1-42. It may retain the same quantitative binding and/or neutralizing ability as a binding member in which the alteration is not made, e.g., as measured in an assay described herein. The binding member comprising a thus-altered amino acid sequence may have an improved ability to bind human Aβ1-42.

Mutation may comprise replacing one or more amino acid residues with a non-naturally occurring or non-standard amino acid, modifying one or more amino acid residue into a non-naturally occurring or non-standard form, or inserting one or more non-naturally occurring or non-standard amino acid into the sequence. Examples of numbers and locations of alterations in sequences of the invention are described elsewhere herein. Naturally occurring amino acids include the 20 "standard" L-amino acids identified as G, A, V, L, I, M, P, F, W, S, T, N, Q, Y, C, K, R, H, D, E by their standard single-letter codes. Non-standard amino acids include any other residue that may be incorporated into a polypeptide backbone or result from modification of an existing amino acid residue. Non-standard amino acids may be naturally occurring or non-naturally occurring. Several naturally occurring non-standard amino acids are known in the art, such as 4-hydroxyproline, 5-hydroxylysine, 3-methyihistidine, N-acetylserine, etc. [Voet & Voet, *Biochemistry*, 2nd Edition, (Wiley) 1995]. Those amino acid residues that are derivatised at their N-alpha position will only be located at the N-terminus of an amino-acid sequence. Normally in the present invention an amino acid is an L-amino acid, but it may be a D-amino acid. Alteration may therefore comprise modifying an L-amino acid into, or replacing it with, a D-amino acid. Methylated, acetylated and/or phosphorylated forms of amino acids are also known, and amino acids in the present invention may be subject to such modification.

Amino acid sequences in antibody domains and binding members of the invention may comprise non-natural or non-standard amino acids described above. Non-standard amino acids (e.g. D-amino acids) may be incorporated into an amino acid sequence during synthesis, or by modification or replacement of the "original" standard amino acids after synthesis of the amino acid sequence.

Use of non-standard and/or non-naturally occurring amino acids increases structural and functional diversity, and can thus increase the potential for achieving desired binding and neutralising properties in a binding member of the invention. Additionally, D-amino acids and analogues have been shown to have different pharmacokinetic profiles compared with standard L-amino acids, owing to in vivo degradation of polypeptides having L-amino acids after administration to an animal, e.g., a human, meaning that D-amino acids are advantageous for some in vivo applications.

Novel VH or VL regions carrying CDR-derived sequences of the invention may be generated using random mutagenesis of one or more selected VH and/or VL genes to generate mutations within the entire variable domain. Such a technique is described by Gram et al. [Gram et al., 1992, *Proc. Natl. Acad. Sci., USA*, 89:3576-3580], who used error-prone PCR. In some embodiments one or two amino acid substitutions are made within an entire variable domain or set of CDRs.

Another method that may be used is to direct mutagenesis to CDR regions of VH or VL genes. Such techniques are disclosed by Barbas et t. [Barbas et al., 1994, *Proc. Natl. Acad. Sci., USA*, 91:3809-3813] and Schier et al. [Schier et al., 1996, *J. Mol. Biol.* 263:551-567].

All the above-described techniques are known as such in the art and the skilled person will be able to use such techniques to provide binding members of the invention using routine methodology in the art.

A further aspect of the invention provides a method for obtaining an antibody antigen-binding site for human Aβ1-42, the method comprising providing byway of substitution, deletion, or insertion of one or more amino acids in the amino acid sequence of a VH domain set out herein a VH domain which is an amino acid sequence variant of the VH domain, optionally combining the VH domain thus provided with one or more VL domains, and testing the VH domain or VH/VL combination or combinations to identify a binding member or an antibody antigen-binding site for Aβ1-42 and optionally with one or more desired properties. Said VL domain may have an amino acid sequence which is substantially as set out herein. An analogous method may be employed in which one or more sequence variants of a VL domain disclosed herein are combined with one or more VH domains.

As noted above, a CDR amino acid sequence substantially as set out herein may be incorporated as a CDR in a human antibody variable domain or a substantial portion thereof. The HCDR3 sequences substantially as set out herein represent embodiments of the present invention and each of these may be incorporated as a HCDR3 in a human heavy chain variable domain or a substantial portion thereof.

Variable domains employed in the invention may be obtained or derived from any germline or rearranged human variable domain, or may be a synthetic variable domain based on consensus or actual sequences of known human variable domains. A variable domain can be derived from a non-human antibody. A CDR sequence of the invention (e.g. CDR3) may be introduced into a repertoire of variable domains lacking a CDR (e.g. CDR3), using recombinant DNA technology. For example, Marks et al. [Marks et al *Bio/Technology,* 1992, 10:779-783] describe methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR3. Marks et al. further describe how this repertoire may be combined with a CDR3 of a particular antibody. Using analogous techniques, the CDR3-derived sequences of the present invention may be shuffled with repertoires of VH or VL domains lacking a CDR3, and the shuffled complete VH or VL domains combined with a cognate VL or VH domain to provide binding members of the invention. The repertoire may then be displayed in a suitable host system, such as the phage display system of WO92/01047, which is herein incorporated by reference in its entirety, or any of a subsequent large body of literature, including Kay, Winter & McCafferty [Kay, B. K., Winter, J., and McCafferty, J. (1996) Phage Display of Peptides and Proteins: A Laboratory Manual, San Diego: Academic Press], so that suitable binding members may be selected. A repertoire may consist of from anything from $10^4$ individual members upwards, for example at least $10^5$, at least $10^6$, at least $10^7$, at least $10^8$, at least $10^9$ or at least $10^{10}$ members or more. Other suitable host systems include, but are not limited to yeast display, bacterial display, T7 display, viral display, cell display, ribosome display and covalent display.

A method of preparing a binding member for human Aβ1-42 is provided, which method comprises:
(a) providing a starting repertoire of nucleic acids encoding a VH domain which either include a CDR3 to be replaced or lack a CDR3 encoding region;
(b) combining said repertoire with a donor nucleic acid encoding an amino acid sequence substantially as set out herein for a VH CDR3, for example a VH CDR3 shown in Table 11, such that said donor nucleic acid is inserted into the CDR3 region in the repertoire, so as to provide a product repertoire of nucleic acids encoding a VH domain;
(c) expressing the nucleic acids of said product repertoire;
(d) selecting a binding member for human Aβ1-42; and
(e) recovering said binding member or nucleic acid encoding it.

Again, an analogous method may be employed in which a VL CDR3 of the invention is combined with a repertoire of nucleic acids encoding a VL domain that either include a CDR3 to be replaced or lack a CDR3 encoding region.

Similarly, one or more, or all three CDRs may be grafted into a repertoire of VH or VL domains that are then screened for a binding member or binding members for human Aβ1-42.

For example, an HCDR1, HCDR2 and/or HCDR3, e.g., a set of HCDRs, from one or more of the antibodies listed in Table 5 or Table 6 may be employed, and/or an LCDR1, LCDR2 and/or LCDR3, e.g., set of LCDRs, from one or more of the antibodies listed herein may be employed.

Similarly, other VH and VL domains, sets of CDRs and sets of HCDRs and/or sets of LCDRs disclosed herein may be employed.

A substantial portion of an immunoglobulin variable domain may comprise at least the three CDR regions, together with their intervening framework regions. The portion may also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally-occurring variable domain regions. For example, construction of binding members of the present invention made by recombinant DNA techniques may result in the introduction of N- or C-terminal residues encoded by linkers introduced to facilitate cloning or other manipulation steps. Other manipulation steps include the introduction of linkers to join variable domains of the invention to further protein sequences including antibody constant regions, other variable domains (for example in the production of diabodies) or detectable/functional labels as discussed in more detail elsewhere herein.

Although in some aspects of the invention, binding members comprise a pair of VH and VL domains, single binding domains based on either VH or VL domain sequences form further aspects of the invention. It is known that single immunoglobulin domains, especially VH domains, are capable of binding target antigens in a specific manner. For example, see the discussion of dAbs above.

In the case of either of the single binding domains, these domains may be used to screen for complementary domains capable of forming a two-domain binding member able to bind Aβ1-42. This may be achieved by phage display screening methods using the so-called hierarchical dual combinatorial approach as disclosed in WO92/01047, herein incorporated by reference in its entirety, in which an individual colony containing either an H or L chain clone is used to infect a complete library of clones encoding the other chain (L or H) and the resulting two-chain binding member is selected in accordance with phage display techniques, such as those described in that reference. This technique is also disclosed in Marks et al., Bio/Technology, 1992, 10:779-783.

Binding members of the present invention may further comprise antibody constant regions or parts thereof, e.g., human antibody constant regions or parts thereof. For example, a VL domain may be attached at its C-terminal end to antibody light chain constant domains including human Cκ or Cλ chains. Similarly, a binding member based on a VH domain may be attached at its C-terminal end to all or part (e.g., a CH1 domain) of an immunoglobulin heavy chain derived from any antibody isotype, e.g. IgG, IgA, IgE and IgM and any of the isotype sub-classes, particularly IgG2, IgG1 and IgG4. IgG2 may be advantageous in some embodiments owing to its lack of effector functions. In other embodiments, IgG1 may be advantageous due to its effector function and ease of manufacture. Any synthetic or other constant region variant that has these properties and stabilizes variable regions may also be useful in the present invention.

Binding members may be labelled with a detectable or functional label. Thus, a binding member or antibody molecule can be present in the form of an immunoconjugate so as to obtain a detectable and/or quantifiable signal. An immunoconjugate may comprise an antibody molecule of the invention conjugated with detectable or functional label. A detectable label as referred to herein may be any label which produces or can be induced to produce a signal, including but not limited to fluorescers, chemiluminescers (e.g., horseradish peroxidase), coloured labels (e.g. latex [blue] or colloidal gold [red]), radiolabels, enzymes, photo-sensitisers and magnetic labels. The amount of label bound at a surface, e.g., a surface of a capillary bore, may therefore be detected and/or measured by detecting fluorescence or luminescence, colour, radioactivity, enzyme activity, light absorbance or changes in magnetic field. Detectable labels may be attached to binding members using conventional chemistry. Preferably, a detectable label is a label detectable by optical interrogation, e.g., with a digital camera or flatbed scanner. Labels that can be detected by optical interrogation include fluorescers, chemiluminescers and coloured labels. The mechanism by which a signal can be generated for optical detection includes (but is not necessarily limited to): light absorption, light scattering, light diffraction, light reflection, fluorescence or luminescence.

Suitable labels include, by way of illustration and not limitation, enzymes, such as alkaline phosphatase, glucose-6-phosphate dehydrogenase ("G6PDH"), alpha-D-galactosidase, glucose oxydase, glucose amylase, carbonic anhydrase, acetylcholinesterase, lysozyme, malate dehydrogenase and peroxidase, e.g., horseradish peroxidase;

dyes;

fluorescent labels or fluorescers, such as fluorescein and its derivatives, fluorochrome, rhodamine compounds and derivatives, GFP (GFP for "Green Fluorescent Protein"), dansyl, umbelliferone, phycoerythrin, phycocyanin, allophycocyanin, o-phthaldehyde, and fluorescamine; fluorophores such as lanthanide cryptates and chelates, e.g., Europium etc (Perkin Elmer and Cis Biointemational), chemoluminescent labels or chemiluminescers, such as isoluminol, luminol and the dioxetanes;

bio-luminescent labels, such as luciferase and luciferin;

sensitizers;

coenzymes;

enzyme substrates;

radiolabels, including but not limited to, bromine$^{77}$, carbon$^{14}$, cobalt$^{57}$, fluorine$^{8}$, gallium$^{67}$, gallium$^{68}$, hydrogen$^{3}$ (tritium), indium$^{111}$, indium$^{113}$, iodine$^{123m}$, iodine$^{125}$, iodine$^{126}$, iodine$^{131}$, iodine$^{133}$, mercury$^{107}$, mercury$^{203}$, phosphorous$^{32}$, rhenium$^{99m}$, rhenium$^{101}$, rhenium$^{105}$, ruthenium$^{95}$, ruthenium$^{97}$, ruthenium$^{103}$, ruthenium$^{105}$, scandium$^{47}$, selenium$^{75}$, sulphur$^{35}$, technetium$^{99}$, technetium$^{99m}$, tellurium$^{121m}$, tellurium$^{122m}$, tellurium$^{125m}$, thulium$^{165}$, thulium$^{167}$, thulium$^{168}$, yttrium$^{199}$ and other radiolabels mentioned herein;

particles, such as latex or carbon particles; metal sol; crystallite; liposomes; cells, etc., which may be further labelled with a dye, catalyst or other detectable group;

molecules such as biotin, digoxygenin or 5-bromodeoxyurdine;

toxin moieties, such as for example a toxin moiety selected from a group of *Pseudomonas* exotoxin (PE or a cytotoxic fragment or mutant thereof), Diptheria toxin or a cytotoxic fragment or mutant thereof, a Botulinum toxin A, B, C, D, E or F, ricin or a cytotoxic fragment thereof e.g. ricin A, abrin or a cytotoxic fragment thereof, saporin or a cytotoxic fragment thereof, pokeweed antiviral toxin or a cytotoxic fragment thereof and bryodin 1 or a cytotoxic fragment thereof.

Examples of suitable enzymes and coenzymes are disclosed in U.S. Pat. Nos. 4,275,149, and 4,318,980. Suitable fluorescers and chemiluminescers are also disclosed in U.S. Pat. No. 4,275,149. Labels further include chemical moieties, such as biotin that may be detected via binding to a specific cognate detectable moiety, e.g., labelled avidin or streptavidin. Detectable labels may be attached to antibodies of the invention using conventional chemistry known in the art.

Immunoconjugates or their functional fragments can be prepared by methods known to the person skilled in the art. They can be coupled to enzymes or to fluorescent labels directly or by the intermediary of a spacer group or of a linking group, such as a polyaldehyde, like glutaraldehyde, ethylenediaminetetraacetic acid (EDTA), diethylene-triaminepentaacetic acid (DPTA), or in the presence of coupling agents, such as those mentioned above for the therapeutic conjugates. Conjugates containing labels of fluorescein type can be prepared by reaction with an isothiocyanate.

The methods known in the art for coupling the therapeutic radioisotopes to the antibodies either directly or via a chelating agent, such as EDTA, DTPA mentioned above may also be used for the radioelements which can be used in diagnosis. It is likewise possible to perform labelling with sodium$^{125}$ by the chloramine T method [Hunter W. M. and Greenwood F. C. (1962) Nature 194:495] or else with technetium$^{99m}$ by the technique of U.S. Pat. No. 4,424,200 or attached via DTPA as described in U.S. Pat. No. 4,479,930.

There are numerous methods by which the label can produce a signal detectable by external means, for example, by visual examination, electromagnetic radiation, heat, and chemical reagents. The label can also be bound to another binding member that binds the antibody of the invention, or to a support.

The label can directly produce a signal, and therefore, additional components are not required to produce a signal. Numerous organic molecules, for example fluorescers, are able to absorb ultraviolet and visible light, where the light absorption transfers energy to these molecules and elevates them to an excited energy state. This absorbed energy is then dissipated by emission of light at a second wavelength. This second wavelength emission may also transfer energy to a labelled acceptor molecule, and the resultant energy dissipated from the acceptor molecule by emission of light for example fluorescence resonance energy transfer (FRET). Other labels that directly produce a signal include radioactive isotopes and dyes.

Alternatively, the label may need other components to produce a signal, and the signal producing system would then include all the components required to produce a measurable signal, which may include substrates, coenzymes, enhancers, additional enzymes, substances that react with enzymic products, catalysts, activators, cofactors, inhibitors, scavengers, metal ions, and a specific binding substance required for binding of signal generating substances. A detailed discussion of suitable signal producing systems can be found in U.S. Pat. No. 5,185,243.

An aspect of the invention provides a method comprising causing or allowing binding of a binding member as provided herein to human Aβ1-42. As noted, such binding may take place in vivo, e.g. following administration of a binding member, or nucleic acid encoding a binding member, or it may take place in vitro, for example in ELISA, Western blotting, immunocytochemistry, immunoprecipitation, affinity chromatography, and biochemical or cell-based assays.

The present invention also provides for measuring levels of antigen directly, e.g., in plasma or CSF, by employing a binding member according to the invention for example in a biosensor system. For instance, a method of detecting and/or measuring binding to human Aβ1-42 may comprise, (i) exposing said binding member to Aβ1-42 and (ii) detecting binding of said binding member to Aβ1-42, wherein binding is detected using any method or detectable label described herein. The Aβ1-42 may be monomeric or oligomeric Aβ1-42, preferably monomeric Aβ1-42. This, and any other binding detection method described herein, may be interpreted directly by the person performing the method, for instance, by visually observing a detectable label. Alternatively, this method, or any other binding detection method described herein, may produce a report in the form of an autoradiograph, a photograph, a computer printout, a flow cytometry report, a graph, a chart, a test tube or container or well containing the result, or any other visual or physical representation of a result of the method.

The amount of binding of the binding member to Aβ1-42 may be determined. Quantitation may be related to the amount of the antigen in a test sample, which may be of diagnostic interest. Screening for Aβ1-42 binding and/or the quantitation thereof may be useful, for instance, in screening patients for diseases or disorders referred to herein and/or any other disease or disorder involving aberrant Aβ1-42 levels and/or activity.

A diagnostic method may comprise (i) obtaining a tissue or fluid sample from a subject, e.g., a patient suspected or believed to have a condition or disease mentioned herein, (ii) exposing said tissue or fluid sample to one or more binding members of the present invention; and (iii) detecting bound Aβ1-42 as compared with a control sample, wherein an increase in the amount of Aβ1-42 binding as compared with the control may indicate an aberrant level of Aβ1-42. Tissue or fluid samples to be tested include blood, serum, plasma, CSF, urine, biopsy material, tumours, or any tissue suspected of containing aberrant Aβ1-42 levels. Subjects testing positive for aberrant Aβ1-42 levels or activity may also benefit from the treatment methods disclosed later herein.

Those skilled in the art are able to choose a suitable mode of determining binding of the binding member to an antigen according to their preference and general knowledge, in light of the methods disclosed herein.

The reactivities of binding members in a sample may be determined by any appropriate means. Radioimmunoassay (RIA) is one possibility. Radioactive labelled antigen is mixed with unlabelled antigen (the test sample) and allowed to bind to the binding member. Bound antigen is physically separated from unbound antigen and the amount of radioactive antigen bound to the binding member determined. The more antigen there is in the test sample the less radioactive antigen will bind to the binding member. A competitive binding assay may also be used with non-radioactive antigen, using antigen or an analogue linked to a reporter molecule. The reporter molecule may be a fluorochrome, phosphor or laser dye with spectrally isolated absorption or emission characteristics. Suitable fluorochromes include fluorescein, rhodamine, phycoerythrin and Texas Red, and lanthanide chelates or cryptates. Suitable chromogenic dyes include diaminobenzidine.

Other reporters include macromolecular colloidal particles or particulate material, such as latex beads that are colored, magnetic or paramagnetic, and biologically or chemically active agents that can directly or indirectly cause detectable signals to be visually observed, electronically detected or otherwise recorded. These molecules may be enzymes, which catalyze reactions that develop, or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

The signals generated by individual binding member-reporter conjugates may be used to derive quantifiable absolute or relative data of the relevant binding member binding in samples (normal and test).

A kit comprising a binding member as described herein is also provided as an aspect of the present invention. In the kit, the binding member may be labelled to allow its reactivity in a sample to be determined, e.g., as described further below. Further, the binding member may or may not be attached to a solid support. Components of a kit are generally sterile and in sealed vials or other containers. Kits may be employed in diagnostic analysis or other methods for which binding members are useful. A kit may be for use in a method described above. A kit may contain instructions for use of the components in a method, e.g., a method in accordance with the present invention. Ancillary materials to assist in or to enable performing such a method may be included within a kit of the invention. The ancillary materials include a second, different binding member which binds to the first binding member and is conjugated to a detectable label (e.g., a fluorescent label, radioactive isotope or enzyme). Antibody-based kits may also comprise beads for conducting an immunoprecipitation. Each component of the kits is generally in its own suitable container. Thus, these kits generally comprise distinct containers suitable for each binding member. Further, the kits may comprise instructions for performing the assay and methods for interpreting and analyzing the data resulting from the performance of the assay.

The present invention also provides the use of a binding member as above for measuring antigen levels in a competition assay, that is to say a method of measuring the level of antigen in a sample by employing a binding member as provided by the present invention in a competition assay. This may be where the physical separation of bound from unbound antigen is not required. Linking a reporter molecule to the binding member so that a physical or optical change occurs on binding is one possibility. The reporter molecule may directly or indirectly generate detectable signals, which may be quantifiable. The linkage of reporter molecules may be directly or indirectly, covalently, e.g., via a peptide bond or non-covalently. Linkage via a peptide bond may be as a result of recombinant expression of a gene fusion encoding antibody and reporter molecule.

Competition between binding members may be assayed easily in vitro, for example using ELISA and/or by a biochemical competition assay such as one tagging a specific reporter molecule to one binding member which can be detected in the presence of one or more other untagged binding members, to enable identification of binding members which bind the same epitope or an overlapping epitope. Such methods are readily known to one of ordinary skill in the art, and are described in more detail herein.

The present invention extends to a binding member that competes for binding to human Aβ1-42 with any binding member defined herein, e.g., any of the antibodies listed in Tables 5 and 6, e.g., in IgG2, IgG1 or IgG1 triple mutation ("TM"; Oganesyan et al. (2008) Acta Crystallogr D Biol Crystallogr. 64(Pt 6):700-4) format. Competition between binding members may be assayed easily in vitro, for example by tagging a specific reporter molecule to one binding member which can be detected in the presence of other untagged binding member(s), to enable identification of binding members which bind the same epitope or an overlapping epitope. Competition may be determined for example using ELISA in which Aβ1-42 is immobilized to a plate and a first tagged or labelled binding member along with one or more other untagged or unlabelled binding members is added to the plate. Presence of an untagged binding member that competes with the tagged binding member is observed by a decrease in the signal emitted by the tagged binding member.

Competition assays can also be used in epitope mapping. In one instance epitope mapping may be used to identify the epitope bound by a binding member which optionally may have optimized neutralizing and/or modulating characteristics. Such an epitope can be linear or conformational. A conformational epitope can comprise at least two different fragments of Aβ, wherein said fragments are positioned in proximity to each other when the Aβ peptide is folded in its tertiary or quaternary structure to form a conformational epitope which is recognized by an inhibitor of Aβ, such as a Aβ-binding member. In testing for competition a peptide fragment of the antigen may be employed, especially a peptide including or consisting essentially of an epitope of interest. A peptide having the epitope sequence plus one or more amino acids at either end may be used. Binding members according to the present invention may be such that their binding for antigen is inhibited by a peptide with or including the sequence given.

In further aspects, the invention provides an isolated nucleic acid which comprises a sequence encoding a binding member, VH domain and/or VL domain according to the present invention, and methods of preparing a binding member, a VH domain and/or a VL domain of the invention, which comprise expressing said nucleic acid under conditions to bring about production of said binding member, VH domain and/or VL domain, and recovering it. Examples of encoding nucleic acid sequences are set out in the Tables and the appended sequence listing. Nucleic acid sequences according to the present invention may comprise DNA or RNA and may be wholly or partially synthetic. Reference to a nucleotide sequence as set out herein encompasses a DNA molecule with the specified sequence, and encompasses a RNA molecule with the specified sequence in which U is substituted for T, unless context requires otherwise The present invention also provides constructs in the form of plasmids, vectors, such as a plasmid or phage vector, transcription or expression cassettes which comprise at least one polynucleotide as above, for example operably linked to a regulatory element.

A further aspect provides a host cell containing or transformed with the nucleic acids and/or vectors of the invention. The present invention also provides a recombinant host cell line that comprises one or more constructs as above. A nucleic acid sequence encoding any CDR or set of CDRs or VH domain or VL domain or antibody antigen-binding site or antibody molecule, e.g. scFv or IgG (e.g. IgG2, IgG1 or IgG1TM) as provided, forms an aspect of the present invention, along with a method of production of the encoded product, which method comprises expression from encoding nucleic acid sequences thereof. Expression may conveniently be achieved by culturing recombinant host cells containing the nucleic acid under appropriate conditions. Following production by expression a VH or VL domain, or binding member may be isolated and/or purified using any suitable technique, then used as appropriate.

Accordingly, another aspect of the invention is a method of production of an antibody VH variable domain, the method including causing expression from encoding nucleic acid sequences. Such a method may comprise culturing host cells under conditions for production of said antibody VH variable domain.

Analogous methods for production of VL variable domains and binding members comprising a VH and/or VL domain are provided as further aspects of the present invention.

A method of production may comprise a step of isolation and/or purification of the product. A method of production may comprise formulating the product into a composition including at least one additional component, such as a pharmaceutically acceptable excipient.

Systems for cloning and expression of a polypeptide in a variety of different host cells are well known. Suitable host cells include bacteria, mammalian cells, plant cells, filamentous fungi, yeast and baculovirus systems and transgenic plants and animals. The expression of antibodies and antibody fragments in prokaryotic cells is well established in the art. For a review, see for example Plückthun [Plückthun, A. Bio/Technology 9: 545-551 (1991)]. A common bacterial host is *E. coli*.

Expression in eukaryotic cells in culture is also available to those skilled in the art as an option for production of a binding member [Chadd H E and Chamow S M (2001) Current Opinion in Biotechnology 12: 188-194; Andersen DC and Krummen L (2002) Current Opinion in Biotechnology 13: 117; Larick J W and Thomas D W (2001) Current Opinion in Biotechnology 12:411-418].

Mammalian cell lines available in the art for expression of a heterologous polypeptide include Chinese hamster ovary (CHO) cells, HeLa cells, baby hamster kidney cells, NS0 mouse melanoma cells, YB2/0 rat myeloma cells, human embryonic kidney cells, human embryonic retina cells and many others.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids e.g. phagemid, or viral, e.g. 'phage, as appropriate [Sambrook and Russell, *Molecular Cloning: a Laboratory Manual:* 3rd edition, 2001, Cold Spring Harbor Laboratory Press]. Many known techniques and protocols for manipulation of nucleic acid, for example in preparation of nucleic acid constructs, mutagenesis, sequencing, introduction of DNA into cells and gene expression, and analysis of proteins, are described in detail in Ausubel et al. [Ausubel et al. eds., *Shot Protocols in Molecular Biology: A Compendium of Methods from Current Protocols in Molecular Biology*, John Wiley & Sons, 4$^{th}$ edition 1999].

A further aspect of the present invention provides a host cell containing nucleic acid as disclosed herein. Such a host cell may be in vitro and may be in culture. Such a host cell may be in vivo. In vivo presence of the host cell may allow intra-cellular expression of the binding members of the present invention as "intrabodies" or intra-cellular antibodies. Intrabodies may be used for gene therapy.

Another aspect provides a method comprising introducing nucleic acid of the invention into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g., Vaccinia, or for insect cells, Baculovirus. Introducing nucleic acid in the host cell, in, particular a eukaryotic cell may use a viral or a plasmid based system. The plasmid system may be maintained episomally or may be incorporated into the host cell or into an artificial chromosome. Incorporation may be either by random or targeted integration of one or more copies at single or multiple loci. For bacterial cells, suitable techniques may include calcium chloride transformation, electroporation and transfection using bacteriophage.

The introduction may be followed by causing or allowing expression from the nucleic acid, e.g., by culturing host cells under conditions for expression of the gene. The purification of the expressed product may be achieved by methods known to one of skill in the art.

Nucleic acid of the invention may be integrated into the genome (e.g., chromosome) of the host cell. Integration may be promoted by inclusion of sequences that promote recombination with the genome, in accordance with standard techniques.

The present invention also provides a method that comprises using a construct as stated above in an expression system in order to express a binding member or polypeptide as above.

Binding members according to the invention may be used in a treatment (which may include prophylactic treatment) of a disease or disorder in the human or animal body (e.g., in a human patient), which comprises administering the binding member to the patient. Conditions treatable according to the invention are described elsewhere herein, including preventative treatment and reduction of severity of the condition or one or more of its symptoms, or delaying or reducing risk of onset.

Accordingly, the invention provides a method of treating or reducing the severity of at least one symptom of any of the conditions mentioned herein, comprising administering to a patient in need thereof an effective amount of one or more binding members of the present invention alone or in a combined therapeutic regimen with another appropriate medicament known in the art or described herein such that the severity of at least one symptom of any of the above disorders is reduced.

The term "effective dose" is defined as an amount sufficient to cure or at least partially arrest the disease and its complications in a patient already suffering from the disease.

The present invention is directed inter alia to treatment of Alzheimer's disease and other amyloidogenic diseases by administration of therapeutic antibody of the invention to a patient under conditions that generate a beneficial therapeutic response in a patient (e.g., a reduction of Aβ1-42 in CSF, a reduction of plaque burden, inhibition of plaque formation, reduction of neuritic dystrophy, improvement in cognitive function, and/or reversal, reduction or prevention of cognitive decline) in the patient, for example, for the prevention or treatment of an amyloidogenic disease.

As used herein, "treatment" is defined as the application or administration of a therapeutic agent to a patient, who has a disease or condition associated with amyloidosis; or a symptom of, or a predisposition towards such disease or condition associated with amyloidosis, with the purpose to cure, heal, alleviate, relieve, after, remedy, ameliorate, improve or affect the disease, condition, symptoms thereof or the predisposition thereto.

The invention provides methods of preventing or treating a disease associated with amyloid deposits of Aβ in the brain of a patient. Such diseases include Alzheimers disease, Down's syndrome, and cognitive impairment. Cognitive impairment can occur with or without other characteristics of an amyloidogenic disease. The invention provides methods of treatment of macular degeneration, a condition which is linked with Aβ. Methods of the invention may involve administering an effective dose to a patient of an antibody that specifically binds to 1-42 Aβ and N-terminal truncates thereof. Such methods are particularly useful for preventing or treating Alzheimer's disease in human patients.

Antibodies of the invention may be used in therapeutic regimes for preventing or ameliorating the neuropathology and, in some patients, the cognitive impairment associated with Alzheimer's disease.

Patients amenable to treatment include patients showing symptoms and also individuals at risk of disease but not showing symptoms. For Alzheimers disease, potentially anyone is at risk if he or she lives for a sufficiently long time. Antibodies of the invention can be administered prophylactically to a subject without any assessment of the risk of the subject patient. Patients amenable to treatment include individuals who have a known genetic risk of Alzheimers disease, for example individuals who have blood relatives with this disease and those whose risk is determined by analysis of genetic or biochemical markers. Genetic markers of predisposition towards Alzheimers disease include mutations in the APP gene, particularly mutations at position 717 and positions 670 and 671 referred to as the Hardy and Swedish mutations respectively. Other markers of risk are mutations in the presenilin genes, PS1 and PS2, and ApoE4, a family history of AD, hypercholesterolemia or atherosclerosis. Individuals suffering from Alzheimer's disease can be diagnosed by the characteristic dementia associated with the disease, as well as by the presence of risk factors described above. A number of diagnostic tests are available to assist in identification Alzheimer's disease in an individual. These include measurement of CSF tau and Aβ1-42 levels. Elevated tau and decreased Aβ1-42 levels may signify the presence of AD. Individuals suffering from Alzheimer's disease can also be diagnosed by NINCDS-ADRDA or DSM-IV-TR criteria.

In asymptomatic patients, treatment can begin at any age (e.g., 10, 20, 30). Generally, treatment is commenced in later life, for example when a patient reaches his or her 40's, 50's, 60's or 70's. Treatment may involve multiple doses over a period of time, which may be for the duration of the remaining life of the patient. The need for administration of repeat doses can be monitored by measuring antibody levels over time.

For prophylaxis, pharmaceutical compositions or medicaments are administered to a patient susceptible to, or otherwise at risk of, Alzheimer's disease in an amount sufficient to eliminate or reduce the risk, lessen the severity, or delay the outset of the disease, including biochemical, histologic, cognitive impairment and/or behavioral symptoms of the disease, its complications and intermediate pathological phenotypes presenting during development of the disease. For therapeutic applications, compositions or medicaments are administered to a patient suspected of, or already suffering from such a disease in an amount sufficient to cure, or at least partially arrest, the symptoms of the disease (biochemical, histologic, cognitive impairment and/ or behavioural), including its complications and intermediate pathological phenotypes in development of the disease.

The invention provides a method of treating an individual comprising administering to an individual in need thereof an effective amount of one or more binding members of the present invention alone or in a combined therapeutic regimen with another appropriate medicament known in the art or described herein. A method of treatment may comprise administering an effective amount of a binding member described herein to a patient in need thereof, wherein levels of Aβ1-42 are decreased in blood plasma and/or CSF.

A method of treatment may comprise (i) identifying a patient having a condition associated with amyloidosis as mentioned herein, and (ii) administering an effective amount of a binding member described herein to the patient, wherein levels of Aβ1-42 are decreased in blood plasma and/or CSF, and amyloidosis is reduced. An effective amount is an amount that decreases the level of Aβ1-42 so as to decrease or lessen the severity of at least one symptom of the particular disease or disorder being treated, but not necessarily cure the disease or disorder.

The invention also provides a method of antagonising at least one effect of Aβ1-42 comprising contacting with or administering an effective amount of one or more binding members of the present invention such that said at least one effect of Aβ1-42 is antagonised.

Accordingly, further aspects of the invention provide methods of treatment comprising administration of a binding member as provided, pharmaceutical compositions comprising such a binding member, and use of such a binding member in the manufacture of a medicament for administration, for example in a method of making a medicament or pharmaceutical composition comprising formulating the binding member with a pharmaceutically acceptable excipient. A pharmaceutically acceptable excipient may be a compound or a combination of compounds entering into a pharmaceutical composition not provoking secondary reactions and which allows, for example, facilitation of the administration of the binding member, an increase in its lifespan and/or in its efficacy in the body, an increase in its solubility in solution or else an improvement in its conservation. These pharmaceutically acceptable vehicles are well known and will be adapted by the person skilled in the art as a function of the nature and of the mode of administration of the active compound(s) chosen.

Binding members as described herein will usually be administered in the form of a pharmaceutical composition, which may comprise at least one component in addition to the binding member. Thus pharmaceutical compositions according to the present invention, and for use in accordance with the present invention, may comprise, in addition to a binding member, a pharmaceutically acceptable excipient, carrier, buffer, stabilizer or other materials well known to those skilled in the art. Such materials should be non-toxic and should not interfere with the efficacy of the active ingredient. The precise nature of the carrier or other material will depend on the route of administration.

For injectable formulations, e.g., for intra-venous or subcutaneous injection, the active ingredient will be in the form of a parenterally acceptable aqueous solution which is pyrogen-free and has suitable pH, isotonicity and stability. Binding members as described herein may be formulated in liquid, semi-solid or solid forms depending on the physicochemical properties of the molecule and the route of delivery. Formulations may include excipients, or combinations of excipients, for example: sugars, amino acids and surfactants. Liquid formulations may include a wide range of antibody concentrations and pH. Solid formulations may be produced by lyophilisation, spray drying, or drying by supercritical fluid technology, for example. Treatment may be given by injection (for example, subcutaneously, or intra-venously. The treatment may be administered by pulse infusion, particularly with declining doses of the binding member. The route of administration can be determined by the physicochemical characteristics of the treatment, by special considerations for the disease or by the requirement to optimize efficacy or to minimize side-effects. One particular route of administration is intra-venous. Another route of administering pharmaceutical compositions of the present invention is subcutaneously. Subcutaneous injection using a needle-free device is also advantageous.

A composition may be administered alone or in combination with other treatments, either simultaneously or sequentially dependent upon the condition to be treated.

A binding member may be used as part of a combination therapy in conjunction with an additional medicinal component. Combination treatments may be used to provide significant synergistic effects, particularly the combination of a binding member with one or more other drugs. A binding member may be administered concurrently or sequentially or as a combined preparation with another therapeutic agent or agents, for the treatment of one or more of the conditions listed herein.

A binding member and one or more of the above additional medicinal components may be used in the manufacture of a medicament. The medicament may be for separate or combined administration to an individual, and accordingly may comprise the binding member and the additional component as a combined preparation or as separate preparations. Separate preparations may be used to facilitate separate and sequential or simultaneous administration, and allow administration of the components by different routes e.g. oral and parenteral administration.

Compositions provided may be administered to mammals. Administration is normally in a "therapeutically effective amount", this being sufficient to show benefit to a patient. Such benefit may be at least amelioration of at least one symptom. The actual amount administered, and rate and time-course of administration, will depend on the nature and severity of what is being treated, the particular mammal being treated, the clinical condition of the individual patient, the cause of the disorder, the site of delivery of the composition, the type of binding member, the method of administration, the scheduling of administration and other factors known to medical practitioners. Prescription of treatment, e.g. decisions on dosage etc, is within the responsibility of general practitioners and other medical doctors and may depend on the severity of the symptoms and/or progression of a disease being treated. A therapeutically effective amount or suitable dose of a binding member of the invention can be determined by comparing its in vitro activity and in vivo activity in an animal model. Methods for extrapolation of effective dosages in test animals to humans are known. The precise dose will depend upon a number of factors, including whether the antibody is for diagnosis, prevention or for treatment, the size and location of the area to be treated, the precise nature of the antibody (e.g., whole antibody, fragment or diabody) and the nature of any detectable label or other molecule attached to the antibody. A typical antibody dose will be in the range 100 µg to 1 g for systemic applications. An initial higher loading dose, followed by one or more lower doses, may be administered. Typically, the antibody will be a whole antibody, e.g., the IgG1 or IgG1-TM isotype. Treatments may be repeated at daily, twice-weekly, weekly or monthly intervals, at the discretion of the physician. Treatments may be every two to four weeks for subcutaneous administration and every four to eight weeks for intra-venous administration. Treatment may be periodic, and the period between administrations is about two weeks or more, e.g., about three weeks or more, about four weeks or more, or about once a month.

Various further aspects and embodiments of the present invention will be apparent to those skilled in the art in view of the present disclosure.

All documents, including database references and accession numbers, patents, patent applications and publications, mentioned in this specification are incorporated herein by reference in their entirety for all purposes.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the accompanying figures and tables.

EXAMPLES

The following sequences have been deposited with NCIMB, Ferguson Building, Cralbstone Estate, Bucksburn, Aberdeen, AB21 9YA. Scotland, UK:
  E. coli TOP10 cells Abet0007=NCIMB 41889
  E. coli TOP10 cells Abet0380-GL=NCIMB 41890
  E. coli TOP10 cells Abet0144-GL=NCIMB 41891
  E. coli TOP10 cells Abet0377-GL=NCIMB 41892
  Date of deposit=2 Nov. 2011

Example 1. Anti-Amyloid Beta 1-42 Specific Antibody Generation and Lead Selection 1.1 Formulation of Amyloid Beta Peptides Biotinylated human Amyloid beta 1-42 peptide (rPeptide, USA; cat: A1117 or Bachem AG, Switzerland; cat: H-5642) was resuspended to 1 mg/ml in 1% ammonium hydroxide solution (v/v) and stored in aliquots at −80° C. until required. An identical procedure was followed for unlabelled human Amyloid beta 1-42 peptide (Anaspec, USA; cat: 64129), unlabelled human Amyloid beta 1-40 peptide (rPeptide, USA; cat: A1155), biotinylated human Amyloid beta 1-40 peptide (rPeptide, USA; cat: A111 or Bachem AG, Switzerland; cat: H-5914), biotinylated murine Amyloid beta 1-42 peptide (Anaspec, USA; cat: 61718-01) and biotinylated murine Amyloid beta 1-40 peptide (Anaspec, USA; cat: 61717).

1.2 Selections

The Fab310-Lambda phage display library (Dyax, USA) cloned into a phagemid vector based on the filamentous phage M13 was used for selections (Hoet et al., 2005). Anti-Amyloid beta 1-42 specific Fab antibodies were isolated from the phage display libraries using a series of selection cycles on synthetic human biotinylated Amyloid beta 1-42 (rPeptide, USA) essentially as previously described (Hawkins et al., 1992; Vaughan et al., 1996). In brief, for the first round of solution-phase selections, biotinylated amyloid-beta 1-42 in Dulbecco's phosphate buffered saline (DPBS, pH 7.4) was added to purified phage particles that had been pre-incubated for 1 hour in Marvel-PBS (3% w/v) containing a 100-fold excess of unlabelled human Amyloid beta 1-40 peptide (Anaspec, USA). Phage particles that bound to the biotinylated Amyloid beta 1-42 peptide were captured using Streptavidin-coupled paramagnetic beads (Invitrogen Life Technologies, UK) and weakly-bound phage were removed by a series of wash cycles using PBS-Tween (0.1% v/v). Bound phage particles were eluted from the beads, infected into E. coli TG1 bacteria and rescued for the next round of selection (Vaughan et al., 1996). Two subsequent rounds of selection were carried out as previously described but with a reduced concentration of biotinylated Amyloid beta 1-42 antigen.

1.3 Identification of Amyloid Beta 1-42 Specific Clones Using a Direct-Binding Assay on Unpurified Fab Fragments To produce soluble single chain Fab fragments (sFab) the geneIII tether was removed from the Fab310-Lambda display cassette using standard cleavage and ligation techniques. Briefly, the phagemid vectors were isolated from the round 3 output using standard DNA purification kits (QIAgen, UK) and the geneIII tether sequence was removed from the vector using a MluI restriction digest (Hoet et al., 2005). Religated vectors were transformed back into TG1 cells and individual colonies were picked for analysis.

Unpurified sFab from periplasmic preparations were screened in a homogeneous time-resolved fluorescence (HTRF™, CisBio International, France) binding assay using an EnVision plate reader (PerkinElmer, USA). In this assay, binding of unpurified sFab to human Amyloid beta 1-42 peptide was assessed by measuring the fluorescence resonance energy transfer (FRET) between the histidine tagged sFab and the biotinylated peptide using streptavidin cryptate and anti-6his-XL665 detection reagents (CisBio International, France; cat: 610SAKLB and 61HISXLB respectively). Selection outputs were screened as unpurified bacterial periplasmic extracts containing sFab, prepared in 50 mM MOPS buffer pH 7.4, 0.5 mM EDTA and 0.5 M sucrose. Ten microlitres of unpurified sFab samples were added to a Costar® 384 well assay plate (Corning, USA; cat: 3676). This was followed by the addition of 5 µl of 20 nM synthetic human Amyloid beta 1-42 and 5 µl of a combined solution of 6 nM streptavidin cryptate and 20 nM anti-his-XL665. Non-specific binding wells (negative controls) were defined for each plate by using a negative control unpurified sFab in place of the test sFab sample. Cross-reactive sFab clones were identified using a concurrent assay with human Amyloid beta 1-40 peptide. All dilutions were performed in 50 mM MOPS pH 7.4 (Sigma, UK; cat: M9381) containing 0.4 M KF (BDH Chemicals, USA; cat: 103444T), 0.1% fatty acid free bovine serum albumin (Sigma, UK; cat: A6003) and 0.1% Tween 20 (v/v) (Sigma, UK; cat: P2287) (assay buffer). Assay plates were incubated for 4 hours at room temperature prior to reading time resolved fluorescence on an EnVision plate reader (PerkinElmer, USA) using an excitation wavelength of 320 nm and measuring the emission at 620 nm and 665 nm (100 flashes).

Data were analysed by calculating % Delta F values for each sample. % Delta F was determined according to equation 1.

$$\% \text{ Delta } F = \frac{(\text{sample 665 nm}/620 \text{ nm ratio}) - (\text{negative control 665 nm}/620 \text{ nm ratio})}{(\text{negative control 665 nm}/620 \text{ nm ratio})} \times 100 \quad \text{Equation 1}$$

1.4 Direct Binding Assay of Purified sFab Fragments

Unpurified sFab periplasm extracts that showed specific binding to human Amyloid beta 1-42 peptide by HTRF™ assay were subjected to DNA sequencing (Osbourn et al., 1996; Vaughan et al., 1996). The sFab with unique protein sequences were expressed in E. coli and purified by affinity chromatography (essentially as described (Bannister et al., 2006)). The Amyloid beta binding profile of each purified sFab was determined by testing a dilution series of the purified sFab in the HTRF™ assay described in section 1.3, substituting the unpurified sFab periplasmic preparation with the purified sFab. The purified sFab were tested concurrently for binding to biotinylated human Amyloid beta 1-42 peptide, biotinylated murine Amyloid beta 1-42 peptide and biotinylated human Amyloid beta 1-40 peptide. In addition, sFab were tested for binding to scrambled human Amyloid beta 1-42 peptide (Anaspec, custom synthesis) in a separate HTRF™ experiment in order to control for any non-specific peptide binding. Data were analysed by calculating the % Delta F values as described in section 1.3.

Figure 1:
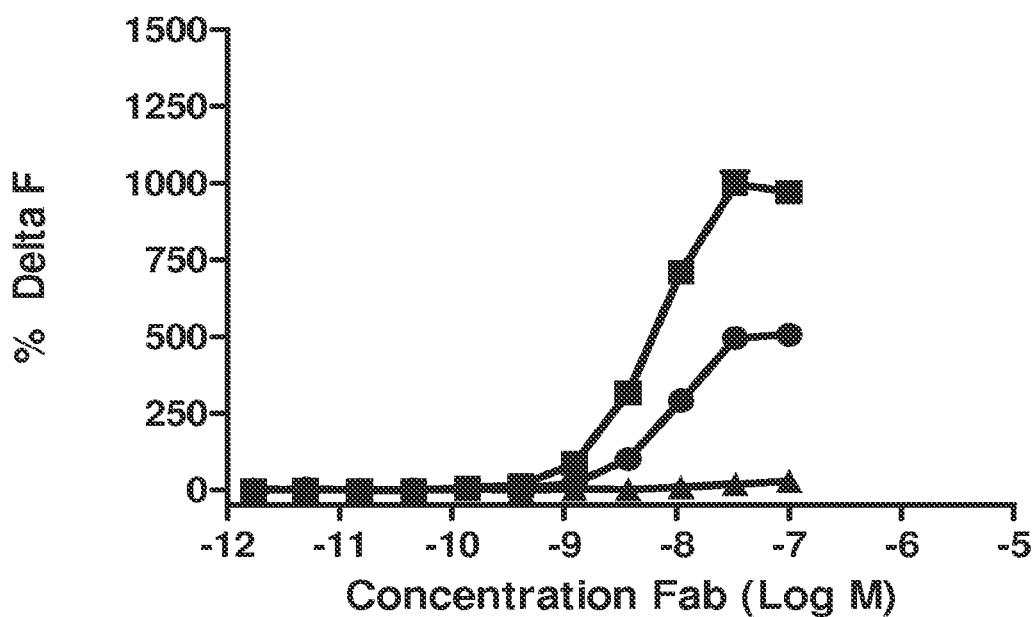
FIG. 1 shows the results of the direct binding HTRF™ assay between the purified Abet0007 Fab and a series of Amyloid beta peptides. The Abet0007 clone (■) shows binding to the human Amyloid beta 1-42 peptide (FIG. 1A) and the murine Amyloid beta 1-42 peptide (FIG. 1C) but shows no binding to the human Amyloid beta 1-40 peptide (FIG. 1B) or the scrambled human Amyloid beta 1-42 peptide (FIG. 1D). The positive control antibody (●) and the negative control antibody (▲) were used to verify the integrity of the assay.
Figure 1:
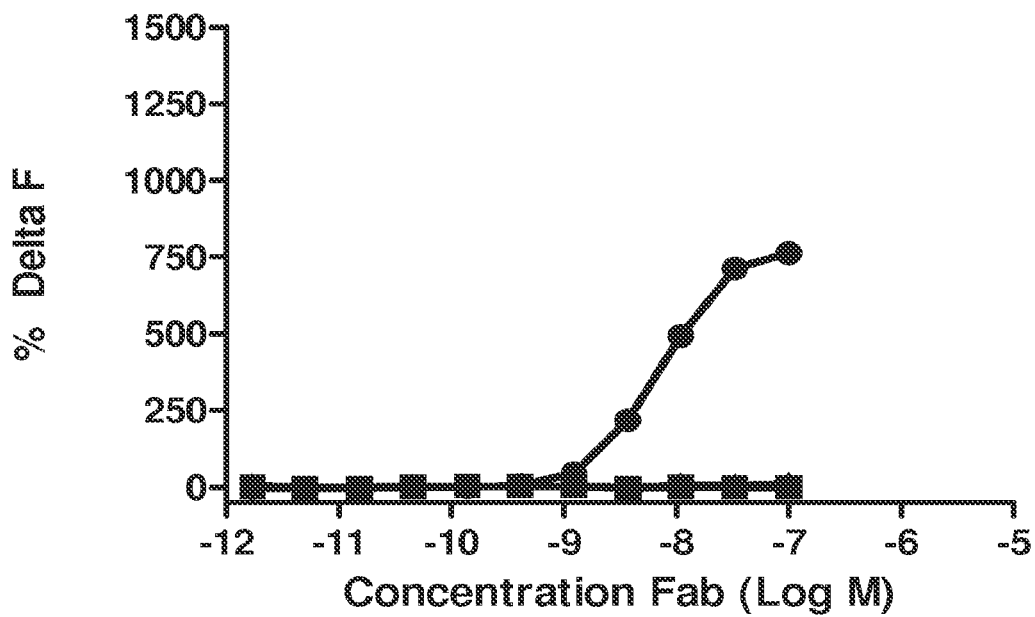

Example results for purified Abet0007 sFab are shown in FIG. 1. These results demonstrate that Abet0007 specifically binds to human Amyloid beta 1-42 peptide over human Amyloid beta 1-40 peptide and scrambled human Amyloid beta 1-42 peptide. In addition, Abet0007 sFab is cross-reactive with murine Amyloid beta 1-42 peptide.

1.5 Reformatting of Amyloid Beta 1-42 Specific Antibody Fabs to IgG2 Format

Thirteen Amyloid beta 1-42 specific clones were converted from Fab to IgG2 by sub-cloning the variable heavy chain ($V_H$) and variable light chain ($V_L$) domains into vectors expressing whole human antibody heavy and light chains respectively. The $V_H$ domains were codon optimised in-house before sub-cloning since the Dyax FAB310 library $V_H$ domains are semi-synthetic and failed to express in sufficient quantities within the mammalian cells described herein. An in-house germline matched $V_H$, which is known to express well as a full-length human IgG in mammalian cells, was used as a template to after the DNA codon usage of the Dyax VH domains whilst retaining the original amino acid sequence. The codon optimised variable heavy chains were cloned into a mammalian expression vector (pEU 9.2) containing the human heavy chain constant domains and regulatory elements to express whole IgG2 heavy chain in mammalian cells. Similarity, the variable light chain domain was cloned into a mammalian expression vector (pEU4.4) for the expression of the human lambda light chain constant domains and regulatory elements to express whole IgG light chain in mammalian cells. Vectors for the expression of heavy chains and light chains were originally described in Persic et al. (Persic et al., 1997). To obtain clones as IgG2, the heavy and light chain IgG expression vectors were transiently transfected into HEK293-EBNA (Invitrogen, UK; cat: R620-07) or CEP6-CHO (produced in-house) mammalian cells where the antibody was expressed and secreted into the medium. Harvested media was filtered prior to purification. The IgGs were purified using Protein A chromatography (Biosepram, Pall, USA or MabSelect SuRe, GE Healthcare, UK). Culture supernatants were loaded onto an appropriate Protein A column pre equilibrated in 50 mM Tris pH 8.0, 250 mM NaCl. Bound IgG was eluted from the column using 0.1 M Sodium citrate pH 3.0 and the eluate was neutralised by the addition of 1 M Tris buffer (pH 10.0). The IgGs were buffer exchanged into Dulbecco's PBS using NAP-10 buffer exchange columns (GE Healthcare, UK; cat: 17-0854-02). The purified IgGs were passed through a 0.2 micrometer filter and the concentration of IgG was determined by absorbance at 280 nm using an extinction coefficient based on the amino acid sequence of the IgG. The purified IgGs were analysed for aggregation or degradation using SEC-HPLC and SDS-PAGE techniques.

1.6 Specificity Determination of Lead Antibodies in an Amyloid Beta Peptide Competition HTRF™ Assay As described above, the purified sFab fragments that bound specifically to the Amyloid beta 1-42 peptide were converted to recombinant IgG. To test the specificity of these IgGs for binding to other human Amyloid beta peptides, a competition assay was developed. In this assay unlabelled human Amyloid beta peptides 1-42 (rPeptide, USA; cat: A1165), 1-40 (rPeptide, USA; cat: A1155), 11-42 (rPeptide, USA; cat: A1063), 17-42 (rPeptide, USA; cat: A1058) and 1-43 (Anaspec, USA; cat: 25356) were incubated with the lead IgG and biotinylated human Amyloid beta peptide 1-42 (rPeptide, USA; cat: A1117). Briefly, a dilution series of each test peptide was combined with 0.3 nM test IgG and 5 nM biotinylated human Amyloid beta 1-42 peptide. The competition of each peptide was assessed by detecting the loss of binding of the lead IgG to the biotinylated 1-42 peptide by measuring the fluorescence resonance energy transfer (FRET) between the IgG and biotinylated 1-42 Amyloid beta using streptavidin cryptate (CisBio International, France; cat: 610SAKLB) and anti-human Fc IgG XL665 (CisBio International, France; cat: 61HFCXLB) detection reagents.

Streptavidin cryptate and anti-human Fc IgG XL665 were combined at 7 nM and 5 nM respectively in assay buffer containing 50 mM MOPS pH 7.4 (Sigma, UK; cat: M9381), 0.4 M KF (BDH Chemicals, USA; cat: 103444T), 0.1% fatty acid free bovine serum albumin (Sigma, UK; cat: A6003) and 0.1% Tween 20 (v/v) (Sigma, UK; cat: P2287). 5 µl of this solution were added to the assay plate (Costar® 384 well black shallow well, Corning Life Sciences; cat: 3676). Amyloid beta peptides were serially diluted in assay buffer using a Greiner 96 well U bottom plate (Greiner BioOne, Germany; cat: 650201). 5 µl of each peptide dilution were transferred in duplicate to the assay plate using a Mini-Trak™ (PerkinElmer, USA) liquid handling robot. The test IgG was diluted to 1.2 nM in assay buffer and 5 µl were added to the assay plate. A 20 nM solution of biotinylated human Amyloid beta 1-42 peptide was prepared in assay buffer and 5 µl of this solution were added to the assay plates. Non-specific binding wells (negative controls) were defined for each plate by replacing the test IgG with 5 µl of assay buffer. Assay plates were incubated for 4 hours at room temperature prior to reading time resolved fluorescence at 620 nm and 665 nm emission wavelengths using an EnVision plate reader (PerkinElmer, USA).

Data were analysed by calculating % Delta F values for each sample. % Delta F was determined according to equation 1. % Delta F values were subsequently used to calculate % specific binding as described in equation 2.

$$\% \text{ specific binding} = \frac{\% \text{ Delta } F \text{ of sample}}{\% \text{ Delta } F \text{ of total binding control}} \times 100 \quad \text{Equation 2}$$

Figure 2:
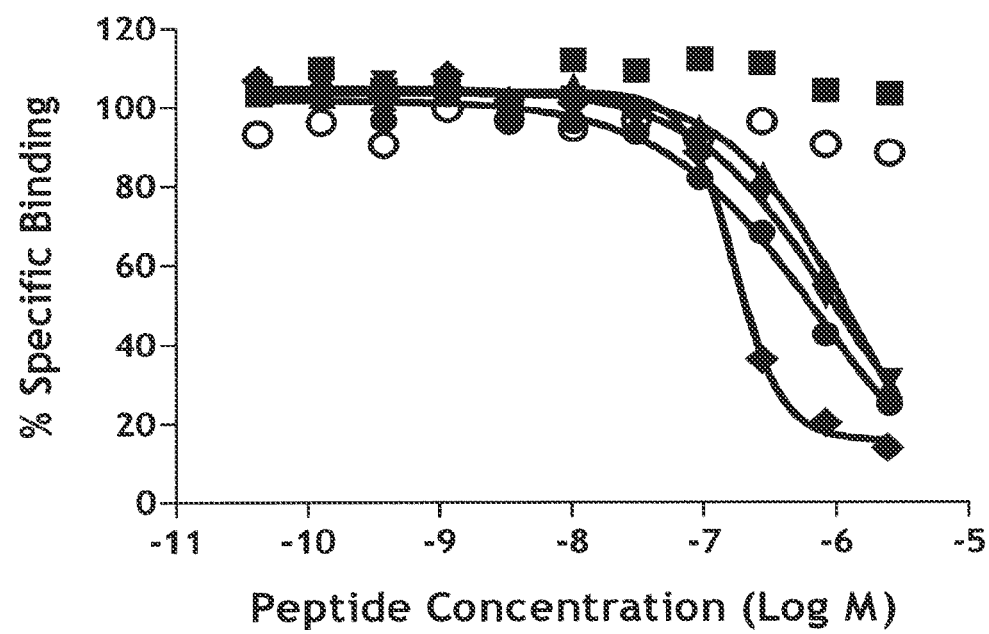
FIG. 2 shows the inhibition of the formation of the biotinylated human Amyloid beta 1-42 peptide and Abet0007 IgG2 complex by increasing concentrations of competitor peptides. Complex formation is inhibited by human Amyloid beta 1-42 (●), 11-42 (▲), 17-42 (▼) and 1-43 (♦) peptides. It is not inhibited by human Amyloid beta 1-40 peptide (■) or by the negative control peptide (○).

Example results for Abet0007 IgG are shown in FIG. 2. These results demonstrate Abet0007 IgG binds to human Amyloid beta 1-42 peptide, but not to human Amyloid beta 1-40 peptide. This antibody also binds to the truncated peptides 11-42 and 17-42 and to the human Amyloid beta 1-43 peptide.

1.7 Determination of Binding Affinities of Lead Antibodies to Human Amyloid Beta 1-42 Using Surface Plasmon Resonance The BIAcore T-100 (GE Healthcare, UK) biosensor instrument was used to assess the kinetic parameters of the interaction between each lead antibody and synthetically produced human Amyloid beta 1-42 peptide. These experiments were performed essentially as described by Karisson et al. (Karisson et al., 1991).

The biosensor uses the optical effects of surface plasmon resonance (SPR) to study changes in surface concentration resulting from the interaction of an analyte molecule that is flowed over a ligand molecule that is immobilised on the dextran layer of a biosensor chip. Typically, a defined concentration of the analyte species is passed over the coupled ligand and any binding is detected as an increase in local SPR signal (association phase). This is followed by a period of buffer flow, during which dissociation of the analyte species from the surface immobilised ligand can be observed as a decrease in signal (dissociation phase). The remaining analyte can then be stripped from the chip-bound ligand and the procedure repeated at several different analyte concentrations. The experiment is designed such that neither the absolute binding capacity nor kinetic profile of the coupled ligand change significantly during the entire experiment and can be monitored using a series of controls employed throughout the experiment. A proprietary HEPES buffered saline containing EDTA (HBS-EP+, GE Healthcare, UK) is typically used as the diluent buffer for the analyte samples and as the flow buffer during the dissociation phase. The experimental data is recorded overtime as 'Resonance Units' (RUs), which are arbitrary units that directly correspond to the SPR signal. The RUs are directly proportional to changes in the refractive index on the chip surface, which in turn is an approximate measure of the mass of analyte bound. The proprietary BIAevaluation software package can then be used to process data and fit binding models to the data sets. Returned association (ka, $M^{-1} s^{-1}$) and dissociation (kd, $s^{-1}$) rate constants allow calculation of dissociation (KD, M) affinity constants.

The affinity of binding between each test IgG and human Amyloid beta 1-42 peptide was estimated using assays in which the antibody was covalently coupled by amine-linkage to a proprietary CM5 chip surface to a final surface density of approximately 2,000 RU. The chip surface was regenerated between cycles by a single 40 second injection of 10 mM Glycine pH 2.0 to remove ligand bound to the antibody. The regeneration did not result in a significant loss of peptide binding activity.

A series of dilutions of synthetic human Amyloid beta 1-42 peptide (1.6-100 nM) were sequentially passed over the antibody surface for a sufficient amount of time to observe sensorgrams that could be fitted to an appropriate binding model with confidence. Blank reference flow-cell data were subtracted from each IgG dataset and a zero-concentration buffer blank was double-reference subtracted from the main data set to reduce the impact of any buffer artefacts or non-specific binding effects. An appropriate binding model was then fitted simultaneously to the data from each analyte titration using the BIAevaluation software.

The validity of the data was assessed using the calculated $Chi^2$ value, with an acceptable value being under 2 $RU^2$. The overall success of the fit was estimated using the residuals, with a deviation of under 2 RUs being acceptable.

Figure 3:
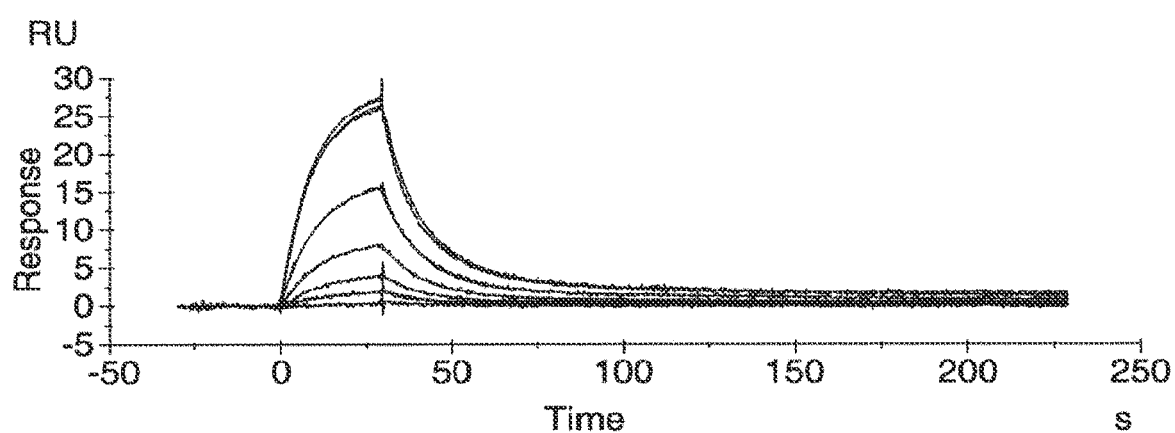
FIG. 3 shows the Surface Plasmon Resonance (BIAcore) traces for the human Amyloid beta 1-42 peptide binding to immobilised Abet0007 IgG2 at concentrations of 100 nM (top trace), 50 nM, 25 nM, 12.5 nM, 6.2 nM and 3.1 nM (bottom trace) peptide. Each trace is fitted to a 1:1 Langmuir model.

Example results for Abet0007 IgG2 are shown in FIG. 3. The mean association rate constant (ka), dissociation rate constant (kd) and dissociation constant (KD) are $1.6 \times 10^5$ M$^{-1}$ s$^{-1}$, 7.4×10$^{-2}$ s$^{-1}$ and 473 nM respectively. These parameters were derived from a 1:1 Langmuir fit to the data.

1.8 Functional Characterisation of Lead Antibodies by Depletion of Amyloid Beta Peptides from Human Plasma The lead antibodies were tested in a plasma depletion assay to investigate their ability to immunoprecipitate human Amyloid beta 1-42 peptide from human blood plasma. This assay was used to provide evidence of functional efficacy for each antibody. Briefly, human plasma samples were incubated with each test IgG for 3 hours after which the antibodies and any bound ligands were removed. The Amyloid beta 1-42 peptide content of the human plasma samples was assayed using standard techniques before and after immunoprecipitation, and these values were used to determine the efficacy of the antibody. The plasma samples were also assayed for any depletion in Amyloid beta 1-40 peptide to assess the specificity of the lead antibodies Each test antibody was separately covalently linked to Dynabeads® M-270 Carboxylic Acid magnetic beads (Invitrogen Life Technologies, UK; cat: 143-05D) according to the manufacturer's instructions. For each test IgG 100 μl of Dynabeads were washed twice with 100 μl of 25 mM MES, pH 5 (Sigma, UK; cat: M5287) using a magnet to separate the beads from the suspension. Immediately before use, EDC (Pierce, Thermo Scientific, USA; cat: 22981) was dissolved in cold 25 mM MES, pH 5 to a final concentration of 50 mg/ml. A 50 mg/ml solution of NHS (Pierce, Thermo Scientific; cat: 24500) was similarly prepared in 25 mM MES, pH 5. 50 μl of NHS solution and 50 μl EDC solution were added to the washed Dynabeads, which were mixed well and incubated with slow-tilt rotation at room temperature for 30 minutes. A magnet was used to pellet the beads and the supernatant was removed. The beads were washed twice with 100 μl of 25 mM MES, pH 5. Each test IgG was diluted to 0.6 mg/ml in a total volume of 100 μl of 25 mM MES, pH 5. The washed beads were resuspended in the ligand solution and were incubated for at least 30 minutes at room temperature with slow tilt rotation. The beads were subsequently pelleted using a magnet and washed once with 100 μl of 50 mM Tris buffer, pH 7.4 (Sigma, UK). The beads were then resuspended in 100 μl of Marvel-PBS (3% w/v) and incubated overnight at 4° C. The beads were washed twice with Dulbecco's PBS (100 μl) and resuspended in PBS (100 μl).

EDTA-plasma samples were isolated from anonymous donors at the AstraZeneca Health Clinic in Södertälje, Sweden. Approximately 100 ml of blood were collected from each donor, and this was pooled into two 50 ml tubes. EDTA was added to a final concentration of 5 mM to prevent clotting, and the tubes were spun at 4,000×g for 10 minutes at 4° C. The supernatant (plasma) was collected, aliquoted into 1 ml tubes, and stored at −80° C. until required. The samples were assayed for both Amyloid beta 1-42 peptide and Amyloid beta 1-40 peptide content as described below.

Each set of antibody coated beads was separately incubated with a 1 ml aliquot of EDTA-plasma for 3 hours at 4° C. with slow tilt rotation, and the beads were then pelleted using a magnet. The supernatant was carefully removed from the beads and was assayed for both Amyloid beta 1-42 peptide and Amyloid beta 1-40 peptide as described below.

Analysis of the Amyloid beta 1-40 peptide content of the plasma samples was performed using the Aβ 40 Human ELISA Kit from Invitrogen (UK; cat: KHB3482) according to the manufacturer's instructions. Briefly, a human Amyloid beta 1-40 standard was used to create a dilution series from 1 ng/ml down to 7.81 μg/ml. The dilutions were made using Standard Dilution Buffer containing 1 protease inhibitor tablet (Roche, UK; cat: 11697498001) per 50 ml diluent. 50 μl of each dilution was then added to a different microtitre well pre-coated with a proprietary monoclonal antibody specific for the N-terminus of the Amyloid beta peptide. EDTA-plasma samples were centrifuged for 10 minutes at 4° C. and 2,000×g and 50 μl of each sample supernatant were added to a separate well in the same microtitre plate as the standards. 50 μl of proprietary Hu Aβ Detection Antibody, which specifically recognises the C-terminus of Amyloid beta 1-40 peptide, were then added to each microtitre well. The plate was covered with a plate seal and incubated for 3 hours at room temperature with shaking. The plate was washed four times with 400 μl of wash buffer, allowing the plate to soak for 15-30 seconds during each wash. The plate was then inverted and tapped dry. 100 μl of proprietary Anti-Rabbit IgG HRP conjugate were added to each well, the plate was covered with a plate seal, and the samples were incubated for 30 minutes at room temperature. Again, the plate was washed four times with 400 μl of wash buffer, allowing the plate to soak for 15-30 seconds during each wash. The plate was then inverted and tapped dry. 100 μl of proprietary Stabilised Chromogen were added to each well, and the plate was incubated in the dark for 20 minutes at room temperature. This was followed by the addition of 100 μl of proprietary Stop Solution to each well. The absorbance of each well was read at 450 nm within 2 hours of adding the Stop Solution. A standard curve was produced from the human Amyloid beta 1-40 dilution series, and this was used to determine the concentration of human Amyloid beta 1-40 in the test EDTA-plasma samples.

Analysis of the Amyloid beta 1-42 peptide content of the plasma samples was performed using the INNOTEST® β-Amyloid$_{(1-42)}$ kit from Innogenetics (Belgium; cat: 80177) essentially according to the manufacturer's instructions. Briefly, a human Amyloid beta 1-42 standard was used to create a dilution series from 1 ng/ml down to 7.81 pg/ml. 100 μl of each dilution was then added to a different microtitre well pre-coated with a proprietary monoclonal antibody specific for the C-terminus of the human Amyloid beta 1-42 peptide. EDTA-plasma samples were centrifuged for 10 minutes at 4° C. and 2,000×g and 100 μl of each sample supernatant were added to a separate well in the same microtitre plate as the standards. The plate was covered with a plate seal and incubated for 3 hours at room temperature with shaking. The plate was washed five times with 400 μl of wash buffer and was then inverted and tapped dry. 100 μl of proprietary conjugate 1 (C1HS), which recognises the N-terminus of the Amyloid beta peptide, were added to each well. The plate was covered with a plate seal, and the samples were incubated for 1 hour at room temperature. Again, the plate was washed five times with 400 μl of wash buffer, and was then inverted and tapped dry. 100 μl of conjugate 2 (C2), a streptavidin-HRP conjugate that binds to the biotinylated C1HS antibody, were then added to each well. The plate was covered with a plate seal and incubated for 30 minutes at room temperature. The plate was washed five times with 400 μl of wash buffer, and was then inverted and tapped dry. 100 μl of proprietary substrate solution were added to each well, the plate was incubated for 30 minutes at room temperature, and then 100 μl of stop solution were added to each well. The absorbance of each well was read at 450 nm within 15 minutes of adding the stop solution. A standard curve was produced from the human Amyloid beta 1-42 dilution series, and this was used to determine the concentration of human Amyloid beta 1-42 in the test EDTA-plasma samples.

In one experiment, the Abet0007 IgG2 antibody reduced the levels of human Amyloid beta 1-42 peptide in plasma from 80.47 pg ml-1 to 60.56 pg ml-1 (a 25% reduction). In a second experiment, the levels were reduced from 197.43 pg ml-1 to 154.45 pg ml-1 (a 22% reduction).

1.9 Identification of Lead Clones with Low Affinity for Native Amyloid Beta Using In Vitro Immunohistochemistry The lead antibodies were tested for their ability to bind to Amyloid beta, with the aim of identifying lead clones with low affinity for native forms of the Amyloid beta peptide. Briefly, the lead antibodies were screened on human Alzheimer's Disease brain sections and Tg2576 mouse brain sections to identify anti Amyloid beta 1-42 antibodies that bound to native Amyloid in vitro.

Tg2576 mice are transgenic mice that over-express the gene for human Amyloid Precursor Protein (APP). This gene carries two point mutations in the gamma-secretase cleavage site (Lys670Asn and Met671Leu) that leads to formation of Amyloid beta plaques in the cortex and hippocampus of the mice, starting at an age of approximately 9 months.

Human brain tissue was isolated from the frontal cortex (inferior frontal gyrus) of two individuals with severe Alzheimer's Disease (ApoE genotype 3/3, Braak stage 6 and ApoE genotype 4/3, Braak stage 5 respectively). As a control, equivalent tissue was isolated from one non-dementia individual (ApoE genotype 3/3, Braak stage 1). All three tissues were supplied by the Netherlands Brain Bank (NBB). The quality of the sections was verified by haematoxylin/eosin staining before use. Mouse brain tissue was isolated from Tg2576 mice at an age of 15 months (2 mice), 18 months (6 mice), and 22 months (2 mice).

Paraffin embedded brain sections, 4-6 µm in width, were prepared for immunohistochemistry by first removing the paraffin support matrix. Sections were washed with Xylene (5 minutes×2), absolute ethanol (3 minutes×2), 95% ethanol (3 minutes×2), 70% ethanol (3 minutes×2), 90% formic acid (Sigma Aldrich, UK; cat: 06440; 10 minutes), tap water (20 minutes×3) and PBS (5 minutes×2). The sections were then boiled in Diva Decloaker solution (Biocare Medical, USA; cat: DV2004 G1) in a microwave oven for 20 minutes at 100° C. The samples were subsequently cooled to 40° C. in a waterbath and then washed with distilled water (5 minutes) and PBS (5 minutes×3).

The lead IgG2 antibodies were tested at concentrations of 2, 5 and 20 µg ml$^{-1}$. Binding of these IgGs was detected using a rabbit anti-human secondary antibody (Dako, Denmark; cat: A0482) at a 1 in 400 dilution, followed by the OmniMap anti-rabbit HRP conjugate antibody (Ventana Medical Systems, USA; cat: 760-4311). The signal was detected using the ChromoMap DAB kit (Ventana Medical Systems, USA; cat: 760-159). These staining steps were performed using a BenchMark automated slide preparation system (Ventana Medical Systems, USA) according to standard protocols.

Scoring of the staining was carried out in a blinded fashion by at least two different people under 20-40× optical magnification. In vitro plaque binding was designated using a scale from 0 (no staining of plaques) up to 4 (intense staining of plaques).

Figure 4:
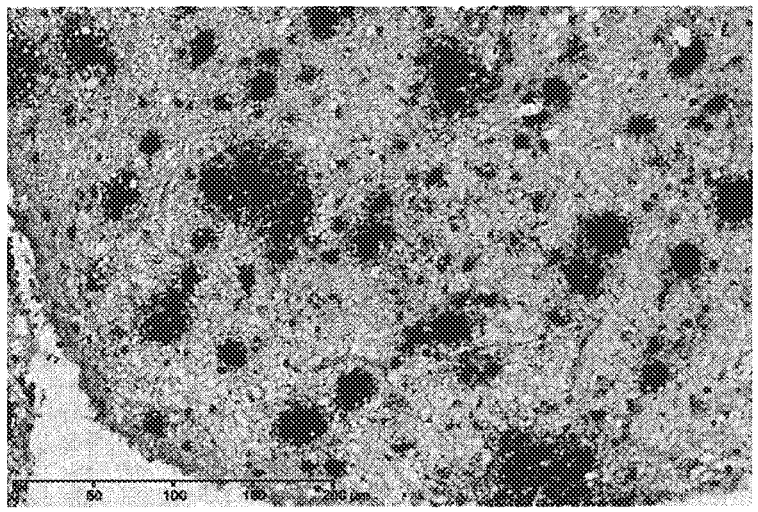
FIG. 4 shows sample images from the in vitro immunohistochemical staining of Abet0007 IgG2. (A) A positive control antibody shows strong plaque recognition (score=4) on human AD brain sections (ApoE genotype 3/3; Braak stage 6; 20 μg/ml antibody). (B) The Abet0007 IgG2 lead clone shows no plaque recognition (score=0) on an adjacent brain section (20 μg/ml). (C) The same positive control antibody shows strong plaque recognition (score=4) on Tg2576 mouse brain sections (18 month old mice; 20 μg/ml antibody). (D) The Abet0007 IgG2 lead clone shows no plaque recognition (score=0) on an adjacent mouse brain section (20 μg/ml).
Figure 4:
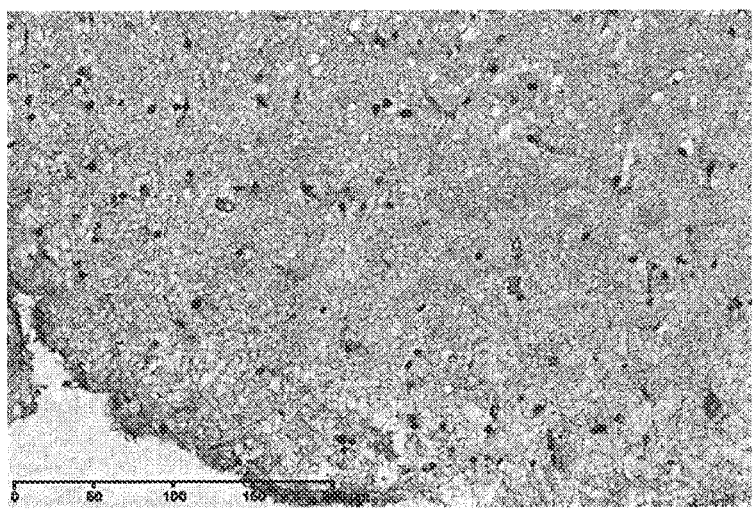
Figure 4:
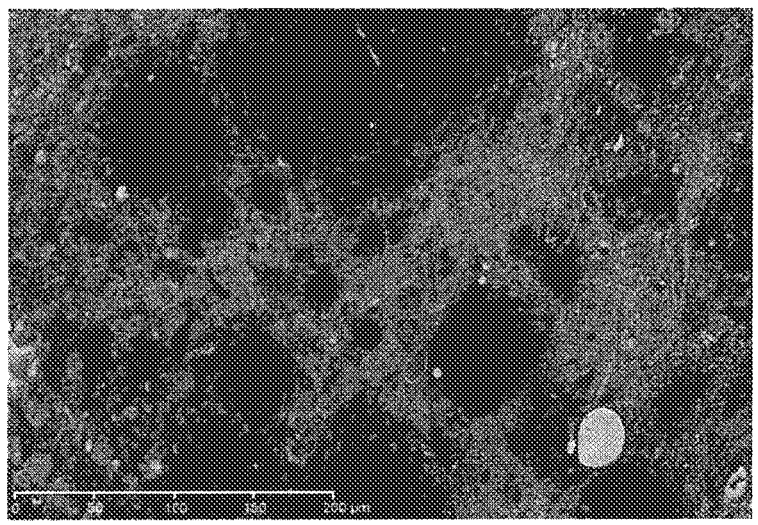
Figure 4:
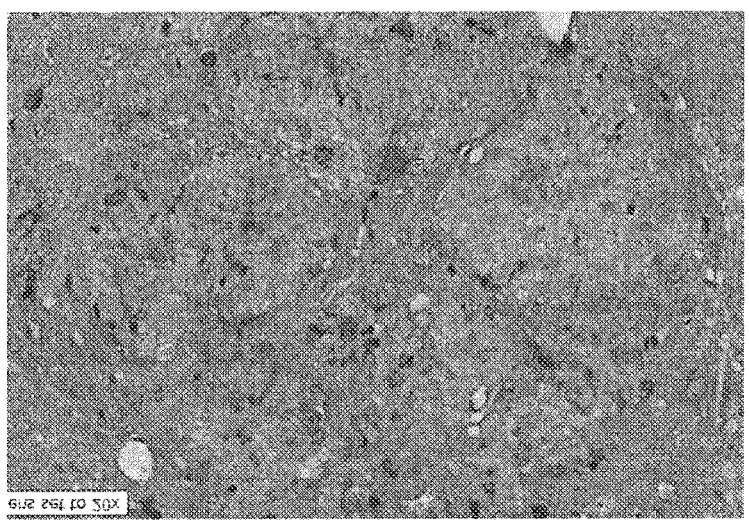

Abet0007 IgG2 showed no staining of plaques in either the human Alzheimer's Disease brains or the mouse Tg2576 brains (score=0). In contrast, a positive control antibody produced a score of 4 on adjacent sections under the same conditions. Representative images are presented in FIG. 4.

Example 2. Antibody Optimisation of Abet0007 Through Directed Mutation of the Complementarity Determining Regions 3 (CDR3)

2.1 Conversion of Abet0007 Parent Done to scFv Format

The parent clone was converted from IgG2 format to single chain variable fragment (scFv) format in preparation for affinity optimisation. The codon-optimised variable heavy ($V_H$) and variable light ($V_L$) domains were amplified separately from their respective IgG vectors with the addition of specific cloning sites and a flexible linker region. Recombinatorial PCR was then performed to generate a complete scFv construct, which was cloned into the pCantab10.5 phagemid vector, essentially as described in Vaughan et al. (Vaughan et al., 1996). The pCantab10.5 vector is a modified version of the pCantab6 vector that contains additional restriction sites to facilitate the addition of tags other than the standard His and myc tags.

2.2 Optimisation of Abet0007 by Targeted Mutagenesis

The lead antibody (Abet0007) was optimised for improved affinity to human Amyloid beta 1-42 peptide using a targeted mutagenesis approach with affinity-based phage display selections. Large scFv-phage libraries derived from Abet0007 were created by oligonucleotide-directed mutagenesis of the variable heavy ($V_H$) and variable light ($V_L$) chain complementarity determining regions 3 (CDR3) using standard molecular biology techniques as described by Clackson and Lowman ((2004) A Practical Approach, Oxford University Press).

The libraries were subjected to affinity-based phage display selections in order to enrich for variants with higher affinity for human Amyloid beta 1-42 peptide. The selections were performed essentially as described previously (Hawkins et al., 1992; Schier et al., 1996; Thompson et al., 1996). In brief, the scFv phage particles were incubated with biotinylated human Amyloid beta 1-42 peptide (rPeptide, USA; cat: A1117) in solution. ScFv-phage that bound to the antigen were then captured on streptavidin-coated paramagnetic beads (Dynabeads® M280, Invitrogen Life Sciences, UK) following the manufacturer's recommendations. The selected scFv-phage particles were then rescued as described previously (Osbourn et al., 1996), and the selection process was repeated in the presence of decreasing concentrations of biotinylated human Amyloid beta 1-42 antigen (200 nM to 2 nM over 3 rounds).

2.3 Identification of Improved Clones Using a Direct Binding Assay

One thousand seven hundred and sixty scFv were randomly selected from selection rounds 2 and 3 from the targeted mutagenesis approach described in section 2.2. These clones were screened using a direct binding assay essentially as described in section 1.3. Briefly, unpurified scFv from periplasmic preparations were tested for increased binding to biotinylated human Amyloid beta 1-42 peptide and detected using HTRF™ technology with streptavidin cryptate and anti-6his-XL665 detection reagents.

Unpurified scFv from periplasmic preparations were prepared in 50 mM MOPS buffer pH 7.4 including 0.5 mM EDTA and 0.5 M sucrose and were subsequently diluted to 1% in assay buffer containing 50 mM MOPS pH 7.4 (Sigma, UK; cat: M9381), 0.4 M potassium fluoride (BDH Chemicals, USA; cat: 103444T), 0.1% fatty acid free bovine serum albumin (Sigma, UK; cat: A6003) and 0.1% Tween 20 (v/v) (Sigma, UK; cat: P2287) using a Greiner 384 well V bottom plate (Greiner BioOne, Germany; cat: 781280). 5 µl of diluted scFv sample were transferred to the assay plate (Costar® 384 well black shallow well, Corning Life Sciences; cat: 3676) using a MiniTrak™ (PerkinElmer, USA) liquid handling robot. 5 µl of assay buffer was then added to each well. A 20 nM solution of biotinylated human Amyloid beta 1-42 peptide (rPeptide, USA; cat: A1117) was prepared in assay buffer and 5 µl this solution were added to the assay plates. Streptavidin cryptate (Cisbio International, France; cat: 610SAKLB) and anti-His6-XL665 (Cisbio International, France; cat: 61HISXLB) detection reagents were combined in assay buffer to give concentrations of 7 nM streptavidin cryptate and 60 nM anti-His6-XL665 and then 5 µl of this detection cocktail were added to all wells of the assay plates. Non-specific binding wells (negative controls) were defined for each plate by replacing scFv sample with 5 µl assay buffer. Assay plates were sealed and incubated for 2.5 hours at room temperature prior to reading time resolved fluorescence at 620 nm and 665 nm emission wavelengths using an EnVision plate reader (PerkinElmer, USA). Data analysis was performed as described previously (Section 1.3) and % Delta F values were used to compare assay signals in adjacent wells. A "hit" was defined as a scFv sample that generated a % Delta F greater than the signal observed for Abet0007 scFv.

2.4 Confirmation of Improved Clones Using an Epitope Competition Assay

Clones that displayed a higher binding to human Amyloid beta 1-42 peptide than the Abet0007 parent clone were subjected to DNA sequencing (Osbourn et al., 1996; Vaughan et al., 1996). The scFv with unique protein sequences were expressed in E. coli and purified by affinity chromatography followed by buffer exchange. The binding affinities of these scFv were then tested in an epitope competition assay against a benchmark antibody called Abet0042, which has a similar affinity for human Amyloid beta 1-42 peptide as Abet0007. In this competition assay, the binding of Abet0042 IgG to biotinylated human Amyloid beta 1-42 peptide is competed against the test scFv samples. The binding of Abet0042 IgG to biotinylated human Amyloid beta 1-42 peptide is detected using the HTRF™ technology as described previously (section 1.6). Briefly, a dilution series of purified scFv are added to a mixture of Abet0042 IgG, biotinylated Amyloid beta 1-42 peptide, streptavidin cryptate and anti-human Fc IgG XL665. The time resolved fluorescence was read after two hours incubation at room temperature.

Purified scFv were serially diluted in assay buffer containing 50 mM MOPS buffer pH 7.4 (Sigma, UK; cat: M9381), 0.4 M potassium fluoride (BDH Chemicals, USA; cat: 103444T), 0.1% fatty acid free bovine serum albumin (Sigma, UK; cat: A6003) and 0.1% Tween 20 (Sigma, UK; cat: P2287) using a Greiner 96 well U bottom plate (Greiner BioOne, Germany; cat: 650201). 5 µl of each dilution of scFv was transferred in duplicate to the assay plate (Costar® 384 well black shallow well, Corning Life Sciences; cat: 3676) using a MiniTrak™ (PerkinElmer, USA) liquid handling robot. A 20 nM solution of biotinylated Amyloid beta 1-42 peptide (rPeptide, USA; cat: A1117) was prepared in assay buffer and 5 µl of the biotinylated peptide solution was added to the assay plates, to give a final concentration of 5 nM peptide in the final assay volume of 20 µl. The assay plates were sealed and incubated at room temperature for 1 hour. Streptavidin cryptate and anti-human Fc IgG XL665 were combined at 7 nM and 20 nM respectively in assay buffer and 5 µl of this solution were added to the assay plate. Abet0042 IgG was diluted to 2.4 nM in assay buffer and 5 µl were added to the assay plate to generate a final IgG concentration of 0.6 nM. Non-specific binding wells (negative controls) were defined for each plate by replacing Abet0042 IgG with 5 µl assay buffer. Assay plates were sealed and incubated for 2 hours at room temperature prior to reading time resolved fluorescence at 620 nm and 665 nm emission wavelengths using an EnVision plate reader (PerkinElmer, USA).

Data were analysed by calculating the % Delta F value and the % specific binding for each sample. % Delta F was determined according to Equation 1 and % specific binding was calculated using Equation 2. $IC_{50}$ values were determined using Prism (Graphpad Software, USA) by curve fitting using a four parameter logistic equation, as described in equation 3.

$$Y = \text{Bottom} + \frac{\text{Top} - \text{Bottom}}{1 + 10\wedge((\text{Log}EC_{50} - X)*\text{HillSlope})} \quad \text{Equation 3}$$

Where Y is specific binding and X is the logarithm of concentration.

Figure 5:
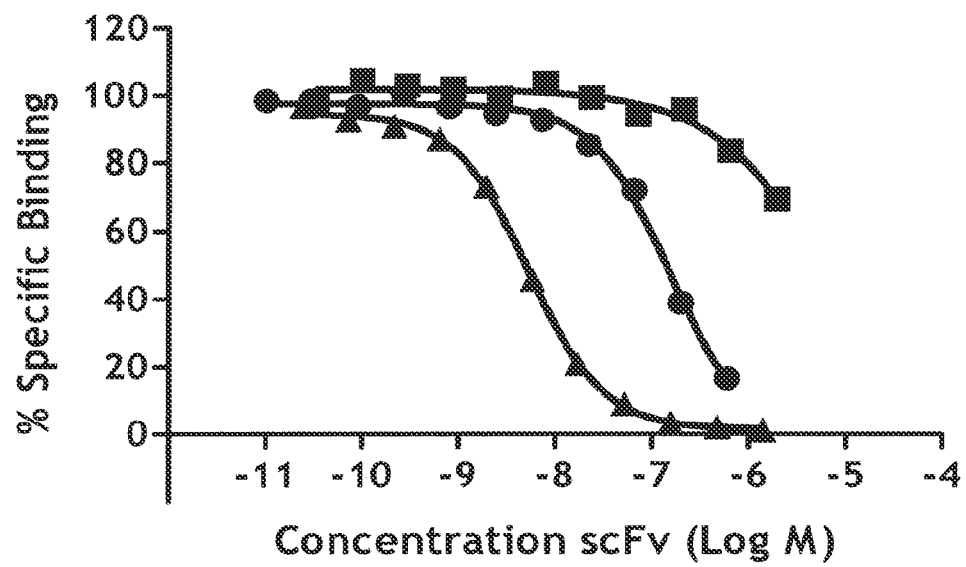
FIG. 5 shows the inhibition of the formation of the human Amyloid beta 1-42 and Abet0042 IgG complex by increasing concentrations of Abet0007 scFv (●) and Abet0144 scFv (▲). The Abet0144 clone is significantly more potent than the Abet0007 parent clone in this assay. A negative control antibody (■) is included for comparison.

Example results are shown in FIG. 5. The original lead, Abet0007, has an $IC_{50}$ of 159 nM while the most improved clone, Abet0144, has an $IC_{50}$ value of 5.5 nM.

2.5 Kinetic Profiling of Affinity Improved Clones in Purified scFv Format by Surface Plasmon Resonance Surface Plasmon Resonance was used to analyse the purified scFv clones that had shown significant improvement in binding affinity for human Amyloid beta 1-42 peptide over the parent sequence, Abet0007, in the HTRF™ epitope competition assay (section 2.4). Briefly, the BIAcore T-100 (GE Healthcare, UK) biosensor instrument was used to assess the kinetic parameters of the interaction between each purified scFv and synthetically-produced human Amyloid beta 1-42 peptide. These experiments were performed essentially as described by Karisson et al. (Karisson et al., 1991). For further details see section 1.7.

The affinity of binding between each test scFv and human Amyloid beta 1-42 was estimated using assays in which biotinylated synthetic human Amyloid beta 1-42 peptide (rPeptide, USA; cat: A1117) was non-covalently bound via a biotin/streptavidin interaction to a proprietary SA sensor chip to a final surface density of approximately 700 RU. The chip surface was regenerated between cycles by a single 20 second injection of 10 mM Glycine pH 2.0 to remove scFv bound to the peptide. The regeneration did not result in a significant loss of peptide binding capacity.

A series of dilutions of each purified scFv (12.5-400 nM) were sequentially passed over the peptide surface for a sufficient amount of time to observe sensorgrams that could be fitted to an appropriate binding model with confidence. A zero-concentration buffer blank was subtracted from the main dataset to reduce the impact of any buffer artefacts or non-specific binding effects. An appropriate binding model was then fitted simultaneously to the data from each analyte titration using the BIAevaluation software.

Figure 6:
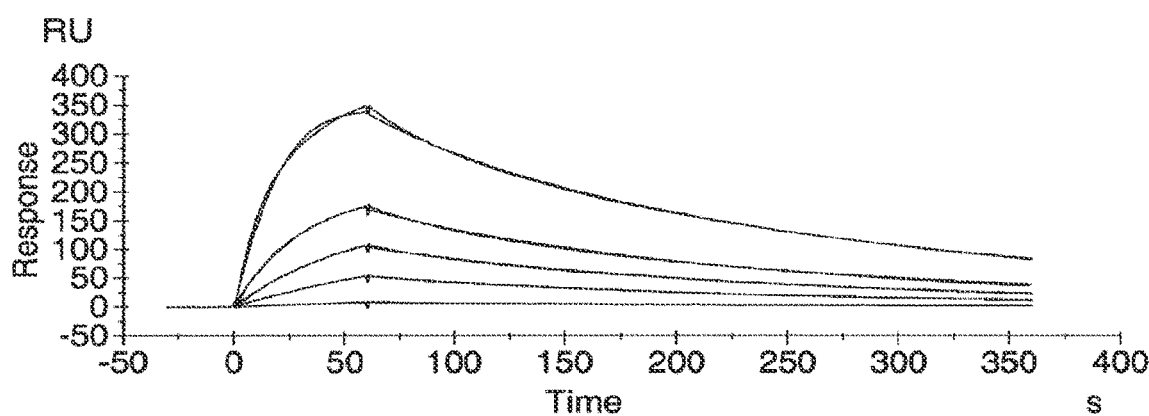
FIG. 6 shows the Surface Plasmon Resonance (BIAcore) traces for the purified Abet0144 scFv binding to immobilised human Amyloid beta 1-42 peptide at concentrations of 400 nM (top trace), 200 nM, 100 nM, 50 nM and 12.5 nM (bottom trace) scFv. Each trace is fitted to a 1:1 Langmuir model.

The validity of the data was assessed using the calculated $\text{Chi}^2$ value, with an acceptable value being under 4 $RU^2$. The overall success of the fit was estimated using the residuals, with a deviation of under 20 RUs being acceptable. Example results for Abet0144 scFv are shown in FIG. 6. The association rate constant (ka), dissociation rate constant (kd) and dissociation constant (KD) are $2.01 \times 10^5$ $M^{-1}$ $s^{-1}$, $6.66 \times 10^{-3}$ $s^{-1}$ and 33.2 nM respectively. These parameters were derived from a 1:1 Langmuir fit to the data.

2.6 Reformatting of Affinity Improved scFv to Human IgG1-TM

The IgG1-TM antibody format is a human IgG1 isotype containing three single amino acid substitutions (Triple Mutant: TM) within the lower hinge and CH2 constant domain (Oganesyan et al., 2008). When introduced into the lower hinge and CH2 domain of human IgG1 molecules, the triple mutation L234F/L235E/P331S ('TM') causes a profound decrease in their binding to human CD64, CD32A, CD16 and C1q. These TM mutations are used to create a human isotype with very low effector function. ScFv were reformatted to IgG1-TM by subcloning the variable heavy chain ($V_H$) and variable light chain ($V_L$) domains into vectors expressing whole human antibody heavy and light chains respectively. The variable heavy chain was cloned into a mammalian expression vector (pEU 1.4) containing the human heavy chain constant domains and regulatory elements to express whole IgG1-TM heavy chain in mammalian cells. Similarly, the variable light chain domain was cloned into a mammalian expression vector (pEU 4.4) for the expression of the human lambda light chain constant domains and regulatory elements to express whole IgG light chain in mammalian cells. IgG antibodies were expressed and purified essentially as described in Section 1.5.

2.7 Germlining

The amino acid sequences of the $V_H$ and $V_L$ domains of the affinity optimised Amyloid beta 1-42 peptide specific antibodies were aligned to the known human germline sequences in the VBASE database (Tomlinson et al., 1992), and the closest germline was identified by sequence similarity. For the $V_H$ domains of the optimised antibody lineage this was Vh3-23 (DP-47) and for the $V_L$ domains it was Vλ3-3r (DPL-23).

The germlining process consisted of reverting framework residues in the $V_H$ and $V_L$ domains to the closest germline sequence to identically match human antibodies. For Abet0144, no residues required changing in the $V_H$ domain (Table 1) but a total of 5 changes were made in the framework of the $V_L$ domain. These changes occurred at Kabat positions 1, 2, 3, 40 and 81 (Table 2). The Vernier residues (Foote et al., 1992), were not germlined, apart from residue 2 in the light chain sequence which was germlined at the same time as the flanking residues 1 and 3. Germlining of these amino acid residues was carried out using standard site directed mutagenesis techniques with the appropriate mutagenic primers as described by Clackson and Lowman (Clackson et al., 2004).

TABLE 1

A sequence alignment of the Abet0144 and Abet0144-GL clones to the VH3-23 (DP47) germline. Residues that are different from germline are italicized. Vernier residues are indicated by circles (•). No changes were made in the $V_H$ domain to germline the Abet0144 clone.

| Kabat Numbering | FW 1 | | | | | | | | | | | | | | | | | | | | | |
|---|---|---|---|---|---|---|---|---|---|---|---|---|---|---|---|---|---|---|---|---|---|---|
| $V_H$ | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
| Vernier | | • | | | | | | | | | | | | | | | | | | | | |
| VH3-23 | E | V | Q | L | L | E | S | G | G | G | L | V | Q | P | G | G | S | L | R | L | S | C |
| Abel0144 | E | V | Q | L | L | E | S | G | G | G | L | V | Q | P | G | G | S | L | R | L | S | C |
| Abel0144-GL | E | V | Q | L | L | E | S | G | G | G | L | V | Q | P | G | G | S | L | R | L | S | C |

| Kabat Numbering | FW 1 | | | | | | | CDR 1 | | | | | FW2 | | | | | | |
|---|---|---|---|---|---|---|---|---|---|---|---|---|---|---|---|---|---|---|---|
| $V_H$ | 23 | 24 | 25 | 26 | 27 | 28 | 29 | 30 | 31 | 32 | 33 | 34 | 35 | 36 | 37 | 38 | 39 | 40 | 41 | 42 | 43 | 44 |
| Vernier | | | | • | • | • | • | | | | | | | | | | | | | | | |
| VH3-23 | A | A | S | G | F | T | F | S | S | Y | A | M | S | W | V | R | Q | A | P | G | K | G |
| Abel0144 | A | A | S | G | F | T | F | S | *V* | Y | *T* | M | *W* | W | V | R | Q | A | P | G | K | G |
| Abel0144-GL | A | A | S | G | F | T | F | S | *V* | Y | *T* | M | *W* | W | V | R | Q | A | P | G | K | G |

| Kabat Numbering | FW2 | | | | | CDR2 | | | | | | | | | | | | | | | |
|---|---|---|---|---|---|---|---|---|---|---|---|---|---|---|---|---|---|---|---|---|---|
| $V_H$ | 45 | 46 | 47 | 48 | 49 | 50 | 51 | 52a | 52 | 53 | 54 | 55 | 56 | 57 | 58 | 59 | 60 | 61 | 62 | 63 | 64 | 65 |
| Vernier | | | • | • | • | | | | • | | | | | | | | | | | | | |
| VH3-23 | L | E | W | V | S | A | I | S | G | S | G | G | S | T | Y | Y | A | D | S | V | K | G |
| Abel0144 | L | E | W | V | S | *V* | I | *G* | *S* | S | G | G | *T* | T | *V* | Y | A | D | S | V | K | G |
| Abel0144-GL | L | E | W | V | S | *V* | I | *G* | *S* | S | G | G | *T* | T | *V* | Y | A | D | S | V | K | G |

| Kabat Numbering | FW 3 | | | | | | | | | | | | | | | | | | |
|---|---|---|---|---|---|---|---|---|---|---|---|---|---|---|---|---|---|---|---|
| $V_H$ | 66 | 67 | 68 | 69 | 70 | 71 | 72 | 73 | 74 | 75 | 76 | 77 | 78 | 79 | 80 | 81 | 82 | 82a | 82b | 82c | 83 | 84 |
| Vernier | | • | | • | | • | | • | | | | | • | | | | | | | | | |
| VH3-23 | R | F | T | I | S | R | D | N | S | K | N | T | L | Y | L | Q | M | N | S | L | R | A |
| Abel0144 | R | F | T | I | S | R | D | N | S | K | N | T | L | Y | L | Q | M | N | S | L | R | A |
| Abel0144-GL | R | F | T | I | S | R | D | N | S | K | N | T | L | Y | L | Q | M | N | S | L | R | A |

TABLE 1-continued

A sequence alignment of the Abet0144 and Abet0144-GL clones to the VH3-23 (DP47) germline. Residues that are different from germline are italicized. Vernier residues are indicated by circles (•). No changes were made in the V$_H$ domain to germline the Abet0144 clone.

| Kabat Numbering | | | FW 3 | | | | | | | | | | CDR 3 | | | | | | | |
|---|---|---|---|---|---|---|---|---|---|---|---|---|---|---|---|---|---|---|---|---|
| V$_H$ | 85 | 86 | 87 | 88 | 89 | 90 | 91 | 92 | 93 | 94 | 95 | 96 | 97 | 98 | 99 | 100 | 100a | 100b | 100c | 100d | 100e | 100f |
| Vernier VH3-23 | E | D | T | A | V | Y | Y | C | A • | K • | • | • | • | • | • | • | • | • | • | • | • | • |
| Abet0144 | E | D | T | A | V | Y | Y | C | A | *R* | E | W | M | D | H | S | R | P | Y | Y | Y | Y |
| Abet0144-GL | E | D | T | A | V | Y | Y | C | A | *R* | E | W | M | D | H | S | R | P | Y | Y | Y | Y |

| Kabat Numbering | | CDR 3 | | | | | | FW 4 | | | | | | |
|---|---|---|---|---|---|---|---|---|---|---|---|---|---|---|
| V$_H$ | 100g | 100h | 101 | 102 | 103 | 104 | 105 | 106 | 107 | 108 | 109 | 110 | 111 | 112 | 113 |
| Vernier VH3-23 | • | • | • | • | • | • | • | • | • | • | • | • | • | • | • |
| Abet0144 | G | M | D | V | W | G | Q | G | T | L | V | T | V | S | S |
| Abet0144-GL | G | M | D | V | W | G | Q | G | T | L | V | T | V | S | S |

TABLE 2

A sequence alignment of the Abet0144 and Abet0144-GL clones to the Vλ3-3R (DPL-23) germline. Residues that are different from germline are italicized. Vernier residues are indicated by circles (•). Five changes were made in the VL domain to germline the Abet0144 clone. The Vernier 2 residue was reverted to germline at the same time as residues 1 and 3. Reverting this residue did not impact on antibody potency.

| Kabat Numbering | | | | | | | | | | FW 1 | | | | | | | | | | | | |
|---|---|---|---|---|---|---|---|---|---|---|---|---|---|---|---|---|---|---|---|---|---|---|
| V$_H$ | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
| Vernier VH3-23 | S | Y • | E • | L | T | Q | P | P | S | | V | S | V | S | P | G | Q | T | A | S | I | T |
| Abet0144 | Q | *S* | *V* | L | T | Q | P | P | S | | V | S | V | S | P | G | Q | T | A | S | I | T |
| Abet0144-LG | S | Y | E | L | T | Q | P | P | S | | V | S | V | S | P | G | Q | T | A | S | I | T |

| Kabat Numbering | FW 1 | | | | | CDR 1 | | | | | | | | | FW 2 | | | | | |
|---|---|---|---|---|---|---|---|---|---|---|---|---|---|---|---|---|---|---|---|---|
| V$_H$ | 23 | 24 | 25 | 26 | 27 | 28 | 29 | 30 | 31 | 32 | 33 | 34 | 35 | 36 | 37 | 38 | 39 | 40 | 41 | 42 | 43 | 44 |
| Vernier VH3-23 | C | S | G | D | K | L | G | D | K | Y | A | C | W | Y | Q | Q • | Q • | K | P | G | Q | S | P |
| Abet0144 | C | S | G | *H* | *N* | L | *E* | D | K | *F* | A | *S* | W | Y | Q | Q | K | S | G | Q | S | P |
| Abet0144-GL | C | S | G | *H* | *N* | L | *E* | D | K | *F* | A | *S* | W | Y | Q | Q | K | P | G | Q | S | P |

| Kabat Numbering | | FW 2 | | | | CDR 2 | | | | | | | FW 3 | | | | | | |
|---|---|---|---|---|---|---|---|---|---|---|---|---|---|---|---|---|---|---|---|---|---|
| V$_H$ | 45 | 46 | 47 | 48 | 49 | 50 | 51 | 52 | 53 | 54 | 55 | 56 | 57 | 58 | 59 | 60 | 61 | 62 | 63 | 64 | 65 | 66 |
| Vernier VH3-23 | V | L • | V • | I • | Y • | Q | D | S | K | R | P | S | G | I | P | E | R | F | S | G • | S | N • |
| Abet0144 | V | L | V | I | Y | *R* | D | *D* | K | R | P | S | G | I | P | E | R | F | S | *A* | S | N |
| Abet0144-GL | V | L | V | I | Y | *R* | D | *D* | K | R | P | S | G | I | P | E | R | F | S | *A* | S | N |

TABLE 2-continued

A sequence alignment of the Abet0144 and Abet0144-GL clones to the Vλ3-3R (DPL-23) germline. Residues that are different from germline are italicized. Vernier residues are indicated by circles (•). Five changes were made in the VL domain to germline the Abet0144 clone. The Vernier 2 residue was reverted to germline at the same time as residues 1 and 3. Reverting this residue did not impact on antibody potency.

| Kabat Numbering | | | | | | | | | | | | FW 3 | | | | | | | | | | |
|---|---|---|---|---|---|---|---|---|---|---|---|---|---|---|---|---|---|---|---|---|---|---|
| $V_H$ | 67 | 68 | 69 | 70 | 71 | 72 | 73 | 74 | 75 | 76 | 77 | 78 | 79 | 80 | 81 | 82 | 83 | 84 | 85 | 86 | 87 | 88 |
| Vernier | | • | • | | • | | | | | | | | | | | | | | | | | |
| VH3-23 | S | G | N | T | A | T | L | T | I | S | G | T | Q | A | M | D | E | A | D | Y | Y | C |
| Abet0144 | S | G | *H* | T | A | T | L | T | I | S | G | T | Q | A | *T* | D | E | A | D | Y | Y | C |
| Abet0144-GL | S | G | *H* | T | A | T | L | T | I | S | G | T | Q | A | M | D | E | A | D | Y | Y | C |

| Kabat Numbering | | | | CDR 3 | | | | | | | | | | FW 4 | | | | | |
|---|---|---|---|---|---|---|---|---|---|---|---|---|---|---|---|---|---|---|---|
| $V_H$ | 89 | 90 | 91 | 92 | 93 | 94 | 95 | 96 | 97 | 98 | 99 | 100 | 101 | 102 | 103 | 104 | 105 | 106 | 107 |
| Vernier | | | | | | | | | | | | | | | | | | | • |
| VH3-23 | Q | A | W | D | • | • | • | • | • | • | • | • | • | • | • | • | • | • | • |
| Abet0144 | Q | A | *Q* | D | S | T | T | R | V | F | G | G | G | T | K | L | T | V | L |
| Abet0144-GL | Q | A | *Q* | D | S | T | T | R | V | F | G | G | G | T | K | L | T | V | L |

2.8 Determination of the Binding Kinetics of Affinity-Optimised IgGs Using Surface Plasmon Resonance Surface Plasmon Resonance was used to analyse the binding kinetics of the affinity-optimised IgGs (section 2.6) and their germlined counterparts (section 2.7). Briefly, the BIAcore T-100 (GE Healthcare, UK) biosensor instrument was used to assess the kinetic parameters of the interaction between each test IgG and synthetically produced human Amyloid beta 1-42 peptide. These experiments were performed essentially as described by Karlsson et al. (Karisson et al., 1991). For further details see section 1.7.

The affinity of binding between each test IgG and human Amyloid beta 1-42 was estimated using assays in which the antibody was covalently coupled by amine linkage to a proprietary CM3 chip surface to a final surface density of approximately 2,000 RU. The chip surface was regenerated between cycles by a single 40 second injection of 10 mM Glycine pH 2.0 to remove ligand bound to the antibody. The regeneration did not result in a significant loss of peptide binding capacity.

A series of dilutions of synthetic human Amyloid beta 1-42 peptide (1.6-50 nM) were sequentially passed over the antibody surface for a sufficient amount of time to observe sensorgrams that could be fitted to an appropriate binding model with confidence. Blank reference flow-cell data were subtracted from each IgG dataset and a zero-concentration buffer blank was double-reference subtracted from the main dataset to reduce the impact of any buffer artefacts or non-specific binding effects. An appropriate binding model was then fitted simultaneously to the data from each analyte titration using the BIAevaluation software.

The validity of the data was assessed using the calculated Chi2 value, with an acceptable value being under 2 RU2. The overall success of the fit was estimated using the residuals, with a deviation of under 2 RUs being acceptable.

Figure 7:
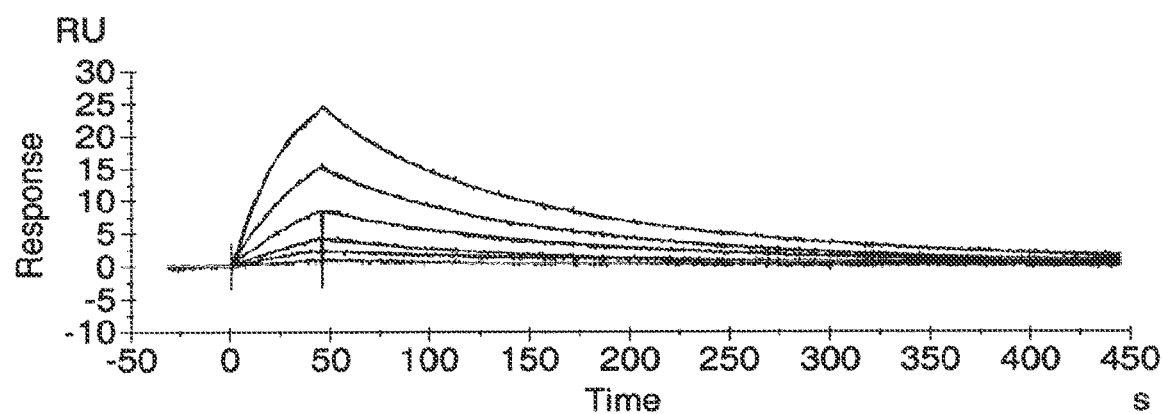
FIG. 7 shows the Surface Plasmon Resonance (BIAcore) traces for human Amyloid beta 1-42 peptide binding to immobilised Abet0144-GL IgG1-TM antibody at concentrations of 50 nM (top trace), 25 nM, 12.5 nM, 6.25 nM, 3.13 nM and 1.56 nM (bottom trace) peptide. Each trace is fitted to a 1:1 Langmuir model.

Example results for Abet0144-GL (germlined) IgG1-TM are shown in FIG. 7. The association rate constant (ka), dissociation rate constant (kd) and dissociation constant (KD) are $2.08 \times 10^5$ $M^{-1}$ $s^{-1}$, $1.97 \times 10^{-3}$ $s^{-1}$ and 9.50 nM respectively. These parameters were derived from a 1:1 Langmuir fit to the data.

2.9 Specificity Profiling of Affinity Optimised IgGs Using Surface Plasmon Resonance Surface Plasmon Resonance was used to verify the specificity of the affinity-optimised IgGs for the human Amyloid beta 1-42 peptide. Briefly, the BIAcore T-100 (GE Healthcare, UK) biosensor instrument was used to assess the kinetic parameters of the interaction between each test IgG and a range of small peptides including synthetically-produced human Amyloid beta 1-42 and human Amyloid beta 1-40. These experiments were performed essentially as described by Karisson et al. (Karisson et al., 1991). For further details see section 1.7.

The affinity of binding between each test IgG and each peptide was estimated using assays in which the antibody was covalently coupled by amine-linkage to a proprietary CM3 chip surface to a final surface density of approximately 2,000 RU. The chip surface was regenerated between cycles by a single 40 second injection of 10 mM Glycine pH 2.0 to remove ligand bound to the antibody. The regeneration did not result in a significant loss of peptide binding capacity.

Each test peptide at 400 nM was sequentially passed over the antibody surface for a sufficient amount of time to observe sensorgrams that either showed no binding or that could be fitted to an appropriate binding model with confidence. Blank reference flow-cell data were subtracted from each IgG dataset and a zero-concentration buffer blank was double-reference subtracted from the main dataset to reduce the impact of any buffer artefacts or non-specific binding effects.

Figure 8:
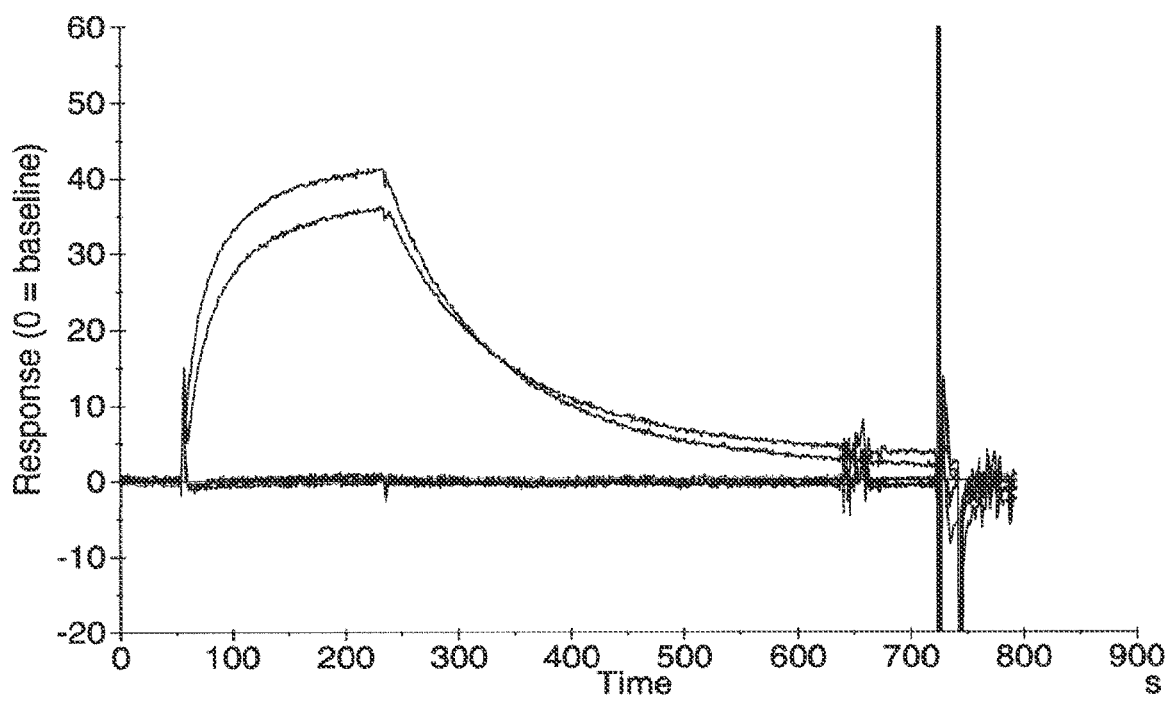
FIG. 8 shows the Surface Plasmon Resonance (BIAcore) traces for a series of Amyloid beta peptides at 400 nM binding to immobilised Abet0144-GL IgG1-TM antibody. There is clear binding to the biotinylated human Amyloid beta 1-42 peptide (top trace) and the unlabelled human Amyloid beta 1-42 peptide (second trace). There is no discernable binding to scrambled biotinylated human Amyloid beta 1-42 peptide, biotinylated human Amyloid beta 1-40 peptide, unlabelled human Amyloid beta 1-40 peptide or biotinylated-insulin (flat lines).

Example results for Abet0144-GL (germlined) IgG1-TM are shown in FIG. 8. Two peptides (biotinylated human Amyloid beta 1-42, (rPeptide, USA; cat: A1117) and unlabelled human Amyloid beta 1-42 (rPeptide, USA; cat: A1165)) showed strong binding to the antibody, whilst three peptides (biotinylated scrambled human Amyloid beta 1-42 (Anaspec, USA; custom synthesis), biotinylated human Amyloid beta 1-40 (rPeptide, USA; cat: A1111) and unlabelled human Amyloid beta 1-40 (Anaspec, USA; cat: 24236)) showed no binding to the antibody.

2.10 Specificity Profiling of Abet0144-GL IgG1-TM in Biochemical Epitope Competition Assay Format To test the specificity of Abet0144-GL IgG1-TM for binding to other human Amyloid beta peptides, a competition assay was developed. In this assay a fixed concentration (1.5 nM) of biotinylated human Amyloid beta 1-42 peptide (rPeptide, USA; cat: A1117) was incubated with a range of different concentrations of unlabelled human Amyloid beta peptides including 1-42, 1-40, 1-16, 12-28, pyro 3-42, pyro 11-42 and scrambled 1-42 (Anaspec cat: 20276, 24236, 24226, 24230, 29907, 29903 and 25383, respectively) in the presence of a fixed concentration (0.28 nM) of Abet0144-GL IgG1-TM. Peptide competition was assessed by detecting the inhibition of binding of Abet0144-GL IgG1-TM to the biotinylated human Amyloid beta 1-42 peptide using time resolved fluorescence resonance energy transfer (TR-FRET). This involved the use of Europium cryptate labelled anti-human Fc IgG (CisBio International, France; cat: 61HFCKLB) and XL665 labelled streptavidin (CisBio International, France; cat: 611SAXLB) TR-FRET detection reagents.

Experiments were set up in Costar 384 well shallow bottom microtitre plates. 5 ul/well of biotinylated human Amyloid beta 1-42 (6 nM) was added to all wells of the assay plate (except for negative binding assay control wells) in order to give a final assay concentration of 1.5 nM. 5 ul of assay buffer only was added to the negative binding assay control wells. A duplicate 11 point 1:3 serial titration was prepared or each test peptide starting at a top concentration of 40 uM in order to give a top final assay peptide concentration of 10 uM. 5 ul per well of each test peptide serial dilution was then transferred onto the 384 well assay plate. 5 ul of assay buffer only was added to the total and negative binding assay control wells. Abet0144-GL IgG1-TM was diluted to give a working solution at 1.12 nM. 5 ul per well of this solution was added to all wells of the 384 well assay plate in order to result in a final assay Abet0144-GL-IgG1-TM concentration of 0.28 nM. Finally, a combined solution was prepared containing Europium cryptate labelled anti-human Fc (2.4 nM) and XL665 labelled streptavidin (60 nM). 5 ul per well of this solution was added to all wells of the 384 well assay plate such that the final concentrations of Europium cryptate labelled anti-human Fc and XL665 labelled streptavidin were 0.6 nM and 15 nM, respectively. Note that the final assay volume was 20 ul and that each individual assay component was added as a 5 ul addition at four times the required final assay concentration. All reagents were diluted in an assay buffer containing 50 mM MOPS pH 7.4 (Sigma, UK; cat: M9381), 0.4 M KF (BDH Chemicals, USA; cat: 103444T), 0.1% fatty acid free bovine serum albumin (Sigma, UK; cat: A6003) and 0.1% Tween 20 (v/v) (Sigma, UK; cat: P2287).

Assay plates were incubated for 2 hours at room temperature prior to reading time resolved fluorescence at 620 nm and 665 nm emission wavelengths using an EnVision plate reader (PerkinElmer, USA). Data was analysed by calculating % Delta F values for each sample. % Delta F was determined according to equation 1.

$$\% \text{ Delta } F = \frac{(\text{sample 665 nm}/620 \text{ nm ratio}) - (\text{negative control 665 nm}/620 \text{ nm ratio})}{(\text{negative control 665 nm}/620 \text{ nm ratio})} \times 100 \quad \text{Equation 1}$$

% Delta F values were used to calculate % specific binding as described in equation 2.

$$\% \text{ specific binding} = \frac{\% \text{ Delta } F \text{ of sample}}{\% \text{ Delta } F \text{ of total binding control}} \times 100 \quad \text{Equation 2}$$

Figure 9:
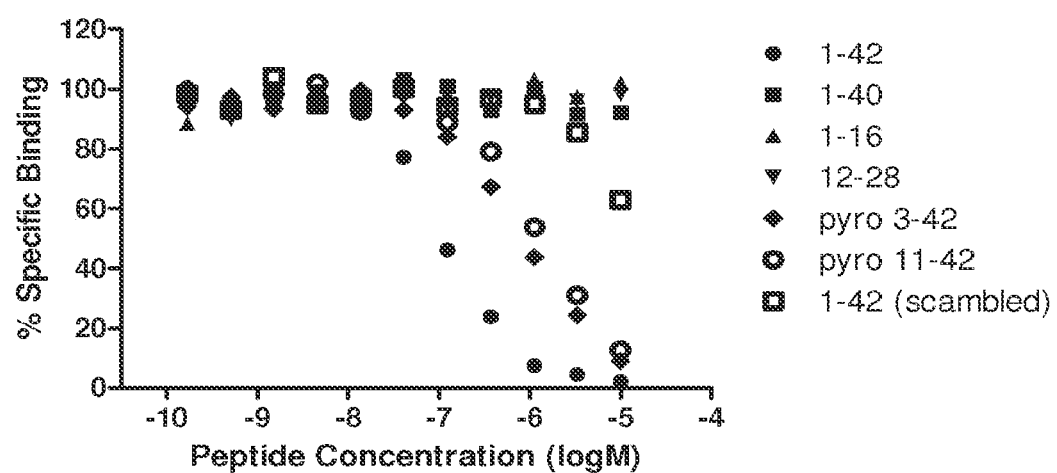
FIG. 9 shows specificity profiling of Abet0144-GL IgG1-TM using a biochemical epitope competition assay in which inhibition of the formation of a complex between biotinylated human Amyloid beta 1-42 peptide and Abet0144-GL IgG1-TM by increasing concentrations of competitor peptides is measured. Complex formation is inhibited by human Amyloid beta 1-42 (●), pyro 3-42 (♦) and pyro 11-42 (○) peptides. No significant inhibition is observed with human Amyloid beta 1-40 peptide (■), 1-16 (▲) and 12-28 (▼) peptide truncates or with the negative control peptide (□).

Example results for Abet0144-GL IgG1-TM are shown in FIG. 9. These results demonstrate that Abet0144-GL IgG1-TM binds to human Amyloid beta 1-42, pyro 3-42 and pyro 11-42 peptides but does not bind to human Amyloid beta 1-40 peptide or to the peptide truncates 1-16 and 12-28.

2.11 Functional Characterisation of Lead Antibodies by Depletion of Amyloid Beta Peptides from Human Plasma The lead antibodies were tested in a plasma depletion assay to investigate their ability to immunoprecipitate human Amyloid beta 1-42 peptide from human blood plasma. This assay was used to provide evidence of functional efficacy for each antibody. The assays were performed exactly as described in Section 1.8.

In one experiment, the Abet0144-GL IgG1-TM antibody reduced the levels of human Amyloid beta 1-42 peptide in plasma from 13.54 pg ml-1 to 9.86 pg ml-1 (a 27% reduction). In a second experiment, the levels were reduced from 40.06 pg ml-1 to 34.65 pg ml-1 (a 14% reduction).

2.12 Identification of Improved Clones with Native Binding for Amyloid Beta Using In Vitro Immunohistochemistry The affinity-optimised IgGs were tested for their ability to bind to Amyloid beta, with the aim of identifying lead clones which recognise native Amyloid beta peptide. Briefly, the lead antibodies were screened on human Alzheimer's Disease brain sections and Tg2576 mouse brain sections to identify anti-Amyloid beta 1-42 antibodies that bound to native Amyloid in vitro. The experiments were performed essentially as described in section 1.9.

In these experiments, human brain tissue was isolated from the frontal cortex and hippocampus of two individuals with severe Alzheimer's Disease (female, ApoE 4/3, 86 years; female, ApoE 3/3, 67 years). Mouse brain tissue was isolated from Tg2576 mice at an age of 18 months (6 mice). Antibodies were tested at concentrations of 2, 5 and 20 ug ml$^{-1}$.

Figure 10:
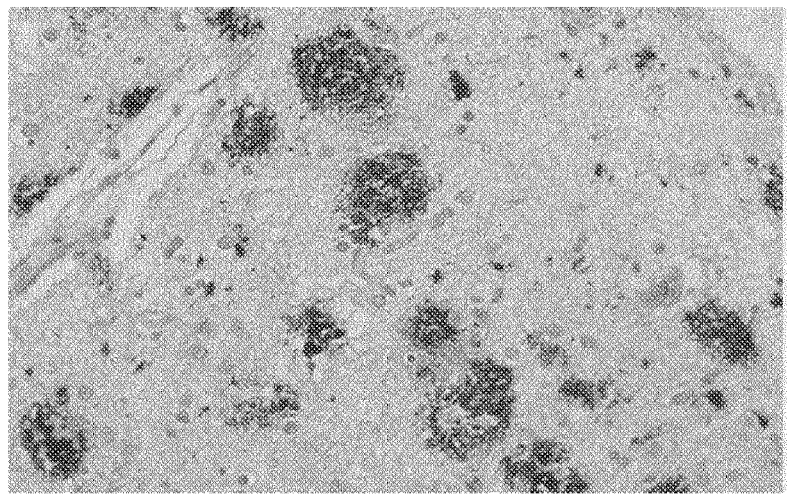
FIG. 10 shows sample images from the in vitro immunohistochemical staining of Abet0144-GL IgG1-TM. (A) A positive control antibody shows strong plaque recognition (score=4) on human AD brain sections (ApoE genotype 3/3; 20 μg/ml antibody). (B) The Abet0144-GL IgG1-TM lead clone shows some plaque recognition (score=1.5) on an adjacent brain section (20 μg/ml). (C) The same positive control antibody shows strong plaque recognition (score=4) on Tg2576 mouse brain sections (18 month old mice; 20 μg/ml antibody). (D) The Abet0144-GL IgG1-TM lead clone shows some plaque recognition (score=1) on an adjacent mouse brain section (20 μg/ml).
Figure 10:
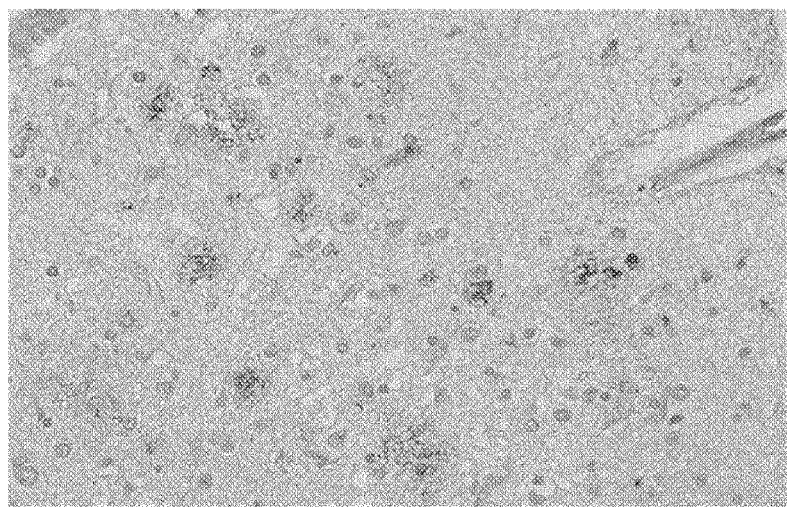
Figure 10:
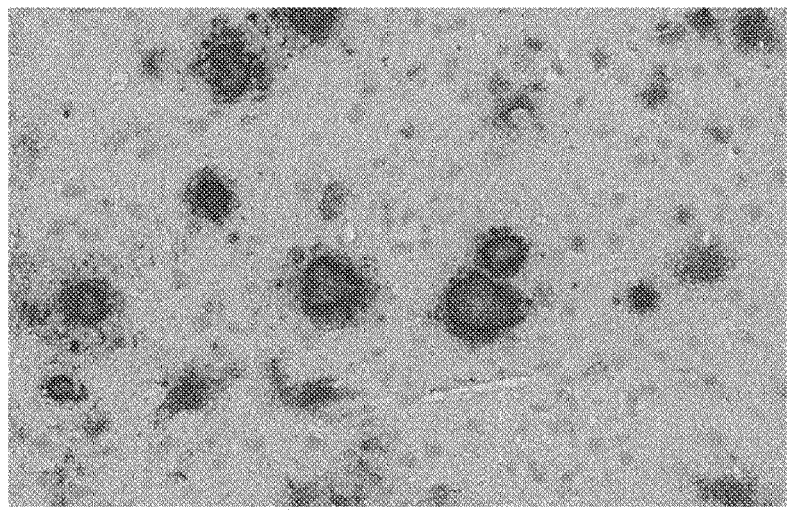
Figure 10:
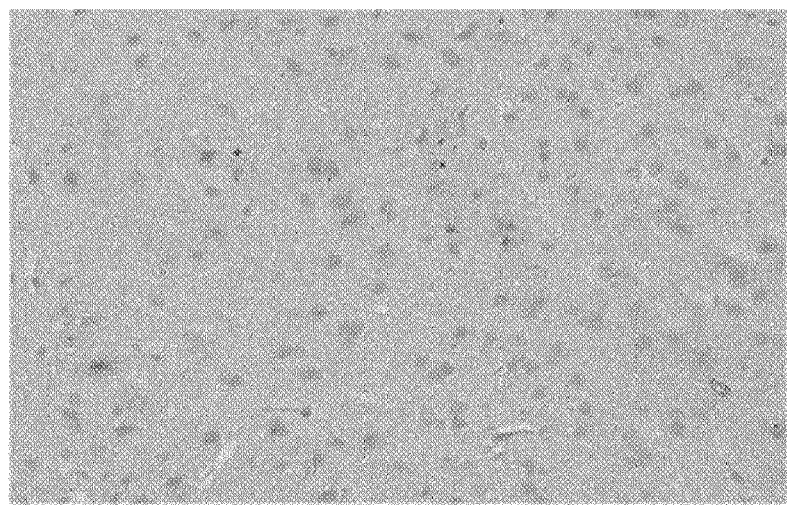

In one experiment, the Abet0144-GL IgG1-TM antibody did not stain diffuse plaques (DP) or cerebral amyloid angiopathy (CAA) plaques (score=0). It did, however, stain core plaques (CP) with a score of 1 on Tg2576 brain sections, and a score of 1.5 on human AD brain sections. In contrast, a positive control antibody produced a score of 3-4 on all plaques (CP, DP, CAA) on adjacent sections under the same conditions. Representative images are shown in FIG. 10.

Example 3. Antibody Optimisation of Abet0144-GL Through Mutation of all Six CDRs Including Flanking Vernier Residues 3.1 Conversion of Abet0144-GL Parent Clone to scFv Format Compatible with Ribosome Display The parent clone was converted from IgG1-TM format to single chain variable fragment (scFv) format in preparation for affinity optimisation. The codon-optimised variable heavy ($V_H$) and variable light ($V_L$) domains were amplified separately from their respective IgG vectors with the addition of specific cloning sites and a flexible linker region. Recombinatorial PCR was then performed to generate a complete scFv construct, which was cloned into a modified pUC vector (pUC-RD) containing the structural features necessary for ribosome display. These features include a 5' and 3' stem loop to prevent degradation of the mRNA transcript by exonucleases, a Shine-Dalgarno sequence to promote ribosome binding to the mRNA transcript, and a geneIII spacer that allows the translated scFv molecule to fold while still remaining attached to the ribosome (Groves et al., 2005).

3.2 Optimisation of Abet0144-GL by Targeted Mutagenesis

The lead antibody (Abet0144-GL) was further optimised for improved affinity to human Amyloid beta 1-42 peptide using a targeted mutagenesis approach with affinity-based ribosome display selections. Large scFv-ribosome libraries derived from Abet0144-GL were created by oligonucleotide-directed mutagenesis of all six variable heavy ($V_H$) and variable light ($V_L$) chain complementarity determining regions (CDRs) using standard molecular biology techniques as described by Clackson and Lowman (Clackson et al., 2004). The mutated sequences from each CDR were affinity optimised as a separate library. The five Vernier residues preceding the $V_H$CDR1 (Kabat residues 26-30) were also randomised using targeted mutagenesis and these sequences were combined and matured with the remaining $V_H$CDR1 library. All libraries were subjected to affinity-based ribosome display selections in order to enrich for variants with higher affinity for human Amyloid beta 1-42 peptide. The selections were performed essentially as described previously (Hanes et al., 2000).

In brief, the six targeted mutagenesis libraries of the Abet0144-GL lead clone, one covering each CDR, were separately transcribed into mRNA. Using a process of stalled translation, mRNA-ribosome-scFv tertiary complexes were formed (Hanes et al., 1997). These complexes were then subjected to four rounds of selection incubated in the presence of decreasing concentrations of synthetic biotinylated human Amyloid beta 1-42 peptide (Bachem, Germany; cat: H-5642) (100 nM to 10 nM) to select for variants with higher affinity for human Amyloid beta 1-42 peptide. Those complexes that bound to the antigen were then captured on streptavidin-coated paramagnetic beads (Dynabeads™, Invitrogen, UK; cat: 112-05D) and non-specific ribosome complexes were washed away. mRNA was subsequently isolated from the bound ribosomal complexes, reverse transcribed to cDNA and then amplified by PCR. This DNA was used for the next round of selection.

After four rounds of affinity maturation, each selection output was cloned out for screening purposes. ScFv isolated by ribosome display were cloned into the phagemid vector pCANTAB6 by NotI/NcoI restriction endonuclease digestion of the ribosome display construct (New England BioLabs, USA; cat: R0189L, R0193L) followed by ligation into NotI/NcoI digested pCANTAB6 using T4 DNA ligase (New England BioLabs, USA; cat: M0202L) essentially as described by McCafferty et al. (McCafferty et al., 1994).

3.3 Identification of Improved Clones Using an Epitope Competition Assay

Two thousand and twenty four scFv chosen at random from selection rounds 3 and 4 of the targeted mutagenesis approach described in section 3.2 were expressed in bacteria to produce unpurified periplasmic scFv. Those scFv capable of binding synthetic human amyloid beta 1-42 peptide via the same epitope as Abet0144-GL IgG1-TM were elucidated in a competition format assay, using the HTRF™ platform. Specifically, fluorescence resonance energy transfer (FRET) was measured between streptavidin cryptate (associated with biotinylated amyloid beta 1-42 peptide) and anti-human Fc XL665 (associated with Abet0144-GL IgG1-TM) in the presence of a single concentration of each unpurified periplasmic test scFv. Successful occupation of the Abet0144-GL IgG1-TM epitope on the peptide by scFv resulted in a reduction in FRET, as measured on a fluorescence plate reader.

A 'Total' binding signal was determined by analysing the binding of Abet0144-GL IgG1-TM to synthetic human Amyloid beta 1-42 peptide in the absence of competitor peptide. The 'Sample' signals were derived from analysing the binding of Abet0144-GL IgG1-TM to synthetic human Amyloid beta 1-42 peptide in the presence of a test scFv sample. Finally, a 'Cryptate Blank' signal was determined by analysing the fluorescence mediated by the detection reagent cocktail alone.

Unpurified periplasmic scFv were supplied in sample buffer consisting of 50 mM MOPS, pH 7.4, 0.5 mM EDTA, and 0.5 M sucrose. For profiling, scFv samples were diluted in a 384-well V-bottom plate to 50% of the original stock concentration in assay buffer, consisting of 50 mM MOPS, pH 7.4, 0.4 M potassium fluoride, 0.1% fatty-acid-free bovine serum albumin and 0.1% Tween 20 (v/v). 5 µl of each newly-diluted scFv was transferred to the 'Sample' wells of a black, shallow, solid bottom, non-binding 384-well assay plate using a liquid handling robot. The remaining reagents (prepared in assay buffer) were added to the assay plate by multichannel pipette in the following order 5 µl sample buffer (to 'Total' and 'Cryptate Blank' wells), 10 µl assay buffer (to 'Cryptate Blank' wells), 5 µl 2 nM Abet0144-GL IgG1-TM (to 'Sample' and 'Total' wells), 5 µl 5 nM biotinylated human Amyloid beta 1-42 peptide (to 'Sample' and 'Total' wells), and 5 µl detection cocktail, consisting of 6 nM streptavidin cryptate and 60 nM anti-His6-XL665 (to all wells). Assay plates were sealed and then incubated for 3 hours at room temperature in the dark, prior to measuring time-resolved fluorescence at 620 and 665 nm emission wavelengths on a fluorescence plate reader.

Data were analysed by calculating % Delta F values for each sample. % Delta F was determined according to equation 4.

$$\% \text{ Delta } F = \frac{(\text{Sample } 665 \text{ nm}/620 \text{ nm ratio}) - (\textit{Cryptate} \text{ Blank } 665 \text{ nm}/620 \text{ nm ratio})}{(\textit{Cryptate} \text{ Blank } 665 \text{ nm}/620 \text{ nm ratio})} \times 100 \quad \text{Equation 4}$$

Delta F values were subsequently used to calculate normalised binding values as described in equation 5.

$$\text{Normalised data (\% Total)} = \frac{\% \text{ Delta } F \text{ of sample}}{\% \text{ Delta } F \text{ of Total binding control}} \times 100 \quad \text{Equation 5}$$

Unpurified periplasmic scFv demonstrating significant inhibition of Abet0144-GL IgG1-TM binding to Amyloid beta 1-42 peptide were subjected to DNA sequencing (Osbourn et al., 1996; Vaughan et al., 1996). The scFv found to have unique protein sequences were expressed in *E. coli* and purified by affinity chromatography followed by buffer exchange.

The potency of each purified scFv was determined by testing a dilution series of the scFv (typically 4 pM-1200 nM) in the epitope competition assay described above. Data were again analysed by calculating the % Delta F and %

Total binding values for each sample. In addition, a % Inhibition value for each concentration of purified scFv was also calculated as described in Equation 6:

% Inhibition=100−% Total Binding        Equation 6:

ScFv sample concentration was plotted against % Inhibition using scientific graphing software, and any concentration-dependent responses were fitted with non-linear regression curves. $IC_{50}$ values were obtained from these analyses with Hill-slopes constrained to a value of −1. The most potent clone from this round of selections, Abet0286, had an $IC_{50}$ of 1.8 nM and came from the $V_L$CDR1 targeted mutagenesis library.

Reagent/Equipment sources: MOPS (Sigma, UK; cat: M9381), potassium fluoride (BDH chemicals, USA; cat: A6003), fatty-acid-free bovine serum albumin (Sigma, UK; cat: A6003), Tween 20 (Sigma, UK; cat: P2287), Abet0144-GL IgG1-TM (produced in-house), biotinylated human Amyloid beta 1-42 peptide (rpeptide, USA; cat: A1117), Streptavidin cryptate (Cisbio, France; cat: 610SAKLB), anti-His6-XL665 (Cisbio, France; cat: 61HISXLB), 384-well assay plates (Corning, Costar Life Sciences; cat: 3676), 384-well dilution plates (Greiner BioOne, Germany; cat: 781280), liquid handling robot (MiniTrak™, Perkin Elmer, USA), fluorescence plate reader (Envision™, Perkin Elmer, USA), HTRF technology (Cisbio International, France), graphing/statistical software (Prism, Graphpad USA).

3.4 Recombination of Successful Selection Outputs to Produce "Binary" Libraries, and their Subsequent Affinity Optimisation The epitope competition assay described in Section 3.3 was used to judge whether a particular scFv-ribosome library had been affinity matured over the first four rounds of selection. Two of the libraries, the $V_H$CDR3 and the $V_L$CDR2 targeted mutagenesis libraries, had shown no improvement over the parent Abet0144-GL clone and were not progressed further.

The remaining four targeted mutagenesis libraries, (covering the $V_H$CDR1, $V_H$CDR2, $V_L$CDR1 and $V_L$CDR3), had shown affinity improvements and were recombined in a pair-wise fashion to produce six "binary" recombination libraries in which two of the six CDRs were mutated. For example, the affinity matured library covering the $V_H$CDR1 was randomly recombined with the affinity matured $V_H$CDR2 library to generate a $V_H1:V_H2$ library. The remaining libraries were produced as: $V_H1:V_L1$, $V_H1:V_L3$, $V_H2:V_L1$, $V_H2:V_L3$ and $V_L1:V_L3$. A subset of each recombination library was cloned out as previously described (Section 3.2) and was sent for sequencing to verify the integrity of each library.

Selections were then continued as previously described (section 3.2) in the presence of decreasing concentrations of biotinylated synthetic human Amyloid beta 1-42 peptide (5 nM and 2 nM for rounds 5 and 6 respectively). As before, each selection output was cloned out for screening purposes (section 3.2).

One thousand nine hundred and thirty-six scFv, randomly selected from selection rounds 5 and 6, were screened in an epitope competition assay as described in section 3.3. Due to the increase in potency of these clones, the unpurified scFv were first diluted to 25% before addition to the assay plates. As previously, clones that showed significant inhibitory properties were sent for DNA sequencing, and unique clones were produced and analysed as purified scFv (section 3.3). The most potent clone from these selections, Abet0303, had a potency of 0.84 nM and came from the $V_H1:V_H2$ recombination library.

3.5 Recombination of Binary Selection Outputs to Produce "Ternary" Libraries, and their Subsequent Affinity Optimisation The epitope competition assay described in Section 3.3 was used to judge whether each binary library had been affinity matured over the previous two rounds of selection (5 and 6). All libraries had shown affinity improvements, and were therefore considered for further affinity maturation.

The six binary libraries (section 3.4) were recombined with the successful round 4 outputs (section 3.2) in a pair-wise fashion to form four "ternary" recombination libraries in which three of the six CDRs were mutated. For example, the $V_H2:V_L3$ binary library (round 6 output) was recombined with the $V_H$CDR1 targeted mutagenesis library (round 4 output) to generate a $V_H1:V_H2:V_L3$ library. Similar constructs were also created by combining the $V_H1:V_H2$ binary library (round 6 output) with the $V_L$CDR3 targeted mutagenesis library (round 4 output). These two individual libraries were pooled to create the $V_H1:V_H2:V_L3$ ternary library.

Care was taken not to destroy the synergy between CDRs that had been co-optimised. For example, the $V_H1:V_L3$ binary library was not recombined with the $V_H$CDR2 targeted mutagenesis library since this manipulation would have destroyed the synergy between the co-optimised $V_H$CDR1 and $V_L$CDR3 sequences. A complete list of all ternary libraries and their derivations is given in Table 3. A subset of each recombination library was cloned out as previously described (Section 3.2) and was sent for sequencing to verify the integrity of each library.

TABLE 3

A description of the four ternary libraries that were matured during rounds 7 and 8 of the second Lead Optimisation campaign. Each library comprised two constituent libraries, generated from a random pairwise recombination of a round 6 output binary library and a round 4 output targeted mutagenesis library.

| Ternary Library | Constituent Libraries | Formed From | |
|---|---|---|---|
| | | Round 6 output | Round 4 output |
| $V_H1:V_H2:V_L1$ | $V_H1:V_H2:V_L1$ a | $V_H1:V_H2$ | $V_L$CDR1 |
| | $V_H1:V_H2:V_L1$ b | $V_H2:V_L1$ | $V_H$CDR1 |
| $V_H1:V_H2:V_L3$ | $V_H1:V_H2:V_L3$ a | $V_H1:V_H2$ | $V_L$CDR3 |
| | $V_H1:V_H2:V_L3$ b | $V_H2:V_L3$ | $V_H$CDR1 |
| $V_H1:V_L1:V_L3$ | $V_H1:V_L1:V_L3$ a | $V_H1:V_L1$ | $V_L$CDR3 |
| | $V_H1:V_L1:V_L3$ b | $V_L1:V_L3$ | $V_H$CDR1 |
| $V_H2:V_L1:V_L3$ | $V_H2:V_L1:V_L3$ a | $V_H2:V_L1$ | $V_L$CDR3 |
| | $V_H2:V_L1:V_L3$ b | $V_L1:V_L3$ | $V_H$CDR2 |

Selections were then continued as previously described (section 3.2) in the presence of decreasing concentrations of biotinylated synthetic human Amyloid beta 1-42 peptide (500 pM and 200 pM for rounds 7 and 8 respectively). As before, each selection output was cloned out for screening purposes (section 3.2).

One thousand four hundred and eight scFv, randomly selected from selection rounds 7 and 8, were screened in an epitope competition assay as described in section 3.3. As with the "binary" screen, the unpurified scFv were first diluted to 25% before addition to the assay plates. As previously, clones that showed significant inhibitory properties were sent for DNA sequencing, and unique clones were produced and analysed as purified scFv (section 3.3). The most potent clone from these selections, Abet0343, had a potency of 0.48 nM and came from the $V_H1:V_H2:V_L3$ recombination library.

3.6 Recombination of Ternary Selection Outputs to Produce "Quaternary" Libraries, and their Subsequent Affinity Optimisation The epitope competition assay described in Section 3.3 was used to judge whether each ternary library had been affinity matured over the previous two rounds of selection (7 and 8). All libraries had shown affinity improvements, and were therefore considered for further affinity maturation.

The $V_H1:V_H2:V_L1$ ternary library (round 8 output) was recombined with the $V_L$CDR3 targeted mutagenesis library (round 4 output) and the $V_H2:V_L1:V_L3$ ternary library (round 8 output) was recombined with the $V_H$CDR1 targeted mutagenesis library (round 4 output). Separately, the $V_H1:V_H2$ binary library (round 6 output) was recombined with the $V_L1:V_L3$ binary library (round 6 output). These three individual libraries were then pooled to create a single "quaternary" library, $V_H1:V_H2:V_L1:V_L3$, in which four of the six CDRs were mutated.

Care was taken not to destroy the synergy between CDRs that had been co-optimised. For example, the $V_H1:V_L2:V_L3$ ternary library was not recombined with the $V_L$CDR1 targeted mutagenesis library since this manipulation would have destroyed the synergy between the co-optimised $V_H$CDR1N$_H$CDR2 and $V_L$CDR3 sequences. A subset of each recombination library was cloned out as previously described (Section 3.2) and was sent for sequencing to verify the integrity of each library.

Selections were then continued as previously described (section 3.2) in the presence of decreasing concentrations of biotinylated synthetic human Amyloid beta 1-42 peptide (50 pM to 10 pM for rounds 9 to 11). As before, each selection output was cloned out for screening purposes (section 3.2).

Figure 11:
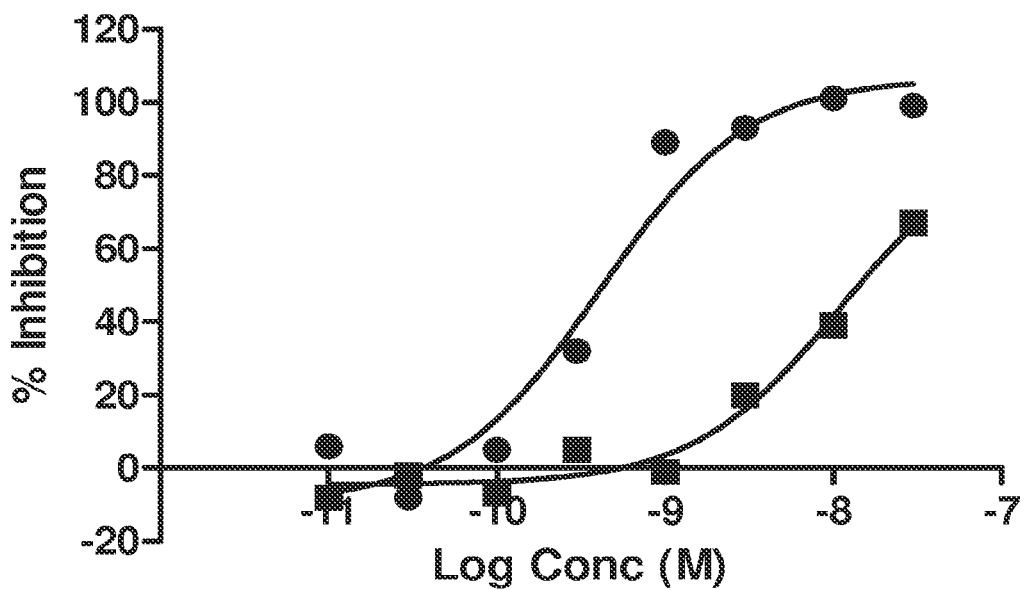
FIG. 11 shows the inhibition of the formation of the human Amyloid beta 1-42 peptide and Abet0144-GL IgG1-TM complex by increasing concentrations of purified competitor scFv (●). Four of the most potent scFv clones, Abet0369 (FIG. 11A), Abet0377 (FIG. 11B), Abet0380 (FIG. 11C) and Abet0382 (FIG. 11D) all show significant improvement in potency over the parent Abet0144-GL scFv sequence (■).
Figure 11:
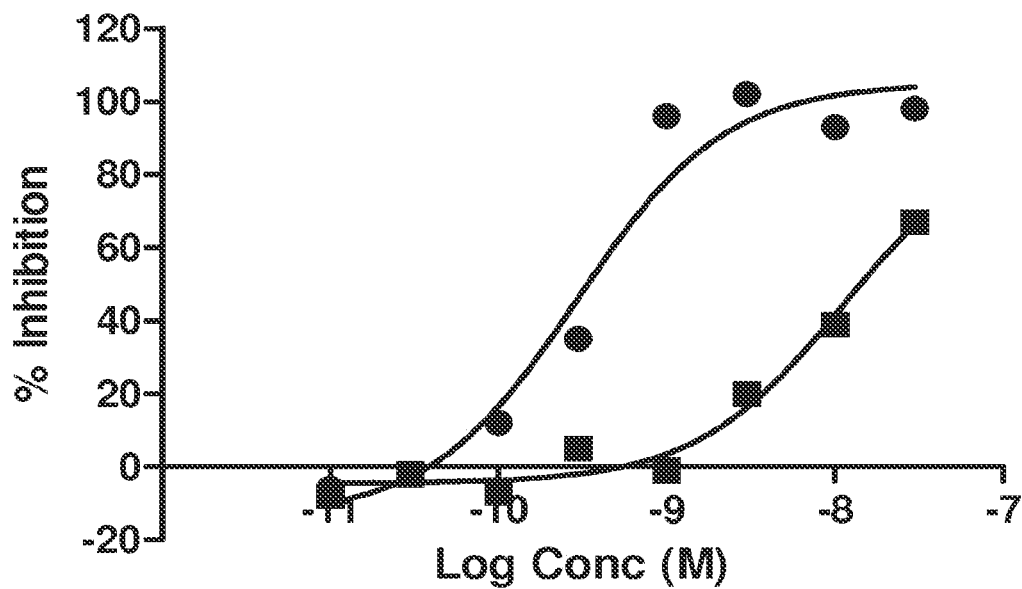
Figure 11:
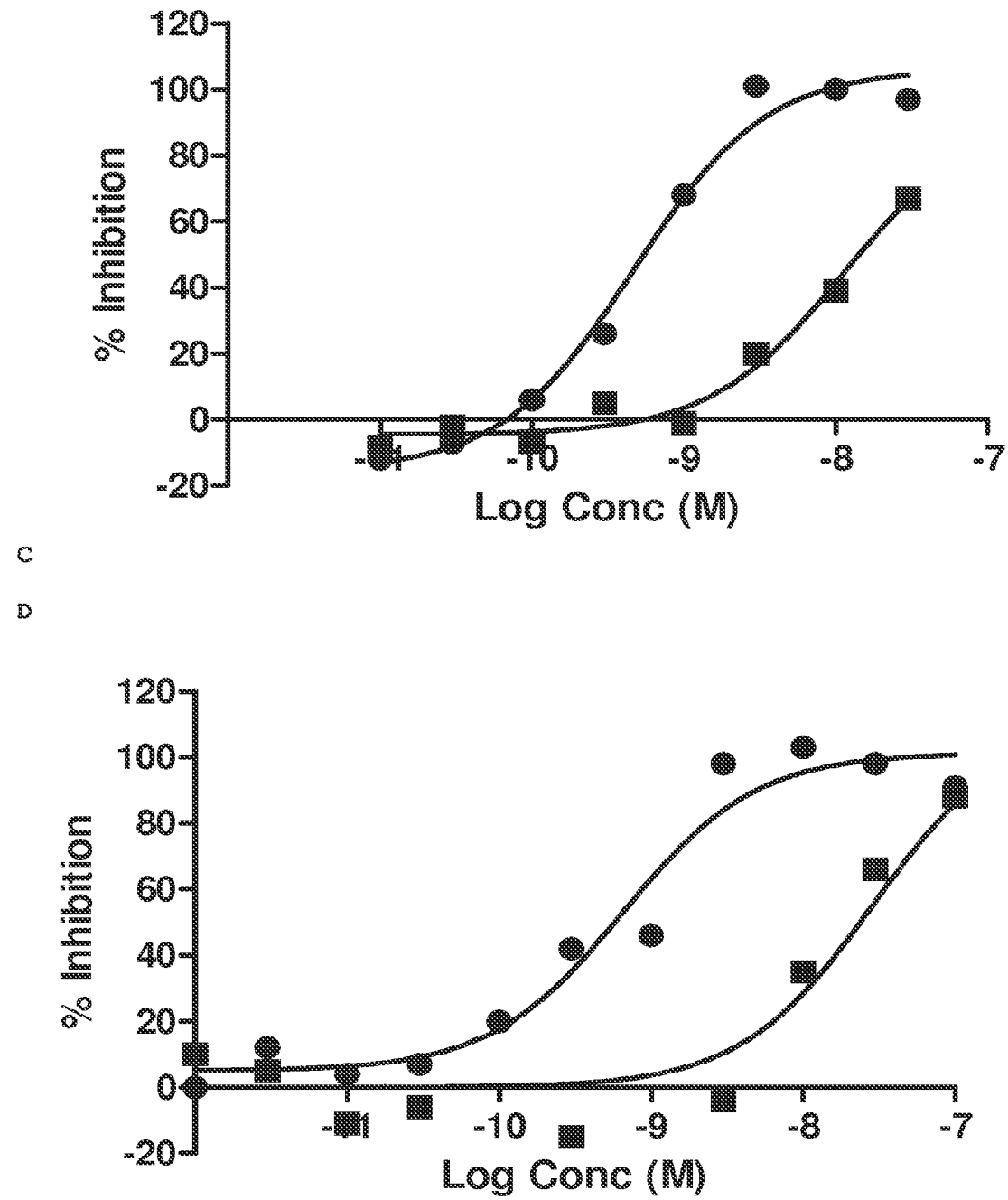

One thousand six hundred and seventy two scFv, randomly selected from selection rounds 9 to 11, were screened in an epitope competition assay as described in section 3.3. Due to the increase in potency of these clones, the unpurified scFv were first diluted to 3.13% before addition to the assay plates. As previously, clones that showed significant inhibitory properties were sent for DNA sequencing, and unique clones were produced and analysed as purified scFv (section 3.3). The most potent clone from these selections, Abet0377, had a potency of 0.32 nM (n=2 data). Sample inhibition curves are shown in FIG. 11, and data for 24 of the highest potency clones are shown in Table 4. The corresponding protein sequences are listed in Tables 5 and 6.

TABLE 4

Example potency data for optimised scFv clones when evaluated in the Abet0144-GL HTRF™ epitope competition assay. Where the assay was performed more than once, the absolute range of $IC_{50}$ values is provided.

| Clone | Selection round | $IC_{50}$ (nM) | Range | Number of repeats |
|---|---|---|---|---|
| Abet0144-GL | — | 14 | 8.1-18 | 7 |
| Abet0319 | 7 | 0.68 | 0.52-0.76 | 3 |
| Abet0321b | 7 | 0.73 | 0.69-0.76 | 2 |
| Abet0322b | 7 | 0.71 | 0.43-0.98 | 2 |
| Abet0323b | 8 | 0.67 | 0.57-0.76 | 2 |
| Abet0328 | 8 | 0.55 | | 1 |
| Abet0329 | 8 | 0.63 | | 1 |
| Abet0332 | 8 | 0.91 | | 1 |
| Abet0342 | 8 | 0.59 | | 1 |
| Abet0343 | 8 | 0.48 | | 1 |
| Abet0344 | 7 | 0.77 | | 1 |
| Abet0368 | 11 | 0.55 | | 1 |
| Abet0369 | 10 | 0.36 | 0.30-0.41 | 3 |
| Abet0370 | 10 | 0.76 | | 1 |
| Abet0371 | 11 | 0.50 | 0.46-0.53 | 2 |
| Abet0372 | 10 | 0.38 | 0.26-0.49 | 2 |
| Abet0373 | 10 | 0.84 | | 1 |
| Abet0374 | 10 | 0.42 | 0.41-0.43 | 2 |
| Abet0377 | 10 | 0.32 | 0.29-0.35 | 2 |
| Abet0378 | 9 | 0.97 | | 1 |
| Abet0379 | 9 | 0.69 | | 1 |
| Abet0380 | 10 | 0.43 | 0.38-0.47 | 2 |
| Abet0381 | 10 | 0.47 | | 1 |
| Abet0382 | 10 | 0.66 | | 1 |
| Abet0383 | 11 | 0.75 | | 1 |

Table 5 (see below): Sequence alignment of the $V_H$ domains of the optimised non-germlined clones described herein. Changes from the parent sequence (Abet0144-GL) are italicized. Residues are designated according to the Kabat numbering system.

Table 6 (see below): Sequence alignment of the VL domains of the optimised non-germlined clones described herein. Changes from the parent sequence (Abet0144-GL) are italicized. Residues are designated according to the Kabat numbering system. Note that Abet0378 has an amber stop codon "B" present in the VL sequence at position 91, which was introduced as a change from glutamine during optimisation. The antibody was produced as an scFv fragment in the *E. coli* strain TG1 used for expression in which the amber stop codon is read as glutamine.

TABLE 5

| Kabat Numbering $V_H$ | | | | | | | | | | | | FW 1 | | | | | | | | | | | | |
|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
| Abet0144-GL | E | V | Q | L | L | E | S | G | G | G | L | V | Q | P | G | G | S | L | R | L | S | C | A | A |
| Abet0319 | | | | | | | | | | | | | | | | | | | | | | | | |
| Abet0321b | | | | | | | | | | | | | | | | | | | | | | | | |
| Abet0322b | | | | | | | | | | | | | | | | | | | | | | | | |
| Abet0323b | | | | | | | | | | | | | | | | | | | | | | | | |
| Abet0328 | | | | | | | | | | | | | | | | | | | | | | | | |
| Abet0329 | | | | | | | | | | | | | | | | | | | | | | | | |

TABLE 5-continued

|  |  |
|---|---|
| Abet0332 | *E* |
| Abet0342 |  |
| Abet0343 |  |
| Abet0344 | *S* |
| Abet0368 |  |
| Abet0369 |  |
| Abet0370 |  |
| Abet0371 | *S* |
| Abet0372 |  |
| Abet0373 | V |
| Abet0374 |  |
| Abet0377 |  |
| Abet0378 |  |
| Abet0379 |  |
| Abet0380 |  |
| Abet0381 |  |
| Abet0382 |  |
| Abet0383 | *K* |

| Kabat | FW 1 | | | | | | CDR 1 | | | | | FW 2 | | | | | | | | | | | | |
|---|---|---|---|---|---|---|---|---|---|---|---|---|---|---|---|---|---|---|---|---|---|---|---|---|
| Numbering V$_H$ | 25 | 26 | 27 | 28 | 29 | 30 | 31 | 32 | 33 | 34 | 35 | 36 | 37 | 38 | 39 | 40 | 41 | 42 | 43 | 44 | 45 | 46 | 47 | 48 |
| Abet0144-GL | S | G | F | T | F | S | V | Y | T | M | W | W | V | R | Q | A | P | G | K | G | L | E | W | V |
| Abet0319 |  | *V* | *S* | *Y* | *Y* | *N* | *K* | *D* |  |  |  |  |  |  |  |  |  |  |  |  |  |  |  |  |
| Abet0321b |  | *A* | *Y* | *H* | *S* | *N* | *H* | *D* | *P* |  |  |  |  |  |  |  |  |  |  |  |  |  |  |  |
| Abet0322b |  | *N* | *E* | *E* |  | *Q* | *Y* | *N* | *P* |  |  |  |  |  |  |  |  |  |  |  |  |  |  |  |
| Abet0323b |  | *T* | *S* |  |  | *Q* | *E* | *D* |  |  |  |  |  |  |  |  |  |  |  |  |  |  |  |  |
| Abet0328 |  | *S* | *D* | *A* |  | *K* | *T* | *D* |  |  |  |  |  |  |  |  |  |  |  | *R* |  |  |  |  |
| Abet0329 |  | *T* |  | *N* | *L* | *K* | *R* | *E* |  |  |  |  |  |  |  |  |  |  |  |  |  |  |  |  |
| Abet0332 |  | *S* | *D* | *S* | *W* | *H* | *T* | *D* | *I* |  |  |  |  |  |  |  |  |  |  | *R* |  |  |  |  |
| Abet0342 |  |  |  | *D* |  | *R* | *R* | *S* | *V* |  |  |  |  |  |  |  |  |  |  |  |  |  |  |  |
| Abet0343 |  |  |  | *N* |  | *N* | *H* | *Q* | *V* |  |  |  |  |  |  |  |  |  |  |  |  |  |  |  |
| Abet0344 |  |  |  |  |  |  |  |  |  |  |  |  |  |  |  |  |  |  |  |  |  |  |  |  |
| Abet0368 |  |  |  | *D* |  | *G* | *P* | *S* | *P* |  |  |  |  |  |  |  |  |  |  |  |  |  |  |  |
| Abet0369 |  | *S* |  | *Q* | *I* |  | *K* | *N* |  |  |  |  |  | *R* |  |  |  |  |  |  |  |  |  |  |
| Abet0370 |  |  |  | *H* |  | *P* | *M* | *S* | *A* |  |  |  |  |  |  |  |  |  |  |  |  |  |  |  |
| Abet0371 |  | *H* | *D* | *A* |  | *P* | *F* | *D* |  |  |  |  |  |  |  |  |  |  |  |  |  |  |  |  |
| Abet0372 |  | *S* | *D* | *M* |  | *N* | *I* | *E* |  |  |  |  |  |  |  |  |  |  |  |  |  |  |  |  |
| Abet0373 |  |  |  | *D* |  | *E* | *R* | *S* | *V* |  |  |  |  |  |  |  |  |  |  | *R* |  |  |  |  |
| Abet0374 |  |  |  | *Q* |  | *K* | *D* | *T* | *P* |  |  |  |  |  |  |  |  |  |  |  |  |  |  |  |
| Abet0377 |  |  |  | *N* |  | *N* | *E* | *Q* |  |  | *L* |  |  |  |  |  |  |  |  |  |  |  |  |  |
| Abet0378 |  |  |  | *P* |  | *E* | *T* | *D* | *I* |  |  |  |  |  |  |  |  |  |  |  |  |  |  |  |
| Abet0379 |  |  |  | *D* |  | *A* | *E* | *T* | *P* |  | *L* |  |  |  |  |  |  |  | *E* | *R* |  |  |  |  |
| Abet0380 |  | *M* | *G* | *N* |  | *N* | *Y* | *Q* |  |  |  |  |  |  |  |  |  |  | *R* |  |  |  |  |  |
| Abet0381 |  | *S* | *P* | *S* |  | *P* | *R* | *E* |  |  |  |  |  |  |  |  |  |  |  |  |  |  |  |  |
| Abet0382 |  |  |  | *H* |  | *T* | *N* | *S* | *I* |  |  |  |  |  |  |  |  |  |  |  |  |  |  |  |
| Abet0383 |  |  |  |  |  | *D* | *W* |  | *P* |  |  |  |  |  |  |  |  |  |  | *R* |  |  |  | *I* |

| Kabat | FW 2 | | | CDR 2 | | | | | | | | | | | | FW 3 | | | | | |
|---|---|---|---|---|---|---|---|---|---|---|---|---|---|---|---|---|---|---|---|---|---|
| Numbering V$_H$ | 49 | 50 | 51 | 52 | 52a | 53 | 54 | 55 | 56 | 57 | 58 | 59 | 60 | 61 | 62 | 63 | 64 | 65 | 66 | 67 | 68 | 69 | 70 | 71 |
| Abet0144-GL | S | V | I | G | S | S | G | G | T | T | V | Y | A | D | S | V | K | G | R | F | T | I | S | R |
| Abet0319 |  |  |  |  |  |  |  |  |  |  |  |  |  |  |  |  |  |  |  |  |  |  |  |  |
| Abet0321b |  |  |  |  |  |  |  |  | *A* |  |  |  |  |  |  |  |  |  |  |  |  |  |  |  |
| Abet0322b |  |  |  |  |  |  | *A* |  |  |  |  |  |  |  | *A* |  |  |  |  |  |  |  |  |  |
| Abet0323b |  |  |  | *P* | *N* | *P* | *K* | *N* | *N* |  | *A* |  |  |  |  |  |  |  |  |  |  |  |  |  |
| Abet0328 |  |  |  | *A* | *H* | *T* | *N* | *N* | *S* |  | *A* |  |  |  |  |  |  |  |  |  |  |  |  |  |
| Abet0329 |  |  |  |  | *H* | *Q* | *E* | *R* |  |  | *S* |  |  |  |  |  |  |  |  |  |  |  |  |  |
| Abet0332 |  |  |  | *N* |  | *N* | *K* | *K* | *I* |  | *A* |  |  |  |  |  |  |  |  |  |  |  |  |  |
| Abet0342 |  |  |  | *A* | *Q* | *T* | *Q* | *N* | *K* |  | *A* |  |  |  |  |  |  |  |  |  |  |  |  |  |
| Abet0343 |  |  |  | *K* | *T* | *N* | *E* | *N* | *I* |  | *A* |  |  |  |  |  |  |  |  |  |  |  |  |  |
| Abet0344 |  |  |  | *G* | *N* | *E* | *T* | *R* | *K* |  | *A* |  |  |  |  |  |  |  |  |  |  |  |  |  |
| Abet0368 |  |  |  | *K* | *D* | *T* | *Q* | *N* | *S* |  | *T* |  |  |  |  |  |  |  |  |  |  |  |  |  |
| Abet0369 |  |  |  | *K* | *D* | *E* | *T* | *R* | *F* |  | *N* |  |  |  |  |  |  |  |  |  |  |  |  |  |
| Abet0370 |  |  |  | *E* | *T* | *P* | *E* | *R* | *Q* |  | *A* |  |  |  |  |  |  |  |  |  |  |  |  |  |
| Abet0371 |  |  |  |  |  |  |  |  |  |  |  |  |  |  |  |  |  |  |  |  |  | *V* |  |  |
| Abet0372 |  |  |  | *K* | *G* | *M* | *N* | *N* | *V* |  | *S* |  |  |  |  |  |  |  |  |  |  |  |  |  |
| Abet0373 |  |  |  |  | *G* | *K* | *T* | *N* | *I* |  | *T* |  |  |  |  |  |  |  |  |  |  |  |  |  |
| Abet0374 |  |  |  | *D* | *Q* | *N* | *H* | *K* | *K* |  | *A* |  |  |  |  |  |  |  |  |  |  |  |  |  |
| Abet0377 |  |  |  | *V* | *G* | *T* | *K* | *N* | *I* |  | *A* |  |  |  | *T* |  |  |  |  |  |  |  |  |  |
| Abet0378 |  |  |  | *T* | *N* | *T* | *D* | *N* | *V* |  | *A* |  |  |  |  |  |  |  |  |  |  |  |  |  |
| Abet0379 |  |  |  |  | *N* | *Q* | *N* | *K* |  |  | *A* |  |  |  |  |  |  |  |  |  |  |  |  |  |
| Abet0380 |  |  |  | *K* | *T* | *N* | *E* | *N* | *I* |  | *A* |  |  |  |  |  |  |  |  |  |  |  |  |  |
| Abet0381 |  |  |  | *T* | *Q* | *P* | *N* | *R* | *L* |  | *T* |  |  |  |  |  |  |  |  |  |  |  |  |  |
| Abet0382 |  |  |  |  | *E* | *A* | *H* | *R* | *V* |  | *T* |  |  |  |  |  |  |  |  |  |  |  |  |  |
| Abet0383 |  |  |  | *A* | *D* | *N* | *A* | *K* | *I* |  | *A* |  |  |  |  |  |  |  |  |  |  |  |  |  |

TABLE 5-continued

| Kabat | FW 3 | | | | | | | | | | | | | | | | | | | | | | | |
|---|---|---|---|---|---|---|---|---|---|---|---|---|---|---|---|---|---|---|---|---|---|---|---|---|
| Numbering V$_H$ | 72 | 73 | 74 | 75 | 76 | 77 | 78 | 79 | 80 | 81 | 82 | 82a | 82b | 82c | 83 | 84 | 85 | 87 | 87 | 88 | 89 | 90 | 91 | 92 |
| Abet0144-GL | D | N | S | K | N | T | L | Y | L | Q | M | N | S | L | R | A | E | D | T | A | V | Y | Y | C |
| Abet0319 | | | | | | | | | | | | | | | | | | | | | | | | |
| Abet0321b | | | | | | | | | | | | | | | | | | | | | | | | |
| Abet0322b | | | | | *E* | | | | | | | | | | | | | | | | | | | |
| Abet0323b | | | | | | | | | | | | | | | | | | | | | | | | |
| Abet0328 | | | | | | | | | | | | | | | | | | | | | | | | |
| Abet0329 | | | | | | | | | | | | | | | | | | | | | | | | |
| Abet0332 | | | | | | | | | | | | | | | | | | | | | | | | |
| Abet0342 | | | | | | | | | | | | | | | | | | | | | | | | |
| Abet0343 | | | | | | | | | | | | | | | | | | | | | | | | |
| Abet0344 | | | | | | *R* | | | | | | | | | | | | | | | | | | |
| Abet0368 | | | | | *D* | | | | | | | | | | | | *K* | | | | | | | |
| Abet0369 | | | | | | | | | | | | | | | | | | | | | | | | |
| Abet0370 | | | | | *S* | | | | | | | | | | | | | | | | | | | |
| Abet0371 | | | | | | | | | | | | | | | | | | | | | | | | |
| Abet0372 | | | | | | | | | | | | | | | | | | | | | | | | |
| Abet0373 | | | | | | | | | | | | | | | | | | | | | | | | |
| Abet0374 | | | | | | | | | | | | | | | | | | | | | | | | |
| Abet0377 | | | | | | | | | | | | | | | | | | | | | | | | |
| Abet0378 | | | | | | | | | | | | | | | | | | | | | | | | |
| Abet0379 | | | | | *D* | | | | | | | | | | | | | | | | | | | |
| Abet0380 | | | | | | | | | | | | | | | | | | | | | | | | |
| Abet0381 | | | | | | | | | | | | | | | | | | | | | | | | |
| Abet0382 | | | | | | | | | | | | | | | | | | | | | | | | |
| Abet0383 | | | | | | | | | | | | | | | | | | | | | | | | |

| Kabat | FW 3 | | CDR 3 | | | | | | | | | | | | | | | FW 4 | | | | | |
|---|---|---|---|---|---|---|---|---|---|---|---|---|---|---|---|---|---|---|---|---|---|---|---|
| Numbering V$_H$ | 93 | 94 | 95 | 96 | 97 | 98 | 99 | 100 | 100a | 100b | 100c | 100d | 100e | 100f | 100g | 100h | 101 | 102 | 103 | 104 | 105 | 106 | 107 | 108 |
| Abet0144-GL | A | R | E | W | M | D | H | S | R | P | Y | Y | Y | Y | G | M | D | V | W | G | Q | G | T | L |
| Abet0319 | | | | | | | | | | | | | | | | | | | | | | | | |
| Abet0321b | | | | | | | | | | | | | | | | | | | | | | | | |
| Abet0322b | | | | | | | | | | | | | | | | | | | | | | | | |
| Abet0323b | | | | | | | | | | | | | | | | | | | | | | | | |
| Abet0328 | | | | | | | | | | *R* | | | | | | | | | | | | | | |
| Abet0329 | | | | | | | | | | | | | | | | | | | | | | | | |
| Abet0332 | | | | | | | | | | | | | | | | | | | | | | | | |
| Abet0342 | | | | | | | | | | | | | | | | | | | | | | | | |
| Abet0343 | | | | | | | | | | | | | | | | | | | | | | | | |
| Abet0344 | | | | | | | | | | | | | | | | | | | | | | | | |
| Abet0368 | | | | | | | | | | | | | | | | | | | | | | | | |
| Abet0369 | | | | | | | | | | | | | | | | | | | | | | | | |
| Abet0370 | | | | | | | | | | | | | | | | | | | | | | | | |
| Abet0371 | | | | | | | | | | | | | | | | | | | | | | | | |
| Abet0372 | | | | | | | | | | | | | | | | | | | | | | | | |
| Abet0373 | | | | | | | | | | | | | | | | | | | | | | | | |
| Abet0374 | | | | | | | | | | | | | | | | | | *A* | | | | | | |
| Abet0377 | | | | | | | | | | | | | | | | | | | | | | | | |
| Abet0378 | | | | | | | | | | | | | | | | | | | | | | | | |
| Abet0379 | | | | | | | | | | | | | | | | | | | | | | | | |
| Abet0380 | | | | | | | | | | | | | | | | | | | | | | | | |
| Abet0381 | | | | | | | | | | | | | | | | | | *I* | | | | | | |
| Abet0382 | | | | | | | | | | | | | | | | | | | | | | | | |
| Abet0383 | | | | | | *G* | | | | | | | | | | | | | | | | | | *P* |

| Kabat | FW 4 | | | | |
|---|---|---|---|---|---|
| Numbering V$_H$ | 109 | 110 | 111 | 112 | 113 |
| Abet0144-GL | V | T | V | S | S |
| Abet0319 | | | | | |
| Abet0321b | | | | | |
| Abet0322b | | | | | |
| Abet0323b | | | | | |
| Abet0328 | | | | | |
| Abet0329 | | | | | |
| Abet0332 | | | | | |
| Abet0342 | | | | | |
| Abet0343 | | | | | |
| Abet0344 | | | | | |
| Abet0368 | | | | | |
| Abet0369 | | | | | |
| Abet0370 | | | | | |
| Abet0371 | | | | | |
| Abet0372 | | | | | |

TABLE 5-continued

|  |  |
|---|---|
| Abet0373 |  |
| Abet0374 |  |
| Abet0377 |  |
| Abet0378 |  |
| Abet0379 |  |
| Abet0380 |  |
| Abet0381 | P |
| Abet0382 |  |
| Abet0383 |  |

TABLE 6

| Kabat Numbering VL | FW 1 | | | | | | | | | | | | | | | | | | | | | | | CDR 1 | | | |
|---|---|---|---|---|---|---|---|---|---|---|---|---|---|---|---|---|---|---|---|---|---|---|---|---|---|---|---|
|  | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 |
| Abet0144-GL | S | Y | E | L | T | Q | P | P | S | — | V | S | V | S | P | G | Q | T | A | S | I | T | C | S | G | H | N |
| Abet0319 |  |  |  |  |  |  |  |  |  |  |  |  |  |  |  |  |  |  |  |  |  |  |  |  |  |  |  |
| Abet0321b |  |  |  |  |  |  |  |  |  |  |  |  |  |  |  |  |  |  |  |  |  |  |  |  |  |  |  |
| Abet0322b |  |  |  |  |  |  |  |  |  |  |  |  |  |  |  |  |  |  |  |  |  |  |  |  |  |  |  |
| Abet0323b |  |  |  |  |  |  |  |  |  |  |  |  |  |  |  |  |  |  |  |  |  |  |  |  |  |  |  |
| Abet0328 |  |  |  |  |  |  |  |  |  |  |  |  |  |  |  |  |  |  | V |  |  |  |  |  |  | R |  |
| Abet0329 |  |  |  |  |  |  |  |  |  |  |  |  |  |  |  |  |  |  |  |  |  |  |  |  |  |  |  |
| Abet0332 |  |  |  |  |  |  |  |  |  |  |  |  |  |  |  |  |  |  |  |  |  |  |  |  |  |  |  |
| Abet0342 |  |  |  |  |  |  |  |  |  |  |  |  |  |  |  |  |  |  |  |  |  |  |  |  |  |  |  |
| Abet0343 | Q | S | V |  |  |  |  |  |  |  |  |  |  |  |  |  |  |  |  |  |  |  |  |  |  |  |  |
| Abet0344 | Q | S | V |  |  |  |  |  |  |  |  |  |  |  |  |  |  |  |  |  |  |  |  |  |  |  |  |
| Abet0368 |  |  |  |  |  |  |  |  |  |  |  |  |  |  |  |  |  |  |  |  |  |  |  |  |  |  |  |
| Abet0369 |  |  | G |  |  |  |  |  |  |  |  |  |  |  |  |  |  |  |  |  |  |  |  |  |  | R |  |
| Abet0370 |  |  |  |  |  |  |  |  |  |  |  |  |  |  |  |  |  |  |  |  |  |  |  | T | T | P | H |
| Abet0371 |  |  |  |  |  |  |  |  |  |  |  |  |  |  |  |  |  |  |  |  |  |  |  |  |  |  |  |
| Abet0372 |  |  |  |  |  |  |  |  |  |  |  |  |  |  |  |  |  |  |  |  |  |  |  |  |  |  |  |
| Abet0373 |  |  |  |  |  |  |  |  |  |  |  |  |  |  |  |  |  |  |  |  |  |  |  |  |  |  |  |
| Abet0374 |  |  |  |  |  |  |  |  |  |  |  |  |  | T |  |  |  |  |  |  |  |  |  |  |  |  |  |
| Abet0377 |  |  |  |  |  |  |  |  |  |  |  |  |  |  |  |  |  |  |  |  |  |  |  |  |  |  |  |
| Abet0378 |  |  |  |  |  |  |  |  |  |  |  |  |  |  |  |  |  |  |  |  |  |  |  |  |  |  |  |
| Abet0379 | Q | S | V |  |  |  |  |  |  |  |  |  |  |  |  |  |  |  |  |  |  |  |  |  |  |  |  |
| Abet0380 |  |  |  |  |  |  |  |  |  |  |  |  |  |  |  |  |  |  |  |  |  |  |  |  |  |  |  |
| Abet0381 |  |  |  |  |  |  |  |  |  |  |  |  | A |  |  |  |  |  |  |  |  |  |  |  |  |  |  |
| Abet0382 |  |  |  |  |  | I |  |  |  |  |  |  |  |  |  |  |  |  |  |  |  |  |  |  |  |  |  |
| Abet0383 |  |  |  |  |  |  |  |  |  |  |  |  |  |  |  |  |  |  |  |  |  |  |  |  |  |  |  |

| Kabat Numbering VL | CDR 1 | | | | | | | FW 2 | | | | | | | | | | | | | | | CDR 2 | | | |
|---|---|---|---|---|---|---|---|---|---|---|---|---|---|---|---|---|---|---|---|---|---|---|---|---|---|---|
|  | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 | 53 | 54 |
| Abet0144-GL | L | E | D | K | F | A | S | W | Y | Q | Q | K | P | G | Q | S | P | V | L | V | I | Y | R | D | D | K | R |
| Abet0319 | I | M |  |  | W | V |  |  |  |  |  |  |  |  | R |  |  | A |  |  |  |  |  |  |  |  |  |
| Abet0321b |  |  |  |  |  |  |  |  |  |  |  |  |  |  |  |  |  |  |  | I |  |  |  |  |  |  |  |
| Abet0322b |  | G |  |  |  |  |  |  |  |  |  |  |  |  |  |  |  |  |  |  |  |  |  |  |  |  |  |
| Abet0323b |  |  |  |  |  |  |  |  |  |  |  |  |  |  |  |  |  |  |  |  |  |  |  |  |  |  |  |
| Abet0328 |  |  |  |  |  |  |  |  |  |  |  |  |  |  |  |  |  |  |  |  |  |  |  |  |  |  |  |
| Abet0329 | V | S |  |  | W | M | T |  |  |  |  |  |  |  |  |  |  |  |  |  |  |  |  |  |  |  |  |
| Abet0332 | I | G | A |  | W | V |  |  |  |  |  |  |  |  |  |  |  |  |  | I |  |  |  |  |  |  |  |
| Abet0342 |  |  |  |  |  |  |  |  |  |  |  |  |  |  |  |  |  |  |  |  |  |  |  |  |  |  |  |
| Abet0343 |  |  |  |  |  |  |  |  |  |  |  | S |  |  |  |  |  |  |  |  |  |  |  |  |  |  |  |
| Abet0344 |  |  |  |  |  |  |  |  |  |  |  | S |  |  |  |  |  |  |  |  |  |  |  |  |  |  |  |
| Abet0368 |  |  |  |  |  | T |  |  |  |  |  | S |  |  |  |  |  |  |  |  |  |  |  |  |  |  |  |
| Abet0369 | I | G |  | S | W | V | A |  |  |  |  |  |  |  |  |  |  |  |  |  |  |  |  |  |  |  |  |
| Abet0370 | F | N | S |  |  |  |  |  |  |  |  |  |  |  |  |  |  |  |  |  |  |  |  |  |  |  |  |
| Abet0371 | I | S | S | S | W | V |  |  |  |  |  |  |  |  |  |  |  |  |  |  |  |  |  |  |  |  |  |
| Abet0372 |  |  |  |  |  |  |  |  |  |  |  |  |  |  |  |  |  |  |  |  |  |  |  |  |  |  |  |
| Abet0373 |  |  |  |  |  |  |  |  |  |  |  |  |  |  |  |  |  |  |  |  |  |  |  |  |  |  |  |
| Abet0374 |  | G | G |  |  |  |  |  |  |  |  |  |  |  |  |  |  |  |  |  |  |  |  |  |  |  |  |
| Abet0377 | T |  | H |  | W | I |  |  |  |  |  |  |  |  |  |  |  |  |  |  |  |  |  |  |  |  |  |
| Abet0378 |  |  |  |  |  |  |  |  |  |  |  |  |  |  |  |  |  |  |  |  |  |  |  |  |  |  |  |
| Abet0379 |  |  |  |  |  |  |  |  |  |  |  | S |  |  |  |  |  |  |  |  |  |  |  |  |  |  |  |
| Abet0380 |  |  |  |  |  |  |  |  |  |  |  |  |  |  |  |  |  |  |  |  |  |  |  |  |  |  |  |
| Abet0381 |  |  |  |  | V |  |  |  |  |  |  |  |  |  |  |  |  |  |  |  |  |  |  |  |  |  |  |
| Abet0382 |  |  |  |  |  |  |  |  |  |  |  |  |  |  |  |  |  |  |  |  |  |  |  |  |  |  |  |
| Abet0383 |  | G |  |  |  |  |  |  |  |  |  |  |  |  |  |  |  |  |  |  |  |  |  |  |  |  |  |

TABLE 6-continued

| Kabat | CDR 2 | | | | | | | | | | | | FW 3 | | | | | | | | | | | | | | |
|---|---|---|---|---|---|---|---|---|---|---|---|---|---|---|---|---|---|---|---|---|---|---|---|---|---|---|---|
| Numbering VL | 55 | 56 | 57 | 59 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 |
| Abet0144-GL | P | S | G | I | P | E | R | F | S | A | S | N | S | G | H | T | A | T | L | T | I | S | G | T | Q | A | M |
| Abet0319 | | | | | | | | | | | | | | | | | | | | | | | | | | | T |
| Abet0321b | | | | | | | | | | | | | | | | | | | | | | | | | | | T |
| Abet0322b | | | E | | | | | | | | | | | | | | | | | | | | | | | | T |
| Abet0323b | | | | V | | | | | | | | | | | | | | | | | | | | | | | T |
| Abet0328 | | | | V | | | | | | | | | | | | | | | | | | | | | | | T |
| Abet0329 | | | | | | | | | | | | | | | | | | | | | | | | | | | T |
| Abet0332 | | | | | | | | | | | | | | | | | | | | | | | | | | | T |
| Abet0342 | | | | | | | | | | | | | | | | D | | | | | | | | | | | |
| Abet0343 | | | | | | | | | | | | | | | | | | | | | | | | | | | T |
| Abet0344 | | | | | | | | | | | | | | | | | | | | | | | | | | | T |
| Abet0368 | | | | | | | | | | | | | | | | | | | | | | | | A | | | T |
| Abet0369 | | | | | | | | | | | | | | | | | | | | | | | | | | | T |
| Abet0370 | | | | | | | | | | | | | | | | | | | | | | | | | | | |
| Abet0371 | | | | | | | | | | | | | | | | | | | | | | | | | | | T |
| Abet0372 | | | | | | | | | | | | | | | | | | | | | | | | | | | T |
| Abet0373 | | | E | | | | | | | | | | | | | | | | | | | | | | | | T |
| Abet0374 | | | | | | | | | | | | | F | | | | | | | | | | | | | | T |
| Abet0377 | | | | | | | | | | | T | | | | | | | | | | | | | | | | T |
| Abet0378 | | | | | | | | | | | | | | | | | | | | | | | | | | | T |
| Abet0379 | | | | | | | | | | | | | | | | | | | | | | | | | | | T |
| Abet0380 | | | | | | | | | | | | | | | | | | | | | | | | | | | T |
| Abet0381 | | | | | | | | | | | | | | | | | | | | | | | | | | | T |
| Abet0382 | | | | | | | | | | | T | | | | | | | | | | | | | | | | T |
| Abet0383 | | | | | | | | | | | | | | | | | | | | | | | | | | | T |

| Kabat | FW 3 | | | | | | | CDR 3 | | | | | | | | | FW 4 | | | | | | | | |
|---|---|---|---|---|---|---|---|---|---|---|---|---|---|---|---|---|---|---|---|---|---|---|---|---|---|
| Numbering VL | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 |
| Abet0144-GL | D | E | A | D | Y | Y | C | Q | A | Q | D | S | T | T | R | V | F | G | G | G | T | K | L | T | V | L |
| Abet0319 | | | | | | | | S | S | | | T | V | | | | | | | | | | | | | |
| Abet0321b | | | | | | | | S | S | | | T | V | | | | | | | | | | | | | |
| Abet0322b | | | | | | | | S | S | | | T | V | | | | | | | | | | | | | |
| Abet0323b | | | | | | | | S | S | | | T | V | | | | | | | | | | | I | | |
| Abet0328 | | | | | | | | S | S | | | T | V | | | | | | | | | | | | | |
| Abet0329 | | | | | | | | S | S | | | T | V | | | | | | | | | | | | | |
| Abet0332 | | | | | | | | | | | G | Q | V | | | S | | | | | | | | | | |
| Abet0342 | | | | | | | | | | | | | | | | | | | | | | | | | | |
| Abet0343 | | | | | | | | S | S | | | T | V | | | | | | | | | | | | | |
| Abet0344 | | | | | | | | A | T | | | N | F | | | | | | | | | | | | | |
| Abet0368 | | | | | | | | S | S | | | T | V | | | | | | | | | | | | | |
| Abet0369 | | | | | | | | S | S | | | T | V | | | | | | | | | | | | | |
| Abet0370 | | | | | | | | | | | | | | | | | | | | | | | | R | | |
| Abet0371 | | | | | | | | S | S | | | T | V | | | | | | | | | | | | | |
| Abet0372 | | | | | | | | S | S | | | T | V | | | | | | | | | | | | | |
| Abet0373 | | | | | | | | S | S | | | T | V | | | | | | | | | | | | | |
| Abet0374 | | | | | | | | S | S | | | T | V | | | | | | | | | | | | | |
| Abet0377 | | | | | | | | S | S | | | T | V | | | | | | | | | | | | | |
| Abet0378 | | | | | | | | S | S | B | | T | V | | | | | | | | | | | | | |
| Abet0379 | | G | | | | | | A | T | | | N | F | | | | | | | | | | | | | |
| Abet0380 | | | | | | | | S | S | | | T | V | | | | | | | | | | | | | |
| Abet0381 | | | | N | | | | S | S | | | T | V | | | A | | | | | | | | | | |
| Abet0382 | | | | | | | | S | S | | | K | V | | | | | | | | | | | | | |
| Abet0383 | | | | | | | | S | S | | | T | V | | | | | | | | | | | | | |

3.7 Kinetic Profiling of Affinity Improved Clones in Purified scFv Format by Surface Plasmon Resonance Surface Plasmon Resonance was used to analyse the purified scFv clones that had shown significant improvement in binding affinity for human Amyloid beta 1-42 peptide over the parent sequence, Abet0144-GL, in the HTRF™ epitope competition assay (sections 3.3-3.6). Briefly, the ProteOn Protein Interaction Array System (Bio-Rad, USA) was used to assess the kinetic parameters of the interaction between each purified scFv and synthetically produced human Amyloid beta 1-42 peptide. These experiments were performed essentially as described by Karisson et al. (Karisson et al., 1991). For further details see section 1.7.

The affinity of binding between each test scFv and human Amyloid beta 1-42 was estimated using assays in which biotinylated synthetic human Amyloid beta 1-42 peptide (rPeptide, USA; cat: A1117) was non-covalently bound via a biotin/streptavidin interaction to a proprietary streptavidin chip (NTA 176-5021) at five different surface densities. The chip surface was regenerated between cycles by a single 60 second injection of 10 mM Glycine pH 2.0 to remove scFv bound to the peptide. The regeneration did not result in a significant loss of scFv binding capacity.

Each scFv at 100-200 nM was sequentially passed over the peptide surface for a sufficient amount of time to observe sensorgrams that could be fitted to an appropriate binding model with confidence. An irrelevant scFv blank was subtracted from the main dataset to reduce the impact of any buffer artefacts or non-specific binding effects. An appropriate binding model was then fitted to the data.

For Abet0380 scFv, the association rate constant (ka), dissociation rate constant (kd) and dissociation constant (KD) are $1.93 \times 10^5$ $M^{-1}$ $s^{-1}$, $2.85 \times 10^{-5}$ $s^{-1}$ and 148 pM respectively. These parameters were derived from a 1:1 Langmuir fit to the data.

TABLE 7

Example kinetic data for optimised scFv clones binding to synthetic biotinylated human Amyloid beta 1-42 peptide, as determined by Surface Plasmon Resonance.

| Clone | $k_a$ ($M^{-1}$ $s^{-1}$) | $k_d$ ($s^{-1}$) | $K_D$ (M) |
|---|---|---|---|
| Abet0144-GL | 1.16E+05 | 6.60E−03 | 5.87E−08 |
| Abet0319 | 3.29E+05 | 1.29E−04 | 3.91E−10 |
| Abet0321b | 1.50E+05 | 3.33E−05 | 2.22E−10 |
| Abet0322b | 2.03E+05 | 1.65E−04 | 8.12E−10 |
| Abet0323b | 2.10E+05 | 1.88E−04 | 8.94E−10 |
| Abet0328 | 1.41E+05 | 1.03E−04 | 7.29E−10 |
| Abet0329 | 1.97E+05 | 1.38E−04 | 7.01E−10 |
| Abet0332 | 3.29E+05 | 1.29E−04 | 3.91E−10 |
| Abet0342 | 1.36E+05 | 5.73E−05 | 4.21E−10 |
| Abet0343 | 1.20E+05 | 2.25E−05 | 1.88E−10 |
| Abet0344 | 7.75E+04 | 5.73E−05 | 7.39E−10 |
| Abet0368 | 1.87E+05 | 9.00E−05 | 4.82E−10 |
| Abet0369 | 3.27E+05 | 4.34E−05 | 1.33E−10 |
| Abet0370 | 1.19E+05 | 7.76E−05 | 6.51E−10 |
| Abet0371 | 3.57E+05 | 2.72E−04 | 7.62E−10 |
| Abet0372 | 2.43E+05 | 1.76E−04 | 7.24E−10 |
| Abet0373 | 1.85E+05 | 8.92E−05 | 4.83E−10 |
| Abet0374 | 2.56E+05 | 6.04E−05 | 2.36E−10 |
| Abet0377 | 1.96E+05 | 3.02E−05 | 1.54E−10 |
| Abet0378 | 1.36E+05 | 6.41E−05 | 4.72E−10 |
| Abet0379 | 1.34E+05 | 4.39E−05 | 3.27E−10 |
| Abet0380 | 1.93E+05 | 2.85E−05 | 1.48E−10 |
| Abet0381 | 2.13E+05 | 5.14E−05 | 2.41E−10 |
| Abet0382 | 2.25E+05 | 7.97E−05 | 3.54E−10 |
| Abet0383 | 1.81E+05 | 3.94E−05 | 2.17E−10 |

3.8 Reformatting of Affinity Improved scFv to Human IgG 1-TM

The IgG1-TM antibody format is discussed in section 2.6. ScFv were reformatted to IgG1-TM by subcloning the variable heavy chain ($V_H$) and variable light chain ($V_L$) domains into vectors expressing whole human antibody heavy and light chains respectively. The variable heavy chain was cloned into a mammalian expression vector (pEU 1.4) containing the human heavy chain constant domains and regulatory elements to express whole IgG1-TM heavy chain in mammalian cells. Similarly, the variable light chain domain was cloned into a mammalian expression vector (pEU 4.4) for the expression of the human lambda light chain constant domains and regulatory elements to express whole IgG light chain in mammalian cells.

To obtain antibodies as IgG, the heavy and light chain IgG expression vectors were transiently transfected into HEK293-EBNA mammalian cells (Invitrogen, UK; cat: R620-07) where the IgGs were expressed and secreted into the medium. Harvests were pooled and filtered prior to purification. The IgG was purified using Protein A chromatography. Culture supernatants were loaded onto an appropriate ceramic Protein A column (BioSepra—Pall, USA) and washed with 50 mM Tris-HCl pH 8.0, 250 mM NaCl. Bound IgG was eluted from the column using 0.1 M Sodium Citrate (pH 3.0) and neutralised by the addition of Tris-HCl (pH 9.0). The eluted material was buffer exchanged into PBS using NAP-10 buffer exchange columns (GE Healthcare, UK; cat: 17-0854-02) and the purified IgGs were passed through a 0.2 μm filter. The concentration of IgG was determined spectrophotometrically using an extinction coefficient based on the amino acid sequence of the IgG. The purified IgGs were analysed for aggregation or degradation using SEC-HPLC and by SDS-PAGE.

3.9 Germlining

Five of the most potent IgGs were selected for germlining, based on an experimental characterisation of their corresponding scFv. Purified scFv of clones Abet0343, Abet0369, Abet0377, Abet0380 and Abet0382 all exhibited $IC_{50}$ values of less than 750 pM, as determined by epitope competition assay (Table 4), and all had an experimental dissociation constant of less than 250 pM, as determined by Surface Plasmon Resonance, Table 7.

The germlining process consisted of reverting framework residues in the $V_H$ and $V_L$ domains to the closest germline sequence to identically match human antibodies. For the $V_H$ domains of the optimised antibody lineage this was Vh3-23 (DP-47) and for the $V_L$ domains it was Vλ3-3r (DPL-23). For Abet0380, 1 residue required changing in the $V_H$ domain at Kabat position 43 (Table 8) and 1 residue required changing in the $V_L$ domain at Kabat position 81 (Table 9). The remaining four sequences required between two and five changes (Tables 8 and 9). The Vernier residues (Foote et al., 1992), were not germlined, apart from residue 2 in the light chain sequence of Abet0343, which was germlined for at the same time as the flanking residues 1 and 3. Germlining of these amino acid residues was carried out using standard site-directed mutagenesis techniques with the appropriate mutagenic primers as described by Clackson and Lowman (Clackson et al., 2004).

TABLE 8

Sequence alignment of the $V_H$ domains of the five clones selected for germlining. The two residues that were reverted to germline are indicated by italicized text. The positions of the Vernier residues are indicated by circles (•).

| Kabat Numbering | | | | | | | | | | | | FW 1 | | | | | | | | |
|---|---|---|---|---|---|---|---|---|---|---|---|---|---|---|---|---|---|---|---|---|
| $V_H$ | 1 | 2 | 3 | 4 | 5 | 6 | 7 | 8 | 9 | 10 | 11 | 12 | 13 | 14 | 15 | 16 | 17 | 18 | 19 | 20 |
| Vernier | | • | | | | | | | | | | | | | | | | | | |
| Abet0144-GL | E | V | Q | L | L | E | S | G | G | G | L | V | Q | P | G | G | S | L | R | L |
| Abet0343 | | | | | | | | | | | | | | | | | | | | |
| Abet0369 | | | | | | | | | | | | | | | | | | | | |
| Abet0377 | | | | | | | | | | | | | | | | | | | | |
| Abet0380 | | | | | | | | | | | | | | | | | | | | |
| Abet0382 | | | | | | | | | | | | | | | | | | | | |

TABLE 8-continued

Sequence alignment of the $V_H$ domains of the five clones selected for germlining. The two residues that were reverted to germline are indicated by italicized text. The positions of the Vernier residues are indicated by circles (•).

| Kabat Numbering | FW 1 | | | | | | | | | | CDR 1 | | | | | FW 2 | | | |
|---|---|---|---|---|---|---|---|---|---|---|---|---|---|---|---|---|---|---|---|
| $V_H$ | 21 | 22 | 23 | 24 | 25 | 26 | 27 | 28 | 29 | 30 | 31 | 32 | 33 | 34 | 35 | 36 | 37 | 38 | 39 | 40 |
| Vernier | | | | | | | • | • | • | • | | | | | | | | | | |
| Abet0144-GL | S | C | A | A | S | G | F | T | F | S | V | Y | T | M | W | W | V | R | Q | A |
| Abet0343 | | | | | | | | N | | N | H | Q | V | | | | | | | |
| Abet0369 | | | | | | S | | Q | I | | K | N | | | | | | | *R* | |
| Abet0377 | | | | | | | | N | | N | E | Q | | L | | | | | | |
| Abet0380 | | | | | | M | G | N | | N | Y | Q | | | | | | | | |
| Abet0382 | | | | | | | | H | | T | N | S | I | | | | | | | |

| Kabat Numbering | FW 2 | | | | | | | | | | CDR 2 | | | | | | | | |
|---|---|---|---|---|---|---|---|---|---|---|---|---|---|---|---|---|---|---|---|
| $V_H$ | 41 | 42 | 43 | 44 | 45 | 46 | 47 | 48 | 49 | 50 | 51 | 52 | 52a | 53 | 54 | 55 | 56 | 57 | 58 | 59 |
| Vernier | | | | | | | • | • | • | | | | | | | | | | | |
| Abet0144-GL | P | G | K | G | L | E | W | V | S | V | I | G | S | S | G | G | T | T | V | Y |
| Abet0343 | | | | | | | | | | | | | K | T | N | E | N | I | A | |
| Abet0369 | | | | | | | | | | | | | K | D | E | T | R | F | N | |
| Abet0377 | | | | | | | | | | | | | V | G | T | K | N | I | A | |
| Abet0380 | | | *R* | | | | | | | | | | K | T | N | E | N | I | A | |
| Abet0382 | | | | | | | | | | | | | E | A | H | R | V | T | | |

| Kabat Numbering | CDR 2 | | | | | | FW 3 | | | | | | | | | | | | | |
|---|---|---|---|---|---|---|---|---|---|---|---|---|---|---|---|---|---|---|---|---|
| $V_H$ | 60 | 61 | 62 | 63 | 64 | 65 | 66 | 67 | 68 | 69 | 70 | 71 | 72 | 73 | 74 | 75 | 76 | 77 | 78 | 79 |
| Vernier | | | | | | | | • | | • | | • | | • | | | | | • | |
| Abet0144-GL | A | D | S | V | K | G | R | F | T | I | S | R | D | N | S | K | N | T | L | Y |
| Abet0343 | | | | | | | | | | | | | | | | | | | | |
| Abet0369 | | | | | | | | | | | | | | | | | | | | |
| Abet0377 | | T | | | | | | | | | | | | | | | | | | |
| Abet0380 | | | | | | | | | | | | | | | | | | | | |
| Abet0382 | | | | | | | | | | | | | | | | | | | | |

| Kabat Numbering | FW 3 | | | | | | | | | | | | | | | | CDR 3 | |
|---|---|---|---|---|---|---|---|---|---|---|---|---|---|---|---|---|---|---|
| $V_H$ | 80 | 81 | 82 | 82a | 82b | 82c | 83 | 84 | 85 | 86 | 87 | 88 | 89 | 90 | 91 | 92 | 93 | 94 | 95 | 96 |
| Vernier | | | | | | | | | | | | | | | | | • | • | | |
| Abet0144-GL | L | Q | M | N | S | L | R | A | E | D | T | A | V | Y | Y | C | A | R | E | W |
| Abet0343 | | | | | | | | | | | | | | | | | | | | |
| Abet0369 | | | | | | | | | | | | | | | | | | | | |
| Abet0377 | | | | | | | | | | | | | | | | | | | | |
| Abet0380 | | | | | | | | | | | | | | | | | | | | |
| Abet0382 | | | | | | | | | | | | | | | | | | | | |

| Kabat Numbering | CDR 3 | | | | | | | | | | | FW 4 | | | | | | |
|---|---|---|---|---|---|---|---|---|---|---|---|---|---|---|---|---|---|---|
| $V_H$ | 97 | 98 | 99 | 100 | 100a | 100b | 100c | 100d | 100e | 100f | 100g | 100h | 101 | 102 | 103 | 104 | 105 | 106 | 107 | 108 |
| Vernier | | | | | | | | | | | | | | | | | | | | |
| Abet0144-GL | M | D | H | S | R | P | Y | Y | Y | Y | G | M | D | V | W | G | D | S | V | K |
| Abet0343 | | | | | | | | | | | | | | | | | | | | |
| Abet0369 | | | | | | | | | | | | | | | | | | | | |
| Abet0377 | | | | | | | | | | | | | | | | | T | | | |
| Abet0380 | | | | | | | | | | | | | | | | | | | | |
| Abet0382 | | | | | | | | | | | | | | | | | | | | |

TABLE 8-continued

Sequence alignment of the V_H domains of the five clones selected for germlining. The two residues that were reverted to germline are indicated by italicized text. The positions of the Vernier residues are indicated by circles (•).

| | Kabat Numbering V_H | FW 4 | | | | |
|---|---|---|---|---|---|---|
| | | 109 | 110 | 111 | 112 | 113 |
| | Vernier | | | | • | |
| Abet0144-GL | | G | R | F | T | I |
| Abet0343 | | | | | | |
| Abet0369 | | | | | | |
| Abet0377 | | | | | | |
| Abet0380 | | | | | | |
| Abet0382 | | | | | | |

TABLE 9

Sequence alignment of the VL domains of the five clones selected for germlining. The thirteen residues that were reverted to germline are indicated by italicized text. The positions of the Vernier residues are indicated by circles (•). The Vernier 2 residue in Abet0343 was reverted to germ-line at the same time as residues 1 and 3. Reverting this residue did not impact on antibody potency.

| Kabat Numbering V_L | FW 1 | | | | | | | | | | | | | | | | | | | | | |
|---|---|---|---|---|---|---|---|---|---|---|---|---|---|---|---|---|---|---|---|---|---|---|
| | 1 | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
| Vernier | | • | | • | | | | | | | | | | | | | | | | | | | |
| Abet0144-GL | S | Y | E | L | T | Q | P | P | S | — | V | S | V | S | P | G | Q | T | A | S | I | T | C |
| Abet0343 | *Q* | *S* | *V* | | | | | | | | | | | | | | | | | | | | |
| Abet0369 | | | *G* | | | | | | | | | | | | | | | | | | | | |
| Abet0377 | | | | | | | | | | | | | | | | | | | | | | | |
| Abet0380 | | | | | | | | | | | | | | | | | | | | | | | |
| Abet0382 | | | | | *I* | | | | | | | | | | | | | | | | | | |

| Kabat Numbering V_L | CDR 1 | | | | | | | | | | | FW 2 | | | | | | | | | | | |
|---|---|---|---|---|---|---|---|---|---|---|---|---|---|---|---|---|---|---|---|---|---|---|---|
| | 23 | 24 | 25 | 26 | 27 | 28 | 29 | 30 | 31 | 32 | 33 | 34 | 35 | 36 | 37 | 38 | 39 | 40 | 41 | 42 | 43 | 44 | 45 |
| Vernier | | | | | | | | | | | | • | • | | | | | | | | | | • |
| Abet0144-GL | S | G | H | N | L | E | D | K | F | A | S | W | Y | Q | Q | K | P | G | Q | S | P | V | L |
| Abet0343 | | | | | | | | | | | | | | | | | *S* | | | | | | |
| Abet0369 | | | R | | I | G | | S | W | V | A | | | | | | | | | | | | |
| Abet0377 | | | | | T | | H | | W | I | | | | | | | | | | | | | |
| Abet0380 | | | | | | | | | | | | | | | | | | | | | | | |
| Abet0382 | | | | | | | | | | | | | | | | | | | | | | | |

| Kabat Numbering V_L | FW 2 | | | CDR 2 | | | | | | FW 3 | | | | | | | | | | | | | |
|---|---|---|---|---|---|---|---|---|---|---|---|---|---|---|---|---|---|---|---|---|---|---|---|
| | 46 | 47 | 48 | 49 | 50 | 51 | 52 | 53 | 54 | 55 | 57 | 58 | 59 | 60 | 61 | 62 | 63 | 64 | 65 | 66 | 67 | 68 | 69 |
| Vernier | • | • | • | | | | | | | | | | | | | | | • | | • | | • | • |
| Abet0144-GL | V | I | Y | R | D | D | K | R | P | S | G | I | P | E | R | F | S | A | S | N | S | G | H |
| Abet0343 | | | | | | | | | | | | | | | | | | | | | | | |
| Abet0369 | | | | | | | | | | | | | | | | | | | | | | | |
| Abet0377 | | | | | | | | | | | | | | | | | | | *T* | | | | |
| Abet0380 | | | | | | | | | | | | | | | | | | | | | | | |
| Abet0382 | | | | | | | | | | | | | | | | | | | *T* | | | | |

| Kabat Numbering V_L | FW 3 | | | | | | | | | | | | | | | | | | CDR 3 | | | |
|---|---|---|---|---|---|---|---|---|---|---|---|---|---|---|---|---|---|---|---|---|---|---|
| | 70 | 71 | 72 | 73 | 74 | 75 | 76 | 77 | 78 | 79 | 80 | 81 | 82 | 83 | 84 | 85 | 86 | 87 | 88 | 89 | 90 | 91 | 92 |
| Vernier | | • | | | | | | | | | | | | | | | | | | | | | |
| Abet0144-GL | T | A | T | L | T | I | S | G | T | Q | A | M | D | E | A | D | Y | Y | C | Q | A | Q | D |
| Abet0343 | | | | | | | | | | | | *T* | | | | | | | | S | S | | |
| Abet0369 | | | | | | | | | | | | *T* | | | | | | | | S | S | | |
| Abet0377 | | | | | | | | | | | | *T* | | | | | | | | S | S | | |
| Abet0380 | | | | | | | | | | | | *T* | | | | | | | | S | S | | |
| Abet0382 | | | | | | | | | | | | *T* | | | | | | | | S | S | | |

TABLE 9-continued

Sequence alignment of the VL domains of the five clones selected for germlining. The thirteen residues that were reverted to germline are indicated by italicized text. The positions of the Vernier residues are indicated by circles (•). The Vernier 2 residue in Abet0343 was reverted to germ-line at the same time as residues 1 and 3. Reverting this residue did not impact on antibody potency.

| Kabat | CDR 3 | | | | | FW 4 | | | | | | | | |
|---|---|---|---|---|---|---|---|---|---|---|---|---|---|---|
| Numbering $V_L$ | 93 | 94 | 95 | 96 | 97 | 98 | 99 | 100 | 101 | 102 | 103 | 104 | 105 | 106 | 107 |
| Vernier | | | | | | | | | | | | | | | • |
| Abet0144-GL | S | T | T | R | V | F | G | G | G | T | K | L | T | V | L |
| Abet0343 | | T | V | | | | | | | | | | | | |
| Abet0369 | | T | V | | | | | | | | | | | | |
| Abet0377 | | T | V | | | | | | | | | | | | |
| Abet0380 | | T | V | | | | | | | | | | | | |
| Abet0382 | | K | V | | | | | | | | | | | | |

3.10 Determination of the Binding Kinetics of Affinity-Optimised IgGs Using Surface Plasmon Resonance Surface Plasmon Resonance was used to analyse the binding kinetics of the affinity-optimised IgGs (section 3.8) and their germlined counterparts (section 3.9). Briefly, the BIAcore T-100 (GE Healthcare, UK) biosensor instrument was used to assess the kinetic parameters of the interaction between each test IgG and synthetically-produced human Amyloid beta 1-42 peptide. These experiments were performed essentially as described by Karlsson et al. (Karlsson et al., 1991). For further details see section 1.7.

The affinity of binding between each test IgG and human Amyloid beta 1-42 was estimated using assays in which each antibody was non-covalently captured by a protein G surface that was itself amine linked to a proprietary CM5 chip. The chip surface was regenerated between cycles by paired 40 second injections of 10 mM Glycine pH 2.0 to remove ligand and bound antibody. The test antibody was then reapplied for each peptide injection.

A series of dilutions of synthetic human Amyloid beta 1-42 peptide (0.063-1024 nM) were sequentially passed over the antibody surface for a sufficient amount of time to observe sensorgrams that could be fitted to an appropriate binding model with confidence. Blank reference flow-cell data were subtracted from each IgG dataset and a zero-concentration antibody-only buffer blank was double-reference subtracted from the main dataset. An appropriate binding model was then fitted simultaneously to the data from each analyte titration using the BIAevaluation software.

The validity of the data was assessed using the calculated Chi$^2$ value, with an acceptable value being under 2 RU$^2$. The overall success of the fit was estimated using the residuals, with a deviation of under 2 RUs being acceptable.

Figure 12:
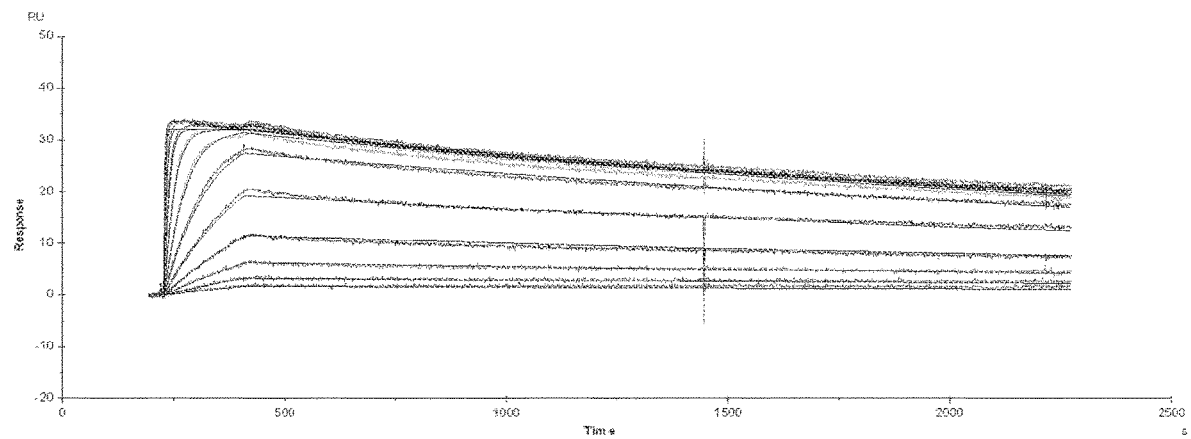
FIG. 12 shows the Surface Plasmon Resonance (BIAcore) traces for human Amyloid beta 1-42 peptide binding to immobilised Abet0380-GL IgG1-TM antibody at concentrations from 1024 nM (top trace) to 63 pM (bottom trace) peptide. Each trace is fitted to a 1:1 Langmuir model.

Example results for Abet0380-GL (germlined) IgG1-TM are shown in FIG. 12. The association rate constant (ka), dissociation rate constant (kd) and dissociation constant (KD) are $9.52 \times 10^5$ M$^{-1}$ s$^{-1}$, $3.07 \times 10^{-4}$ s$^{-1}$ and 322 pM respectively. These parameters were derived from a 1:1 Langmuir fit to the data.

3.11 Specificity Profiling of Affinity-Optimised IgGs Using Surface Plasmon Resonance Surface Plasmon Resonance was used to verify the specificity of the affinity-optimised IgGs for the human Amyloid beta 1-42 peptide. Briefly, the BIAcore2000 (GE Healthcare, UK) biosensor instrument was used to assess the kinetic parameters of the interaction between each test IgG and a range of small peptides including synthetically-produced human Amyloid beta 1-42 and human Amyloid beta 1-40. These experiments were performed essentially as described by Karlsson et al. (Karlsson et al., 1991). For further details see section 1.7.

The interaction between each test IgG and each peptide was estimated using assays in which the antibody was non-covalently captured by a protein G surface that was itself amine linked to a proprietary CM5 chip. The interaction between antibody and peptide was observed using a 5 application single cycle approach. The chip surface was regenerated between cycles by paired 40 second injections of 10 mM Glycine pH 2.0 to remove ligand and bound antibody. The test antibody was then reapplied for each peptide injection cycle.

Each test peptide (between 64 and 1024 nM) was sequentially passed over the antibody surface for a sufficient amount of time to observe sensorgrams that either showed no binding or that could be fitted to an appropriate binding model with confidence. Blank reference flow-cell data were subtracted from each IgG dataset and a zero-concentration antibody-only buffer blank was double-reference subtracted from the main dataset.

Figure 13:
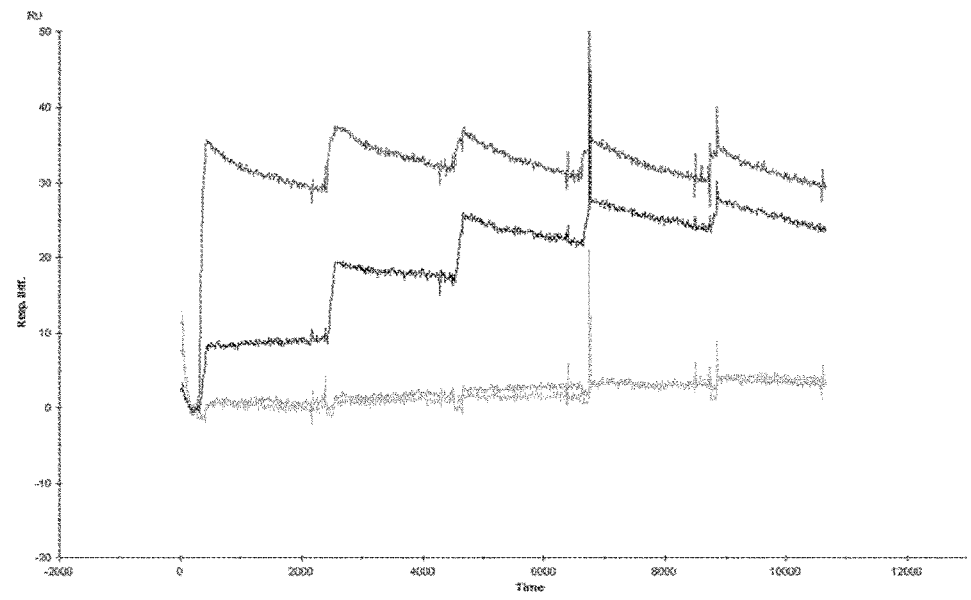
FIG. 13 shows the Surface Plasmon Resonance (BIAcore) traces for a series of Amyloid beta peptides binding to immobilised Abet0380-GL IgG1-TM antibody. There is clear binding to the biotinylated human Amyloid beta 1-42 peptide (top trace) and the unlabelled murine Amyloid beta 1-42 peptide (second trace). There is no discemable binding to biotinylated human Amyloid beta 1-40 peptide or unlabelled murine Amyloid beta 1-40 peptide (flat lines).

Example results for Abet0380-GL (germlined) IgG1-TM are shown in FIG. 13. Two peptides (biotinylated human Amyloid beta 1-42, (rPeptide, USA; cat: A1117) and unlabelled murine Amyloid beta 1-42 (rPeptide, USA; cat: A1008) showed strong binding to the antibody, whilst two peptides biotinylated human Amyloid beta 1-40 (rPeptide, USA; cat: A1111) and unlabelled murine Amyloid beta 1-40 (rPeptide, USA; cat: A1007) showed no binding to the antibody.

3.12 Affinity of the Most Potent IgGs for Native Amyloid Beta Using In Vitro Immunohistochemistry The most potent IgGs were tested for their ability to bind to Amyloid beta, with the aim of estimating the affinity of these clones for native forms of the Amyloid beta peptide. Briefly, the lead antibodies were screened on human Alzheimer's Disease brain sections and Tg2576 mouse brain sections to identify anti-Amyloid beta 1-42 antibodies that bound to Amyloid plaques in vitro. The experiments were performed essentially as described in section 1.9.

In these experiments, human brain tissue was isolated from the frontal cortex of two individuals with severe Alzheimer's Disease (ApoE genotype 3/3, Braak stage 6 and ApoE genotype 4/3, Braak stage 5). As a control, equivalent tissue was isolated from one non-dementia individual (ApoE genotype 3/3, Braak stage 1). Mouse brain tissue was isolated from Tg2576 mice at an age of 15 months (2 mice) and 22 months (2 mice). Antibodies were tested at concentrations of 2, 5, 10 and 20 ug ml$^{-1}$.

Figure 14:
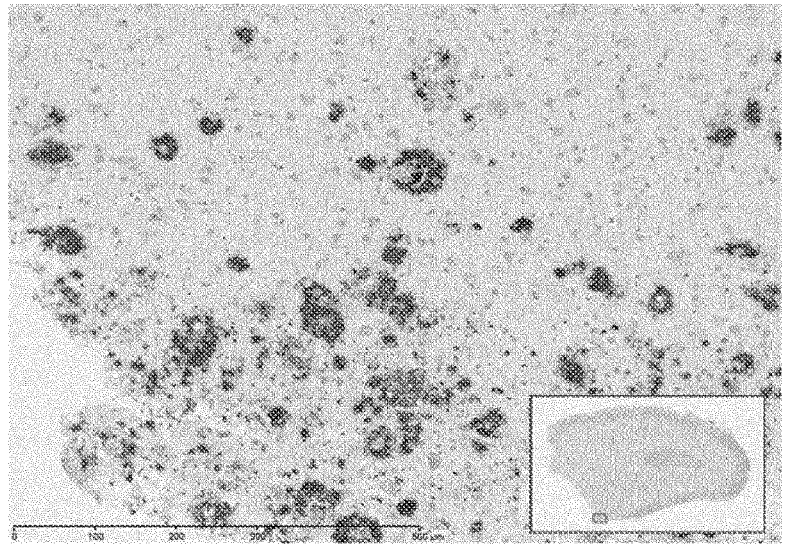
FIG. 14 shows sample images from the in vitro immunohistochemical staining of Abet0380-GL IgG1-TM. (A) A positive control antibody shows strong plaque recognition (score=4) on human AD brain sections (ApoE genotype 3/3, Braak stage 6; 5 μg/ml antibody). (B) The Abet0380-GL IgG1-TM lead clone shows strong plaque recognition (score=3) on an adjacent brain section (10 μg/ml). (C) The same positive control antibody shows strong plaque recognition (score=4) on Tg2576 mouse brain sections (22 month old mice; 20 μg/ml antibody). (D) The Abet0380-GL IgG1-TM lead clone shows strong plaque recognition (score=4) on an adjacent mouse brain section (20 μg/ml).
Figure 14:
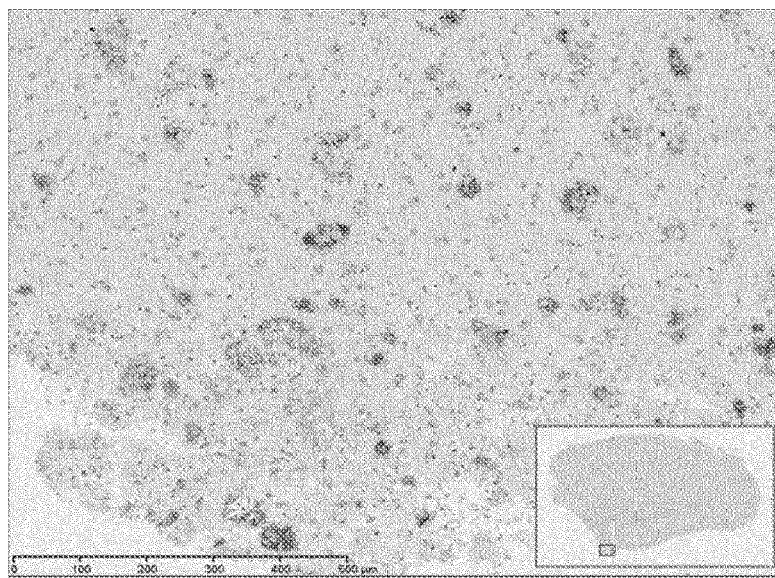
Figure 14:
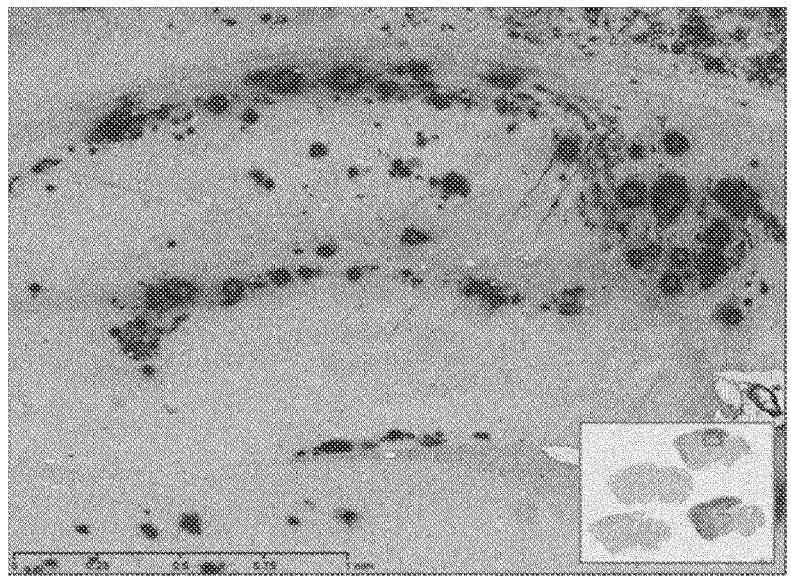
Figure 14:
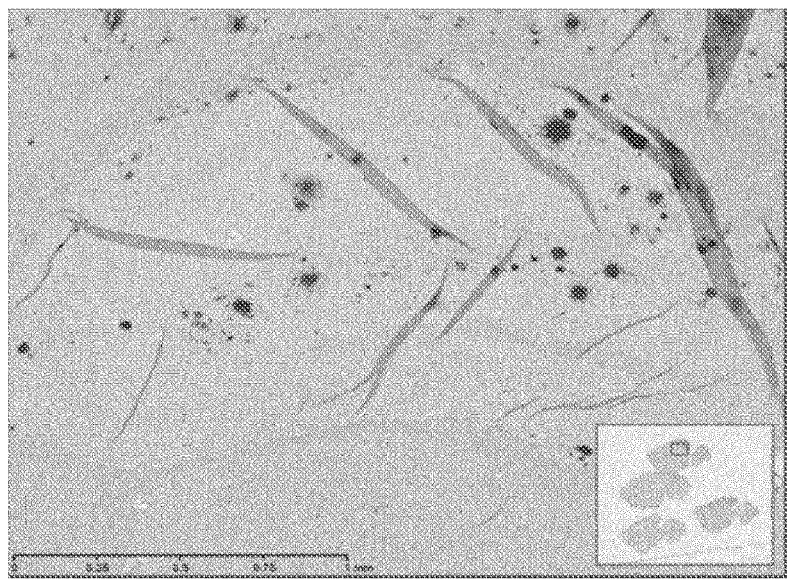

In one experiment, the Abet0380-GL IgG1-TM antibody stained core plaques (CP) with a score of 4 on Tg2576 brain sections, and a score of 3 on human AD brain sections. It also stained diffuse plaques (DP) and cerebral amyloid angiopathy (CAA) plaques, but to a lesser extent. In contrast, a positive control antibody produced a score of 3-4 on all plaques (CP, DP, CAA) on adjacent sections under the same conditions. Representative images are shown in FIG. 14.

3.13 Demonstrating Abet0380-GL IgG1-TM Abeta42 Recognition Profile by Western Blot To cross-link the Aβ42 oligomers before SDS-PAGE, PICUP (photo-induced cross-linking of peptides) was carried out as follows. A 1 mM solution of Ru(Bpy) was created by adding 2 µl of stock (at 10 mM) to 18 µl of 1×PBS. In addition, a 20 mM solution of ammonium persulphate (APS) was created by adding 2 µl of stock (at 200 mM) to 18 µl of 1×PBS. Unused stock was immediately snap-frozen on dry ice and returned to the −80° C. freezer. In the dark room, 5 µl of Ru(Bpy) was added to 80 ul of aggregate (neat 10 uM sample), followed by 5 µl of APS. Samples were irradiated with a lamp in the dark room for 10 secs. 30 uls of (4×) LDS Sample buffer was added immediately.

SDS-PAGE was then performed on cross-linked (PICUP) and non-cross-linked Aβ1-42 aggregate. The solutions were incubated in a hot block at 70° C. for 10 minutes. Meanwhile, a marker was created by combining 5 µl of Magic Mark XP Western Protein Standard, 5 µl of Novex Sharp Pre-stained Protein Standard. After the ten-minute incubation, the samples plus marker were loaded onto a NuPAGE Novex 4-12% Bis-Tris Gels (1.0 mm, 15 well, 15 µl per well) with MES running buffer. The gels were run at 200 V for 35 minutes.

The gel was then blotted onto a PVDF membrane using an iBlot machine from Invitrogen, for 7 minutes at 20V (program P3).

Once blotting was complete, the gel stack was disassembled and the PVDF membrane was then blocked in 50 ml of 4% MPBST (4% Marvel in PBST) for one hour at room temperature with gentle rotation. The blots were then cut with a scalpel for probing with individual antibodies. This was a 1 hour incubation with the primary antibody solution (2 ug/ml in 10 ml of 3% MPBST).

Next, the membrane was washed 5× with PBST, 5 minutes each, and was then incubated in secondary antibody solution (1 µl anti-human Fc specific—HRP conjugate in 10 ml of PBST) for 1 hour at room temperature. The membrane was washed 3× with PBST and 2× with PBS, 5 minutes each.

Figure 15:
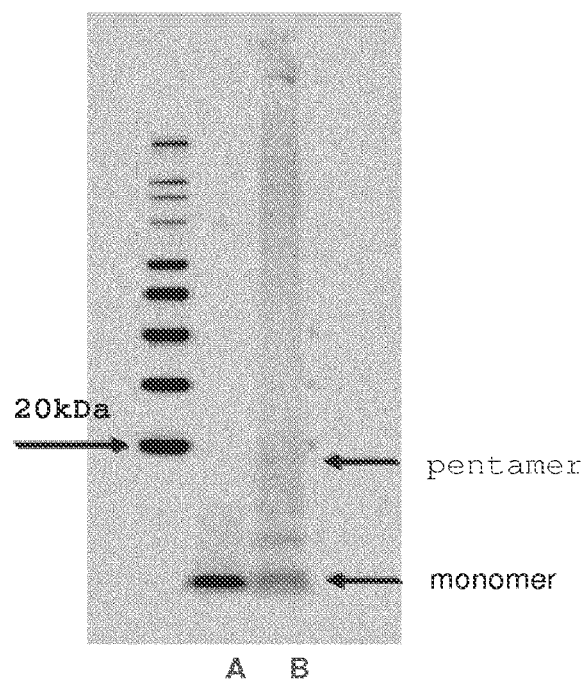
FIG. 15 shows Western Blot analysis of Abeta 42 aggregate preparation and detection using the Abet0380-GL IgG1TM. (A) Abet0380-GL IgG1TM detection of non-photo cross-linked (non PICUP) Aβ42 aggregate. (B) Abet0380-GL IgG1TM detection of photo cross-linked Aβ42 aggregate (PICUP). Here we demonstrate that Abet0380-GL IgG1TM specifically recognises Aβ1-42 monomer and low n oligomer species up to and including pentamer.

During the final washes, the chemi-luminescence SuperSignal West Dura substrate (Thermo Scientific; 34075) were allowed to warm to room temperature. 600 ul of each of the 2 solutions were combined. The PBS was decanted from the PVDF membrane, and then a pipette was used to cover the membrane with the mixed Dura reagents. The reaction was allowed to proceed for ~5 minutes (during which time the VerscDoc Imaging System was set up) and then an image was taken with 30 sec exposure (with enhancement using the transform filter). A representative image is shown in FIG. 15.

Example 4. Studies Demonstrating a Specific Functional Response of Abet0380-GL IgG1-TM Antibody In Vivo 4.1 Functional Characterisation of Abet0380-GL IgG1-TM by Reduction of Fee Amyloid Beta 1-42 Peptide In Vivo Eight-week old male albino Harlan Sprague-Dawley rats (n=8-12) received a single dose of Abet0380-GL IgG1-TM antibody by intravenous injection with a dosing vehicle of 25 mM Histidine, 7% Sucrose, 0.02% p80 surfactant, pH 6.0 at 5 ml/kg. Dosing solutions were made just before dosing. Animals were anaesthetised at the time indicated and cerebrospinal fluid (CSF) was aspirated from the cisterna magna. CSF samples were centrifuged for 10 minutes at approximately 3000× g at 4° C. within 20 minutes of sampling to remove cells or debris. Samples were then frozen on dry ice and stored at −70° C. for subsequent analysis.

Animals were sacrificed by decapitation, brain tissue was dissected and Amyloid beta peptides were extracted from brain tissue in diethylamine (DEA; Fluka, Sigma, UK; cat: 31729). Briefly, frozen brain tissue was homogenised in 0.2% DEA and 50 mM NaCl (Merck, USA; cat: 1.06404.1000). Brain homogenates were ultracentrifuged at 133,000×g, for 1 hour. Recovered supernatants were neutralised to pH 8.0 with 2 M Tris-HCl (TRIZMA®-hydrochloride; Sigma, UK; cat: 93363) and stored at −70° C. until analysis. Animal experimentations were performed in accordance with relevant guidelines and regulations provided by the Swedish Board of Agriculture. The ethical permission was provided by an ethical board specialised in animal experimentations: the Stockholm Södra Animal Research Ethical Board.

Measurement of free Amyloid beta 1-42 peptide in rat CSF was conducted using immunoprecipitation to remove Abet0380-GL bound Amyloid beta 1-42 peptide, followed by analysis by a commercial ELISA kit obtained from Invitrogen. Briefly, a solution of protein A beads (Dynabeads® Protein A; Invitrogen, UK; cat: 100-02D) was added to a 96 well non-skirted plate (polypropylene 0.2 ml; VWR International, UK; cat: 10732-4828) and washed twice with TBST (50 mM TBS; Sigma, UK; cat: T6664 plus 0.1% Tween20) using a magnet (DynaMag™ 96 side; Invitrogen, UK; cat: 123.31D) to separate the beads from the solution. Thawed rat CSF samples (40 µl) were added to each well and incubated at 40° C. with tilt rotation for 1 hour. The beads were then pelleted using the magnet and 30 µl of immunoprecipitated CSF samples were transferred to a 96 well plate from the ELISA kit (mouse Amyloid beta (1-42) colorimetric ELISA kit; Invitrogen, UK; cat: KMB3441) with 70 µl of the Standard Diluent Buffer already added (supplemented with protease inhibitor; Roche, UK; cat: 11836153001). Calibration standard samples were added to the plate in duplicate and the plate was incubated for 2 hours at room temperature with shaking. The plate was washed 4 times with 400 µl of wash buffer, 100 µl of the detection antibody solution was added to each well and the plate was incubated for 1 hour at room temperature with shaking. Again, the plate was washed 4 times with 400 µl of wash buffer, 100 µl of the secondary antibody working solution was added to each well and the plate was incubated for 30 minutes at room temperature with shaking. Finally, the plate was washed 4 times with 400 µl of wash buffer, 100 µl of stabilised Chromogen was added to each well and the plate was incubated for 30 minutes at room temperature in the dark. To stop the reaction, 100 µl of Stop Solution was added to each well and the plate was read within 2 hours at an absorbance of 450 nm. Single CSF samples were analyzed and data analysis was performed using Prism 4 (GraphPad, USA) with one-way ANOVA on log transformed data without adjustment for multiple comparisons.

Measurement of total (free and Abet0380-GL bound) Amyloid beta 1-42 peptide in rat brain homogenates was performed using modifications of the mouse Amyloid beta (1-42) colorimetric ELISA kit (Invitrogen, UK; cat: KMB3441). The kit detection antibody was replaced by an excess of Abet0380-GL IgG1-TM antibody and the secondary antibody by an anti-human IgG HRP-conjugate antibody (Jackson ImmunoResearch, UK; cat: 109-035-098). Briefly, thawed brain homogenates of 50 µl diluted 1:2 in Sample Diluent (supplemented with protease inhibitor; Roche, UK; cat: 11836153001) and standard samples were added in duplicate to the 96 well ELISA plate. An excess of Abet0380-GL IgG1-TM antibody (50 µl, 4 pg/ml) was added to each well and the plate was then incubated for 3 hours at room temperature. The plate was washed 4 times with 400 µl of wash buffer, 100 µl of the secondary antibody working solution was added to each well and the plate was incubated for 30 minutes at room temperature. Finally, the plate was washed 4 times with 400 µl of wash buffer, 100 µl of stabilised Chromogen was added to each well and the plate was incubated for 15 minutes at room temperature in the dark. To stop the reaction, 100 µl of Stop Solution was added to each well and the plate was read within 2 hours at an absorbance of 450 nm. Data analysis was performed using Prism 4 (GraphPad, USA) with one-way ANOVA on log transformed data without adjustment for multiple comparisons.

Measurement of total Amyloid beta 1-40 peptide in rat brain homogenates was performed using the mouse Amyloid beta (1-40) colorimetric ELISA kit (Invitrogen, UK; cat: KMB3481). Briefly, thawed brain homogenates of 50 µl and standard samples, diluted in Sample Diluent (supplemented with protease inhibitor; Roche, UK; cat: 11836153001), were added in duplicate to the 96 well ELISA plate. 50 µl of the detection antibody solution were added to each well and the plate was incubated for 3 hours at room temperature. The plate was washed 4 times with 400 µl of wash buffer, 100 µl of the secondary antibody working solution was added to each well and the plate was incubated for 30 minutes at room temperature. Finally, the plate was washed 4 times with 400 µl of wash buffer, 100 µl of stabilised Chromogen was added to each well and the plate was incubated for 30 minutes at room temperature in the dark. To stop the reaction, 100 µl of Stop Solution was added to each well and the plate was read within 2 hours at an absorbance of 450 nm. Data analysis was performed using Prism 4 (GraphPad, USA) with one-way ANOVA on log transformed data without adjustment for multiple comparisons.

4.2 Functional Characterisation of Abet0380-GL IgG1-TM by Reduction of Free Amyloid Beta 1-42 Peptide In Vivo A single dose of the Abet0380-GL IgG1-TM antibody at 20 mg/kg reduced the CSF level of free Amyloid beta 1-42 peptide in rats to the limit of quantification at 72 or 168 hours after dose in the assay described in Section 4.1 (data not shown). To further investigate the effect of the Abet0380-GL IgG1-TM antibody in vivo, rats were administered weekly doses of 0.25, 0.5, 1, 5 or 10 mg/kg over 14 days. Animals were euthanized 168 hours after the second dose to measure levels of free Amyloid beta 1-42 peptide in CSF as well as total Amyloid beta 1-42 or 1-40 peptides in brain tissue.

Figure 16:
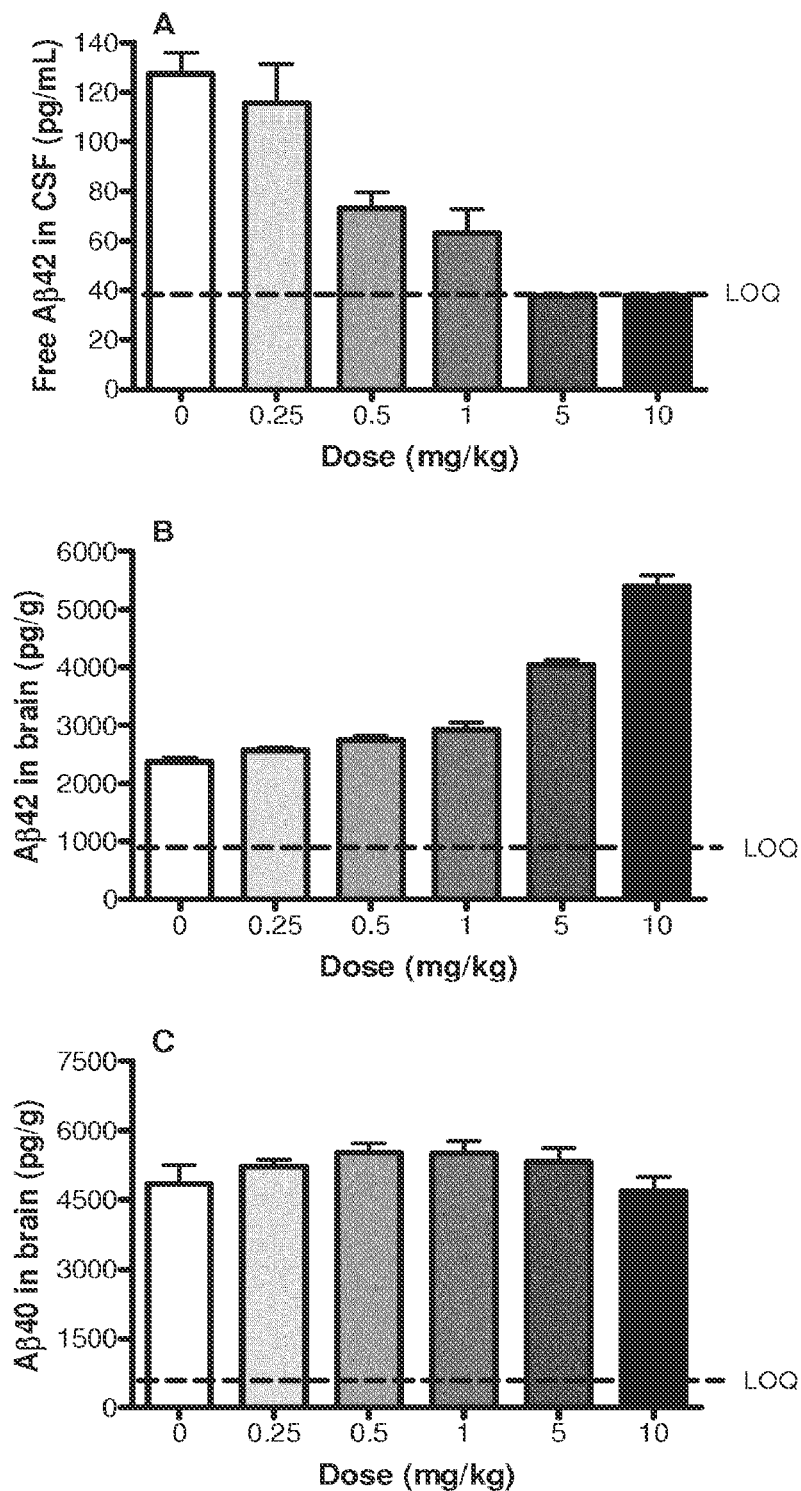
FIG. 16 shows the dose-dependent reduction of the level of free Amyloid beta 1-42 peptide in the CSF (A), the increase of total Amyloid beta 1-42 peptide in brain tissue (B) and the unaffected levels of total Amyloid beta 1-40 peptide in brain tissue (C) by increasing doses of Abet0380-GL IgG1-TM antibody in Sprague-Dawley rats receiving repeated weekly doses over 14 days.

A dose-dependent decrease of free Amyloid beta 1-42 was demonstrated in CSF (FIG. 16A). The two highest doses of 5 and 10 mg/kg reduced Amyloid beta 1-42 peptide to the limit of quantification in the assay used, whereas doses of 0.5 and 1 mg/kg significantly reduced Amyloid beta 1-42 peptide by 47% and 61% respectively when compared to the vehicle control. The lowest dose, 0.25 mg/kg, gave a 14% reduction of free Amyloid beta 1-42 peptide in CSF, but failed to reach statistical significance. Due to sequestration of Amyloid beta 1-42 peptide by Abet0380-GL IgG1-TM antibody, a dose-dependent increase of total Amyloid beta 1-42 peptide was demonstrated in brain tissue (FIG. 16B). However, the level of total Amyloid beta 1-40 peptide in brain tissue was unaffected (FIG. 16C), thus demonstrating the specificity of Abet0380-GL IgG1-TM for Amyloid beta 1-42 peptide. In summary, the above results from rat studies showed that the Abet0380-GL IgG1-TM antibody reduced the level of free Amyloid beta 1-42 peptide in CSF with an $ED_{50}$ between 0.5 and 1 mg/kg.

4.3 Functional Characterisation of Abet0380-GL IgG1TM—Demonstration of Non Plaque Binding In Vivo—No Binding of Abet0380-GL IgG1-TM to Amyloid Beta Plaques In Vivo 168 Hours after a Peripheral Dose to Aged Tg2576 Mice Abet0380-GL IgG1-TM was tested for its ability to bind to Amyloid beta plaques in aged Tg2576 mice after a single peripheral dose. Animal experimentations were performed in accordance with relevant guidelines and regulations provided by the Swedish Board of Agriculture. The ethical permission was provided by an ethical board specialised in animal experimentations: the Stockholm Södra Animal Research Ethical Board.

Seventeen-month old female Tg2576 mice (n=5) received a single dose of vehicle, a positive control antibody at 30 mg/kg or the Abet0380-GL IgG1-TM antibody at 10 or 30 mg/kg by intravenous injection with a dosing vehicle of 25 mM Histidine, 7% Sucrose, 0.02% p80 surfactant, pH 6.0 at 5 mL/kg. At 168 hours after dose, animals were deeply anaesthetised and perfused with room temperature PBS followed by cold (4° C.) phosphate buffered 4% paraformaldehyde (PFA). Animals were then sacrificed by decapitation and brains were dissected and immersions fix in PFA at 4° C. for 72 hours. The fixative was exchanged to PBS containing 0.1% sodium azide and tissues were stored at 4° C. until further processed.

Immunohistochemistry was performed on brain sections to evaluate the degree of binding of Abet0380-GL IgG1-TM to Amyloid beta plaques in vivo. Briefly, paraffin embedded brain sections were prepared for immunohistochemistry as described in section 1.9. Detection of Abet0380-GL IgG1-TM or the positive control antibody deposited within brain parenchyma was conducted using a rabbit-anti-mouse IgG1 and IgG2-specific secondary antibody from Epitomics. The staining was performed on the Ventana robot, using the OmniMap detection system (Ventana Medical Systems, USA). For spiking ex vivo, consecutive tissue sections were stained in vitro with the injected Abet0380-GL IgG1-TM or positive control antibody in excess. Secondary antibodies and chromogenes were the same as above.

Scoring of the staining was carried out in a blinded fashion under 10× optical magnification. The distribution of decorated plaques was noted. The intensity of plaque labelling was scored according to a relative intensity scale from 0 (no staining of plaques) up to 4 (intense decoration of plaques).

Figure 17:
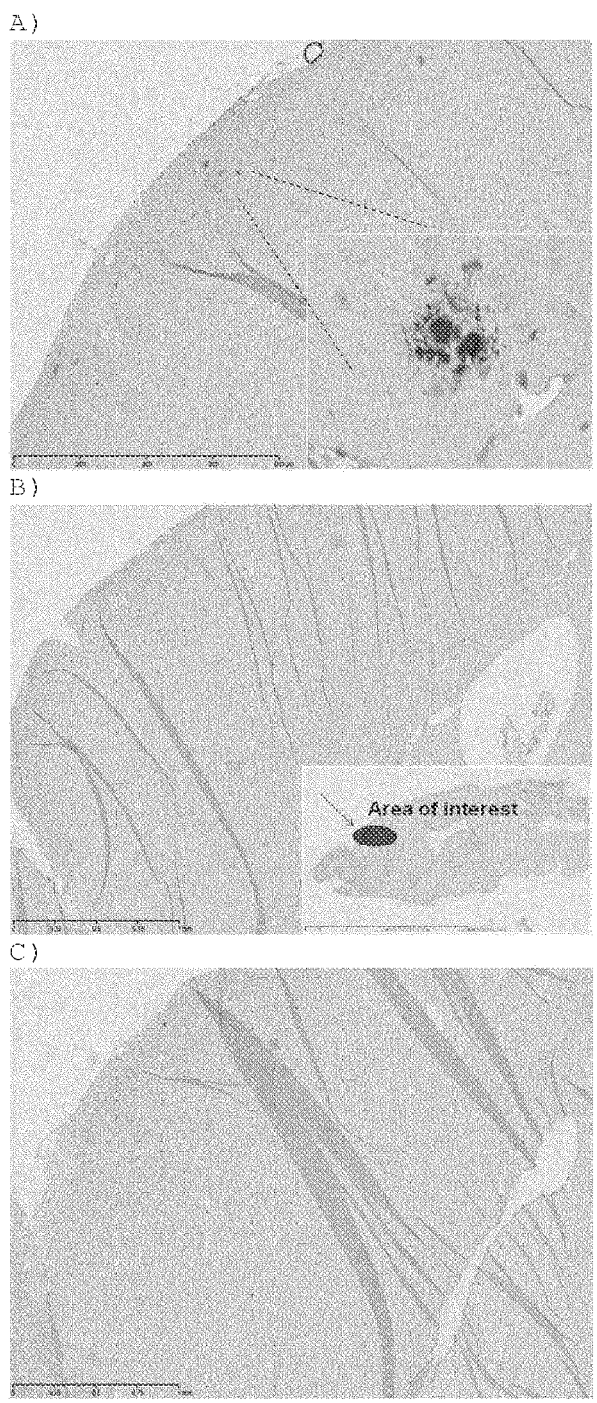
FIG. 17 shows sample images from the immunohistochemical analysis of binding of Abet0380-GL IgG1-TM to Amyloid beta plaques in vivo 168 hours after a peripheral dose to aged Tg2576 mice. A positive control antibody given at 30 mg/kg shows strong in vivo plaque recognition (A), whereas Abet0380-GL IgG1-TM given at 30(B) or 10(C) mg/kg does not show any in vivo plaque decoration.

Abet0380-GL IgG1-TM did not decorate Amyloid beta plaques or cerebral amyloid angiopathy (CAA) in vivo at 168 hours after a peripheral dose of 10 or 30 mg/kg. The positive control antibody demonstrated intense to low in vivo plaque decoration. A partial and focal distribution pattern was apparent, with core plaques, diffuse plaques and CAA in all animals. Representative images are shown in FIG. 17. Spiking ex vivo of brain tissue from the same animals with Abet0380-GL IgG1-TM and the positive control antibody confirmed the previously demonstrated ex vivo plaque binding capacity of the injected antibodies (not shown).

Example 5. Anti-AB1-42 Sequences

Examples of sequences of antibody molecules are listed in the appended sequence listing, including example antibody $V_H$ domains, VL domains, individual CDR sequences, sets of HCDRs, sets of LCDRs, and framework regions.

Sequences of the 24 optimised clones listed in Table 7 were compared. Tables 10 and 11 show % sequence identity between the $V_H$ and VL domains respectively.

TABLE 10

Sequence identity across the entire $V_H$ sequence (Kabat residues 1→113) of the twenty four non-germlined and the five germ-lined antibodies described herein. All sequences are within 86.4% of the Abet0380-GL lead clone.

| Homology of the $V_H$ domain | | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|
| | | | | | | | | Percent Identity | | | | | | | | |
| Abet0144-GL | 1 | | 94.4 | 92.8 | 92.0 | 90.4 | 88.0 | 91.2 | 87.2 | 90.4 | 90.4 | 92.8 | 88.8 | 89.6 | 89.6 | 93.6 |
| Abet0319 | 2 | 5.8 | | 94.4 | 91.2 | 90.4 | 88.0 | 90.4 | 88.0 | 88.0 | 88.8 | 87.2 | 86.4 | 88.8 | 87.2 | 93.6 |
| Abet0321b | 3 | 7.6 | 5.8 | | 91.2 | 89.6 | 88.0 | 89.6 | 88.8 | 88.8 | 90.4 | 87.2 | 87.2 | 87.2 | 88.8 | 92.0 |
| Abet0322b | 4 | 8.5 | 9.4 | 9.4 | | 88.0 | 85.6 | 88.0 | 85.6 | 87.2 | 87.2 | 85.6 | 86.4 | 86.4 | 86.4 | 90.4 |
| Abet0323b | 5 | 10.3 | 10.3 | 11.2 | 13.1 | | 90.4 | 89.6 | 88.8 | 90.4 | 90.4 | 90.4 | 88.0 | 88.0 | 89.6 | 88.8 |
| Abet0328 | 6 | 13.1 | 13.1 | 13.1 | 16.0 | 10.3 | | 88.8 | 88.8 | 90.4 | 88.8 | 87.2 | 88.0 | 87.2 | 87.2 | 88.8 |
| Abet0329 | 7 | 9.4 | 10.3 | 11.2 | 13.1 | 11.2 | 12.2 | | 86.4 | 89.6 | 90.4 | 88.8 | 87.2 | 89.6 | 89.6 | 88.8 |
| Abet0332 | 8 | 14.1 | 13.1 | 12.2 | 16.0 | 12.2 | 12.2 | 15.0 | | 87.2 | 88.8 | 85.6 | 84.8 | 86.4 | 86.4 | 87.2 |
| Abet0342 | 9 | 10.3 | 13.1 | 12.2 | 14.1 | 10.3 | 10.3 | 11.2 | 14.1 | | 92.8 | 90.4 | 92.8 | 88.0 | 91.2 | 87.2 |
| Abet0343 | 10 | 10.3 | 12.2 | 10.3 | 14.1 | 10.3 | 12.2 | 10.3 | 12.2 | 7.6 | | 89.6 | 90.4 | 88.8 | 92.0 | 87.2 |
| Abet0344 | 11 | 7.6 | 14.1 | 14.1 | 16.0 | 10.3 | 14.1 | 12.2 | 16.0 | 10.3 | 11.2 | | 87.2 | 90.4 | 89.6 | 86.4 |
| Abet0368 | 12 | 12.2 | 15.0 | 14.1 | 15.0 | 13.1 | 13.1 | 14.1 | 17.0 | 7.6 | 10.3 | 14.1 | | 88.0 | 89.6 | 85.6 |
| Abet0369 | 13 | 11.2 | 12.2 | 14.1 | 15.0 | 13.1 | 14.1 | 11.2 | 15.0 | 13.1 | 12.2 | 10.3 | 13.1 | | 88.0 | 86.4 |
| Abet0370 | 14 | 11.2 | 14.1 | 12.2 | 15.0 | 11.2 | 14.1 | 11.2 | 15.0 | 9.4 | 8.5 | 11.2 | 11.2 | 13.1 | | 87.2 |
| Abet0371 | 15 | 6.7 | 6.7 | 8.5 | 10.3 | 12.2 | 12.2 | 12.2 | 14.1 | 14.1 | 14.1 | 15.0 | 16.0 | 15.0 | 14.1 | |
| Abet0372 | 16 | 11.2 | 11.2 | 12.2 | 14.1 | 10.3 | 9.4 | 10.3 | 13.1 | 11.2 | 9.4 | 13.1 | 12.2 | 11.2 | 13.1 | 12.2 |
| Abet0373 | 17 | 11.2 | 14.1 | 14.1 | 15.0 | 13.1 | 15.0 | 12.2 | 14.1 | 7.6 | 9.4 | 13.1 | 10.3 | 14.1 | 12.2 | 15.0 |
| Abet0374 | 18 | 11.2 | 14.1 | 12.2 | 14.1 | 12.2 | 13.1 | 12.2 | 13.1 | 8.5 | 9.4 | 11.2 | 12.2 | 13.1 | 11.2 | 15.0 |
| Abet0377 | 19 | 11.2 | 13.1 | 13.1 | 15.0 | 9.4 | 12.2 | 12.2 | 14.1 | 9.4 | 6.7 | 12.2 | 12.2 | 14.1 | 12.2 | 15.0 |
| Abet0378 | 20 | 10.3 | 12.2 | 11.2 | 14.1 | 8.5 | 9.4 | 12.2 | 11.2 | 7.6 | 8.5 | 10.3 | 10.3 | 13.1 | 10.3 | 13.1 |
| Abel0379 | 21 | 12.2 | 15.0 | 13.1 | 15.0 | 13.1 | 16.0 | 13.1 | 15.0 | 12.2 | 13.1 | 14.1 | 12.2 | 17.0 | 13.1 | 16.0 |
| Abet0380 | 22 | 12.2 | 12.2 | 12.2 | 14.1 | 10.3 | 12.2 | 11.2 | 13.1 | 11.2 | 4.1 | 13.1 | 13.1 | 13.1 | 11.2 | 14.1 |
| Abet0381 | 23 | 13.1 | 14.1 | 15.0 | 16.0 | 12.2 | 13.1 | 11.2 | 15.0 | 12.2 | 14.1 | 14.1 | 15.0 | 13.1 | 12.2 | 14.1 |
| Abct0382 | 24 | 9.4 | 12.2 | 11.2 | 13.1 | 12.2 | 14.1 | 10.3 | 14.1 | 9.4 | 10.3 | 11.2 | 10.3 | 12.2 | 8.5 | 13.1 |
| Abet0383 | 25 | 13.1 | 18.0 | 16.0 | 18.0 | 15.0 | 17.0 | 17.0 | 14.1 | 13.1 | 12 2 | 13.1 | 15.0 | 17.0 | 15.0 | 19.1 |
| Abet0343-GL | 26 | 10.3 | 12.2 | 10.3 | 14.1 | 10.3 | 12.2 | 10.3 | 12.2 | 7.6 | 0.0 | 11.2 | 10.3 | 12.2 | 8.5 | 14.1 |
| Abet0369-GL | 27 | 10.3 | 11.2 | 13.1 | 14.1 | 12.2 | 13.1 | 10.3 | 14.1 | 12.2 | 11.2 | 9.4 | 12.2 | 0.8 | 12.2 | 14.1 |
| Abet0377-GL | 28 | 11.2 | 13.1 | 13.1 | 15.0 | 9.4 | 12.2 | 12.2 | 14.1 | 9.4 | 6.7 | 12.2 | 12.2 | 14.1 | 12.2 | 15.0 |
| Abet0380-GL | 29 | 11.2 | 11.2 | 11.2 | 13.1 | 9.4 | 11.2 | 10.3 | 12.2 | 10.3 | 3.3 | 12.2 | 12.2 | 12.2 | 10.3 | 13.1 |
| Abet0382-GL | 30 | 9.4 | 12.2 | 11.2 | 13.1 | 12.2 | 14.1 | 10.3 | 14.1 | 9.4 | 10.3 | 11.2 | 10.3 | 12.2 | 8.5 | 13.1 |
| | | | | | | | | Percent Divergence | | | | | | | | |

| Homology of the $V_H$ domain | | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|
| | | | | | | | | Percent Identity | | | | | | | | |
| Abet0144-GL | 1 | 89.6 | 89.6 | 89.6 | 89.6 | 90.4 | 88.8 | 88.8 | 88.0 | 91.2 | 88.0 | 90.4 | 90.4 | 89.6 | 89.6 | 91.2 |
| Abet0319 | 2 | 89.6 | 87.2 | 87.2 | 88.0 | 88.8 | 86.4 | 88.8 | 87.2 | 88.8 | 84.0 | 88.8 | 89.6 | 88.0 | 89.6 | 88.8 |
| Abet0321b | 3 | 88.8 | 87.2 | 88.8 | 88.0 | 89.6 | 88.0 | 88.8 | 86.4 | 89.6 | 85.6 | 90.4 | 88.0 | 88.0 | 89.6 | 89.6 |
| Abet0322b | 4 | 87.2 | 86.4 | 87.2 | 86.4 | 87.2 | 86.4 | 87.2 | 85.6 | 88.0 | 84.0 | 87.2 | 87.2 | 86.4 | 88.0 | 88.0 |
| Abet0323b | 5 | 90.4 | 88.0 | 88.8 | 91.2 | 92.0 | 88.0 | 90.4 | 88.8 | 88.8 | 86.4 | 90.4 | 88.8 | 91.2 | 91.2 | 88.8 |
| Abet0328 | 6 | 91.2 | 86.4 | 88.0 | 88.8 | 91.2 | 85.6 | 88.8 | 88.0 | 87.2 | 84.8 | 88.8 | 88.0 | 88.8 | 89.6 | 87.2 |
| Abet0329 | 7 | 90.4 | 88.8 | 88.8 | 88.8 | 88.8 | 88.0 | 89.6 | 89.6 | 90.4 | 84.8 | 90.4 | 90.4 | 88.8 | 90.4 | 90.4 |
| Abet0332 | 8 | 88.0 | 87.2 | 88.0 | 87.2 | 89.6 | 86.4 | 88.0 | 86.4 | 87.2 | 87.2 | 88.8 | 87.2 | 87.2 | 88.8 | 87.2 |
| Abet0342 | 9 | 89.6 | 92.8 | 92.0 | 91.2 | 92.8 | 88.8 | 89.6 | 88.8 | 91.2 | 88.0 | 92.8 | 88.8 | 91.2 | 90.4 | 91.2 |
| Abet0343 | 10 | 91.2 | 91.2 | 91.2 | 93.6 | 92.0 | 88.0 | 96.0 | 87.2 | 90.4 | 88.8 | 100.0 | 89.6 | 93.6 | 96.8 | 90.4 |
| Abet0344 | 11 | 88.0 | 88.0 | 89.6 | 88.8 | 90.4 | 87.2 | 88.0 | 87.2 | 89.6 | 88.0 | 89.6 | 91.2 | 88.8 | 88.8 | 89.6 |
| Abet0368 | 12 | 88.8 | 90.4 | 88.8 | 88.8 | 90.4 | 88.8 | 88.0 | 86.4 | 90.4 | 86.4 | 90.4 | 88.8 | 88.8 | 88.8 | 90.4 |
| Abet0369 | 13 | 89.6 | 87.2 | 88.0 | 87.2 | 88.0 | 84.8 | 88.0 | 88.0 | 88.8 | 84.8 | 88.8 | 99.2 | 87.2 | 88.8 | 88.8 |
| Abet0370 | 14 | 88.0 | 88.8 | 89.6 | 88.8 | 90.4 | 88.0 | 89.6 | 88.8 | 92.0 | 86.4 | 92.0 | 88.8 | 88.8 | 90.4 | 92.0 |
| Abet0371 | 15 | 88.8 | 86.4 | 86.4 | 86.4 | 88.0 | 85.6 | 87.2 | 87.2 | 88.0 | 83.2 | 87.2 | 87.2 | 86.4 | 88.0 | 88.0 |
| Abet0372 | 16 | | 88.8 | 88.0 | 90.4 | 90.4 | 86.4 | 91.2 | 90.4 | 89.6 | 84.8 | 91.2 | 90.4 | 90.4 | 92.0 | 89.6 |
| Abet0373 | 17 | 12.2 | | 88.0 | 89.6 | 90.4 | 88.8 | 88.0 | 87.2 | 91.2 | 87.2 | 91.2 | 88.0 | 89.6 | 88.8 | 91.2 |
| Abet0374 | 18 | 13.1 | 13.1 | | 88.8 | 90.4 | 89.6 | 88.8 | 87.2 | 90.4 | 88.8 | 91.2 | 88.8 | 88.8 | 89.6 | 90.4 |
| Abet0377 | 19 | 10.3 | 11.2 | 12.2 | | 91.2 | 88.0 | 92.0 | 86.4 | 88.8 | 86.4 | 93.6 | 88.0 | 100.0 | 92.8 | 88.8 |
| Abet0378 | 20 | 10.3 | 10.3 | 10.3 | 9.4 | | 88.8 | 89.6 | 88.0 | 92.0 | 87.2 | 92.0 | 88.8 | 91.2 | 90.4 | 92.0 |
| Abel0379 | 21 | 15.0 | 12.2 | 11.2 | 12.2 | 12.2 | | 86.4 | 84.8 | 88.0 | 87.2 | 88.0 | 85.6 | 88.8 | 86.4 | 88.0 |
| Abet0380 | 22 | 9.4 | 13.1 | 12.2 | 8.5 | 11.2 | 15.0 | | 87.2 | 88.0 | 86.4 | 96.0 | 88.8 | 92.0 | 99.2 | 88.0 |
| Abet0381 | 23 | 10.3 | 14.1 | 14.1 | 15.0 | 13.1 | 17.0 | 14.1 | | 88.8 | 83.2 | 87.2 | 88.8 | 86.4 | 88.0 | 88.8 |
| Abct0382 | 24 | 11.2 | 9.4 | 10.3 | 12.2 | 8.5 | 13.1 | 13.1 | 12.2 | | 86.4 | 90.4 | 89.6 | 88.8 | 88.8 | 100.0 |

TABLE 10-continued

Sequence identity across the entire $V_H$ sequence (Kabat residues 1→113) of the twenty four non-germlined and the five germlined antibodies described herein. All sequences are within 86.4% of the Abet0380-GL lead clone.

| | | | | | | | | | | | | | | | | | |
|---|---|---|---|---|---|---|---|---|---|---|---|---|---|---|---|---|---|
| Abet0383 | 25 | 17 0 | 14.1 | 12.2 | 15.0 | 14.1 | 14.1 | 15.0 | 19.1 | 15.0 | | | 88.8 | 85.6 | 86.4 | 87.2 | 86.4 |
| Abet0343-GL | 26 | 9.4 | 9.4 | 9.4 | 6.7 | 8.5 | 13.1 | 4.1 | 14.1 | 10.3 | 12.2 | | | 89.6 | 93.6 | 96.8 | 90.4 |
| Abet0369-GL | 27 | 10.3 | 13.1 | 12.2 | 13.1 | 12.2 | 16.0 | 12.2 | 12.2 | 11.2 | 16.0 | 11.2 | | | 88.0 | 89.6 | 89.6 |
| Abet0377-GL | 28 | 10.3 | 11.2 | 12.2 | 0.0 | 9.4 | 12.2 | 8.5 | 15.0 | 12.2 | 15.0 | 6.7 | 13.1 | | | 92.8 | 88.8 |
| Abet0380-GL | 29 | 8.5 | 12.2 | 11.2 | 7.6 | 10.3 | 15.0 | 0.8 | 13.1 | 12.2 | 14.1 | 3.3 | 11.2 | 7.6 | | | 88.8 |
| Abet0382-GL | 30 | 11.2 | 9.4 | 10.3 | 12.2 | 8.5 | 13.1 | 13.1 | 12.2 | 0.0 | 15.0 | 10.3 | 11.2 | 12.2 | 12.2 | | |
| | | | | | | | | Percent Divergence | | | | | | | | | |

TABLE 11

Sequence identity across the entire VL sequence (Kabat residues 1→107) of the twenty four non-germlined and the five germlined antibodies described herein. All sequences are within 88.7% of the Abet0380-GL lead clone.

| Homology of the $V_L$ domain | | Percent Identity | | | | | | | | | | | | | |
|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 |
| Abet0144-GL | 1 | | 89.6 | 94.3 | 93.4 | 93.4 | 92.5 | 90.6 | 89.6 | 99.1 | 91.5 | 91.5 | 92.5 | 87.7 | 92.5 | 89.6 |
| Abet0319 | 2 | 11.2 | | 93.4 | 93.4 | 92.5 | 91.5 | 94.3 | 91.5 | 88.7 | 90.6 | 86.8 | 92.5 | 93.4 | 84.0 | 95.3 |
| Abet0321b | 3 | 5.9 | 6.9 | | 97.2 | 97.2 | 96.2 | 94.3 | 88.7 | 93.4 | 95.3 | 91.5 | 96.2 | 91.5 | 86.8 | 93.4 |
| Abet0322b | 4 | 6.9 | 6.9 | 2.9 | | 96.2 | 95.3 | 94.3 | 89.6 | 92.5 | 94.3 | 90.6 | 95.3 | 92.5 | 86.8 | 93.4 |
| Abet0323b | 5 | 6.9 | 8.0 | 2.9 | 3.9 | | 97.2 | 93.4 | 87.7 | 92.5 | 94.3 | 90.6 | 95.3 | 90.6 | 85.8 | 92.5 |
| Abet0328 | 6 | 8.0 | 9.0 | 3.9 | 4.9 | 2.9 | | 92.5 | 86.8 | 91.5 | 93.4 | 89.6 | 94.3 | 91.5 | 85.8 | 91.5 |
| Abet0329 | 7 | 10.1 | 5.9 | 5.9 | 5.9 | 6.9 | 8.0 | | 89.6 | 89.6 | 91.5 | 87.7 | 93.4 | 93.4 | 84.9 | 95.3 |
| Abet0332 | 8 | 11.2 | 9.0 | 12.3 | 11.2 | 13.4 | 14.6 | 11.2 | | 88.7 | 85.8 | 84.9 | 87.7 | 89.6 | 84.9 | 91.5 |
| Abet0342 | 9 | 0.9 | 12.3 | 6.9 | 8.0 | 8.0 | 9.0 | 11.2 | 12.3 | | 90.6 | 90.6 | 91.5 | 86.8 | 91.5 | 88.7 |
| Abet0343 | 10 | 9.0 | 10.1 | 4.9 | 5.9 | 5.9 | 6.9 | 9.0 | 15.7 | 10.1 | | 96.2 | 95.3 | 89.6 | 84.0 | 90.6 |
| Abet0344 | 11 | 9.0 | 14.6 | 9.0 | 10.1 | 10.1 | 11.2 | 13.4 | 16.9 | 10.1 | 3.9 | | 91.5 | 85.8 | 84.0 | 86.8 |
| Abet0368 | 12 | 8.0 | 8.0 | 3.9 | 4.9 | 4.9 | 5.9 | 6.9 | 13.4 | 9.0 | 4.9 | 9.0 | | 90.6 | 84.9 | 92.5 |
| Abet0369 | 13 | 13.4 | 6.9 | 9.0 | 8.0 | 10.1 | 9.0 | 6.9 | 11.2 | 14.6 | 11.2 | 15.7 | 10.1 | | 83.0 | 95.3 |
| Abet0370 | 14 | 8.0 | 18.1 | 14.6 | 14.6 | 15.7 | 15.7 | 16.9 | 16.9 | 9.0 | 18.1 | 18.1 | 16.9 | 19.3 | | 85.8 |
| Abet0371 | 15 | 11.2 | 4.9 | 6.9 | 6.9 | 8.0 | 9.0 | 4.9 | 9.0 | 12.3 | 10.1 | 14.6 | 8.0 | 4.9 | 15.7 | |
| Abet0372 | 16 | 4.9 | 5.9 | 0.9 | 1.9 | 1.9 | 2.9 | 4.9 | 11.2 | 5.9 | 3.9 | 8.0 | 2.9 | 8.0 | 13.4 | 5.9 |
| Abet0373 | 17 | 5.9 | 6.9 | 1.9 | 0.9 | 2.9 | 3.9 | 5.9 | 12.3 | 6.9 | 4.9 | 9.0 | 3.9 | 9.0 | 14.6 | 6.9 |
| Abet0374 | 18 | 9.0 | 9.0 | 4.0 | 3.9 | 5.9 | 6.9 | 8.0 | 12.3 | 10.1 | 8.0 | 12.3 | 6.9 | 10.1 | 15.7 | 8.0 |
| Abet0377 | 19 | 10.1 | 6.9 | 5.9 | 6.9 | 6.9 | 8.0 | 5.9 | 11.2 | 11.2 | 9.0 | 13.4 | 6.9 | 9.0 | 16.9 | 5.9 |
| Abet0378 | 20 | 5.9 | 6.9 | 1.9 | 2.9 | 2.9 | 3.9 | 5.9 | 12.3 | 6.9 | 4.9 | 9.0 | 3.9 | 9.0 | 14.6 | 6.9 |
| Abet0379 | 21 | 10.1 | 15.7 | 10.1 | 11.2 | 11.2 | 12.3 | 14.6 | 18.1 | 11.2 | 4.9 | 0.9 | 10.1 | 16.9 | 19.3 | 15.7 |
| Abet0380 | 22 | 4.9 | 5.9 | 0.9 | 1.9 | 1.9 | 2.9 | 4.9 | 11.2 | 5.9 | 3.9 | 8.0 | 2.9 | 8.0 | 13.4 | 5.9 |
| Abet0381 | 23 | 9.0 | 8.0 | 4.9 | 5.9 | 5.9 | 6.9 | 8.0 | 12.3 | 10.1 | 8.0 | 12.3 | 5.9 | 10.1 | 18.1 | 8.0 |
| Abet0382 | 24 | 5.9 | 9.0 | 3.9 | 4.9 | 4.9 | 5.9 | 8.0 | 13.4 | 6.9 | 6.9 | 10.1 | 5.9 | 11.2 | 14.6 | 9.0 |
| Abet0383 | 25 | 5.9 | 5.9 | 1.9 | 0.9 | 2.9 | 3.9 | 4.9 | 10.1 | 6.9 | 4.9 | 9.0 | 3.9 | 6.9 | 13.4 | 5.9 |
| Abet0343-GL | 26 | 3.9 | 6.9 | 1.9 | 2.9 | 2.9 | 3.9 | 5.9 | 12.3 | 4.9 | 4.9 | 9.0 | 3.9 | 9.0 | 12.3 | 6.9 |
| Abet0369-GL | 27 | 11.2 | 6.9 | 9.0 | 8.0 | 10.1 | 9.0 | 6.9 | 11.2 | 12.3 | 12.3 | 16.9 | 10.1 | 1.9 | 16.9 | 4.9 |
| Abet0377-GL | 28 | 8.0 | 6.9 | 5.9 | 6.9 | 6.9 | 8.0 | 5.9 | 11.2 | 9.0 | 9.0 | 13.4 | 6.9 | 9.0 | 14.6 | 5.9 |
| Abet0380-GL | 29 | 3.9 | 6.9 | 1.9 | 2.9 | 2.9 | 3.9 | 5.9 | 12.3 | 4.9 | 4.9 | 9.0 | 3.9 | 9.0 | 12.3 | 6.9 |
| Abet0382-GL | 30 | 3.9 | 6.9 | 1.9 | 2.9 | 2.9 | 3.9 | 5.9 | 12.3 | 4.9 | 4.9 | 9.0 | 3.9 | 9.0 | 12.3 | 6.9 |
| | | | | | | | | Percentage Divergence | | | | | | | | |

| Hemology of the $V_L$ domain | | Percent Identity | | | | | | | | | | | | | |
|---|---|---|---|---|---|---|---|---|---|---|---|---|---|---|---|
| | | 16 | 17 | 18 | 19 | 20 | 21 | 22 | 23 | 24 | 25 | 26 | 27 | 28 | 29 | 30 |
| Abet0144-GL | 1 | 95.3 | 94.3 | 91.5 | 90.6 | 94.3 | 90.6 | 95.3 | 91.5 | 94.3 | 94.3 | 96.2 | 89.6 | 92.5 | 96.2 | 96.2 |
| Abet0319 | 2 | 94.3 | 93.4 | 91.5 | 93.4 | 93.4 | 85.8 | 94.3 | 92.5 | 91.5 | 94.3 | 93.4 | 93.4 | 93.4 | 93.4 | 93.4 |
| Abet0321b | 3 | 99.1 | 98.1 | 95.3 | 94.3 | 98.1 | 90.6 | 99.1 | 95.3 | 96.2 | 98.1 | 98.1 | 91.5 | 94.3 | 98.1 | 98.1 |
| Abet0322b | 4 | 98.1 | 99.1 | 96.2 | 93.4 | 97.2 | 89.6 | 98.1 | 94.3 | 95.3 | 99.1 | 97.2 | 92.5 | 93.4 | 97.2 | 97.2 |
| Abet0323b | 5 | 98.1 | 97.2 | 94.3 | 93.4 | 97.2 | 89.6 | 98.1 | 94.3 | 95.3 | 97.2 | 97.2 | 90.6 | 93.4 | 97.2 | 97.2 |
| Abet0328 | 6 | 97.2 | 96.2 | 93.4 | 92.5 | 96.2 | 88.7 | 97.2 | 93.4 | 94.3 | 96.2 | 96.2 | 91.5 | 92.5 | 96.2 | 96.2 |
| Abet0329 | 7 | 95.3 | 94.3 | 92.5 | 94.3 | 94.3 | 86.8 | 95.3 | 92.5 | 92.5 | 95.3 | 94.3 | 93.4 | 94.3 | 94.3 | 94.3 |
| Abet0332 | 8 | 89.6 | 88.7 | 88.7 | 89.6 | 88.7 | 84.0 | 89.6 | 88.7 | 87.7 | 90.6 | 88.7 | 89.6 | 89.6 | 88.7 | 88.7 |
| Abet0342 | 9 | 94.3 | 93.4 | 90.6 | 89.6 | 93.4 | 89.6 | 94.3 | 90.6 | 93.4 | 93.4 | 95.3 | 88.7 | 91.5 | 95.3 | 95.3 |
| Abet0343 | 10 | 96.2 | 95.3 | 92.5 | 91.5 | 95.3 | 95.3 | 96.2 | 92.5 | 93.4 | 95.3 | 95.3 | 88.7 | 91.5 | 95.3 | 95.3 |
| Abet0344 | 11 | 92.5 | 91.5 | 88.7 | 87.7 | 91.5 | 99.1 | 92.5 | 88.7 | 90.6 | 91.5 | 91.5 | 84.9 | 87.7 | 91.5 | 91.5 |
| Abet0368 | 12 | 97.2 | 96.2 | 93.4 | 93.4 | 96.2 | 90.6 | 97.2 | 94.3 | 94.3 | 96.2 | 96.2 | 90.6 | 93.4 | 96.2 | 96.2 |
| Abet0369 | 13 | 92.5 | 91.5 | 90.6 | 91.5 | 91.5 | 84.9 | 92.5 | 90.6 | 89.6 | 93.4 | 91.5 | 98.1 | 91.5 | 91.5 | 91.5 |
| Abet0370 | 14 | 87.7 | 86.8 | 85.8 | 84.9 | 86.8 | 83.0 | 87.7 | 84.0 | 86.8 | 87.7 | 88.7 | 84.9 | 86.8 | 88.7 | 88.7 |
| Abet0371 | 15 | 94.3 | 93.4 | 92.5 | 94.3 | 93.4 | 85.8 | 94.3 | 92.5 | 91.5 | 94.3 | 93.4 | 95.3 | 94.3 | 93.4 | 93.4 |
| Abet0372 | 16 | | 99.1 | 96.2 | 95.3 | 99.1 | 91.5 | 100.0 | 96.2 | 97.2 | 99.1 | 99.1 | 92.5 | 95.3 | 99.1 | 99.1 |
| Abet0373 | 17 | 0.9 | | 95.3 | 94.3 | 98.1 | 90.6 | 99.1 | 95.3 | 96.2 | 98.1 | 98.1 | 91.5 | 94.3 | 98.1 | 98.1 |
| Abet0374 | 18 | 3.9 | 4.9 | | 92.5 | 95.3 | 87.7 | 96.2 | 92.5 | 93.4 | 97.2 | 95.3 | 90.6 | 92.5 | 95.3 | 95.3 |
| Abet0377 | 19 | 4.9 | 5.9 | 8.0 | | 94.3 | 86.8 | 95.3 | 92.5 | 94.3 | 94.3 | 94.3 | 91.5 | 98.1 | 94.3 | 94.3 |
| Abet0378 | 20 | 0.9 | 1.9 | 4.9 | 5.9 | | 90.6 | 99.1 | 95.3 | 96.2 | 98.1 | 98.1 | 91.5 | 94.3 | 98.1 | 98.1 |
| Abet0379 | 21 | 9.0 | 10.1 | 13.4 | 14.6 | 10.1 | | 91.5 | 87.7 | 89.6 | 90.6 | 90.6 | 84.0 | 86.8 | 90.6 | 90.6 |

TABLE 11-continued

Sequence identity across the entire VL sequence (Kabat residues 1→107) of the twenty four non-germlined and the five germlined antibodies described herein. All sequences are within 88.7% of the Abet0380-GL lead clone.

| | | | | | | | | | | | | | | | | | |
|---|---|---|---|---|---|---|---|---|---|---|---|---|---|---|---|---|---|
| Abet0380 | 22 | 0.0 | 0.9 | 3.9 | 4.9 | 0.9 | 9.0 | | 96.2 | 97.2 | 99.1 | 99.1 | 92.5 | 95.3 | 99.1 | 99.1 |
| Abet0381 | 23 | 3.9 | 4.9 | 8.0 | 8.0 | 4.9 | 13.4 | 3.9 | | 93.4 | 95.3 | 95.3 | 90.6 | 92.5 | 95.3 | 95.3 |
| Abet0382 | 24 | 2.9 | 3.9 | 6.9 | 5.9 | 3.9 | 11.2 | 2.9 | 6.9 | | 96.2 | 96.2 | 89.6 | 92.5 | 96.2 | 96.2 |
| Abet0383 | 25 | 0.9 | 1.9 | 2.9 | 5.9 | 1.9 | 10.1 | 0.9 | 4.9 | 3.9 | | 98.1 | 93.4 | 94.3 | 98.1 | 98.1 |
| Abet0343-GL | 26 | 0.9 | 1.9 | 4.9 | 5.9 | 1.9 | 10.1 | 0.9 | 4.9 | 3.9 | 1.9 | | 93.4 | 96.2 | 100.1 | 100.1 |
| Abet0369-GL | 27 | 8.0 | 9.0 | 10.1 | 9.0 | 9.0 | 18.1 | 8.0 | 10.1 | 11.2 | 6.9 | 6.9 | | 93.4 | 93.4 | 93.4 |
| Abet0377-GL | 28 | 4.9 | 5.9 | 8.0 | 1.9 | 5.9 | 14.6 | 4.9 | 8.0 | 8.0 | 5.9 | 3.9 | 6.9 | | 96.2 | 96.2 |
| Abet0380-GL | 29 | 0.9 | 1.9 | 4.9 | 5.9 | 1.9 | 10.1 | 0.9 | 4.9 | 3.9 | 1.9 | 0.0 | 6.9 | 3.9 | | 100.0 |
| Abet0382-GL | 30 | 0.9 | 1.9 | 4.9 | 5.9 | 1.9 | 10.1 | 0.9 | 4.9 | 3.9 | 1.9 | 0.0 | 6.9 | 3.9 | 0.0 | |

Percent Divergence

TABLE 12

Examples of residues at each position within the VH CDRs and Vernier Residues.

| | Kabat number | Abet0380-GL | Other example residues | | | | |
|---|---|---|---|---|---|---|---|
| VH FW1 | 26 | M | G | S | | | |
| | 27 | G | F | D | | | |
| | 28 | N | T | D | H | | |
| | 29 | F | | | | | |
| | 30 | N | S | K | P | | |
| VH CDR1 | 31 | Y | V | R | E | T | |
| | 32 | Q | Y | D | S | E | |
| | 33 | T | P | I | V | | |
| | 34 | M | | | | | |
| | 35 | W | | | | | |
| VH CDR2 | 50 | V | | | | | |
| | 51 | I | | | | | |
| | 52 | G | | | | | |
| | 52a | K | S | A | | | |
| | 53 | T | S | N | D | G | Q |
| | 54 | N | G | T | P | | |
| | 55 | E | G | N | K | T | |
| | 56 | N | T | R | K | | |
| | 57 | I | T | K | V | | |
| | 58 | A | V | T | | | |
| | 59 | Y | | | | | |
| | 60 | A | | | | | |
| | 61 | D | | | | | |
| | 62 | S | | | | | |
| | 63 | V | | | | | |
| | 64 | K | | | | | |
| | 65 | G | | | | | |
| VH CDR3 | 95 | E | | | | | |
| | 96 | W | | | | | |
| | 97 | M | | | | | |
| | 98 | D | | | | | |
| | 99 | H | | | | | |
| | 100 | S | | | | | |
| | 100a | R | | | | | |
| | 100b | P | | | | | |
| | 100c | Y | | | | | |
| | 100d | Y | | | | | |
| | 100e | Y | | | | | |
| | 100f | Y | | | | | |
| | 100g | G | | | | | |
| | 100h | M | | | | | |
| | 101 | D | | | | | |
| | 102 | V | | | | | |

TABLE 13

Examples of residues at each position within the $V_L$ CDRs.

| | Kabat number | Abet0380-GL | Other example residues |
|---|---|---|---|
| VL CDR1 | 24 | S | |
| | 25 | G | |
| | 26 | H | |
| | 27 | N | |
| | 28 | L | I |
| | 29 | E | G |
| | 30 | D | |
| | 31 | K | |
| | 32 | F | W |
| | 33 | A | V |
| | 34 | S | |
| VL CDR2 | 50 | R | |
| | 51 | D | |
| | 52 | D | |
| | 53 | K | |
| | 54 | R | |
| | 55 | P | |
| | 56 | S | |
| VL CDR3 | 89 | S | Q |
| | 90 | S | A |
| | 91 | Q | |
| | 92 | D | |
| | 93 | T | S |
| | 94 | V | T |
| | 95 | T | |
| | 96 | R | |
| | 97 | V | |

TABLE 14

Substitutions observed in VH CDRs and FW1 in 24 optimised clones

| | Kabat number | 0380-GL | Substitutions in other optimised clones |
|---|---|---|---|
| VH FW1 | 26 | M | G, S, V, A, N, T, H |
| | 27 | G | F, S, Y, E, D, P |
| | 28 | N | Q, H, V, E, T, A, S, D, M, P |
| | 29 | F | I, Y, S, L, W |
| | 30 | N | S, T, Q, K, H, R, G, P, E, K, A, D |
| VH CDR1 | 31 | Y | H, K, E, N, T, R, V, P, M, F, I, D, W |
| | 32 | Q | Y, D, N, S, E, T |
| | 33 | T | P, I, V, A, I |
| | 34 | M | L |
| | 35 | W | |
| VH CDR2 | 50 | V | |
| | 51 | I | |
| | 52 | G | |
| | 52a | K | S, P, A, N, G, E, D, V, T |
| | 53 | T | S, N, H, Q, D, G, E |
| | 54 | N | G, P, T, Q, E, M, K, A |
| | 55 | E | G, K, N, Q, T, H, D, A |
| | 56 | N | T, A, R, K |
| | 57 | I | T, N, S, K, F, Q, V, L |
| | 58 | A | V, S, T, N |
| | 59 | Y | |

TABLE 14-continued

Substitutions observed in VH CDRs and FW1 in 24 optimised clones

|  | Kabat number | 0380-GL | Substitutions in other optimised clones |
|---|---|---|---|
|  | 60 | A |  |
|  | 61 | D |  |
|  | 62 | S | A, T |
|  | 63 | V |  |
|  | 64 | K |  |
|  | 65 | G |  |
| VH CDR3 | 95 | E |  |
|  | 96 | W |  |
|  | 97 | M |  |
|  | 98 | D | G |
|  | 99 | H | R |
|  | 100 | S |  |
|  | 100a | R |  |
|  | 100b | P |  |
|  | 100c | Y |  |
|  | 100d | Y |  |
|  | 100e | Y |  |
|  | 100f | Y |  |
|  | 100g | G |  |
|  | 100h | M | I |
|  | 101 | D |  |
|  | 102 | V | A |

TABLE 15

Substitutions observed in VL CDRs in 24 optimised clones

|  | Kabat number | 0380-GL | Substitutions in other optimised clones |
|---|---|---|---|
| VL CDR1 | 24 | S | T |
|  | 25 | G | T |
|  | 26 | H | R, P |
|  | 27 | N | H |
|  | 28 | L | I, V, F, T |
|  | 29 | E | M, G, S, N |
|  | 30 | D | A, S, G, H |
|  | 31 | K | S |
|  | 32 | F | W |
|  | 33 | A | V, M, T, I |
|  | 34 | S | T, A |
| VL CDR2 | 50 | R |  |
|  | 51 | D |  |
|  | 52 | D |  |
|  | 53 | K |  |
|  | 54 | R |  |
|  | 55 | P |  |
|  | 56 | S |  |
| VL CDR3 | 89 | S | Q, A |
|  | 90 | S | A, T |
|  | 91 | Q |  |
|  | 92 | D | G |
|  | 93 | T | Q, S, N, K |
|  | 94 | V | T, F |
|  | 95 | T |  |
|  | 96 | R |  |
|  | 97 | V | S, A |

TABLE 16

Correspondence between the antibody sequences mentioned herein and the sequences in the Sequence Listing at the end of this document.

| 1 | Abet0007 | VH DNA |
|---|---|---|
| 2 | Abet0007 | VH PRT |
| 3 | Abet0007 | CDR1 PRT |
| 4 | Abet0007 | CDR2 PRT |
| 5 | Abet0007 | CDR3 PRT |
| 6 | Abet0007 | FW1 PRT |
| 7 | Abet0007 | FVV2 PRT |
| 8 | Abet0007 | FVV3 PRT |
| 9 | Abet0007 | FW4 PRT |
| 10 | Abet0007 | VL DNA |
| 11 | Abet0007 | VL PRT |
| 12 | Abet0007 | CDR1 PRT |
| 13 | Abet0007 | CDR2 PRT |
| 14 | Abet0007 | CDR3 PRT |
| 15 | Abet0007 | FW1 PRT |
| 16 | Abet0007 | FVV2 PRT |
| 17 | Abet0007 | FVV3 PRT |
| 18 | Abet0007 | FW4 PRT |
| 19 | Abet0144-GL | VH DNA |
| 20 | Abet0144-GL | VH PRT |
| 21 | Abet0144-GL | CDR1 PRT |
| 22 | Abet0144-GL | CDR2 PRT |
| 23 | Abet0144-GL | CDR3 PRT |
| 24 | Abet0144-GL | FW1 PRT |
| 25 | Abet0144-GL | FVV2 PRT |
| 26 | Abet0144-GL | FVV3 PRT |
| 27 | Abet0144-GL | FW4 PRT |
| 28 | Abet0144-GL | VL DNA |
| 29 | Abet0144-GL | VL PRT |
| 30 | Abet0144-GL | CDR1 PRT |
| 31 | Abet0144-GL | CDR2 PRT |
| 32 | Abet0144-GL | CDR3 PRT |
| 33 | Abet0144-GL | FW1 PRT |
| 34 | Abet0144-GL | FVV2 PRT |
| 35 | Abet0144-GL | FVV3 PRT |
| 36 | Abet0144-GL | FW4 PRT |
| 37 | Abet0319 | VH DNA |
| 38 | Abet0319 | VH PRT |
| 39 | Abet0319 | CDR1 PRT |
| 40 | Abet0319 | CDR2 PRT |
| 41 | Abet0319 | CDR3 PRT |
| 42 | Abet0319 | FW1 PRT |
| 43 | Abet0319 | FVV2 PRT |
| 44 | Abet0319 | FVV3 PRT |
| 45 | Abet0319 | FW4 PRT |
| 46 | Abet0319 | VL DNA |
| 47 | Abet0319 | VL PRT |
| 48 | Abet0319 | CDR1 PRT |
| 49 | Abet0319 | CDR2 PRT |
| 50 | Abet0319 | CDR3 PRT |
| 51 | Abet0319 | FW1 PRT |
| 52 | Abet0319 | FVV2 PRT |
| 53 | Abet0319 | FVV3 PRT |
| 54 | Abet0319 | FW4 PRT |
| 55 | Abet0321b | VH DNA |
| 56 | Abet0321b | VH PRT |
| 57 | Abet0321b | CDR1 PRT |
| 58 | Abet0321b | CDR2 PRT |
| 59 | Abet0321b | CDR3 PRT |
| 60 | Abet0321b | FW1 PRT |
| 61 | Abet0321b | FVV2 PRT |
| 62 | Abet0321b | FVV3 PRT |
| 63 | Abet0321b | FW4 PRT |
| 64 | Abet0321b | VL DNA |
| 65 | Abet0321b | VL PRT |
| 66 | Abet0321b | CDR1 PRT |
| 67 | Abet0321b | CDR2 PRT |
| 68 | Abet0321b | CDR3 PRT |
| 69 | Abet0321b | FW1 PRT |
| 70 | Abet0321b | FVV2 PRT |
| 71 | Abet0321b | FVV3 PRT |
| 72 | Abet0321b | FW4 PRT |
| 73 | Abet0322b | VH DNA |
| 74 | Abet0322b | VH PRT |
| 75 | Abet0322b | CDR1 PRT |
| 76 | Abet0322b | CDR2 PRT |
| 77 | Abet0322b | CDR3 PRT |
| 78 | Abet0322b | FW1 PRT |
| 79 | Abet0322b | FVV2 PRT |
| 80 | Abet0322b | FVV3 PRT |
| 81 | Abet0322b | FW4 PRT |
| 82 | Abet0322b | VL DNA |
| 83 | Abet0322b | VL PRT |
| 84 | Abet0322b | CDR1 PRT |

TABLE 16-continued

Correspondence between the antibody sequences mentioned herein and the sequences in the Sequence Listing at the end of this document.

| | | |
|---|---|---|
| 85 | Abet0322b | CDR2 PRT |
| 86 | Abet0322b | CDR3 PRT |
| 87 | Abet0322b | FW1 PRT |
| 88 | Abet0322b | FVV2 PRT |
| 89 | Abet0322b | FVV3 PRT |
| 90 | Abet0322b | FW4 PRT |
| 91 | Abet0323b | VH DNA |
| 92 | Abet0323b | VH PRT |
| 93 | Abet0323b | CDR1 PRT |
| 94 | Abet0323b | CDR2 PRT |
| 95 | Abet0323b | CDR3 PRT |
| 96 | Abet0323b | FW1 PRT |
| 97 | Abet0323b | FVV2 PRT |
| 98 | Abet0323b | FVV3 PRT |
| 99 | Abet0323b | FW4 PRT |
| 100 | Abet0323b | VL DNA |
| 101 | Abet0323b | VL PRT |
| 102 | Abet0323b | CDR1 PRT |
| 103 | Abet0323b | CDR2 PRT |
| 104 | Abet0323b | CDR3 PRT |
| 105 | Abet0323b | FW1 PRT |
| 106 | Abet0323b | FVV2 PRT |
| 107 | Abet0323b | FVV3 PRT |
| 108 | Abet0323b | FW4 PRT |
| 109 | Abet0328 | VH DNA |
| 110 | Abet0328 | VH PRT |
| 111 | Abet0328 | CDR1 PRT |
| 112 | Abet0328 | CDR2 PRT |
| 113 | Abet0328 | CDR3 PRT |
| 114 | Abet0328 | FW1 PRT |
| 115 | Abet0328 | FVV2 PRT |
| 116 | Abet0328 | FVV3 PRT |
| 117 | Abet0328 | FW4 PRT |
| 118 | Abet0328 | VL DNA |
| 119 | Abet0328 | VL PRT |
| 120 | Abet0328 | CDR1 PRT |
| 121 | Abet0328 | CDR2 PRT |
| 122 | Abet0328 | CDR3 PRT |
| 123 | Abet0328 | FW1 PRT |
| 124 | Abet0328 | FVV2 PRT |
| 125 | Abet0328 | FVV3 PRT |
| 126 | Abet0328 | FW4 PRT |
| 127 | Abet0329 | VH DNA |
| 128 | Abet0329 | VH PRT |
| 129 | Abet0329 | CDR1 PRT |
| 130 | Abet0329 | CDR2 PRT |
| 131 | Abet0329 | CDR3 PRT |
| 132 | Abet0329 | FW1 PRT |
| 133 | Abet0329 | FVV2 PRT |
| 134 | Abet0329 | FVV3 PRT |
| 135 | Abet0329 | FW4 PRT |
| 136 | Abet0329 | VL DNA |
| 137 | Abet0329 | VL PRT |
| 138 | Abet0329 | CDR1 PRT |
| 139 | Abet0329 | CDR2 PRT |
| 140 | Abet0329 | CDR3 PRT |
| 141 | Abet0329 | FW1 PRT |
| 142 | Abet0329 | FVV2 PRT |
| 143 | Abet0329 | FVV3 PRT |
| 144 | Abet0329 | FW4 PRT |
| 145 | Abet0332 | VH DNA |
| 146 | Abet0332 | VH PRT |
| 147 | Abet0332 | CDR1 PRT |
| 148 | Abet0332 | CDR2 PRT |
| 149 | Abet0332 | CDR3 PRT |
| 150 | Abet0332 | FW1 PRT |
| 151 | Abet0332 | FVV2 PRT |
| 152 | Abet0332 | FVV3 PRT |
| 153 | Abet0332 | FW4 PRT |
| 154 | Abet0332 | VL DNA |
| 155 | Abet0332 | VL PRT |
| 156 | Abet0332 | CDR1 PRT |
| 157 | Abet0332 | CDR2 PRT |
| 158 | Abet0332 | CDR3 PRT |
| 159 | Abet0332 | FW1 PRT |
| 160 | Abet0332 | FVV2 PRT |
| 161 | Abet0332 | FVV3 PRT |
| 162 | Abet0332 | FW4 PRT |
| 163 | Abet0342 | VH DNA |
| 164 | Abet0342 | VH PRT |
| 165 | Abet0342 | CDR1 PRT |
| 166 | Abet0342 | CDR2 PRT |
| 167 | Abet0342 | CDR3 PRT |
| 168 | Abet0342 | FW1 PRT |
| 169 | Abet0342 | FVV2 PRT |
| 170 | Abet0342 | FVV3 PRT |
| 171 | Abet0342 | FW4 PRT |
| 172 | Abet0342 | VL DNA |
| 173 | Abet0342 | VL PRT |
| 174 | Abet0342 | CDR1 PRT |
| 175 | Abet0342 | CDR2 PRT |
| 176 | Abet0342 | CDR3 PRT |
| 177 | Abet0342 | FW1 PRT |
| 178 | Abet0342 | FVV2 PRT |
| 179 | Abet0342 | FVV3 PRT |
| 180 | Abet0342 | FW4 PRT |
| 181 | Abet0343 | VH DNA |
| 182 | Abet0343 | VH PRT |
| 183 | Abet0343 | CDR1 PRT |
| 184 | Abet0343 | CDR2 PRT |
| 185 | Abet0343 | CDR3 PRT |
| 186 | Abet0343 | FW1 PRT |
| 187 | Abet0343 | FVV2 PRT |
| 188 | Abet0343 | FVV3 PRT |
| 189 | Abet0343 | FW4 PRT |
| 190 | Abet0343 | VL DNA |
| 191 | Abet0343 | VL PRT |
| 192 | Abet0343 | CDR1 PRT |
| 193 | Abet0343 | CDR2 PRT |
| 194 | Abet0343 | CDR3 PRT |
| 195 | Abet0343 | FW1 PRT |
| 196 | Abet0343 | FVV2 PRT |
| 197 | Abet0343 | FVV3 PRT |
| 198 | Abet0343 | FW4 PRT |
| 199 | Abet0344 | VH DNA |
| 200 | Abet0344 | VH PRT |
| 201 | Abet0344 | CDR1 PRT |
| 202 | Abet0344 | CDR2 PRT |
| 203 | Abet0344 | CDR3 PRT |
| 204 | Abet0344 | FW1 PRT |
| 205 | Abet0344 | FVV2 PRT |
| 206 | Abet0344 | FVV3 PRT |
| 207 | Abet0344 | FW4 PRT |
| 208 | Abet0344 | VL DNA |
| 209 | Abet0344 | VL PRT |
| 210 | Abet0344 | CDR1 PRT |
| 211 | Abet0344 | CDR2 PRT |
| 212 | Abet0344 | CDR3 PRT |
| 213 | Abet0344 | FW1 PRT |
| 214 | Abet0344 | FVV2 PRT |
| 215 | Abet0344 | FVV3 PRT |
| 216 | Abet0344 | FW4 PRT |
| 217 | Abet0368 | VH DNA |
| 218 | Abet0368 | VH PRT |
| 219 | Abet0368 | CDR1 PRT |
| 220 | Abet0368 | CDR2 PRT |
| 221 | Abet0368 | CDR3 PRT |
| 222 | Abet0368 | FW1 PRT |
| 223 | Abet0368 | FVV2 PRT |
| 224 | Abet0368 | FVV3 PRT |
| 225 | Abet0368 | FW4 PRT |
| 226 | Abet0368 | VL DNA |
| 227 | Abet0368 | VL PRT |
| 228 | Abet0368 | CDR1 PRT |
| 229 | Abet0368 | CDR2 PRT |
| 230 | Abet0368 | CDR3 PRT |
| 231 | Abet0368 | FW1 PRT |
| 232 | Abet0368 | FVV2 PRT |
| 233 | Abet0368 | FVV3 PRT |
| 234 | Abet0368 | FW4 PRT |
| 235 | Abet0369 | VH DNA |
| 236 | Abet0369 | VH PRT |
| 237 | Abet0369 | CDR1 PRT |
| 238 | Abet0369 | CDR2 PRT |

TABLE 16-continued

Correspondence between the antibody sequences mentioned herein and the sequences in the Sequence Listing at the end of this document.

| | | |
|---|---|---|
| 239 | Abet0369 | CDR3 PRT |
| 240 | Abet0369 | FW1 PRT |
| 241 | Abet0369 | FVV2 PRT |
| 242 | Abet0369 | FVV3 PRT |
| 243 | Abet0369 | FW4 PRT |
| 244 | Abet0369 | VL DNA |
| 245 | Abet0369 | VL PRT |
| 246 | Abet0369 | CDR1 PRT |
| 247 | Abet0369 | CDR2 PRT |
| 248 | Abet0369 | CDR3 PRT |
| 249 | Abet0369 | FW1 PRT |
| 250 | Abet0369 | FVV2 PRT |
| 251 | Abet0369 | FVV3 PRT |
| 252 | Abet0369 | FW4 PRT |
| 253 | Abet0370 | VH DNA |
| 254 | Abet0370 | VH PRT |
| 255 | Abet0370 | CDR1 PRT |
| 256 | Abet0370 | CDR2 PRT |
| 257 | Abet0370 | CDR3 PRT |
| 258 | Abet0370 | FW1 PRT |
| 259 | Abet0370 | FVV2 PRT |
| 260 | Abet0370 | FVV3 PRT |
| 261 | Abet0370 | FW4 PRT |
| 262 | Abet0370 | VL DNA |
| 263 | Abet0370 | VL PRT |
| 264 | Abet0370 | CDR1 PRT |
| 265 | Abet0370 | CDR2 PRT |
| 266 | Abet0370 | CDR3 PRT |
| 267 | Abet0370 | FW1 PRT |
| 268 | Abet0370 | FVV2 PRT |
| 269 | Abet0370 | FVV3 PRT |
| 270 | Abet0370 | FW4 PRT |
| 271 | Abet0371 | VH DNA |
| 272 | Abet0371 | VH PRT |
| 273 | Abet0371 | CDR1 PRT |
| 274 | Abet0371 | CDR2 PRT |
| 275 | Abet0371 | CDR3 PRT |
| 276 | Abet0371 | FW1 PRT |
| 277 | Abet0371 | FVV2 PRT |
| 278 | Abet0371 | FVV3 PRT |
| 279 | Abet0371 | FW4 PRT |
| 280 | Abet0371 | VL DNA |
| 281 | Abet0371 | VL PRT |
| 282 | Abet0371 | CDR1 PRT |
| 283 | Abet0371 | CDR2 PRT |
| 284 | Abet0371 | CDR3 PRT |
| 285 | Abet0371 | FW1 PRT |
| 286 | Abet0371 | FVV2 PRT |
| 287 | Abet0371 | FVV3 PRT |
| 288 | Abet0371 | FW4 PRT |
| 289 | Abet0372 | VH DNA |
| 290 | Abet0372 | VH PRT |
| 291 | Abet0372 | CDR1 PRT |
| 292 | Abet0372 | CDR2 PRT |
| 293 | Abet0372 | CDR3 PRT |
| 294 | Abet0372 | FW1 PRT |
| 295 | Abet0372 | FVV2 PRT |
| 296 | Abet0372 | FVV3 PRT |
| 297 | Abet0372 | FW4 PRT |
| 298 | Abet0372 | VL DNA |
| 299 | Abet0372 | VL PRT |
| 300 | Abet0372 | CDR1 PRT |
| 301 | Abet0372 | CDR2 PRT |
| 302 | Abet0372 | CDR3 PRT |
| 303 | Abet0372 | FW1 PRT |
| 304 | Abet0372 | FVV2 PRT |
| 305 | Abet0372 | FVV3 PRT |
| 306 | Abet0372 | FW4 PRT |
| 307 | Abet0373 | VH DNA |
| 308 | Abet0373 | VH PRT |
| 309 | Abet0373 | CDR1 PRT |
| 310 | Abet0373 | CDR2 PRT |
| 311 | Abet0373 | CDR3 PRT |
| 312 | Abet0373 | FW1 PRT |
| 313 | Abet0373 | FVV2 PRT |
| 314 | Abet0373 | FVV3 PRT |
| 315 | Abet0373 | FW4 PRT |
| 316 | Abet0373 | VL DNA |
| 317 | Abet0373 | VL PRT |
| 318 | Abet0373 | CDR1 PRT |
| 319 | Abet0373 | CDR2 PRT |
| 320 | Abet0373 | CDR3 PRT |
| 321 | Abet0373 | FW1 PRT |
| 322 | Abet0373 | FVV2 PRT |
| 323 | Abet0373 | FVV3 PRT |
| 324 | Abet0373 | FW4 PRT |
| 325 | Abet0374 | VH DNA |
| 326 | Abet0374 | VH PRT |
| 327 | Abet0374 | CDR1 PRT |
| 328 | Abet0374 | CDR2 PRT |
| 329 | Abet0374 | CDR3 PRT |
| 330 | Abet0374 | FW1 PRT |
| 331 | Abet0374 | FVV2 PRT |
| 332 | Abet0374 | FVV3 PRT |
| 333 | Abet0374 | FW4 PRT |
| 334 | Abet0374 | VL DNA |
| 335 | Abet0374 | VL PRT |
| 336 | Abet0374 | CDR1 PRT |
| 337 | Abet0374 | CDR2 PRT |
| 338 | Abet0374 | CDR3 PRT |
| 339 | Abet0374 | FW1 PRT |
| 340 | Abet0374 | FVV2 PRT |
| 341 | Abet0374 | FVV3 PRT |
| 342 | Abet0374 | FW4 PRT |
| 343 | Abet0377 | VH DNA |
| 344 | Abet0377 | VH PRT |
| 345 | Abet0377 | CDR1 PRT |
| 346 | Abet0377 | CDR2 PRT |
| 347 | Abet0377 | CDR3 PRT |
| 348 | Abet0377 | FW1 PRT |
| 349 | Abet0377 | FVV2 PRT |
| 350 | Abet0377 | FVV3 PRT |
| 351 | Abet0377 | FW4 PRT |
| 352 | Abet0377 | VL DNA |
| 353 | Abet0377 | VL PRT |
| 354 | Abet0377 | CDR1 PRT |
| 355 | Abet0377 | CDR2 PRT |
| 356 | Abet0377 | CDR3 PRT |
| 357 | Abet0377 | FW1 PRT |
| 358 | Abet0377 | FVV2 PRT |
| 359 | Abet0377 | FVV3 PRT |
| 360 | Abet0377 | FW4 PRT |
| 361 | Abet0378 | VH DNA |
| 362 | Abet0378 | VH PRT |
| 363 | Abet0378 | CDR1 PRT |
| 364 | Abet0378 | CDR2 PRT |
| 365 | Abet0378 | CDR3 PRT |
| 366 | Abet0378 | FW1 PRT |
| 367 | Abet0378 | FVV2 PRT |
| 368 | Abet0378 | FVV3 PRT |
| 369 | Abet0378 | FW4 PRT |
| 370 | Abet0378 | VL DNA |
| 371 | Abet0378 | VL PRT |
| 372 | Abet0378 | CDR1 PRT |
| 373 | Abet0378 | CDR2 PRT |
| 374 | Abet0378 | CDR3 PRT |
| 375 | Abet0378 | FW1 PRT |
| 376 | Abet0378 | FVV2 PRT |
| 377 | Abet0378 | FVV3 PRT |
| 378 | Abet0378 | FW4 PRT |
| 379 | Abet0379 | VH DNA |
| 380 | Abet0379 | VH PRT |
| 381 | Abet0379 | CDR1 PRT |
| 382 | Abet0379 | CDR2 PRT |
| 383 | Abet0379 | CDR3 PRT |
| 384 | Abet0379 | FW1 PRT |
| 385 | Abet0379 | FVV2 PRT |
| 386 | Abet0379 | FVV3 PRT |
| 387 | Abet0379 | FW4 PRT |
| 388 | Abet0379 | VL DNA |
| 389 | Abet0379 | VL PRT |
| 390 | Abet0379 | CDR1 PRT |
| 391 | Abet0379 | CDR2 PRT |
| 392 | Abet0379 | CDR3 PRT |

TABLE 16-continued

Correspondence between the antibody sequences mentioned herein and the sequences in the Sequence Listing at the end of this document.

| | | |
|---|---|---|
| 393 | Abet0379 | FW1 PRT |
| 394 | Abet0379 | FVV2 PRT |
| 395 | Abet0379 | FVV3 PRT |
| 396 | Abet0379 | FW4 PRT |
| 397 | Abet0380 | VH DNA |
| 398 | Abet0380 | VH PRT |
| 399 | Abet0380 | CDR1 PRT |
| 400 | Abet0380 | CDR2 PRT |
| 401 | Abet0380 | CDR3 PRT |
| 402 | Abet0380 | FW1 PRT |
| 403 | Abet0380 | FVV2 PRT |
| 404 | Abet0380 | FVV3 PRT |
| 405 | Abet0380 | FW4 PRT |
| 406 | Abet0380 | VL DNA |
| 407 | Abet0380 | VL PRT |
| 408 | Abet0380 | CDR1 PRT |
| 409 | Abet0380 | CDR2 PRT |
| 410 | Abet0380 | CDR3 PRT |
| 411 | Abet0380 | FW1 PRT |
| 412 | Abet0380 | FVV2 PRT |
| 413 | Abet0380 | FVV3 PRT |
| 414 | Abet0380 | FW4 PRT |
| 415 | Abet0381 | VH DNA |
| 416 | Abet0381 | VH PRT |
| 417 | Abet0381 | CDR1 PRT |
| 418 | Abet0381 | CDR2 PRT |
| 419 | Abet0381 | CDR3 PRT |
| 420 | Abet0381 | FW1 PRT |
| 421 | Abet0381 | FVV2 PRT |
| 422 | Abet0381 | FVV3 PRT |
| 423 | Abet0381 | FW4 PRT |
| 424 | Abet0381 | VL DNA |
| 425 | Abet0381 | VL PRT |
| 426 | Abet0381 | CDR1 PRT |
| 427 | Abet0381 | CDR2 PRT |
| 428 | Abet0381 | CDR3 PRT |
| 429 | Abet0381 | FW1 PRT |
| 430 | Abet0381 | FVV2 PRT |
| 431 | Abet0381 | FVV3 PRT |
| 432 | Abet0381 | FW4 PRT |
| 433 | Abet0382 | VH DNA |
| 434 | Abet0382 | VH PRT |
| 435 | Abet0382 | CDR1 PRT |
| 436 | Abet0382 | CDR2 PRT |
| 437 | Abet0382 | CDR3 PRT |
| 438 | Abet0382 | FW1 PRT |
| 439 | Abet0382 | FVV2 PRT |
| 440 | Abet0382 | FVV3 PRT |
| 441 | Abet0382 | FW4 PRT |
| 442 | Abet0382 | VL DNA |
| 443 | Abet0382 | VL PRT |
| 444 | Abet0382 | CDR1 PRT |
| 445 | Abet0382 | CDR2 PRT |
| 446 | Abet0382 | CDR3 PRT |
| 447 | Abet0382 | FW1 PRT |
| 448 | Abet0382 | FVV2 PRT |
| 449 | Abet0382 | FVV3 PRT |
| 450 | Abet0382 | FW4 PRT |
| 451 | Abet0383 | VH DNA |
| 452 | Abet0383 | VH PRT |
| 453 | Abet0383 | CDR1 PRT |
| 454 | Abet0383 | CDR2 PRT |
| 455 | Abet0383 | CDR3 PRT |
| 456 | Abet0383 | FW1 PRT |
| 457 | Abet0383 | FVV2 PRT |
| 458 | Abet0383 | FVV3 PRT |
| 459 | Abet0383 | FW4 PRT |
| 460 | Abet0383 | VL DNA |
| 461 | Abet0383 | VL PRT |
| 462 | Abet0383 | CDR1 PRT |
| 463 | Abet0383 | CDR2 PRT |
| 464 | Abet0383 | CDR3 PRT |
| 465 | Abet0383 | FW1 PRT |
| 466 | Abet0383 | FVV2 PRT |
| 467 | Abet0383 | FVV3 PRT |
| 468 | Abet0383 | FW4 PRT |
| 469 | Abet0343-GL | VH DNA |
| 470 | Abet0343-GL | VH PRT |
| 471 | Abet0343-GL | CDR1 PRT |
| 472 | Abet0343-GL | CDR2 PRT |
| 473 | Abet0343-GL | CDR3 PRT |
| 474 | Abet0343-GL | FW1 PRT |
| 475 | Abet0343-GL | FVV2 PRT |
| 476 | Abet0343-GL | FVV3 PRT |
| 477 | Abet0343-GL | FW4 PRT |
| 478 | Abet0343-GL | VL DNA |
| 479 | Abet0343-GL | VL PRT |
| 480 | Abet0343-GL | CDR1 PRT |
| 481 | Abet0343-GL | CDR2 PRT |
| 482 | Abet0343-GL | CDR3 PRT |
| 483 | Abet0343-GL | FW1 PRT |
| 484 | Abet0343-GL | FVV2 PRT |
| 485 | Abet0343-GL | FVV3 PRT |
| 486 | Abet0343-GL | FW4 PRT |
| 487 | Abet0369-GL | VH DNA |
| 488 | Abet0369-GL | VH PRT |
| 489 | Abet0369-GL | CDR1 PRT |
| 490 | Abet0369-GL | CDR2 PRT |
| 491 | Abet0369-GL | CDR3 PRT |
| 492 | Abet0369-GL | FW1 PRT |
| 493 | Abet0369-GL | FVV2 PRT |
| 494 | Abet0369-GL | FVV3 PRT |
| 495 | Abet0369-GL | FW4 PRT |
| 496 | Abet0369-GL | VL DNA |
| 497 | Abet0369-GL | VL PRT |
| 498 | Abet0369-GL | CDR1 PRT |
| 499 | Abet0369-GL | CDR2 PRT |
| 500 | Abet0369-GL | CDR3 PRT |
| 501 | Abet0369-GL | FW1 PRT |
| 502 | Abet0369-GL | FVV2 PRT |
| 503 | Abet0369-GL | FVV3 PRT |
| 504 | Abet0369-GL | FW4 PRT |
| 505 | Abet0377-GL | VH DNA |
| 506 | Abet0377-GL | VH PRT |
| 507 | Abet0377-GL | CDR1 PRT |
| 508 | Abet0377-GL | CDR2 PRT |
| 509 | Abet0377-GL | CDR3 PRT |
| 510 | Abet0377-GL | FW1 PRT |
| 511 | Abet0377-GL | FVV2 PRT |
| 512 | Abet0377-GL | FVV3 PRT |
| 513 | Abet0377-GL | FW4 PRT |
| 514 | Abet0377-GL | VL DNA |
| 515 | Abet0377-GL | VL PRT |
| 516 | Abet0377-GL | CDR1 PRT |
| 517 | Abet0377-GL | CDR2 PRT |
| 518 | Abet0377-GL | CDR3 PRT |
| 519 | Abet0377-GL | FW1 PRT |
| 520 | Abet0377-GL | FVV2 PRT |
| 521 | Abet0377-GL | FVV3 PRT |
| 522 | Abet0377-GL | FW4 PRT |
| 523 | Abet0380-GL | VH DNA |
| 524 | Abet0380-GL | VH PRT |
| 525 | Abet0380-GL | CDR1 PRT |
| 526 | Abet0380-GL | CDR2 PRT |
| 527 | Abet0380-GL | CDR3 PRT |
| 528 | Abet0380-GL | FW1 PRT |
| 529 | Abet0380-GL | FVV2 PRT |
| 530 | Abet0380-GL | FVV3 PRT |
| 531 | Abet0380-GL | FW4 PRT |
| 532 | Abet0380-GL | VL DNA |
| 533 | Abet0380-GL | VL PRT |
| 534 | Abet0380-GL | CDR1 PRT |
| 535 | Abet0380-GL | CDR2 PRT |
| 536 | Abet0380-GL | CDR3 PRT |
| 537 | Abet0380-GL | FW1 PRT |
| 538 | Abet0380-GL | FVV2 PRT |
| 539 | Abet0380-GL | FVV3 PRT |
| 540 | Abet0380-GL | FW4 PRT |
| 541 | Abet0382-GL | VH DNA |
| 542 | Abet0382-GL | VH PRT |
| 543 | Abet0382-GL | CDR1 PRT |
| 544 | Abet0382-GL | CDR2 PRT |
| 545 | Abet0382-GL | CDR3 PRT |
| 546 | Abet0382-GL | FW1 PRT |

TABLE 16-continued

Correspondence between the antibody sequences mentioned herein and the sequences in the Sequence Listing at the end of this document.

| 547 | Abet0382-GL | FVV2 PRT |
|---|---|---|
| 548 | Abet0382-GL | FVV3 PRT |
| 549 | Abet0382-GL | FW4 PRT |
| 550 | Abet0382-GL | VL DNA |
| 551 | Abet0382-GL | VL PRT |
| 552 | Abet0382-GL | CDR1 PRT |
| 553 | Abet0382-GL | CDR2 PRT |
| 554 | Abet0382-GL | CDR3 PRT |
| 555 | Abet0382-GL | FW1 PRT |
| 556 | Abet0382-GL | FVV2 PRT |
| 557 | Abet0382-GL | FVV3 PRT |
| 558 | Abet0382-GL | FW4 PRT |

Example 6: Specificity of Abet0380-GL IgG 1-TM in Competition Binding Experiments The specificity of Abet0380-GL IgG1-TM was examined in competition binding experiments. In brief Abet0380-GL IgG1-TM (0.5 nM) was incubated (1 hr at room temperature) with a range of different concentrations (10 uM down to 0.17 nM) of a panel of full length, truncate and pyro human Abeta peptides (Abeta 1-42, Abeta 1-43, Abeta 1-16, Abeta 12-28, Abeta 17-42, Abeta pyro-3-42, or Abeta pyro-11-42).

Following the incubation between Abet0380-GL IgG1-TM and the Abeta peptides N-terminal biotin Abeta 1-42 (1.5 nM) was added followed by a europium cryptate labelled anti-human Fc antibody (0.8 nM) (CisBio Cat. No. 61HFCKLB) and streptavidin-XL$^{ent!}$ (5 nM) (CisBio Cat. No. 611SAXLB). The assay was then incubated for a further 2 hrs at room temperature before reading on an Envision plate reader (PerkinElmer) using a standard homogeneous time resolved fluorescence (HTRF) read protocol. In the absence of competition, the interaction of N-terminal biotin Abeta 1-42 with Abet0380-GL IgG1-TM (in complex with streptavidin-XL$^{ent!}$ and and europium cryptate labelled anti-human Fc antibody, respectively) could then be measured via time resolved fluorescence resonance energy transfer (TR-FRET) due to the proximity of the europium cryptate donor and XL$^{665}$ acceptor fluorophores. Competition of the Abet0380-GL IgG1-TM: N-terminal biotin Abeta 1-42 interaction by test peptides therefore resulted in a reduction in assay signal. Results were expressed as % specific binding where 100% specific binding was derived from wells containing streptavidin-XL$^{ent!}$ (5 nM), N-terminal biotin Abeta 1-42 (1.5 nM), Abet0380-GL IgG1-TM (0.5 nM) & europium crptate labelled anti-human Fc antibody (0.8 nM). 0% specific binding was derived from wells in which Abet0380-GL IgG1-TM had been omitted.

The final assay volume was 20 µl and all reagents were prepared in an assay buffer comprising MOPS pH7.4 (50 mM), potassium fluoride (0.4M), tween 20 (0.1%) & fatty acid free BSA (0.1%). The assay was performed in low volume 384 well black assay plates (Costar 3676).

Figure 18:
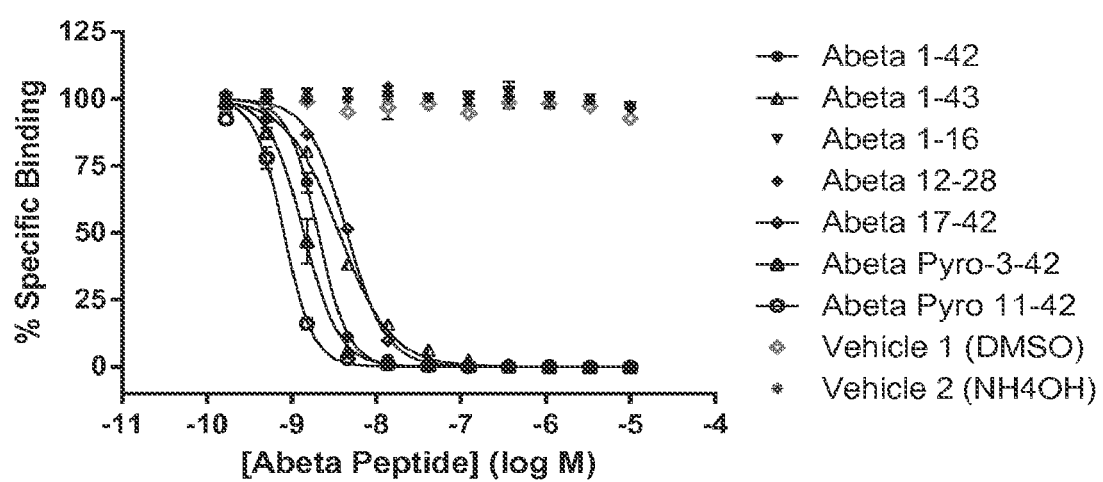
FIG. 18 shows the specificity of Abet0380-GL IgG1-TM in competition binding experiments with a range of different concentrations (10 uM down to 0.17 nM) of a panel of full length, truncate and pyro human Abeta peptides (Abeta 1-42, Abeta 1-43, Abeta 1-16, Abeta 12-28, Abeta 17-42, Abeta pyro-3-42, or Abeta pyro-11-42). Key.

In summary, inhibition of Abet0380-GL IgG1-TM: N-terminal Biotin Abeta 1-42 binding was observed with Abeta 1-42, Abeta 1-43, Abeta 17-42, Abeta Pyro-3-42 & Abeta Pyro-11-42 with IC$_{50}$ values ranging from 10$^{-8}$ to 10$^{-9}$ molar for this group. No inhibition of Abet0380-GL IgG1-TM: N-terminal Biotin Abeta 1-42 binding was observed with Abeta 1-16 or Abeta 12-28 (FIG. 18).

Example 7: Ability of Antibody Abet0144-GL to Sequester Amyloid Beta 1-42 in a Normal Rat PK-PD Study The ability of antibody Abet0144-GL to sequester amyloid beta 1-42 was investigated in a PK-PD study in normal rats. Rats were intravenously administered Abet0144-GL (10 or 40 mg/kg) or vehicle weekly for 2 weeks (on days 0 and 7), and sacrificed a week after the 2nd dose. CSF was sampled for free and total amyloid beta 1-42, and brain was sampled for total amyloid beta 1-42 measurement. Free and total amyloid beta 1-42 levels were measured using assays described above.

As shown in FIG. 19, free amyloid beta 1-42 in CSF was not significantly altered by either 10 or 40 mg/kg of Abet0144-GL (5 and 18% increase, respectively when compared with vehicle; FIG. 19). Total amyloid beta 1-42 in CSF was significantly increased by 38% at 10 mg/kg, and by 139% at 40 mg/kg. Total amyloid beta 1-42 in brain tissue was also significantly increased, by 16% and 50% at 10 and 40 mg/kg, respectively. In summary, data from this study in normal rats, demonstrated that Abet0144-GL had no significant effect on free amyloid beta 1-42 levels in CSF, whilst increasing total amyloid beta 1-42 levels in both CSF and brain. This was the profile that would be expected from an antibody with an affinity for target in the tens of nM range.

REFERENCES

Bannister, D., Wilson, A., Prowse, L., Walsh, M., Holgate, R., Jermutus, L. and Wilkinson, T. (2006). Parallel, high-throughput purification of recombinant antibodies for in vivo cell assays. *Biotechnol. Bioeng.* 94, 931-937.

Bard, F., Cannon, C., Barbour, R., Burke, R. L., Games, D., Grajeda, H., Guido, T., Hu, K., Huang, J., Johnson-Wood, K., Khan, K., Kholodenko, D., Lee, M., Lieberburg, I., Motter, R., Nguyen, M., Soriano, F., Vasquez, N., Weiss, K., Welch, B., Seubert, P., Schenk, D. and Yednock, T. (2000). Peripherally administered antibodies against amyloid beta-peptide enter the central nervous system and reduce pathology in a mouse model of Alzheimer disease. *Nat. Med.* 6, 916-919.

Borchelt, D. R., Thinakaran, G., Eckman, C. B., Lee, M. K., Davenport, F., Ratovitsky, T., Prada, C. M., Kim, G., Seekins, S., Yager, D., Slunt, H. H., Wang, R., Seeger, M., Levey, A. I., Gandy, S. E., Copeland, N. G., Jenkins, N. A., Price, D. L., Younkin, S. G. and Sisodia, S. S. (1996). Familial Alzheimer's disease-linked presenilin 1 variants elevate Abeta1-42/1-40 ratio in vitro and in vivo. *Neuron* 17, 1005-1013.

Citron, M., Eckman, C. B., Diehl, T. S., Corcoran, C., Ostaszewski, B. L., Xia, W., Levesque, G., St George Hyslop, P., Younkin, S. G. and Selkoe, D. J. (1998). Additive effects of PS1 and APP mutations on secretion of the 42-residue amyloid beta-protein. *Neurobiol. Dis.* 5, 107-116.

Clackson, T. and Lowman, H. B. (2004). *Phage display: a practical approach*, Oxford University Press.

De Strooper, B. (2007). Loss-of-function presenilin mutations in Alzheimer disease. Talking Point on the role of presenilin mutations in Alzheimer disease. *EMBO Rep.* 8, 141-146.

DeMattos, R. B., Bales, K. R., Cummins, D. J., Dodart, J. C., Paul, S. M. and Holtzman, D. M. (2001). Peripheral anti-A beta antibody alters CNS and plasma A beta clearance and decreases brain A beta burden in a mouse model of Alzheimer's disease. *Proc. Natl. Acad. Sci. USA* 98, 8850-8855.

Duff, K., Eckman, C., Zehr, C., Yu, X., Prada, C. M., Perez-tur, J., Hutton, M., Buee, L., Harigaya, Y., Yager, D., Morgan, D., Gordon, M. N., Holcomb, L., Refolo, L., Zenk, B., Hardy, J. and Younkin, S. (1996). Increased amyloid-beta42(43) in brains of mice expressing mutant presenilin 1. *Nature* 383, 710-713.

Foote, J. and Winter, G. (1992). Antibody framework residues affecting the conformation of the hypervariable loops. *J. Mol. Biol.* 224, 487-499.

Gilman, S., Koller, M., Black, R. S., Jenkins, L., Griffith, S. G., Fox, N. C., Eisner, L., Kirby, L., Rovira, M. B., Forette, F. and Orgogozo, J. M. (2005). Clinical effects of Abeta immunization (AN1792) in patients with AD in an interrupted trial. *Neurology* 64, 1553-1562.

Glabe, C. (2000). Does Alzheimer disease tilt the scales of amyloid degradation versus accumulation? *Nat. Med.* 6, 133-134.

Golde, T. E., Das, P. and Levites, Y. (2009). Quantitativeand Mechanistic Studies of Ab Immunotherapy. CNS & Neuro. Dis.—Drug Targets 8, 31-49

Greeve, I., Kretzschmar, D., Tschape, J. A., Beyn, A., Brellinger, C., Schweizer, M., Nitsch, R. M. and Reifegerste, R. (2004). Age-dependent neurodegeneration and Alzheimer-amyloid plaque formation in transgenic Drosophila. *J. Neurosci.* 24, 3899-3906.

Groves, M. A. and Osbourn, J. K. (2005). Applications of ribosome display to antibody drug discovery. *Expert Opin. Biol. Ther.* 5, 125-135.

Hanes, J., Jermutus, L. and Pluckthun, A. (2000). Selecting and evolving functional proteins in vitro by ribosome display. *Methods Enzymol.* 328, 404-430.

Hanes, J. and Pluckthun, A. (1997). In vitro selection and evolution of functional proteins by using ribosome display. *Proc. Natl. Acad. Sci. USA* 94, 4937-4942.

Hawkins, R. E., Russell, S. J. and Winter, G. (1992). Selection of phage antibodies by binding affinity. Mimicking affinity maturation. *J. Mol. Biol.* 226, 889-896.

Hoet, R. M., Cohen, E. H., Kent, R. B., Rookey, K., Schoonbroodt, S., Hogan, S., Rem, L., Frans, N., Daukandt, M., Pieters, H., van Hegelsom, R., Neer, N. C., Nastri, H. G., Rondon, I. J., Leeds, J. A., Hufton, S. E., Huang, L., Kashin, I., Devlin, M., Kuang, G., Steukers, M., Viswanathan, M., Nixon, A. E., Sexton, D. J., Hoogenboom, H. R. and Ladner, R. C. (2005). Generation of high-affinity human antibodies by combining donor-derived and synthetic complementarity-determining-region diversity. *Nat. Biotechnol.* 23, 344-348.

Iijima, K., Liu, H. P., Chiang, A. S., Hearn, S. A., Konsolaki, M. and Zhong, Y. (2004). Dissecting the pathological effects of human Abeta40 and Abeta42 in Drosophila: a potential model for Alzheimer's disease. *Proc. Natl. Acad. Sci. USA* 101, 6623-6628.

Karisson, R., Michaelsson, A. and Mattsson, L. (1991). Kinetic analysis of monoclonal antibody-antigen interactions with a new biosensor based analytical system. *J. Immunol Methods* 145, 229-240.

Kuperstein, I., Broersen, K., Benilova, I., Rozenski, J., Jonckheere, W., Debulpaep, M., Vandersteen, A., Segers-Nolten, I., Van Der Werf, K., Subramaniam, V., Braeken, D., Callewaert, G., Bartic, C., D'Hooge, R., Martins, I. C., Rousseau, F., Schymkowitz, J. and De Strooper, B. (2010). Neurotoxicity of Alzheimer's disease Abeta peptides is induced by small changes in the Abeta42 to Abeta40 ratio. *EMBO J.* 29, 3408-3420.

Lambert, M. P., Barlow, A. K., Chromy, B. A., Edwards, C., Freed, R., Liosatos, M., Morgan, T. E., Rozovsky, I., Trommer, B., Viola, K. L., Wals, P., Zhang, C., Finch, C. E., Krafft, G. A. and Klein, W. L. (1998). Diffusible, nonfibrillar ligands derived from Abeta1-42 are potent central nervous system neurotoxins. *Proc. Natl. Acad. Sci. USA* 95, 6448-6453.

Levites, Y., Das, P., Price, R. W., Rochette, M. J., Kostura, L. A., McGowan, E. M., Murphy, M. P. and Golde, T. E. (2006). Anti-Abeta42- and anti-Abeta40-specific mAbs attenuate amyloid deposition in an Alzheimer disease mouse model. *J. Clin. Invest.* 116, 193-201.

Matsuoka, Y., Saito, M., LaFrancois, J., Saito, M., Gaynor, K., Olm, V., Wang, L., Casey, E., Lu, Y., Shiratori, C., Lemere, C. and Duff, K. (2003). Novel therapeutic approach for the treatment of Alzheimer's disease by peripheral administration of agents with an affinity to beta-amyloid. *J. Neurosci.* 23, 29-33.

McCafferty, J., Fitzgerald, K. J., Earnshaw, J., Chiswell, D. J., Link, J., Smith, R. and Kenten, J. (1994). Selection and rapid purification of murine antibody fragments that bind a transition-state analog by phage display. *Appl. Biochem. Biotechnol.* 47, 157-171; discussion 171-153.

McGowan, E., Pickford, F., Kim, J., Onstead, L., Eriksen, J., Yu, C., Skipper, L., Murphy, M. P., Beard, J., Das, P., Jansen, K., Delucia, M., Lin, W. L., Dolios, G., Wang, R., Eckman, C. B., Dickson, D. W., Hutton, M., Hardy, J. and Golde, T. (2005). Abeta42 is essential for parenchymal and vascular amyloid deposition in mice. *Neuron* 47, 191-199.

Mucke, L., Masliah, E., Yu, G. Q., Mallory, M., Rockenstein, E. M., Tatsuno, G., Hu, K., Kholodenko, D., Johnson-Wood, K. and McConlogue, L. (2000). High-level neuronal expression of abeta 1-42 in wild-type human amyloid protein precursor transgenic mice: synaptotoxicity without plaque formation. *J. Neurosci.* 20, 4050-4058.

Oganesyan, V., Gao, C., Shirinian, L., Wu, H. and Dal'Acqua, W. F. (2008). Structural characterization of a human Fc fragment engineered for lack of effector functions. *Acta Crystallogr. D Biol. Crystallogr.* 64, 700-704.

Orgogozo, J. M., Gilman, S., Dartigues, J. F., Laurent, B., Puel, M., Kirby, L. C., Jouanny, P., Dubois, B., Eisner, L., Flitman, S., Michel, B. F., Boada, M., Frank, A. and Hock, C. (2003). Subacute meningoencephalitis in a subset of patients with AD after Abeta42 immunization. *Neurology* 61, 46-54.

Osbourn, J. K., Field, A., Wilton, J., Derbyshire, E., Earnshaw, J. C., Jones, P. T., Allen, D. and McCafferty, J. (1996). Generation of a panel of related human scFv antibodies with high affinities for human CEA. *Immunotechnology* 2, 181-196.

Persic, L., Roberts, A., Wilton, J., Cattaneo, A., Bradbury, A. and Hoogenboom, H. R. (1997). An integrated vector system for the eukaryotic expression of antibodies or their fragments after selection from phage display libraries. *Gene* 187, 9-18.

Portelius, E., Bogdanovic, N., Gustavsson, M. K., Volkmann, I., Brinkmalm, G., Zetterberg, H., Winblad, B. and Blennow, K. (2010). Mass spectrometric characterization of brain amyloid beta isoform signatures in familial and sporadic Alzheimer's disease. *Acta Neuropathol.* 120, 185-193.

Pride, M., Seubert, P., Grundman, M., Hagen, M., Eldridge, J. and Black, R. S. (2008). Progress in the active immunotherapeutic approach to Alzheimer's disease: clinical investigations into AN1792-associated meningoencephalitis. *Neurodegener. Dis.* 5, 194-196.

Schenk, D., Barbour, R., Dunn, W., Gordon, G., Grajeda, H., Guido, T., Hu, K., Huang, J., Johnson-Wood, K., Khan, K., Kholodenko, D., Lee, M., Liao, Z., Lieberburg, I., Motter, R., Mutter, L., Soriano, F., Shopp, G., Vasquez, N., Vandevert, C., Walker, S., Wogulis, M., Yednock, T., Games, D. and Seubert, P. (1999). Immunization with amyloid-beta attenuates Alzheimer-disease-like pathology in the PDAPP mouse. Nature 400, 173-177.

Schenk, D. B., Seubert, P., Lieberburg, I. and Wallace, J. (2000). beta-peptide immunization: a possible new treatment for Alzheimer disease. Arch. Neurol. 57, 934-936.

Scheuner, D., Eckman, C., Jensen, M., Song, X., Citron, M., Suzuki, N., Bird, T. D., Hardy, J., Hutton, M., Kukull, W., Larson, E., Levy-Lahad, E., Viitanen, M., Peskind, E., Poorkaj, P., Schellenberg, G., Tanzi, R., Wasco, W., Lannfelt, L., Selkoe, D. and Younkin, S. (1996). Secreted amyloid beta-protein similar to that in the senile plaques of Alzheimer's disease is increased in vivo by the presenilin 1 and 2 and APP mutations linked to familial Alzheimer's disease. Nat. Med. 2, 864-870.

Schier, R., Bye, J., Apell, G., McCall, A., Adams, G. P., Malmqvist, M., Weiner, L. M. and Marks, J. D. (1996). Isolation of high-affinity monomeric human anti-c-erbB-2 single chain Fv using affinity-driven selection. J. Mol. Biol. 255, 28-43.

Selkoe, D. J. (1999). Translating cell biology into therapeutic advances in Alzheimer's disease. Nature 399, A23-31.

Thompson, J., Pope, T., Tung, J. S., Chan, C., Hollis, G., Mark, G. and Johnson, K. S. (1996). Affinity maturation of a high-affinity human monoclonal antibody against the third hypervariable loop of human immunodeficiency virus: use of phage display to improve affinity and broaden strain reactivity. J. Mol. Biol. 256, 77-88.

Tomlinson, I. M., Walter, G., Marks, J. D., Llewelyn, M. B. and Winter, G. (1992). The repertoire of human germline $V_H$ sequences reveals about fifty groups of $V_H$ segments with different hypervariable loops. J. Mol. Biol. 227, 776-798.

Vassar, R., Bennett, B. D., Babu-Khan, S., Kahn, S., Mendiaz, E. A., Denis, P., Teplow, D. B., Ross, S., Amarante, P., Loeloff, R., Luo, Y., Fisher, S., Fuller, J., Edenson, S., Lile, J., Jarosinski, M. A., Biere, A. L., Curran, E., Burgess, T., Louis, J. C., Collins, F., Treanor, J., Rogers, G. and Citron, M. (1999). Beta-secretase cleavage of Alzheimer's amyloid precursor protein by the transmembrane aspartic protease BACE. Science 286, 735-741.

Vaughan, T. J., Williams, A. J., Pritchard, K., Osbourn, J. K., Pope, A. R., Earnshaw, J. C., McCafferty, J., Hodits, R. A., Wilton, J. and Johnson, K. S. (1996). Human antibodies with sub-nanomolar affinities isolated from a large non-immunized phage display library. Nat. Biotechnol. 14, 309-314.

Walsh, D. M., Klyubin, I., Fadeeva, J. V., Cullen, W. K., Anwyl, R., Wolfe, M. S., Rowan, M. J. and Selkoe, D. J. (2002). Naturally secreted oligomers of amyloid beta protein potently inhibit hippocampal long-term potentiation in vivo. Nature 416, 535-539.

Walsh, D. M., Klyubin, I., Shankar, G. M., Townsend, M., Fadeeva, J. V., Betts, V., Podlisny, M. B., Cleary, J. P., Ashe, K. H., Rowan, M. J. and Selkoe, D. J. (2005a). The role of cell-derived oligomers of Abeta in Alzheimer's disease and avenues for therapeutic intervention. Biochem. Soc. Trans. 33, 1087-1090.

Walsh, D. M., Townsend, M., Podlisny, M. B., Shankar, G. M., Fadeeva, J. V., El Agnaf, O., Hartley, D. M. and Selkoe, D. J. (2005b). Certain inhibitors of synthetic amyloid beta-peptide (Abeta) fibrillogenesis block oligomerization of natural Abeta and thereby rescue long-term potentiation. J. Neurosci. 25, 2455-2462.

Wang, H. W., Pasternak, J. F., Kuo, H., Ristic, H., Lambert, M. P., Chromy, B., Viola, K. L., Klein, W. L., Stine, W. B., Krafft, G. A. and Trommer, B. L. (2002). Soluble oligomers of beta amyloid (1-42) inhibit long-term potentiation but not long-term depression in rat dentate gyrus. Brain Res. 924, 133-140.

Weller, R. O. and Nicoll, J. A. (2003). Cerebral amyloid angiopathy: pathogenesis and effects on the ageing and Alzheimer brain. Neurol. Res. 25, 611-616.

Wilcock, D. M., Alamed, J., Gottschall, P. E., Grimm, J., Rosenthal, A., Pons, J., Ronan, V., Symmonds, K., Gordon, M. N. and Morgan, D. (2006). Deglycosylated anti-amyloid-beta antibodies eliminate cognitive deficits and reduce parenchymal amyloid with minimal vascular consequences in aged amyloid precursor protein transgenic mice. J. Neurosci. 26, 5340-5346.

Wilcock, D. M. and Colton, C. A. (2009). Immunotherapy, vascular pathology, and microhemorrhages in transgenic mice. CNS Neurol. Disord. Drug. Targets. 8, 50-64.

Younkin, S. G. (1995). Evidence that A beta 42 is the real culprit in Alzheimer's disease. Ann. Neurol. 37, 287-288.

Younkin, S. G. (1998). The role of A beta 42 in Alzheimer's disease. J. Physiol. Paris 92, 289-292.

Other references are included in the text.

What is claimed is:

1. An isolated antibody molecule that is selective for binding human amyloid beta 1-42 peptide (Aβ1-42) over human amyloid beta 1-40 peptide (Aβ1-40), wherein the antibody molecule comprises a $V_H$ domain having an amino acid sequence that is at least 90% identical to the amino acid sequence of SEQ ID NO: 524 and a $V_L$ domain having an amino acid sequence that is at least 90% identical to the amino acid sequence of SEQ ID NO: 533, wherein the $V_H$ domain of the antibody molecule comprises:
a) HCDR1 of SEQ ID NO: 525, HCDR2 of SEQ ID NO: 526, and HCDR3 of SEQ ID NO: 527;
b) wherein FW1 of the $V_H$ domain comprises:
a methionine residue at the amino acid position corresponding to position 26 of SEQ ID NO: 524;
a glycine residue at the amino acid position corresponding to position 27 of SEQ ID NO: 524;
an asparagine residue at the amino acid position corresponding to position 28 of SEQ ID NO: 524; and
an asparagine residue at the amino acid position corresponding to position 30 of SEQ ID NO: 524;
and wherein the $V_L$ domain of the antibody molecule comprises LCDR1 of SEQ ID NO: 534, LCDR2 of SEQ ID NO: 535, and LCDR3 of SEQ ID NO: 536.

2. The isolated antibody molecule of claim 1, wherein the antibody molecule comprises a VH domain having an amino acid sequence that is at least 95%, 98% or 99% identical to the amino acid sequence of SEQ ID NO: 524 and a VL domain having an amino acid sequence that is at least 95%, 98%, or 99% identical to the amino acid sequence of SEQ ID NO: 533.

3. The isolated antibody molecule of claim 1, wherein the antibody molecule is a monoclonal antibody.

4. The isolated antibody molecule of claim 3, wherein the monoclonal antibody is a recombinant antibody, a humanized antibody, a human antibody, a multispecific antibody, or an antibody fragment thereof.

5. The isolated antibody molecule of claim 4, wherein the antibody molecule is an scFv.

6. The isolated antibody molecule of claim 4, wherein the antibody molecule is a Fab.

7. The isolated antibody molecule of claim 3, wherein the antibody molecule is of the IgG1-, IgG2-, or IgG4-type.

8. The isolated antibody molecule of claim 1, wherein the antibody molecule is a chimeric antibody.

9. A composition comprising an isolated antibody molecule according to claim 1, and a pharmaceutically acceptable excipient.

10. A method of treating a human or animal subject having an amyloidosis associated with amyloid beta, the method comprising administering to the subject an antibody according to claim 1.

11. The method of claim 10, wherein the treatment at least reduces amyloidosis; treats Alzheimer's disease; improves cognition or reduces cognitive decline in an Alzheimer's disease or Down's syndrome patient; or treats macular degeneration.

12. A method of at least reducing amyloidosis, treating Alzheimer's disease; improving cognition or reducing cognitive decline in an Alzheimer's disease or Down's syndrome patient; and/or treating macular degeneration in an individual, the method comprising administering to the subject an antibody according to claim 1.

* * * * *